US008673916B2

(12) United States Patent
Bacon et al.

(10) Patent No.: US 8,673,916 B2
(45) Date of Patent: Mar. 18, 2014

(54) METHODS OF TREATING DISORDERS MEDIATED BY HISTAMINE $H_3$ RECEPTORS USING PYRIDAZINONE DERIVATIVES

(75) Inventors: Edward R. Bacon, Audubon, PA (US); Thomas R. Bailey, Phoenixville, PA (US); Nadine C. Becknell, Coatesville, PA (US); Sankar Chatterjee, Wynnewood, PA (US); Derek D. Dunn, Coatesville, PA (US); Greg A. Hostetler, Newark, DE (US); Robert L. Hudkins, Chester Springs, PA (US); Kurt A. Josef, Radnor, PA (US); Lars J. S. Knutsen, West Chester, PA (US); Ming Tao, Maple Glen, PA (US); Allison L. Zulli, Wayne, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 13/197,243

(22) Filed: Aug. 3, 2011

(65) Prior Publication Data
US 2011/0288075 A1 Nov. 24, 2011

Related U.S. Application Data

(60) Division of application No. 12/815,800, filed on Jun. 15, 2010, now Pat. No. 8,207,168, which is a continuation of application No. 11/881,001, filed on Jul. 25, 2007, now Pat. No. 8,247,414.

(60) Provisional application No. 60/833,164, filed on Jul. 25, 2006.

(51) Int. Cl.
*A61K 31/501* (2006.01)
*A61P 3/04* (2006.01)
*A61P 25/28* (2006.01)
*A61P 25/18* (2006.01)
*A61P 25/08* (2006.01)
*A61P 25/06* (2006.01)
*A61P 25/24* (2006.01)

(52) U.S. Cl.
USPC .................................................. 514/252.05

(58) Field of Classification Search
USPC ................. 514/248, 252.02, 252.03, 252.04, 514/252.05, 252.06, 247
See application file for complete search history.

(56) References Cited

U.S. PATENT DOCUMENTS

| | | |
|---|---|---|
| 3,931,177 A | 1/1976 | Coates et al. |
| 4,011,321 A | 3/1977 | Coates et al. |
| 4,053,601 A | 10/1977 | Coates et al. |
| 4,082,843 A | 4/1978 | Coates et al. |
| 4,111,935 A | 9/1978 | Coates et al. |
| 4,111,936 A | 9/1978 | Coates et al. |
| 4,353,905 A | 10/1982 | Sircar et al. |
| 4,397,854 A | 8/1983 | Sircar |
| 4,404,203 A | 9/1983 | Sircar |
| 4,666,902 A | 5/1987 | Zoller et al. |
| 4,734,415 A | 3/1988 | Sircar et al. |
| 4,816,454 A | 3/1989 | Zoller et al. |
| 4,843,072 A | 6/1989 | Yasuda et al. |
| 4,921,856 A | 5/1990 | Schickaneder et al. |
| 4,925,845 A | 5/1990 | Mertens et al. |
| 4,954,501 A | 9/1990 | Herter et al. |
| 4,968,683 A | 11/1990 | Morsdorf et al. |
| 5,053,338 A | 10/1991 | Bray et al. |
| 5,135,932 A | 8/1992 | Hauel et al. |
| 5,153,210 A | 10/1992 | Ainsworth et al. |
| 5,204,463 A | 4/1993 | Wheeler et al. |
| 5,698,554 A | 12/1997 | Ishida et al. |
| 6,531,496 B1 | 3/2003 | Uhr et al. |
| 6,677,333 B1 | 1/2004 | Seko et al. |
| 7,727,989 B2 | 6/2010 | Schoenafinger et al. |
| 2006/0178375 A1 | 8/2006 | Ohtake et al. |
| 2007/0072866 A1 | 3/2007 | Schoenafinger et al. |
| 2007/0173503 A1 | 7/2007 | Hoelder et al. |
| 2008/0027041 A1 | 1/2008 | Hudkins et al. |
| 2008/0262226 A1 | 10/2008 | Chen |
| 2008/0293719 A1 | 11/2008 | Dorsch et al. |
| 2009/0011994 A1 | 1/2009 | Stein et al. |
| 2009/0042880 A1 | 2/2009 | Hoelder et al. |
| 2009/0163545 A1 | 6/2009 | Goldfarb |

(Continued)

FOREIGN PATENT DOCUMENTS

| | | |
|---|---|---|
| AT | 389108 | 10/1989 |
| AU | 198547661 A | 4/1986 |

(Continued)

OTHER PUBLICATIONS

Ting, et al., Bioorganic & Medicinal Chemistry Letters, 12 (2002) 2643-2646.*
Leurs, et al., TiPS—May 1998 (vol. 19), 177-183.*
Medhurst, et al., J. Pharmacol. & Experiment. Therapeut., vol. 321, No. 3, 1032-1045.*
Seki et al., "Studies on Agents with Vasodilator and B-Blocking Activities. IV", Chem. Pharm. Bull. (1996), vol. 44(11), pp. 2061-2069.
Davis et al., "Strategic approaches to drug design. II. Modelling studies on phosphodiesterase substrates and inhibitors", J. Computer-Aided Mol. Design (1987), vol. 1, pp. 97-120.

(Continued)

*Primary Examiner* — James O Wilson
*Assistant Examiner* — Cecilia M Jaisle
(74) *Attorney, Agent, or Firm* — John P. White; Gary J. Gershik; Cooper & Dunham LLP

(57) ABSTRACT

The present invention is directed to methods of treating disorders mediated by Histamine $H_3$ receptors by administering novel pyridazinone derivatives. In particular, the pyridazinone compounds may be effective in the treatment of diseases or disease states related to the activity of the histamine $H_3$ receptor, including, for example, neurodegenerative disorders, sleep/wake disorders, attention deficit hyperactivity disorder and cognition/cognitive disorders.

21 Claims, No Drawings

(56) References Cited

U.S. PATENT DOCUMENTS

| | | |
|---|---|---|
| 2010/0130738 A1 | 5/2010 | Kohno et al. |
| 2010/0160335 A1 | 6/2010 | Kohno et al. |
| 2010/0179149 A1 | 7/2010 | Stieber et al. |
| 2010/0184746 A1 | 7/2010 | Umemura et al. |
| 2010/0261697 A1 | 10/2010 | Dorsch et al. |
| 2010/0286390 A1 | 11/2010 | Shigeta et al. |
| 2010/0298332 A1 | 11/2010 | Dandu et al. |
| 2010/0311752 A1 | 12/2010 | Hudkins et al. |
| 2011/0003759 A1 | 1/2011 | Stein et al. |
| 2011/0071131 A1 | 3/2011 | Bacon et al. |

FOREIGN PATENT DOCUMENTS

| | | |
|---|---|---|
| DE | 2556918 | 6/1977 |
| EP | 0 051 215 | 5/1982 |
| EP | 0 051 217 | 5/1982 |
| EP | 0 075 436 | 3/1983 |
| EP | 0 084 250 | 7/1983 |
| EP | 0 129 791 | 2/1985 |
| EP | 0 138 344 | 4/1985 |
| EP | 0 175 363 | 3/1986 |
| EP | 0 194 548 | 9/1986 |
| EP | 0 201 988 | 11/1986 |
| EP | 0 259 835 | 3/1988 |
| EP | 0 259 835 A | 3/1988 |
| EP | 0 280 224 | 8/1988 |
| EP | 0 304 534 | 3/1989 |
| EP | 0 304 534 A | 3/1989 |
| EP | 0 327 800 | 8/1989 |
| EP | 0 339 208 | 11/1989 |
| EP | 0 400 519 | 5/1990 |
| EP | 0 383 449 | 8/1990 |
| EP | 0 412 814 | 2/1991 |
| EP | 0 412 814 A | 2/1991 |
| EP | 0 751 132 | 1/1997 |
| EP | 1 311 482 B1 | 2/2007 |
| GB | 1 488 330 | 10/1977 |
| GB | 1 548 601 | 7/1979 |
| GB | 2 228 004 | 8/1990 |
| JP | 57-46966 | 3/1982 |
| JP | 60-87283 | 5/1985 |
| JP | 61-212582 | 9/1986 |
| JP | 63-145272 | 6/1988 |
| JP | 63-154673 | 6/1988 |
| JP | 63-215672 | 9/1988 |
| JP | 10-236954 | 9/1998 |
| JP | 2008-222580 | 9/2008 |
| JP | 2008-222648 | 9/2008 |
| JP | 2008-239558 | 10/2008 |
| WO | 90/01479 | 2/1990 |
| WO | 99/31071 | 6/1999 |
| WO | 99/47505 | 9/1999 |
| WO | 00/21935 | 4/2000 |
| WO | 00/64881 | 11/2000 |
| WO | 01/64652 A1 | 9/2001 |
| WO | 01/68611 A1 | 9/2001 |
| WO | 01/74771 A1 | 10/2001 |
| WO | 02/32897 A1 | 4/2002 |
| WO | 03/040096 A2 | 5/2003 |
| WO | 2004/022540 A2 | 3/2004 |
| WO | 2004/089373 A1 | 10/2004 |
| WO | 2005/085230 A1 | 9/2005 |
| WO | 2005/085231 A1 | 9/2005 |
| WO | 2006/060122 A2 | 6/2006 |
| WO | 2006/060127 A2 | 8/2006 |
| WO | WO 2006/103045 | 10/2006 |
| WO | WO 2006/103057 | 10/2006 |
| WO | WO 2006/103546 A2 | 10/2006 |
| WO | WO 2006/117609 A2 | 11/2006 |
| WO | WO 2006/124874 A2 | 11/2006 |
| WO | WO 2007/065518 A1 | 6/2007 |
| WO | WO 2007/130383 A2 | 11/2007 |
| WO | WO 2008/013838 | 1/2008 |
| WO | WO 2008/029882 A1 | 3/2008 |
| WO | WO 2008/077597 A1 | 7/2008 |
| WO | WO 2008/137087 A1 | 11/2008 |
| WO | WO 2008/017361 A2 | 12/2008 |
| WO | WO 2009/082698 A1 | 7/2009 |
| WO | WO 2009/142732 A2 | 11/2009 |
| WO | WO 2010/129242 A2 | 11/2010 |

OTHER PUBLICATIONS

Loynes et al., "New Sulfonamides", J. Med. Chem. (1965), vol. 8(5), pp. 691-694.

Mertens et al., "Nonsteroidal Cardiotonics. 3. New 4,5-Dihydro-6-(1H-indol-5-yl)pyridazin-3(2H)-ones and Related Compounds with Positive Inotropic Activities", J. Med. Chem. (1990), vol. 33, pp. 2870-2875.

Sircar, "Cardiotonic Agents. 7. Inhibition of Separated Forms of Cyclic Nucleotide Phosphodiesterase from Guinea Pig Cardiac Muscle by 4,5-Dihydro-6-[4-(1H-imidazol-1-yl)phenyl]-3(2H)-pyridazinones and Related Compounds. Structure-Activity Relationships and Correlation with in Vivo Positive Inotropic Activity", J. Med. Chem. (1987), vol. 30, pp. 1955-1962.

Coates et al., "One-Pot Preparation of 6-Substituted 3(2H-Pyridazinones from Ketones", Synthesis (1993), pp. 334-342.

Van der Mey et al., "Novel Selective PDE4 Inhibitors. 2. Synthesis and Structure-Activity Relationships of 4-Aryl-Substituted cis-Tetra- and cis-Hexahydrophthalazinones", J. Med. Chem. (2001), vol. 44, pp. 2523-2535.

Van der Mey et al., "Synthesis and Structure-Activity Relationships of cis-Tetrahydrophthalazinone/Pyridazinone Hybrids: A Novel Series of Potent Dual PDE3/PDE4 Inhibitory Agents", J. Med. Chem. (2003), vol. 46, pp. 2008-2016.

Saunders et al., "Syntheses of carbon-14-labeled prizidilol dihydrochloride", J. Labelled Compounds and Radiopharmaceuticals (1985), vol. 22(9), pp. 869-881 (Abstract only).

Shang et al., "Investigation on exposy resin adhesive containing phthalazinone", Zhongguo Jiaoniangi (2002), vol. 11 (2), pp. 1-3 (Abstract only).

Kuehmstedt et al., "Synthesis of tetrahydropyranyl and tetrahydrofuryl derivatives of various 3-pyridazones and 3-thiopyridazones", Zeitschrift fuer Chemie (1965), vol. 5(7), pp. 269-270 (Abstract only).

Eurasian Office Action for EA Appln. No. 200970156/28 dated Sep. 21, 2010 (English translation included).

European Communication for EP Appln. No. 07810758.8-2117 dated Dec. 8, 2009.

Singapore Office Action for SG Appln. No. 200900331-0 dated Oct. 22, 2010.

New Zealand Office Action for NZ Appln. No. 574873 dated Jul. 16, 2010.

China Office Action for CN Appln. No. 200780034555.6 dated Nov. 22, 2010 (English translation included).

Alguacil, L.F. et al., Histamine H3 Receptor: A potential drug target for the treatment of central nervous system disorders. Current Drug Targets—CNS & Neurological Disorders 2003, 2, 303-131.

Arrang, J. M. et al., Auto-inhibition of brain histamine release mediated by a novel class ($H_3$) of histamine receptor. Nature 1983, 302, (5911), 832-7.

Celanire, S. et al., Keynote review: histamine H3 receptor antagonists reach out for the clinic. Drug Discov. Today 2005, 10, (23-24), 1613-27.

Chazot, P.L. et al., H3 histamine receptor isoforms: New therapeutic targets in the CNS? Current Opinions in Investigational Drugs 2001, 2, 1428-1431.

Chen, Z. Effect of histamine $H_3$-receptor antagonist clobenprobit on spatial memory of radial maze performance in rats. Acta Pharmacol. Sin. 2000, 21, 905-910.

Esbenshade, T.A. et al., Histamine H3 receptor antagonists: Preclinical promise for treating obesity and cognitive disorders. Molecular interventions 2006, 6, 77-88.

Fox, G.B. et al., Effects of histamine H3 receptor ligands GT-2331 and ciproxifan in a repeated acquisition response in the spontaneously hypertensive rat pup. Behav. Brain Res. 2002, 131, 151-161.

(56) References Cited

OTHER PUBLICATIONS

Fox, G.B. et al., Two novel and selective nonimidazole H3 receptor Antagonists A-304121 and A-317920: II. In vivo behavioral and neurophysiological characterization. J. Pharmacol. Exper. Ther. 2003, 305, 897-908.

Hancock, A.A. et al., Genetic and pharmacological aspects of histamine H3 receptor heterogeneity. Life Sci. 2003, 73, (24), 3043-72.

Hancock, A.A. et al., Perspectives on cognitive domains, H3 receptor ligands and neurological disease. Expert Opin. Investig. Drugs, 2004, 13, 1237-1248.

Komater, V.A. et al., H3 receptor blockade by thioperamide enhances cognition in rats without inducing locomotor sensitization. Psychopharmacology 2003, 167, 363-372.

Leurs, R. et al., Therapeutic potential of histamine H3 receptor agonists and antagonists. Trends in Pharmacology 1998, 19, 177-183.

Leurs, R. et al., The histamine H3 receptor: from gene cloning to H3 receptor drugs. Nat. Rev. Drug Discov. 2005, 4, (2), 107-20.

Lin, J. S. et al., Involvement of histaminergic neurons in arousal mechanisms demonstrated with $H_3$-receptor ligands in the cat. Brain Res. 1990, 523, (2), 325-30.

Lloyd, G.K. et al., Neuronal nicotinic acetylcholine receptors as novel drug targets. J. Pharmacol. Exp. Ther. 2000, 292, 461-467.

Monti, J.M. et al., Sleep and waking during acute histamine H3 agonist BP 2.94 or H3 antagonist carboperamide (MR 16155) administration in rats. Neuropsychopharmacology 1996, 15, 31-5.

Orsetti, M. et al., Histamine $H_3$-receptor blockade in the rat nucleus basalis magnocellularis improves place recognition memory. Psychopharmacology 2002, 159, 133-137.

Parmentier, R. et al., Anatomical, physiological, and pharmacological characteristics of histidine decarboxylase knock-out mice: evidence for the role of brain histamine in behavioral and sleep-wake control. J. Neurosci. 2002, 22, 7695-7711.

Passani, M.B. et al., The histamine H3 receptor as a novel therapeutic target for cognitive and sleep disorders. Trends Pharmacol. Sci. 2004, 25, 618-25.

Repka-Ramirez, M.S. New concepts of histamine receptors and actions. Current Allergy and Asthma Reports 2003, 3, 227-231.

Ritz, A. et al., J. Anxiety and cognition in histamine H3 receptor -/- mice. Eur. J. Neurosci. 2004, 19, 1992-1996.

Rouleau, A. et al., Cloning and expression of the mouse histamine H3 receptor: evidence for multiple isoforms. J. Neurochem. 2004, 90, 1331-8.

Vanni-Merci, G. et al., Waking selective neurons in the posterior hypothalamus and their response to histamine $H_3$-receptor ligands: an electrophysiological study in freely moving cats. Behav. Brain Res. 2003, 144, 227-241.

Witkin, J. M. et al., Selective histamine H3 receptor antagonists for treatment of cognitive deficiencies and other disorders of the central nervous system. Pharmacol. Ther. 2004, 103, 1-20.

Yao, B. B. et al., Cloning and pharmacological characterization of the monkey histamine H3 receptor. Eur. J. Pharmacol. 2003, 482, (1-3), 49-60.

Lehninger, A.L. Biochemistry, $2^{rd}$ ed.; Worth Publishers: New York, 1975; 71-77.

Heterocycles, 2002, 57, 39.

Chem. Pharm. Bull., 1980, 42, 1850.

Van der Mey, M. et al. Synthesis and structure-activity relationships of cis-tetrahydrophthalazinone/pyridazinone hybrids: a novel series of potent dual PDE3/PDE4 inhibitory agents, J. Med. Chem. 2003, 46, 2008-2016.

Indian J. Chem, 1977, 16B, 631.

Wermuth, C.G. et al., Synthesis and structure-activity relationships of a series of aminopyridazine derivatives of .gamma.-aminobutyric acid acting as selective GABA-A antagonists, J. Med. Chem., 1987, 30, 239-249.

Pinna, G.A. et al., Synthesis and Pharmacological Study of 5-aryl-6-methyl-4,5-dihydro-pyridazin-3(2H)ones and related 5-aryl-6-methyl-pyridazin-3(2H)ones, Farmaco, 1987, 43, 539-549.

Genbank file #NM_053506.

Edgar & Seidel, Journal of Pharmacology and Experimental Therapeutics, 283: 757-769, 1997.

Kraly, F.S. et al., 1982 Physiol. Behav. 28: 841.

Leibowitz, S.F. 1973 Brain Res. 63:440.

Ligneau, X. et al., 1998 J. Pharmcol. Exp. Ther. 287:658-66.

Clapham, J. and Kilpatrick G.J. 1993 Eur. J. Pharmacol. 232:99-103.

Ennaceur, A. and Delacour, J. (1988) Behav. Brain Res. 31: 47-59.

Thor and Holloway (1982). Thor, D. and Holloway, W. (1982) J. Comp. Physiolog. Psychcol. 96: 1000-1006.

Okushima, Hiromi et al., "A novel class of cardiotonics. Synthesis and pharmacological properties of [4-(substituted-amino)phenyl]pyridazinones and related derivatives," J. Med. Chem., 1987, 30(7), 1157-1161.

Steck, Edgar A. et al., "Pyridazines. VI. 6 Substituted 3(2H)pyridazinones," J. Heterocyclic Chem., 1974, 11(5), 755-761.

Li, Wenxin et al., "Synthesis and platelet aggregation inhibitory activity of 6-(4-substituted phenyl-4,5-dihydro-3-(2H)-pyridazinones," Zhongguo Yaowu Huaxue Zazhi, 1997, 7(1), 12-17.

Zhu, Jin et al., "Synthesis and platelet aggregation inhibitory activity of 4,5-dihydro-3(2H)-pyridazinones," Zhongguo Yaowu Huaxue Zazhi, 2004, 14(1), 23-26.

Xu, Youjun et al., "Synthesis and platelet aggregation inhibitory activity of 6-(substituted phenyl)-4,5-dihydro-3(2H)-pryidazinones," Zhongguo Yaowu Huaxue Zazhi, 1997, 7(4), 240-245.

Apelt, J. et al., "Search for histamine H3 receptor antagonists with combined inhibitory potency at N-methyltransferase: ether derivatives," Pharmazie, Die, Govi Verlag, Eschborn, DE, vol. 60, No. 2, 2005, pp. 97-106.

Mori et al., "Oxygen-Saving Effect of a New Cardiotonic Agent, MCI-154, in Diseased Human Hearts", J. Am. Coll. Cardiol. (1997), 29(3), 613-622.

Seki, et al., "Studies on Agents with Vasodilator and β-Blocking Activities. IV", Chem. Pharm. Bull. (1996), 44(11), 2061-2069.

Genbank file #NM 053506 (Jan. 25, 2009).

* cited by examiner

METHODS OF TREATING DISORDERS MEDIATED BY HISTAMINE H₃ RECEPTORS USING PYRIDAZINONE DERIVATIVES

CROSS-REFERENCE TO RELATED APPLICATIONS

This application is a divisional application of U.S. application Ser. No. 12/815,800 filed Jun. 15, 2010 which is a continuing application of U.S. application Ser. No. 11/881,001 filed Jul. 25, 2007, which claims the benefit of U.S. Provisional Application Ser. No. 60/833,164 filed Jul. 25, 2006, the disclosure of which is incorporated herein by reference in its entirety.

FIELD OF THE INVENTION

The present invention is related to pyridazinone derivatives, their use as $H_3$ inhibitors, processes for their preparation, and pharmaceutical compositions thereof.

BACKGROUND OF THE INVENTION

Histamine is a well established modulator of neuronal activity. At least four subtypes of histamine receptors have been reported in the literature—$H_1$, $H_2$, $H_3$, $H_4$. The histamine $H_3$ receptors play a key role in neurotransmission in the central nervous system. The $H_3$ receptor was discovered in 1983 originally on histamine-containing neurons where it was shown to function presynaptically, regulating the release and synthesis of the biogenic amine histamine (Arrang et al, 1983) now a well established neurotransmitter. $H_3$ receptors are predominately expressed in the brain, localizing to the cerebral cortex, amygdala, hippocampus, striatum, thalamus and hypothalamus. $H_3$ receptors are also localized presynaptically on histaminergic nerve terminals and act as inhibitory autoreceptors (Alguacil and Perez-Garcia, 2003; Passani et al, 2004; Leurs at al, 2005; Celanire et al, 2005; Witkin and Nelson, 2004). When these receptors are activated by histamine, histamine release is inhibited. $H_3$ receptors can also be found in the periphery (skin, lung, cardiovascular system, intestine, GI tract, etc). $H_3$ receptors are also involved in presynaptic regulation of the release of acetylcholine, dopamine, GABA, glutamate and serotonin (see Repka-Ramirez, 2003; Chazot and Hann, 2001; Leurs et al, 1998). The $H_3$ receptor demonstrates a high degree of constitutive or spontaneous activity (e.g., receptor is active in the absence of agonist stimulation) in vitro and in vivo, thus, ligands to the receptor can display, agonist, neutral antagonist or inverse agonist effects.

The location and function of histaminergic neurons in the CNS suggests that compounds interacting with the $H_3$ receptor may have utility in a number of therapeutic applications including narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders and epilepsy (Leers et al, 2005; Witkin and Nelson, 2004, Hancock and Fox 2004; Esbenshade et al. 2006). An $H_3$ antagonist/inverse agonist could be important for gastrointestinal disorders, respiratory disorders such as asthma, inflammation, and myocardial infarction.

Ohtake et al. (US 2006/0178375 A1) disclosed compounds that reportedly exhibit histamine receptor $H_3$ antagonist or inverse agonist activity and may be useful for the treatment or prevention of obesity, diabetes, hormonal secretion abnormality, or sleep disorders.

Celanire et al. (WO 2006/103057 A1 and WO 2006/103045) have disclosed compounds comprising an oxazoline or thiazoline moiety, processes for preparing them, their pharmaceutical compositions and their uses as $H_3$ ligands.

Bertrand et al. (WO 2006/117609 A2) disclosed novel histamine $H_3$ receptor ligands, processes for their preparation, and their therapeutic applications.

Schwartz et al. (WO 2006/103546 A2) disclosed certain methods of treatment for Parkinson's disease, obstructive sleep apnea, narcolepsy, dementia with Lewy bodies, and/or vascular dementia using non-imidazole alkylamine derivatives that are antagonists of the $H_3$ receptors of histamine.

Apodaca et al. (EP 1 311 482 B1) disclosed certain non-imidazole aryloxypiperidines as $H_3$ receptor ligands, their synthesis, and their use for the treatment of disorders and conditions mediated by the histamine receptor.

Xu et al. disclosed certain 6-substituted phenyl-4,5-dihydro-3(2H)-pyridazinones, their synthesis, and rabbit platelet aggregation inhibitory activity induced by ADP in vitro.

Thus, there is a need for novel classes of compounds that possess the beneficial properties. It has been discovered that currently disclosed class of compounds, referred to herein as substituted pyridazinone derivatives, are useful as agents for treating or preventing various diseases or disorders disclosed herein.

SUMMARY OF THE INVENTION

Accordingly, the present invention is directed, in part, to novel pyridazinone compounds which may be useful as $H_3$ inhibitors, and thus may be useful, inter alia, in methods for treating diseases, disorders, and/or conditions that may be mediated or modulated by inhibition of $H_3$, or otherwise associated with the $H_3$ receptor system, including, for example, narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders (such as asthma), inflammation, and myocardial infarction. In preferred form, the novel compounds of the invention have the following formula I*:

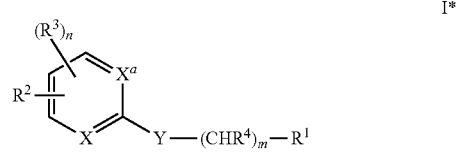

or a stereoisomeric form, mixture of stereoisomeric forms, or a pharmaceutically acceptable salt forms thereof, wherein:

X and $X^a$ are each independently CH or N;

Y is $S(O)_q$, O, or $NR^{15}$;

$R^1$ is $NR^{10}R^{11}$ or a 4- to 9-membered heterocycloalkyl ring containing 1 or 2 nitrogen atoms and optionally substituted with 1 to 3 $R^{20}$ groups;

$R^2$ is (i) 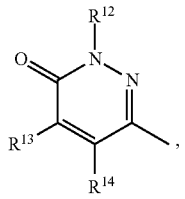

(ii) 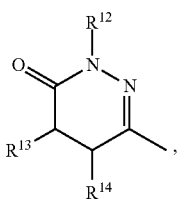

(iii) 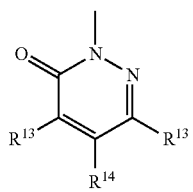

(iv) 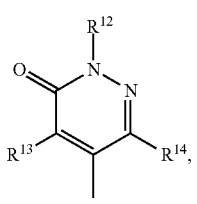

(v) 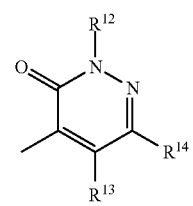

(vi) 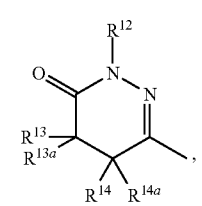

(vii) 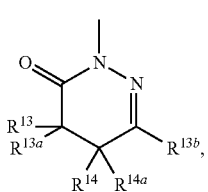

(viii) 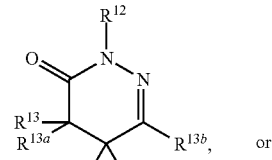

(ix) 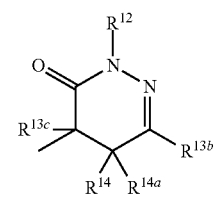

wherein:
when X and $X^a$ are both CH, then $R^2$ is meta or para to the $Y-(CHR^4)_m-R^1$ group;
and
when either X or $X^a$ are N, then $R^2$ is para to the $Y-(CHR^4)_m-R^1$ group;
each $R^3$ is:
independently H, F, Cl, Br, I, $OR^{21}$, $NR^{23}R^{24}$, $NO_2$, CN, $CF_3$, $C_1$-$C_6$alkyl, $C(=O)R^{21}$, $CO_2R^{21}$, or $C(=O)NR^{23}R^{24}$; or
when $R^3$ is ortho to $R^2$, and $R^2$ is (i), (ii), (iv), (vi), or (ix), then $R^3$ and $R^{14}$ taken together may form $-(CH_2)_s-$, $-CH_2Z-$, $-ZCH_2-$, $-ZCH_2CH_2-$ or $CH_2CH_2Z-$; wherein Z is O, $S(O)_y$, or $NR^{27}$; or
when $R^3$ is ortho to $R^2$, and $R^2$ is (iv), (v), or (viii), then $R^3$ and $R^{13}$ taken together may form $-(CH_2)_s-$, $-CH_2Z-$, $-ZCH_2-$, $-ZCH_2CH_2-$ or $CH_2CH_2Z-$; or
when $R^3$ is ortho to $R^2$, and $R^2$ is (viii), then $R^3$ and $R^{13b}$ taken together may form $-(CH_2)_s-$, $-CH_2Z-$, $-ZCH_2-$, $-ZCH_2CH_2-$ or $CH_2CH_2Z-$; or
when $R^3$ is ortho to $X^a$ and $R^2$ is ortho to $R^3$ and meta to $X^a$, then $R^2$ and $R^3$ taken together may form:

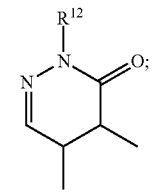

each $R^4$ is independently H, $C_1$-$C_6$alkyl, or $OR^{21}$, wherein the alkyl group is optionally substituted with 1 to 3 $R^{20}$ groups;
$R^{10}$ and $R^{11}$ are each independently H, $C_1$-$C_6$alkyl, or $C_3$-$C_6$cycloalkyl, wherein the alkyl or cycloalkyl group is optionally substituted with 1 to 3 $R^{20}$ groups;
$R^{12}$ is H, $C_1$-$C_6$alkyl, cycloalkyl, aryl, arylalkyl, heteroaryl, heterocycloalkyl, $C(=O)R^{27}$, or $CO_2R^{27}$, wherein the alkyl, cycloalkyl, aryl, arylalkyl, heteroaryl, or heterocycloalkyl group is optionally substituted with 1 to 3 $R^{20}$ groups;
$R^{13}$ and $R^{14}$ are each independently H, $C_1$-$C_6$alkyl, aryl, arylalkyl $C_1$-$C_6$alkoxyl, $S(=O)_y-C_1$-$C_6$alkyl, cycloalkyl, heterocycloalkyl, or heteroaryl;
$R^{13a}$, $R^{13b}$, $R^{13c}$, and $R^{14a}$ are each independently H, $C_1$-$C_6$alkyl; or $R^{13}$ and $R^{14}$, taken together with the carbon atoms through which they are connected form a fused phenyl, thienyl, pyrrolyl, oxazolyl, pyridinyl, or $C_3$-$C_6$cycloalkyl ring; or $R^{13b}$ and $R^{14}$, or $R^{13}$ and $^{14a}$ or $R^{13b}$ and $^{14a}$, or $R^{13c}$ and $R^{14a}$, taken together with the carbon atoms through which they are connected form a fused $C_3$-$C_6$cycloalkyl ring; or $R^{13}$ and $R^{13a}$, or $R^{14}$ and $R^{14a}$, taken together with the carbon atom to which they are attached form a $C_3$-$C_8$cycloalkyl ring; provided that no more than one pair of $R^{13}$ and $R^{14}$, $R^{13b}$ and $R^{14}$, $R^{13}$ and $R^{14a}$, $R^{13b}$ and $R^{14a}$, $R^{13c}$ and $R^{14a}$, $R^{13}$ and $R^{13a}$, and $R^{14}$ and $R^{14a}$ are taken together with the carbon atoms through which they are connected or to which they are attached to form a ring; and wherein the fused phenyl, thienyl, pyrrolyl, oxazolyl, pyridinyl, or cycloalkyl ring is optionally substituted with 1 to 3 $R^{20}$ groups;

$R^{15}$ is H, $C_1$-$C_6$ alkyl, C(=O)$R^{25}$, $CO_2R^{25}$;

$R^{20}$ at each occurrence is independently, H, F, Cl, Br, I, $OR^{21}$, $OR^{22}$, $NR^{23}R^{24}$, NHOH, $NO_2$, CN, $CF_3$, $C_1$-$C_6$ alkyl optionally substituted with $OR^{26}$, $C_2$-$C_6$ alkenyl, $C_2$-$C_6$ alkynyl, $C_3$-$C_7$cycloalkyl$C_0$-$C_4$alkyl, 3- to 7-membered heterocycloalkyl$C_0$-$C_4$alkyl, phenyl, 5- or 6-membered heteroaryl$C_0$-$C_4$alkyl, arylalkyl, (=O), C(=O)$R^{21}$, $CO_2R^{21}$, OC(=O)$R^{21}$, C(=O)$NR^{23}R^{24}$, $NR^{27}$C(=O)$R^{21}$, $NR^{27}$C(=O)$OR^{21}$, OC(=O)$NR^{23}R^{24}$, $NR^{27}$C(=S)$R^{21}$, or S(O)$_q R^{21}$;

each $R^{21}$ is independently H, $C_1$-$C_6$alkyl, aryl, or arylalkyl;
each $R^{22}$ is independently the residue of an amino acid after the hydroxyl group of the carboxyl group is removed;
each $R^{23}$ and $R^{24}$ is independently selected from H, $C_1$-$C_6$alkyl, and aryl, or $R^{23}$ and $R^{24}$, together with the nitrogen atom to which they are attached, form a 3 to 7 membered heterocyclic ring optionally substituted with =O;
$R^{25}$ is $C_1$-$C_6$alkyl, aryl, or alkylaryl;
$R^{26}$ is H, $C_1$-$C_6$alkyl, aryl, or alkylaryl;
$R^{27}$ is H or $C_1$-$C_6$alkyl;
m is 1, 2, 3, 4, or 5 when $R^1$ is attached via a nitrogen atom, and m is 0, 1, 2, 3, 4, or 5 when $R^1$ is attached via a carbon atom;
n is 1, 2, or 3;
q is 0, 1, or 2;
s is 1, 2, or 3; and
y is 0, 1, or 2.

In another aspect, the present invention is directed to pharmaceutical compositions which comprise a pharmaceutically acceptable carrier and a compound of the present invention, preferably in a therapeutically effective amount.

In other aspects, the present invention is directed to methods for treating a disorder selected from the group consisting of narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders, inflammation, and myocardial infarction in a patient in need thereof comprising administering to the patient a therapeutically effective amount of a compound of the present invention.

These and other aspects of the invention will become more apparent from the following detailed description.

DETAILED DESCRIPTION OF ILLUSTRATIVE EMBODIMENTS

The invention is generally directed to pyridazinone derivatives, processes for their preparation, and pharmaceuticals compositions their and methods of their pharmaceutical use.

As employed above and throughout the disclosure, the following terms, unless otherwise indicated, shall be understood to have the following meanings.

As used herein, the term "about" refers to a range of values from ±10% of a specified value. For example, the phrase "about 50" includes ±10% of 50, or from 45 to 55. The phrase "from about 10 to 100" includes ±10% of 10 and ±10% of 100, or from 9 to 110.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1 to 2, 1 to 3, 1 to 4, 1 to 5, 2 to 3, 2 to 4, 2 to 5, 2 to 6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, "substituted" refers to any one or more hydrogen atoms on the indicated atom is replaced with a selected group referred to herein as a "substituent", provided that the substituted atom's valency is not exceeded, and that the substitution results in a stable compound. A substituted group has 1 to 5, preferably 1 to 3, and more preferably 1 independently selected substituents. Preferred substituents include, but are not limited to F, Cl, Br, I, OH, OR, $NH_2$, NHR, $NR_2$, NHOH, $NO_2$, CN, $CF_3$, $CF_2CF_3$, $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, heterocyclyl, $C_6$-$C_{10}$ aryl, heteroaryl, arylalkyl, =O, C(=O)R, COOH, $CO_2R$, O—C(=O)R, C(=O)NRR', NRC(=O)R', $NRCO_2R'$, OC(=O)NRR', —NRC(=O)NRR', —NRC(=S)NRR', and —$SO_2NRR'$, wherein R and R' are each independently hydrogen, $C_1$-$C_6$ alkyl, or $C_6$-$C_{10}$ aryl.

As used herein, the term "alkyl" refers to a straight-chain, or branched alkyl group having 1 to 8 carbon atoms, preferably from 1 to 6, with 1 to 3 more preferred. Exemplary alkyl groups include methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms. Alkyl groups may be optionally substituted.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc. Alkenyl groups may be optionally substituted.

As used herein, the term "alkynyl" refers to a straight chain, or branched hydrocarbon chains of 2 to 8 carbon atoms having at least one carbon-carbon triple bond. A designation "$C_2$-$C_8$ alkynyl" refers to an alkynyl radical containing from 2 to 8 carbon atoms. Examples include ethynyl, propynyl, isopropynyl, 3,5-hexadiynyl, etc. Alkynyl groups may be optionally substituted.

As used herein, the term "cycloalkyl" refers to a saturated or partially saturated mono- or bicyclic alkyl ring system containing 3 to 10 carbon atoms. Certain embodiments contain 3 to 6 carbon atoms, preferably 3 or 4 carbon atoms, and other embodiments contain 5 or 6 carbon atoms. A designation such as "$C_5$-$C_7$ cycloalkyl" refers to a cycloalkyl radical containing from 5 to 7 ring carbon atoms. Examples of cycloalkyl groups include such groups as cyclopropyl, cyclobutyl, cyclopentyl, cyclohexyl, cycloheptyl, cyclooctyl, pinenyl, pinanyl, and adamantanyl. Cycloalkyl groups may be optionally substituted.

As used herein, the term "aryl" refers to a substituted or unsubstituted, mono- or bicyclic hydrocarbon aromatic ring system having 6 to 12 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene. Aryl groups may be optionally substituted.

As used herein, the terms "heterocycle", "heterocyclic" or "heterocyclyl" refer to a substituted or unsubstituted carbocyclic group in which one or more ring carbon atoms are replaced by at least one hetero atom such as —O—, —N—, or —S—. Certain embodiments include 4 to 9 membered rings preferably 3 to 7 membered rings, and other embodiments include 5 or 6 membered rings. The nitrogen and sulfur heteroatoms may be optionally oxidized, and the nitrogen may be optionally substituted in non-aromatic rings. Heterocycles are intended to include heteroaryl and heterocycloalkyl groups. Heterocyclic groups may be optionally substituted.

As used herein, the term "heteroaryl" refers to an aromatic group containing 5 to 10 ring carbon atoms in which one or more ring carbon atoms are replaced by at least one hetero atom such as —O—, —N—, or —S—. Certain embodiments include 5 or 6 membered rings. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene. Heteroaryl groups may be optionally substituted. In certain preferred embodiments, heteroaryl is pyridinyl, more preferably pyridine-2-yl, or thienyl As used herein, the term "heterocycloalkyl" refers to a cycloalkyl group in which one or more ring carbon atoms are replaced by at least one hetero atom such as —O—, —N—, or —S—. Certain embodiments include 4 to 9 membered rings, preferably 3 to 7, more preferably 3 to 6 membered rings, and other embodiments include 5 or 6 membered rings. Examples of heterocycloalkyl groups include pyrrolidinyl, pyrrolinyl, imidazolidinyl, imidazolinyl, pirazolidinyl, pirazolinyl, pyrazolyl, piperidinyl, piperazinyl, hexahydropyrimidinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl, preferably pyrrolidinyl, morpholinyl, piperidinyl, orazapanyl, more preferably pyrrolidinyl or piperidinyl. Heterocycloalkyl groups may be optionally substituted.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl, etc. preferably benzyl. Arylalkyl groups may be optionally substituted.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-NH$_2$. The amino acids can be in their D, L or racemic configurations Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, 2$^{nd}$ ed.; Worth Publishers: New York, 1975; 71-77, the disclosure of which is incorporated herein by reference. Non-naturally occurring amino acids also include α-amino acids wherein the side chains are replaced with synthetic derivatives. In certain embodiments, substituent groups for the compounds of the present invention include the residue of an amino acid after removal of the hydroxyl moiety of the carboxyl group thereof; i.e., groups of formula —C(=O)CH (side chain)-NH$_2$. Representative side chains of naturally occurring and non-naturally occurring α-amino acids include are shown below in Table A.

TABLE A

H
CH$_3$—
HO—CH$_2$—
C$_6$H$_5$—CH$_2$—
HO—C$_6$H$_4$—CH$_2$—

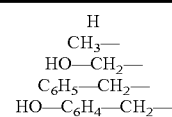

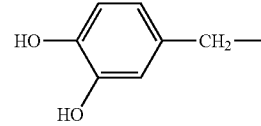

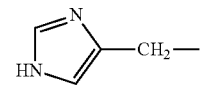

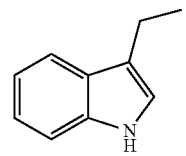

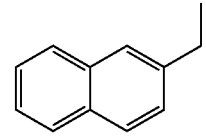

TABLE A-continued

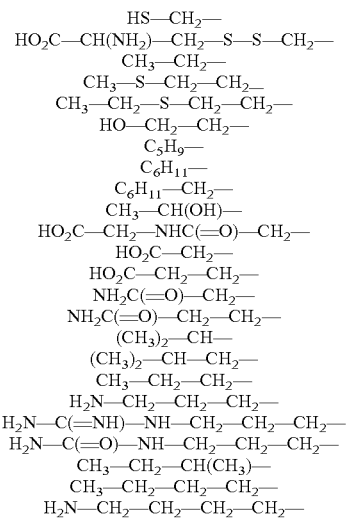

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—
HO—CH$_2$—CH$_2$—
C$_5$H$_9$—
C$_6$H$_{11}$—
C$_6$H$_{11}$—CH$_2$—
CH$_3$—CH(OH)—
HO$_2$C—CH$_2$—NHC(=O)—CH$_2$—
HO$_2$C—CH$_2$—
HO$_2$C—CH$_2$—CH$_2$—
NH$_2$C(=O)—CH$_2$—
NH$_2$C(=O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(=NH)—NH—CH$_2$—CH$_2$—CH$_2$—
H$_2$N—C(=O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

As used herein, the term "subject" or "patient" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

As used herein, "prodrug" refers to compounds specifically designed to maximize the amount of active species that reaches the desired site of reaction, which are of themselves typically inactive or minimally active for the activity desired, but through biotransformation are converted into biologically active metabolites.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, cycloalkyl, aryl, and alkylaryl esters such as methyl, ethyl, propyl, isopropyl, butyl, isobutyl, sec-butyl, tert-butyl, cyclopropyl, phenyl, benzyl, and phenethyl esters, and the like.

Compounds described herein may contain one or more asymmetrically substituted carbon atoms, and may be isolated in optically active or racemic forms. Thus, all isomeric forms of a structure, including all stereogenic (such as enantiomeric, diastereomeric, and/or meso forms, whether chiral or racemic), all achiral, all geometric, and/or all conformational isomeric forms are intended, unless the specific stereochemical or other isomeric form is specifically indicated and/or achiral. It is well known in the art how to prepare and isolate such isomeric forms of a structure including those having stereogenic centers including those stereogenic forms wherein the structure is present in optically active form. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As used herein, the term "stereoisomers" refers to compounds that have identical chemical constitution, but differ as regards the arrangement of the atoms or groups in space.

The terms "treatment" and "treating" as used herein include preventative (e.g., prophylactic), curative and/or palliative treatment.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

Accordingly, the present invention is directed, in part, to novel pyridazinone compounds which have the following formula I*:

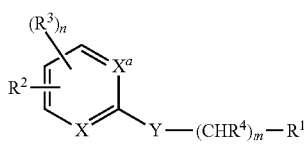

I* or a stereoisomeric form, mixture of stereoisomeric forms, or a pharmaceutically acceptable salt forms thereof, wherein:

X and $X^a$ are each independently CH or N;

Y is $S(O)_q$, O, or $NR^{15}$;

$R^1$ is $NR^{10}R^{11}$ or a 4- to 9-membered heterocycloalkyl ring containing 1 or 2 nitrogen atoms and optionally substituted with 1 to 3 $R^{20}$ groups;

$R^2$ is

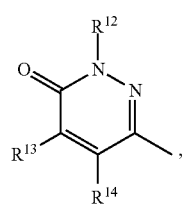

(i)

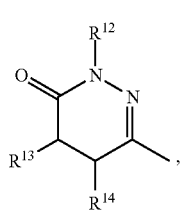

(ii)

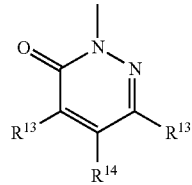

(iii)

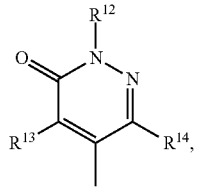

(iv)

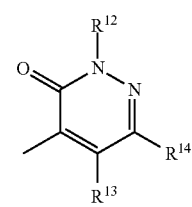

(v)

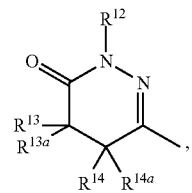

(vi)

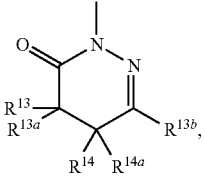

(vii)

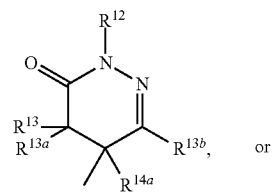

(viii)

or

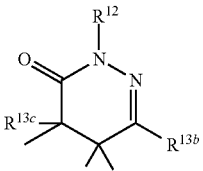

(ix)

wherein:

when X and $X^a$ are both CH, then $R^2$ is meta or para to the Y—$(CHR^4)_m$—$R^1$ group;

and when either X or $X^a$ are N, then $R^2$ is para to the Y—$(CHR^4)_m$—$R^1$ group;

each $R^3$ is:
  independently H, F, Cl, Br, I, $OR^{21}$, $NR^{23}R^{24}$, $NO_2$, CN, $CF_3$, $C_1$-$C_6$alkyl, $C(=O)R^{21}$, $CO_2R^{21}$, or $C(=O)NR^{23}R^{24}$; or
  when $R^3$ is ortho to $R^2$, and $R^2$ is (i), (ii), (iv), (vi), or (ix), then $R^3$ and $R^{14}$ taken together may form —$(CH_2)_s$—, —$CH_2Z$—, —$ZCH_2$—, —$ZCH_2CH_2$— or $CH_2CH_2Z$—; wherein Z is O, $S(O)_y$, or $NR^{27}$; or
  when $R^3$ is ortho to $R^2$, and $R^2$ is (iv), (v), or (viii), then $R^3$ and $R^{13}$ taken together may form —$(CH_2)_s$—, —$CH_2Z$—, —$ZCH_2$—, —$ZCH_2CH_2$— or $CH_2CH_2Z$—; or
  when $R^3$ is ortho to $R^2$, and $R^2$ is (viii), then $R^3$ and $R^{13b}$ taken together may form —$(CH_2)_s$—, —$CH_2Z$—, —$ZCH_2$—, —$ZCH_2CH_2$— or $CH_2CH_2Z$—; or
  when $R^3$ is ortho to $X^a$ and $R^2$ is ortho to $R^3$ and meta to $X^a$, then $R^2$ and $R^3$ taken together may form:

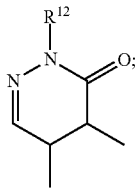

each $R^4$ is independently H, $C_1$-$C_6$alkyl, or $OR^{21}$, wherein the alkyl group is optionally substituted with 1 to 3 $R^{20}$ groups;

$R^{10}$ and $R^{11}$ are each independently H, $C_1$-$C_6$alkyl, or $C_3$-$C_6$cycloalkyl, wherein the alkyl or cycloalkyl group is optionally substituted with 1 to 3 $R^{20}$ groups;

$R^{12}$ is H, $C_1$-$C_6$alkyl, cycloalkyl, aryl, arylalkyl, heteroaryl, heterocycloalkyl, $C(=O)R^{27}$, or $CO_2R^{27}$, wherein the alkyl, cycloalkyl, aryl, arylalkyl, heteroaryl, or heterocycloalkyl group is optionally substituted with 1 to 3 $R^{20}$ groups;

$R^{13}$ and $R^{14}$ are each independently H, $C_1$-$C_6$alkyl, aryl, arylalkyl $C_1$-$C_6$alkoxyl, $S(=O)_y$—$C_1$-$C_6$alkyl, cycloalkyl, heterocycloalkyl, or heteroaryl;

$R^{13a}$, $R^{13b}$, $R^{13c}$, and $R^{14a}$ are each independently H, $C_1$-$C_6$alkyl; or $R^{13}$ and $R^{14}$, taken together with the carbon atoms through which they are connected form a fused phenyl, thienyl, pyrrolyl, oxazolyl, pyridinyl, or $C_3$-$C_6$cycloalkyl ring; or $R^{13b}$ and $R^{14}$, or $R^{13}$ and $^{14a}$ or $R^{13b}$ and $^{14a}$, or $R^{13c}$ and $R^{14a}$, taken together with the carbon atoms through which they are connected form a fused $C_3$-$C_6$cycloalkyl ring; or $R^{13}$ and $R^{13a}$, or $R^{14}$ and $R^{14a}$, taken together with the carbon atom to which they are attached form a $C_3$-$C_8$cycloalkyl ring; provided that no more than one pair of $R^{13}$ and $R^{14}$, $R^{13b}$ and $R^{14}$, $R^{13}$ and $R^{14a}$, $R^{13b}$ and $R^{14a}$, $R^{13c}$ and $R^{14a}$, $R^{13}$ and $R^{13a}$, and $R^{14}$ and $R^{14a}$ are taken together with the carbon atoms through which they are connected or to which they are attached to form a ring; and wherein the fused phenyl, thienyl, pyrrolyl, oxazolyl, pyridinyl, or cycloalkyl ring is optionally substituted with 1 to 3 $R^{20}$ groups;

$R^{15}$ is H, $C_1$-$C_6$ alkyl, $C(=O)R^{25}$, $CO_2R^{25}$;

$R^{20}$ at each occurrence is independently, H, F, Cl, Br, I, $OR^{21}$, $OR^{22}$, $NR^{23}R^{24}$, NHOH, $NO_2$, CN, $CF_3$, $C_1$-$C_6$ alkyl optionally substituted with $OR^{26}$, $C_2$-$C_6$ alkenyl, $C_2$-$C_6$ alkynyl, $C_3$-$C_7$cycloalkyl$C_0$-$C_4$alkyl, 3- to 7-membered heterocycloalkyl$C_0$-$C_4$alkyl, phenyl, 5- or 6-membered heteroaryl$C_0$-$C_4$alkyl, arylalkyl, (=O), $C(=O)R^{21}$, $CO_2R^{21}$, $OC(=O)R^{21}$, $C(=O)NR^{23}R^{24}$, $NR^{27}C(=O)R^{21}$, $NR^{27}C(=O)OR^{21}$, $OC(=O)NR^{23}R^{24}$, $NR^{27}C(=S)R^{21}$, or $S(O)_qR^{21}$;

each $R^{21}$ is independently H, $C_1$-$C_6$alkyl, aryl, or arylalkyl;

each $R^{22}$ is independently the residue of an amino acid after the hydroxyl group of the carboxyl group is removed;

each $R^{23}$ and $R^{24}$ is independently selected from H, $C_1$-$C_6$alkyl, and aryl, or $R^{23}$ and $R^{24}$, together with the nitrogen atom to which they are attached, form a 3 to 7 membered heterocyclic ring optionally substituted with =O;

$R^{25}$ is $C_1$-$C_6$alkyl, aryl, or alkylaryl;

$R^{26}$ is H, $C_1$-$C_6$alkyl, aryl, or alkylaryl;

$R^{27}$ is H or $C_1$-$C_6$alkyl;

m is 1, 2, 3, 4, or 5 when $R^1$ is attached via a nitrogen atom, and m is 0, 1, 2, 3, 4, or 5 when $R^1$ is attached via a carbon atom;

n is 1, 2, or 3;

q is 0, 1, or 2;

s is 1, 2, or 3; and y is 0, 1, or 2.

In certain preferred embodiments, the compounds of formula I or I* are other than 6-[4-(3-Diethylamino-propoxy)-phenyl]-4,5-dihydro-2H-pyridazin-3-one. In other preferred embodiments of the compounds of formula I or I*; when $X^a$ and X are each CH, Y is O, n is 0, each $R^4$ is H, m is 2, 3, or 4, $R^1$ is methylamino, hydroxyethylamino, pyrrolidin-1-yl, piperidin-1-yl, morpholin-4-yl, and $R^2$ is para to the Y—$(CHR^4)_m$—$R^1$ group, then $R^2$ is other than 4,5-dihydro-2H-pyridazin-3-one-6-yl.

In some preferred embodiments, the present invention provides a novel of formula I:

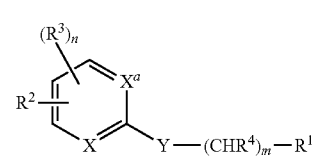

and stereoisomeric forms, mixtures of stereoisomeric forms or pharmaceutically acceptable salt forms thereof, wherein:

X and $X^a$ are each independently CH or N;

Y is selected from $S(O)_q$, O, and $NR^{15}$;

$R^1$ is $NR^{10}R^{11}$ or a 4 to 9 membered heterocycloalkyl ring containing 1 or 2 nitrogen atoms and optionally substituted with 1 to 3 $R^{20}$ groups;

$R^2$ is

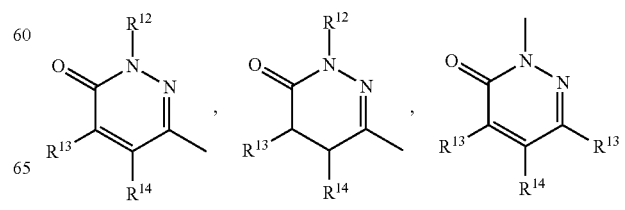

-continued

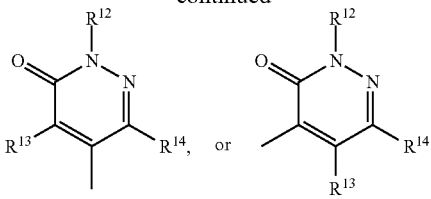

wherein:
when X and $X^a$ are both CH, then $R^2$ is meta or para to the Y—$(CHR^4)_m$—$R^1$ group;
and
when either X or $X^a$ are N, then $R^2$ is para to the Y—$(CHR^4)_m$—$R^1$ group;
$R^3$ is:
at each occurrence is independently, H, F, Cl, Br, I, $OR^{21}$, $NR^{23}R^{24}$, $NO_2$, CN, $CF_3$, $C_1$-$C_6$ alkyl, C(=O)$R^{21}$, $CO_2R^{21}$, or C(=O)$NR^{23}R^{24}$; or
when $R^3$ is ortho to $R^2$, then $R^3$ and $R^{14}$ can combine to form —$(CH_2)_s$—, —$CH_2Z$—, $CH_2CH_2Z$—; wherein Z is O, $S(O)_y$, $NR^{27}$; or
when $R^3$ is ortho to $X^a$ and $R^2$ is ortho to $R^3$ and meta to $X^a$, then $R^2$ and $R^3$ combine to form:

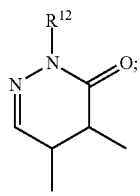

$R^4$ is H, $C_1$-$C_6$ alkyl, or $OR^{21}$, wherein the alkyl group is optionally substituted with 1 to 3 $R^{20}$ groups;
$R^{10}$ and $R^{11}$ are each, independently H or $C_1$-$C_6$ alkyl, wherein the alkyl group is optionally substituted with 1 to 3 $R^{20}$ groups;
$R^{12}$ is H, $C_1$-$C_6$ alkyl, cycloalkyl, aryl, arylalkyl, heteroaryl, heterocycloalkyl, C(=O)$R^{27}$, or $CO_2R^{27}$, wherein the alkyl, cycloalkyl, aryl, arylalkyl, heteroaryl, and heterocycloalkyl groups are optionally substituted with 1 to 3 $R^{20}$ groups;
$R^{13}$ and $R^{14}$ are independently H, $C_1$-$C_6$ alkyl, aryl, or arylalkyl or $R^{13}$ and $R^{14}$ can combine to form a fused phenyl, thienyl, pyrrolyl, cyclopentyl or cyclohexyl ring; wherein the phenyl, thienyl, pyrrolyl, cyclopentyl or cyclohexyl rings are optionally substituted with 1 to 3 $R^{20}$ groups;
$R^{15}$ is H, $C_1$-$C_6$ alkyl, C(=O)$R^{25}$, $CO_2R^{25}$;
$R^{20}$ at each occurrence is independently, H, F, Cl, Br, I, $OR^{21}$, $OR^{22}$, $NR^{23}R^{24}$, NHOH, $NO_2$, CN, $CF_3$, $C_1$-$C_6$ alkyl optionally substituted with $OR^{26}$, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, (=O), C(=O)$R^{21}$, $CO_2R^{21}$, OC(=O)$R^{21}$, C(=O)$NR^{23}R^{24}$, $NR^{27}$C(=O)$R^{21}$, $NR^{27}$C(=O)$OR^{21}$, OC(=O)$NR^{23}R^{24}$, $NR^{27}$C(=S)$R^{21}$, or $S(O)_qR^{21}$;
$R^{21}$ at each occurrence is independently H, $C_1$-$C_6$ alkyl, aryl, or arylalkyl;
$R^{22}$ at each occurrence is independently the residue of an amino acid after the hydroxyl group of the carboxyl group is removed;
$R^{23}$ and $R^{24}$ at each occurrence are each independently selected from H, $C_1$-$C_6$ alkyl, and aryl, or $R^{23}$ and $R^{24}$, together with the nitrogen atom to which they are attached, form a 3 to 7 membered heterocyclic ring optionally substituted with =O;
$R^{25}$ is $C_1$-$C_6$ alkyl, aryl, or alkylaryl;
$R^{26}$ is H, $C_1$-$C_6$ alkyl, aryl, or alkylaryl;
$R^{27}$ is H or $C_1$-$C_6$ alkyl;
m is 1, 2, 3, 4, or 5 when $R^1$ is attached via a nitrogen atom, and m is 0, 1, 2, 3, 4, or 5 when $R^1$ is attached via a carbon atom;
n is 0, 1, 2, or 3;
q is 0, 1, or 2;
s is 1, 2, or 3.
Embodiments of the present invention include those compounds of formula I having the structure I**:

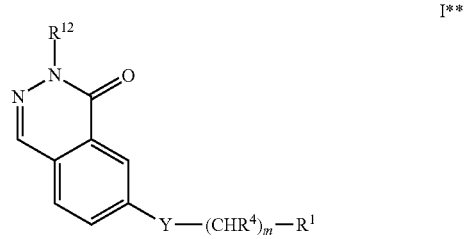

wherein:
Y is O;
$R^1$ is $NR^{10}R^{11}$ or a 5 to 6 membered heterocycloalkyl ring containing 1 or 2 nitrogen atoms and optionally substituted with 1 to 3 $R^{20}$ groups; or $R^1$ is $NR^{10}R^{11}$, pyrrolidinyl or piperidyl, wherein the pyrrolidinyl and piperidyl groups are optionally substituted with 1 to 3 $R^{20}$ groups; or $R^1$ is pyrrolidinyl or piperidyl, wherein the pyrrolidinyl and piperidyl groups are optionally substituted with 1 to 3 $R^{20}$ groups;
$R^4$ is H or $C_1$-$C_6$ alkyl, wherein the alkyl group is optionally substituted with 1 to 3 $R^{20}$ groups;
$R^{10}$ and $R^{11}$ are each, independently H or $C_1$-$C_6$ alkyl, wherein the alkyl group is optionally substituted with 1 to 3 $R^{20}$ groups;
$R^{12}$ is H, $C_1$-$C_6$ alkyl, phenyl, or benzyl, wherein the alkyl, phenyl and benzyl groups are optionally substituted with 1 to 3 $R^{20}$ groups;
$R^{20}$ at each occurrence is independently, H, F, Cl, Br, I, $OR^{21}$, $OR^{22}$, $NR^{23}R^{24}$, NHOH, $NO_2$, CN, $CF_3$, $C_1$-$C_6$ alkyl optionally substituted with $OR^{26}$, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, (=O), C(=O)$R^{21}$, $CO_2R^{21}$, OC(=O)$R^{21}$, C(=O)$NR^{23}R^{24}$, $NR^{27}$C(=O)$R^{21}$, $NR^{27}$C(=O)$OR^{21}$, OC(=O)$NR^{23}R^{24}$, $NR^{27}$C(=S)$R^{21}$, or $S(O)_qR^{21}$;
$R^{21}$ at each occurrence is independently H, $C_1$-$C_6$ alkyl, aryl, or arylalkyl;
$R^{22}$ at each occurrence is independently the residue of an amino acid after the hydroxyl group of the carboxyl group is removed;
$R^{23}$ and $R^{24}$ at each occurrence are each independently selected from H, $C_1$-$C_6$ alkyl, and aryl, or $R^{23}$ and $R^{24}$, together with the nitrogen atom to which they are attached, form a 3 to 7 membered heterocyclic ring optionally substituted with =O;
$R^{26}$ is H, $C_1$-$C_6$ alkyl, aryl, or alkylaryl;
$R^{27}$ is H or $C_1$-$C_6$ alkyl;

m is 3 when $R^1$ is attached via a nitrogen atom, and m is 0 or 1 when $R^1$ is attached via a carbon atom;

n is 0 or 1;

q is 0, 1, or 2.

In another embodiment, the present invention includes compounds of formula (Ia):

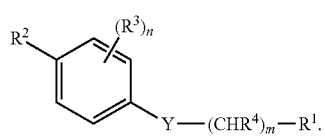

(Ia)

wherein each variable is defined in formula I. Additional aspects of the present invention include compounds of formula (Ia) which incorporate the embodiments described above for compounds of formula I, as is appropriate. For example, additional embodiments include compound of formula (Ia) with the preferred moieties of groups $R^1$ and $R^2$; or $R^1$ and Y; or $R^1$, $R^2$ and Y; etc.

In another embodiment, the present invention includes compounds of formula (Ib):

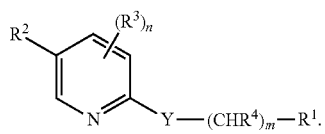

(Ib)

wherein each variable is defined in formula I. Additional aspects of the present invention include compounds of formula (Ib) which incorporate the embodiments described above for compounds of formula I, as is appropriate. For example, additional embodiments include compound of formula (Ib) with the preferred moieties of groups $R^1$ and $R^2$; or $R^1$ and Y; or $R^1$, $R^2$ and Y; etc.

In another embodiment, the present invention includes compounds of formula (Ic):

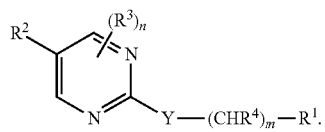

(Ic)

wherein each variable is defined in formula I. Additional aspects of the present invention include compounds of formula (Ic) which incorporate the embodiments described above for compounds of formula I, as is appropriate. For example, additional embodiments include compound of formula (Ic) with the preferred moieties of groups $R^1$ and $R^2$; or $R^1$ and Y; or $R^1$, $R^2$ and Y; etc.

In another embodiment, the present invention includes compounds of formula (Id):

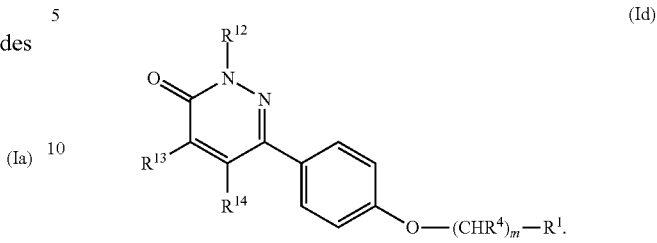

(Id)

wherein each variable is defined in formula I. Additional aspects of the present invention include compounds of formula (Id) which incorporate the embodiments described above for compounds of formula I, as is appropriate. For example, additional embodiments include compound of formula (Id) with the preferred moieties of groups $R^1$; or $R^1$ and m; or $R^1$, $R^{13}$ and $R^{14}$; etc.

In another embodiment, the present invention includes compounds of formula (Ie):

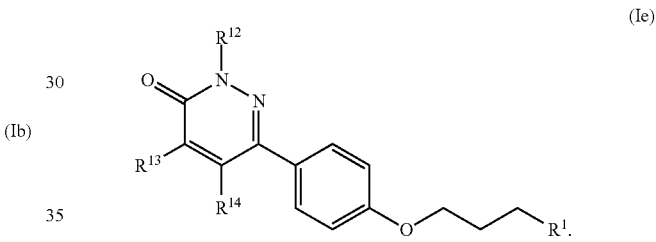

(Ie)

wherein each variable is defined in formula I. Additional aspects of the present invention include compounds of formula (Ie) which incorporate the embodiments described above for compounds of formula I, as is appropriate. For example, additional embodiments include compound of formula (Ie) with the preferred moieties of groups $R^1$; or $R^1$, $R^{13}$ and $R^{14}$; etc.

In another embodiment, the present invention includes compounds of formula (If):

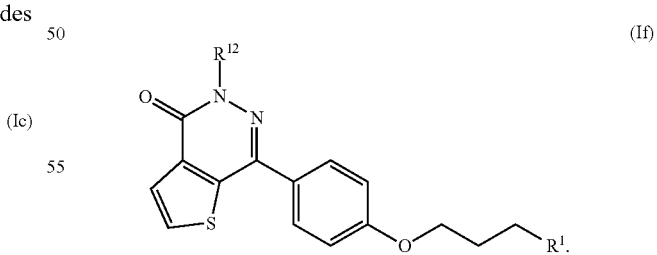

(If)

wherein each variable is defined in formula I. Additional aspects of the present invention include compounds of formula (If) which incorporate the embodiments described above for compounds of formula I, as is appropriate. For example, additional embodiments include compound of formula (If) with the preferred moieties of groups $R^1$; or $R^{12}$; or $R^1$ and $R^{12}$.

In another embodiment, the present invention includes compounds of formula (Ig):

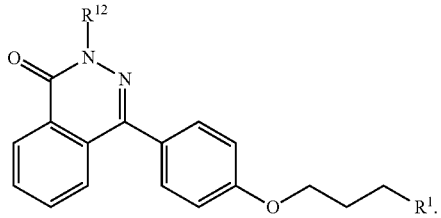

wherein each variable is defined in formula I. Additional aspects of the present invention include compounds of formula (Ig) which incorporate the embodiments described above for compounds of formula I, as is appropriate. For example, additional embodiments include compound of formula (Ig) with the preferred moieties of groups $R^1$; or $R^{12}$; or $R^1$ and $R^{12}$.

In another embodiment, the present invention includes compounds of formula (Ih):

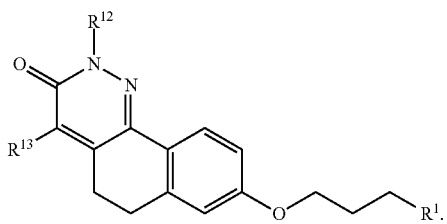

wherein each variable is defined in formula I. Additional aspects of the present invention include compounds of formula (Ih) which incorporate the embodiments described above for compounds of formula I, as is appropriate. For example, additional embodiments include compound of formula (Ih) with the preferred moieties of groups $R^1$; or $R^1$ and $R^{13}$; or $R^1$, $R^{23}$ and $R^{24}$.

In another embodiment, the present invention includes compounds of formula (Ii):

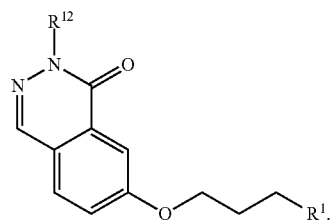

wherein each variable is defined in formula I. Additional aspects of the present invention include compounds of formula (II) which incorporate the embodiments described above for compounds of formula I, as is appropriate. For example, additional embodiments include compound of formula (II) with the preferred moieties of the $R^1$ and $R^{12}$ groups.

In a further embodiment of the present invention, there are included compounds having a structure of Formula II:

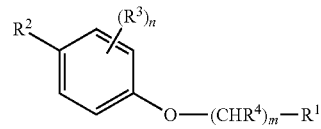

and stereoisomeric forms, mixtures of stereoisomeric forms or pharmaceutically acceptable salt forms thereof,
wherein:
$R^1$ is $NR^{10}R^{11}$ or a 5 to 6 membered heterocycloalkyl ring containing 1 or 2 nitrogen atoms and optionally substituted with 1 to 3 $R^{20}$ groups;
$R^2$ is

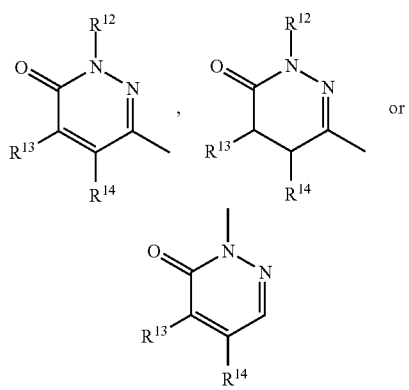

$R^3$ is:
at each occurrence is independently, H, F, Cl, Br, I, $OR^{21}$, $NR^{23}R^{24}$, $NO_2$, CN, $CF_3$, $C_1$-$C_6$ alkyl, $C(=O)R^{21}$, $CO_2R^{21}$, or $C(=O)NR^{23}R^{24}$; or
when $R^3$ is ortho to $R^2$, then $R^3$ and $R^{14}$ can combine to form —$CH_2CH_2$—; or
when $R^3$ is ortho to $X^a$ and $R^2$ is ortho to $R^3$ and meta to $X^a$, then $R^2$ and $R^3$ combine to form:

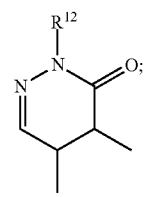

$R^4$ is H or $C_1$-$C_6$ alkyl, wherein the alkyl group is optionally substituted with 1 to 3 $R^{20}$ groups;
$R^{10}$ and $R^{11}$ are each, independently H or $C_1$-$C_6$ alkyl, wherein the alkyl group is optionally substituted with 1 to 3 $R^{20}$ groups;
$R^{12}$ is H, $C_1$-$C_6$ alkyl, phenyl, or benzyl, wherein the alkyl, phenyl and benzyl groups are optionally substituted with 1 to 3 $R^{20}$ groups;
$R^{13}$ and $R^{14}$ are independently H, $C_1$-$C_6$ alkyl, phenyl, or benzyl, or $R^{13}$ and $R^{14}$ can combine to form a fused phenyl, thienyl, cyclopentyl or cyclohexyl ring; wherein the phenyl, thienyl, pyrrolyl, cyclopentyl or cyclohexyl rings are optionally substituted with 1 to 3 $R^{20}$ groups;
$R^{20}$ at each occurrence is independently, H, F, Cl, Br, I, $OR^{21}$, $OR^{22}$, $NR^{23}R^{24}$, NHOH, $NO_2$, CN, $CF_3$, $C_1$-$C_6$ alkyl optionally substituted with $OR^{26}$, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, (=O), C(=O)$R^{21}$, $CO_2R^{21}$, OC(=O)$R^{21}$, C(=O)$NR^{23}R^{24}$, $NR^{27}$C(=O)$R^{21}$, $NR^{27}$C(=O)O$R^{21}$, OC(=O)$NR^{23}R^{24}$, $NR^{27}$C(=S)$R^{21}$, or S(O)$_q$$R^{21}$;

$R^{21}$ at each occurrence is independently H, $C_1$-$C_6$ alkyl, aryl, or arylalkyl;

$R^{22}$ at each occurrence is independently the residue of an amino acid after the hydroxyl group of the carboxyl group is removed;

$R^{23}$ and $R^{24}$ at each occurrence are each independently selected from H, $C_1$-$C_6$ alkyl, and aryl, or $R^{23}$ and $R^{24}$, together with the nitrogen atom to which they are attached, form a 3 to 7 membered heterocyclic ring optionally substituted with =O;

$R^{26}$ is H, $C_1$-$C_6$ alkyl, aryl, or alkylaryl;

$R^{27}$ is H or $C_1$-$C_6$ alkyl;

m is 3 when $R^1$ is attached via a nitrogen atom, and m is 0 or 1 when $R^1$ is attached via a carbon atom;

n is 0 or 1;

q is 0, 1, or 2.

As used herein, "embodiments of the present invention" is intended to include the full scope of compounds of any of formulas I, I*, I**, I(a-i), and II, or any combination or subcombination thereof, unless specifically otherwise provided.

Embodiments of the present invention include those compounds where Y is O. In other embodiments Y is S(O)$_q$, or Y is $NR^{15}$.

Embodiments of the present invention include those compounds where $R^1$ is $NR^{10}R^{11}$, and those compounds where $R^{10}$ and $R^{11}$ are each, independently H or $C_1$-$C_6$ alkyl, preferably both are $C_1$-$C_6$ alkyl.

Embodiments of the present invention include those compounds where $R^1$ is a 4- to 9-membered heterocycloalkyl ring, preferably a 5- to 6-membered heterocycloalkyl ring containing 1 or 2 nitrogen atoms, more preferably 1 nitrogen atom, and optionally substituted with 1 to 3 $R^{20}$ groups. In certain embodiments $R^1$ is an optionally substituted 5-membered heterocycloalkyl ring containing 1 or 2 nitrogen atoms, such as pyrrolidinyl, imidazolidinyl, or pyrazolidinyl. In other embodiments, $R^1$ is an optionally substituted 6-membered heterocycloalkyl ring containing 1 or 2 nitrogen atoms, such as piperidinyl, piperazinyl, or hexahydropyrimidinyl. In certain preferred embodiments, $R^1$ is attached to Y through a ring nitrogen atom. In other preferred embodiments, $R^1$ is attached to Y through a ring carbon atom.

In other preferred embodiments, $R^1$ is:

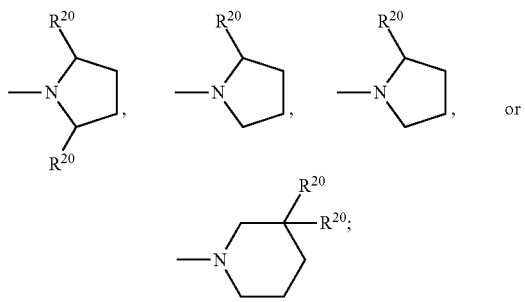

more preferably:

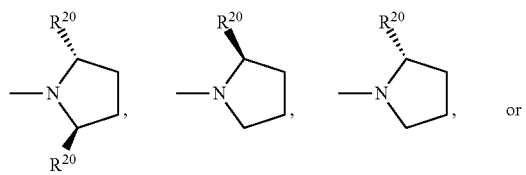

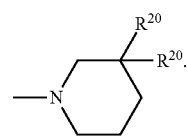

In certain preferred embodiments of the moiety Y—(CHR$^4$)$_m$—$R^1$, one or more of the carbon centers [(i.e., the subgroup "—(CHR$^4$)$_m$—"), said subgroup which is present in the Y—(CHR$^4$)$_m$—$R^1$ moiety "m" times] may have the potential to be chiral in nature. That is to say, there may be 4 different groups attached to a carbon center in the subgroup. Each —(CHR$^4$)— independently may be chiral and all possible stereoisomeric combinations are within the scope of the present invention. In certain more preferable embodiments, m is 3, more preferably the moiety Y—(CHR$^4$)$_m$—$R^1$ is

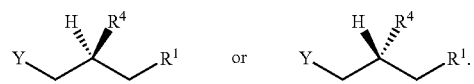

Embodiments of the present invention include those compounds where $R^2$ is

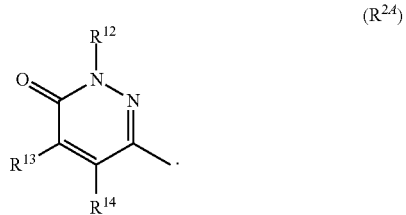

(R$^{2A}$)

In certain embodiments $R^2$ is

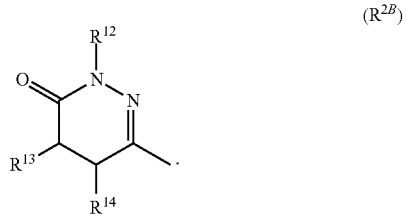

(R$^{2B}$)

In other embodiments, $R^2$ is

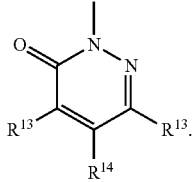 ($R^{2C}$)

In other embodiments, $R^2$ is

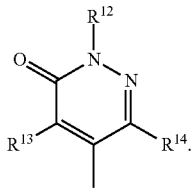 ($R^{2D}$)

In other embodiments, $R^2$ is

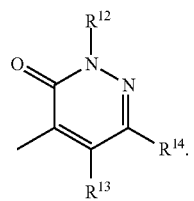 ($R^{2E}$)

In other embodiments, the $R^2$ can be a combination of $R^{2A}$ through $R^{2E}$. For example, such combinations include: $R^{2A}$, $R^{2C}$, $R^{2D}$, and $R^{2E}$; $R^{2A}$, $R^{2B}$, $R^{2D}$, and $R^{2E}$; $R^{2A}$, $R^{2B}$, and $R^{2C}$; $R^{2A}$, $R^{2D}$, and $R^{2E}$; $R^{2A}$, $R^{2D}$, and $R^{2E}$; $R^{2A}$ and $R^{2B}$; $R^{2B}$ and $R^{2C}$; $R^{2D}$ and $R^{2E}$; etc.

In other embodiments, $R^2$ is:

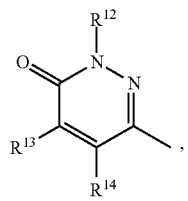 (i)

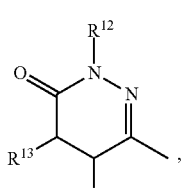 (ii)

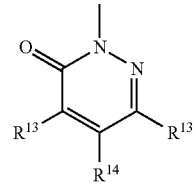 (iii)

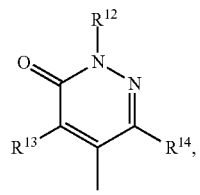 (iv)

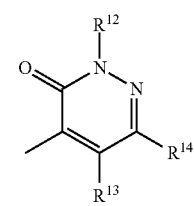 (v)

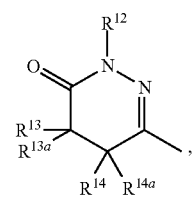 (vi)

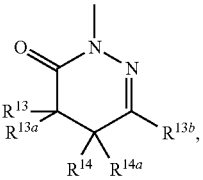 (vii)

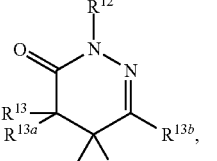 (viii)

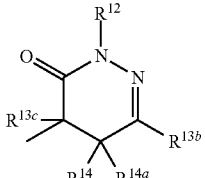 (ix)

wherein:
when X and $X^a$ are both CH, then $R^2$ is meta or para to the $Y$—$(CHR^4)_m$—$R^1$ group;
and
when either X or $X^a$ are N, then $R^2$ is para to the $Y$—$(CHR^4)_m$—$R^1$ group;

each $R^3$ is:

independently H, F, Cl, Br, I, $OR^{21}$, $NR^{23}R^{24}$, $NO_2$, CN, $CF_3$, $C_1$-$C_6$alkyl, $C(=O)R^{21}$, $CO_2R^{21}$, or $C(=O)NR^{23}R^{24}$; or;

when $R^3$ is ortho to $R^2$, and $R^2$ is (i), (ii), (iv), (vi), or (ix), then $R^3$ and $R^{14}$ taken together may form —$(CH_2)_s$—, —$CH_2Z$—, —$ZCH_2$—, —$ZCH_2CH_2$— or $CH_2CH_2Z$—; wherein Z is O, $S(O)_y$, or $NR^{27}$; or when $R^3$ is ortho to $R^2$, and $R^2$ is (iv), (v), or (viii), then $R^3$ and $R^{13}$ taken together may form —$(CH_2)_s$—, —$CH_2Z$—, —$ZCH_2$—, —$ZCH_2CH_2$— or $CH_2CH_2Z$—; or when $R^3$ is ortho to $R^2$, and $R^2$ is (viii), then $R^3$ and $R^{13b}$ taken together may form —$(CH_2)_s$—, —$CH_2Z$—, —$ZCH_2$—, —$ZCH_2CH_2$— or $CH_2CH_2Z$—; or when $R^3$ is ortho to $X^a$ and $R^2$ is ortho to $R^3$ and meta to $X^a$, then $R^2$ and $R^3$ taken together may form:

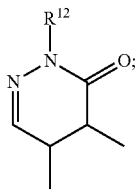

preferably wherein $R^2$ is (i), (ii), (iv), (vi), (viii), or (ix). In certain more preferred embodiments, $R^2$ is (iv); or it is (i); more preferably

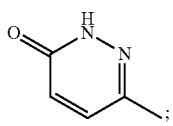

or it is (iii) and one of $R^{13}$ is cyclopropyl. In other alternatively preferred embodiments, R2 is (vi), (viii), or (ix).

In some preferred embodiments, $R^2$ is:

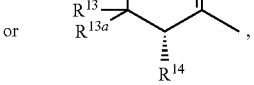

more preferably

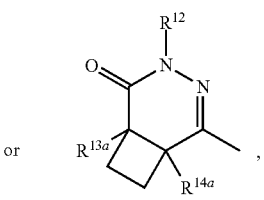

still more preferably

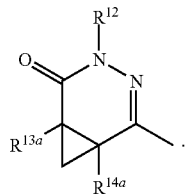

Alternatively preferred in some embodiments, $R^2$ is:

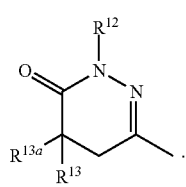

In still other embodiments, $R^2$ is:

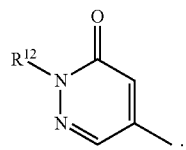

In further embodiments of the present invention, $R^2$ is para to the Y—$(CHR^4)$—$R^1$ group. In certain embodiments when X and $X^a$ are both CH, then $R^2$ is meta to the Y—$(CHR^4)$—$R^1$ group, or $R^2$ is para to the Y—$(CHR^4)$—$R^1$ group. In other embodiments when X and $X^a$ are both CH, then $R^2$ is meta or para to the Y—$(CHR^4)$—$R^1$ group. In other embodiments in combination with any of the three $R^2$ groups, $R^{13}$ and $R^{14}$ are independently H, or they are each independently $C_1$-$C_6$ alkyl, or they are each independently aryl, or they are each independently arylalkyl. In further embodiments of $R^2$, $R^{13}$ and $R^{14}$ can combine to form a fused phenyl ring, or they can form a fused thienyl ring, or they can form a fused pyrrolyl ring, or they can form a fused cyclopentyl ring or they can form a fused cyclohexyl ring. An example of $R^{13}$ and $R^{14}$ combining to form a fused thienyl ring has the following structure:

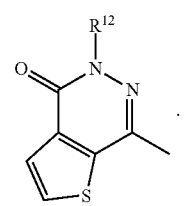

Embodiments of the present invention include those compounds where n is 0. Certain embodiments include those compounds where n is 1. Still other embodiments include those compounds where n is 2.

Embodiments of the present invention include those compounds where $R^3$ at each occurrence is independently, H, F, Cl, Br, I, $OR^{21}$, $NR^{23}R^{24}$, $NO_2$, CN, $CF_3$, $C_1$-$C_6$ alkyl, $C(=O)R^{21}$, $CO_2R^{21}$, or $C(=O)NR^{23}R^{24}$, preferably F, Cl, Br, or $C_1$-$C_6$alkyl, more preferably F. In other preferred embodiments when $R^3$ is ortho to $R^2$, then $R^3$ and $R^{14}$ can combine to form —$CH_2CH_2$—. In certain embodiments $R^3$ at each occurrence is independently, H, F, Cl, Br, I, $OR^{21}$, $NR^{23}R^{24}$, $NO_2$, CN, $CF_3$, $C_1$-$C_6$ alkyl, C(=O)$R^{21}$, $CO_2R^{21}$, or C(=O)$NR^{23}R^{24}$. In other embodiments, $R^3$ is ortho to $R^2$, then $R^3$ and $R^{14}$ can combine to form —$(CH_2)_s$—. An example includes a compound where s is 2, which has the following structure:

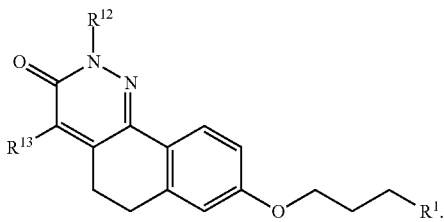

In certain embodiments of the present invention, s is 2, or s is 3. In other embodiments, $R^3$ and $R^{14}$ can combine to form —$CH_2Z$— or $CH_2CH_2Z$—; wherein Z is O, S(O)$_y$, $NR^{27}$. In particular, $R^3$ and $R^{14}$ can combine to form —$CH_2Z$— or they can combine to form $CH_2CH_2Z$—. In particular embodiments, Z is O and in others, Z is —S—.

In further embodiments of the present invention, $R^3$ is ortho to $X^a$ and $R^2$ is ortho to $R^3$ and meta to $X^a$, then $R^2$ and $R^3$ combine to form:

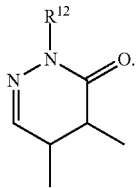

An example includes a compound of the following structure:

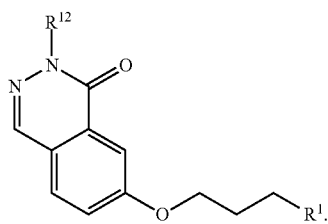

Embodiments of the present invention include those compounds where $R^4$ is H, optionally substituted $C_1$-$C_6$alkyl, or optionally substituted $C_1$-$C_6$ alkoxyl, preferably H or optionally substituted $C_1$-$C_6$alkyl. In certain embodiments. $R^4$ is optionally substituted $C_1$-$C_6$ alkyl. In embodiments where R4 is alkyl, it is preferably $C_1$-$C_3$alkyl, more preferably, $C_1C_6$alkyl, with methyl being even more preferred.

Embodiments of the present invention include those compounds where m is 1, 2, 3, 4, or 5 when $R^1$ is attached via a nitrogen atom. In particular, m is 1, or m is 2, or m is 3, or m is 4, or m is 5, or m can be any combination of the above including, 1 and 2; 1 and 3; 2 and 3; 1, 2, and 3; etc. Other embodiments include those compounds where m is 0, 1, 2, 3, 4, or 5 when $R^1$ is attached via a carbon atom. In particular, m is 0, or m is 1, or m is 2, or m is 3, or m is 4, or m is 5, or m can be any combination of the above including, 0 and 1; 0 and 2; 0, 1, and 2; 1, 2, and 3; etc.

In certain preferred embodiments of the present invention, s is 2.

In other preferred embodiments of the present invention, $R^{12}$ is H, $C_1$-$C_6$alkyl, cycloalkyl, aryl, arylalkyl, or heteroaryl, more preferably H or heteroaryl, with heteroaryl being even more preferred. Alternatively, $C_1$-$C_6$alkyl, aryl, arylalkyl, or heteroaryl is preferred in some embodiments.

In certain preferred embodiments of the present invention, $R^{13}$, $R^{14}R^{13a}$, $R^{13b}$, $R^{13c}$, and $R^{14a}$ are each independently H or $C_1$-$C_6$alkyl, more preferably wherein at least one of is $R^{13}$, $R^{14}R^{13a}$, $R^{13b}$, $R^{13c}$, and $R^{14a}$ is $C_1$-$C_6$alkyl. In other alternatively preferred embodiments, $R^{13a}$ and $R^{13}$ are each independently $C_1$-$C_3$ alkyl; or $R^{14a}$ and $R^{14}$ are each independently $C_1$-$C_3$ alkyl.

In still other preferred embodiments of the present invention, $R^{13}$ and $R^{14}$, taken together with the carbon atoms through which they are connected form a fused phenyl, thienyl, oxazolyl, pyridinyl, or $C_3$-$C_6$cycloalkyl ring; or $R^{13b}$ and $R^{14}$, or $R^{13}$ and $^{14a}$, or $R^{13b}$ and $^{14a}$, or $R^{13c}$ and $R^{14a}$, taken together with the carbon atoms through which they are connected form a fused $C_3$-$C_6$cycloalkyl ring; or $R^{13}$ and $R^{13a}$, or $R^{14}$ and $R^{14a}$, taken together with the carbon atom to which they are attached form a $C_3$-$C_8$cycloalkyl ring; provided that no more than one pair of $R^{13}$ and $R^{14}$, $R^{13b}$ and $R^{14}$, $R^{13}$ and $R^{14a}$, $R^{13b}$ and $R^{14a}$, $R^{13c}$ and $R^{14a}$, $R^{13}$ and $R^{13a}$, and $R^{14}$ and $R^{14a}$ are taken together with the carbon atoms through which they are connected or to which they are attached to form a ring; and wherein the fused phenyl, thienyl, pyrrolyl, oxazolyl, pyridinyl, or cycloalkyl ring is optionally substituted with 1 to 3 $R^{20}$ groups. More preferably, $R^{13}$ and $R^{14}$, $R^{13b}$ and $R^{14}$, or $R^{13}$ and $^{14a}$, or $R^{13b}$ and $^{14a}$, or $R^{13c}$ and $R^{14a}$, taken together with the carbon atoms through which they are connected form a fused $C_3$-$C_6$cycloalkyl ring; or $R^{13}$ and $R^{13a}$, or $R^{14}$ and $R^{14a}$, taken together with the carbon atom to which they are attached form a $C_3$-$C_8$cycloalkyl ring; then the cycloalkyl ring is a is $C_3$-$C_4$cycloalkyl ring.

In some preferred embodiments of the present invention, $R^{14}$ is heteroaryl.

In some preferred embodiments of the present invention, $R^{20}$ is alkyl; in others it is cycloalkyl, more preferably cyclobutyl. In still others, $R^{20}$ is F, Cl, $CF_3$, $NR^{23}R^{24}$, or $C_1$-$C_6$alkyl optionally substituted with $OR^{26}$, cycloalkyl$C_0$-$C_4$alkyl, or heterocycloalkyl$C_0$-$C_4$alkyl, more preferably $C_1$-$C_6$alkyl optionally substituted with $OR^{26}$.

In certain other preferred embodiments of the present invention, $R^{21}$ is H or $C_1$-$C_6$alkyl.

In some preferred embodiments of the present invention, $R^{23}$ and $R^{24}$ are each independently $C_1$-$C_6$alkyl.

In yet other preferred embodiments of the present invention, $R^{26}$ is H or $C_1$-$C_6$alkyl.

In some preferred embodiments of the present invention, at least one of X and $X_a$ is CH, more preferably X and $X_a$ are each CH.

Embodiments of the present invention include those compounds of formula I
wherein:
X and $X^a$ are CH;
Y is O;
$R^1$ is $NR^{10}R^{11}$ or a 5 to 6 membered heterocycloalkyl ring containing 1 or 2 nitrogen atoms and optionally substituted with 1 to 3 $R^{20}$ groups; or $R^1$ is $NR^{10}R^{11}$, pyrrolidinyl or piperidyl, wherein the pyrrolidinyl and piperidyl groups are optionally substituted with 1 to 3 $R^{20}$ groups; or $R^1$ is pyrrolidinyl or piperidyl, wherein the pyrrolidinyl and piperidyl groups are optionally substituted with 1 to 3 $R^{20}$ groups;

$R^2$ is

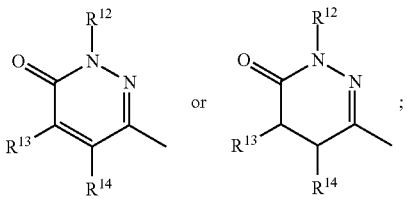

or $R^2$ is

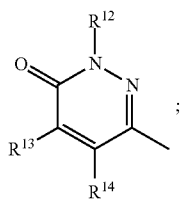

$R^3$ at each occurrence is independently, H, F, Cl, Br, I, $OR^{21}$, $NR^{23}R^{24}$, $NO_2$, CN, $CF_3$, $C_1$-$C_6$ alkyl, $C(=O)R^{21}$, $CO_2R^{21}$, or $C(=O)NR^{23}R^{24}$; or when $R^3$ is ortho to $R^2$, then $R^3$ and $R^{14}$ can combine to form —$CH_2CH_2$—; or $R^3$ at each occurrence is independently, H; F; Cl; Br; I; $OR^{21}$; $NR^{23}R^{24}$; $NO_2$; CN; $CF_3$; $C_1$-$C_6$ alkyl; $C(=O)R^{21}$; $CO_2R^{21}$; or $C(=O)NR^{23}R^{24}$;

$R^4$ is H or $C_1$-$C_6$ alkyl, wherein the alkyl group is optionally substituted with 1 to 3 $R^{20}$ groups;

$R^{10}$ and $R^{11}$ are each, independently H or $C_1$-$C_6$ alkyl, wherein the alkyl group is optionally substituted with 1 to 3 $R^{20}$ groups;

$R^{12}$ is H, $C_1$-$C_6$ alkyl, phenyl, or benzyl, wherein the alkyl, phenyl and benzyl groups are optionally substituted with 1 to 3 $R^{20}$ groups;

$R^{13}$ and $R^{14}$ are independently H, $C_1$-$C_6$ alkyl, phenyl, or benzyl, or $R^{13}$ and $R^{14}$ can combine to form a fused phenyl, thienyl, cyclopentyl or cyclohexyl ring; wherein the phenyl, thienyl, pyrrolyl, cyclopentyl or cyclohexyl rings are optionally substituted with 1 to 3 $R^{20}$ groups; or $R^{13}$ and $R^{14}$ are independently H, $C_1$-$C_6$ alkyl, phenyl, or benzyl; or $R^{13}$ and $R^{14}$ can combine to form a fused phenyl, thienyl, cyclopentyl or cyclohexyl ring;

$R^{20}$ at each occurrence is independently, H, F, Cl, Br, I, $OR^{21}$, $OR^{22}$, $NR^{23}R^{24}$, NHOH, $NO_2$, CN, $CF_3$, $C_1$-$C_6$ alkyl optionally substituted with $OR^{26}$, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, (=O), $C(=O)R^{21}$, $CO_2R^{21}$, $OC(=O)R^{21}$, $C(=O)NR^{23}R^{24}$, $NR^{27}C(=O)R^{21}$, $NR^{27}C(=O)OR^{21}$, $OC(=O)NR^{23}R^{24}$, $NR^{27}C(=S)R^{21}$, or $S(O)_qR^{21}$;

$R^{21}$ at each occurrence is independently H, $C_1$-$C_6$ alkyl, aryl, or arylalkyl;

$R^{22}$ at each occurrence is independently the residue of an amino acid after the hydroxyl group of the carboxyl group is removed;

$R^{23}$ and $R^{24}$ at each occurrence are each independently selected from H, $C_1$-$C_6$ alkyl, and aryl, or $R^{23}$ and $R^{24}$, together with the nitrogen atom to which they are attached, form a 3 to 7 membered heterocyclic ring optionally substituted with =O;

$R^{26}$ is H, $C_1$-$C_6$ alkyl, aryl, or alkylaryl;

$R^{27}$ is H or $C_1$-$C_6$ alkyl;

m is 3 when $R^1$ is attached via a nitrogen atom, and m is 0 or 1 when $R^1$ is attached via a carbon atom;

n is 0 or 1;

q is 0, 1, or 2.

Embodiments of the present invention include those compounds of formula I wherein:

X is N and $X^a$ is N or CH; or X and $X^a$ are each N; or X is N and $X^a$ is CH;

Y is O;

$R^1$ is $NR^{10}R^{11}$ or a 5 to 6 membered heterocycloalkyl ring containing 1 or 2 nitrogen atoms and optionally substituted with 1 to 3 $R^{20}$ groups; or $R^1$ is $NR^{10}R^{11}$, pyrrolidinyl or piperidyl, wherein the pyrrolidinyl and piperidinyl groups are optionally substituted with 1 to 3 $R^{20}$ groups; or $R^1$ is pyrrolidinyl or piperidinyl, wherein the pyrrolidinyl and piperidyl groups are optionally substituted with 1 to 3 $R^{20}$ groups;

$R^2$ is

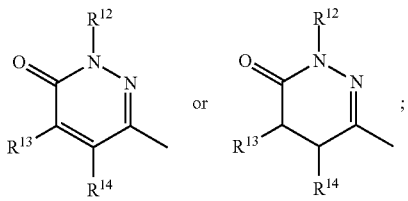

or $R^2$ is

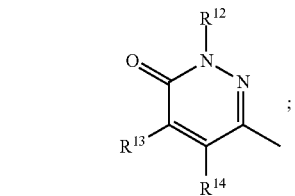

$R^3$ at each occurrence is independently, H, F, Cl, Br, I, $OR^{21}$, $NR^{23}R^{24}$, $NO_2$, CN, $CF_3$, $C_1$-$C_6$ alkyl, $C(=O)R^{21}$, $CO_2R^{21}$, or $C(=O)NR^{23}R^{24}$; or when $R^3$ is ortho to $R^2$, then $R^3$ and $R^{14}$ can combine to form —$CH_2CH_2$—; or $R^3$ at each occurrence is independently, H; F; Cl; Br; I; $OR^{21}$; $NR^{23}R^{24}$; $NO_2$; CN; $CF_3$; $C_1$-$C_6$ alkyl; $C(=O)R^{21}$; $CO_2R^{21}$; or $C(=O)NR^{23}R^{24}$;

$R^4$ is H or $C_1$-$C_6$ alkyl, wherein the alkyl group is optionally substituted with 1 to 3 $R^{20}$ groups;

$R^{10}$ and $R^{11}$ are each, independently H or $C_1$-$C_6$ alkyl, wherein the alkyl group is optionally substituted with 1 to 3 $R^{20}$ groups;

$R^{12}$ is H, $C_1$-$C_6$ alkyl, phenyl, or benzyl, wherein the alkyl, phenyl and benzyl groups are optionally substituted with 1 to 3 $R^{20}$ groups;

$R^{13}$ and $R^{14}$ are independently H, $C_1$-$C_6$ alkyl, phenyl, or benzyl, or $R^{13}$ and $R^{14}$ can combine to form a fused phenyl, thienyl, cyclopentyl or cyclohexyl ring; wherein the phenyl, thienyl, pyrrolyl, cyclopentyl or cyclohexyl rings are optionally substituted with 1 to 3 $R^{20}$ groups; or $R^{13}$ and $R^{14}$ are independently H, $C_1$-$C_6$ alkyl, phenyl, or benzyl; or $R^{13}$ and $R^{14}$ can combine to form a fused phenyl, thienyl, cyclopentyl or cyclohexyl ring;

$R^{20}$ at each occurrence is independently, H, F, Cl, Br, I, $OR^{21}$, $OR^{22}$, $NR^{23}R^{24}$, NHOH, $NO_2$, CN, $CF_3$, $C_1$-$C_6$ alkyl optionally substituted with $OR^{26}$, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, (=O), C(=O)$R^{21}$, $CO_2R^{21}$, OC(=O)$R^{21}$, C(=O)$NR^{23}R^{24}$, $NR^{27}$C(=O)$R^{21}$, $NR^{27}$C(=O)$OR^{21}$, OC(=O)$NR^{23}R^{24}$, $NR^{27}$C(=S)$R^{21}$, or $S(O)_qR^{21}$;

$R^{21}$ at each occurrence is independently H, $C_1$-$C_6$ alkyl, aryl, or arylalkyl;

$R^{22}$ at each occurrence is independently the residue of an amino acid after the hydroxyl group of the carboxyl group is removed;

$R^{23}$ and $R^{24}$ at each occurrence are each independently selected from H, $C_1$-$C_6$ alkyl, and aryl, or $R^{23}$ and $R^{24}$, together with the nitrogen atom to which they are attached, form a 3 to 7 membered heterocyclic ring optionally substituted with =O;

$R^{26}$ is H, $C_1$-$C_6$ alkyl, aryl, or alkylaryl;

$R^{27}$ is H or $C_1$-$C_6$ alkyl;

m is 3 when $R^1$ is attached via a nitrogen atom, and m is 0 or 1 when $R^1$ is attached via a carbon atom;

n is 0 or 1;

q is 0, 1, or 2.

Embodiments of the present invention include those compounds of formula I wherein:

X and $X^a$ are CH;

Y is O;

$R^1$ is $NR^{10}R^{11}$, pyrrolidinyl or piperidyl, wherein the pyrrolidinyl and piperidyl groups are optionally substituted with 1 to 3 $R^{20}$ groups;

$R^2$ is para to the Y—(CHR$^4$)$_m$—$R^1$ group;

$R^3$ at each occurrence is independently, H, F, Cl, Br, I, $OR^{21}$, $NR^{23}R^{24}$, $NO_2$, CN, $CF_3$, $C_1$-$C_6$ alkyl, C(=O)$R^{21}$, $CO_2R^{21}$, or C(=O)$NR^{23}R^{24}$; or when $R^3$ is ortho to $R^2$, then $R^3$ and $R^{14}$ can combine to form —$CH_2CH_2$—;

m is 3 when $R^1$ is attached via a nitrogen atom, and m is 0 or 1 when $R^1$ is attached via a carbon atom;

n is 0 or 1.

In particular, a first embodiment includes those compounds wherein:

$R^1$ is attached by the nitrogen atom;

$R^2$ is:

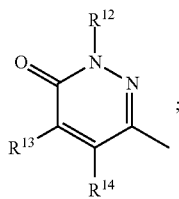

and $R^{13}$ and $R^{14}$ combine to form a fused phenyl or thienyl ring; and m is 3.

In other embodiments, $R^2$ is:

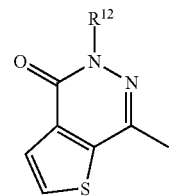

In further embodiments, $R^2$ is:

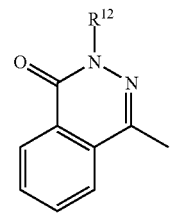

In a second particular embodiment:

$R^1$ is attached by the nitrogen atom;

$R^2$ is:

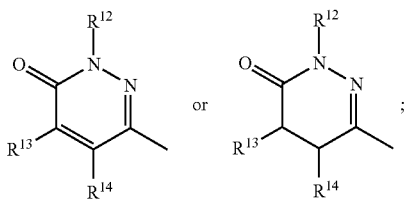

$R^{13}$ and $R^{14}$ combine to form a fused cyclopentyl or cyclohexyl ring; and m is 3.

In a third particular embodiment:

$R^1$ is attached by the nitrogen atom;

$R^2$ is:

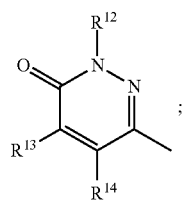

$R^{13}$ and $R^{14}$ are independently H, $C_1$-$C_6$ alkyl, phenyl, or benzyl; and m is 3.

In a fourth particular embodiment:

$R^1$ is pyrrolidinyl or piperidyl, wherein the pyrrolidinyl and piperidyl groups are attached by a ring carbon atom and each are optionally substituted with 1 to 3 $R^{20}$ groups;

$R^2$ is:

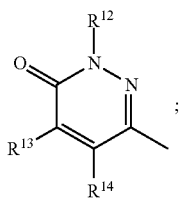

$R^4$ is H;
$R^{13}$ and $R^{14}$ are independently H, $C_1$-$C_6$ alkyl, phenyl, or benzyl;
m is 0 or 1.

In a fifth particular embodiment:
$R^1$ is attached by the nitrogen atom;
$R^2$ is:

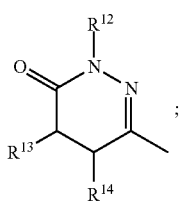

$R^{13}$ and $R^{14}$ are independently H, $C_1$-$C_6$ alkyl, phenyl, or benzyl;
m is 3.

In a sixth particular embodiment:
$R^1$ is attached by the nitrogen atom;
$R^2$ is:

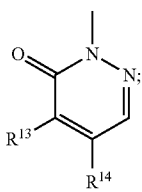

$R^{13}$ and $R^{14}$ are independently H, $C_1$-$C_6$ alkyl, phenyl, or benzyl;
m is 3.

In a seventh particular embodiment:
$R^1$ is attached by the nitrogen atom;
$R^2$ is ortho to $R^3$, and $R^2$ is:

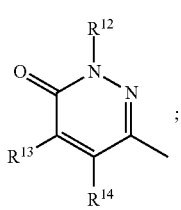

$R^3$ and $R^{14}$ combine to form —$CH_2CH_2$—;
m is 3.

Embodiments of the present invention include those compounds of formula I wherein:
X and $X^a$ are CH;
Y is O;
$R^1$ is $NR^{10}R^{11}$, pyrrolidinyl or piperidyl, wherein the pyrrolidinyl and piperidyl groups are optionally substituted with 1 to 3 $R^{20}$ groups;
$R^2$ is para to the Y—$(CHR^4)_m$—$R^1$ group;
$R^3$ at each occurrence is independently, H, F, Cl, Br, I, $OR^{21}$, $NR^{23}R^{24}$, $NO_2$, CN, $CF_3$, $C_1$-$C_6$ alkyl, C(=O)$R^{21}$, $CO_2R^{21}$, or C(=O)$NR^{23}R^{24}$; or
when $R^3$ is ortho to $R^2$, then $R^3$ and $R^{14}$ can combine to form —$CH_2CH_2$—;
m is 3 when $R^1$ is attached via a nitrogen atom, and m is 0 or 1 when $R^1$ is attached via a carbon atom;
n is 0 or 1.

Additional aspects of the present invention include compounds of formula II which incorporate the embodiments described above for compounds of formula I, as is appropriate. For example, additional embodiments include compound of formula II with the preferred moieties of groups $R^1$; or $R^1$ and $R^{13}$; or $R^1$, $R^{23}$ and $R^{24}$, etc.

For example, in certain embodiments of compounds of formula II:
$R^1$ is $NR^{10}R^{11}$, pyrrolidinyl or piperidyl, wherein the pyrrolidinyl and piperidyl groups are optionally substituted with 1 to 3 $R^{20}$ groups.

For example, in other embodiments of compounds of formula II:
$R^3$ at each occurrence is independently, H, F, Cl, Br, I, $OR^{21}$, $NR^{23}R^{24}$, $NO_2$, CN, $CF_3$, $C_1$-$C_6$ alkyl, C(=O)$R^{21}$, $CO_2R^{21}$; or C(=O)$NR^{23}R^{24}$; or
when $R^3$ is ortho to $R^2$, then $R^3$ and $R^{14}$ can combine to form —$CH_2CH_2$—.

In certain embodiments, the compounds of the formula I*:

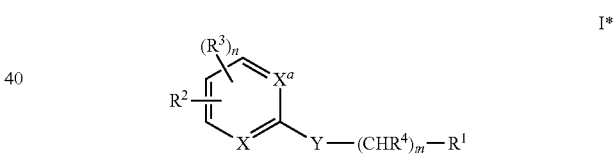

are selected from the group consisting of:
2-methyl-6-{4-[(R)-2-methyl-3-((R)-2-methyl-pyrrolidin-1-yl)-propoxy]-phenyl}-2H-pyridazin-3-one;
6-[4-(1-cyclopentyl-piperidin-4-yloxy)-phenyl]-2-methyl-2H-pyridazin-3-one;
6-{3,5-difluoro-4-[3-((R)-2-methyl-pyrrolidin-1-yl)-propoxy]-phenyl}-2-methyl-2H-pyridazin-3-one;
6-{3-chloro-4-[3-((R)-2-methyl-pyrrolidin-1-yl)-propoxy]-phenyl}-2-methyl-2H-pyridazin-3-one;
2,6-dimethyl-5-{4-[3-((R)-2-methyl-pyrrolidin-1-yl)-propoxy]-phenyl}-2H-pyridazin-3-one;
2,6-dimethyl-5-[4-(3-piperidin-1-yl-propoxy)-phenyl]-2H-pyridazin-3-one;
6-methyl-5-{4-[3-((R)-2-methyl-pyrrolidin-1-yl)-propoxy]-phenyl}-2H-pyridazin-3-one;
6-methyl-5-[4-(3-piperidin-1-yl-propoxy)-phenyl]-2H-pyridazin-3-one;
5-[4-(3-azepan-1-yl-propoxy)-phenyl]-6-methyl-2H-pyridazin-3-one;
2-methyl-5-{4-[3-((R)-2-methyl-pyrrolidin-1-yl)-propoxy]-phenyl}-2H-pyridazin-3-one;
2-methyl-5-[4-(3-piperidin-1-yl-propoxy)-phenyl]-2H-pyridazin-3-one;

5-[4-(3-azepan-1-yl-propoxy)-phenyl]-2-methyl-2H-pyridazin-3-one;
5-{4-[3-((R)-2-methyl-pyrrolidin-1-yl)-propoxy]-phenyl}-2-pyridin-2-yl-2H-pyridazin-3-one;
5-[4-(3-piperidin-1-yl-propoxy)-phenyl]-2-pyridin-2-yl-2H-pyridazin-3-one;
5-[4-(3-azepan-1-yl-propoxy)-phenyl]-2-pyridin-2-yl-2H-pyridazin-3-one;
2-methyl-5-[4-(3-piperidin-1-yl-propoxy)-phenyl]-2H-pyridazin-3-one;
2-(6-methyl-pyridin-2-yl)-5-{4-[3-((R)-2-methyl-pyrrolidin-1-yl)-propoxy]-phenyl}-2H-pyridazin-3-one;
2-(3-methyl-pyridin-2-yl)-5-{4-[3-((R)-2-methylpyrrolidin-1-yl)-propoxy]-phenyl}-2H-pyridazin-3-one;
6-methyl-5-{4-[3-((R)-2-methyl-pyrrolidin-1-yl)-propoxy]-phenyl}-2-pyridin-2-yl-2H-pyridazin-3-one;
6-methyl-2-(3-methyl-pyridin-2-yl)-5-{4-[3-((R)-2-methyl-pyrrolidin-1-yl)-propoxy]-phenyl}-2H-pyridazin-3-one;
6-methyl-5-[4-(piperidin-4-yloxy)-phenyl]-2H-pyridazin-3-one; hydrochloride;
5-[4-(1-cyclobutyl-piperidin-4-yloxy)-phenyl]-6-methyl-2H-pyridazin-3-one;
5-[4-(1-cyclobutyl-piperidin-4-yloxy)-phenyl]-6-methyl-2-pyridin-2-yl-2H-pyridazin-3-one;
5-[4-(piperidin-4-yloxy)-phenyl]-2H-pyridazin-3-one;
5-[4-(1-cyclobutyl-piperidin-4-yloxy)-phenyl]-2H-pyridazin-3-one;
5-[4-(1-cyclobutyl-piperidin-4-yloxy)-phenyl]-6-methyl-2-thiophen-3-yl-2H-pyridazin-3-one;
6-methyl-5-{4-[3-((R)-2-methyl-pyrrolidin-1-yl)-propoxy]-phenyl}-2-thiophen-3-yl-2H-pyridazin-3-one;
5-{4-[3-((S)-2-methyl-pyrrolidin-1-yl)-propoxy]-phenyl}-2-pyridin-2-yl-2H-pyridazin-3-one;
5-[4-(1-cyclobutyl-piperidin-4-yloxy)-phenyl]-6-methyl-4,5-dihydro-2H-pyridazin-3-one;
6-{4-[3-((R)-2-methyl-pyrrolidin-1-yl)-propoxy]-phenyl}-5-pyridin-2-yl-4,5-dihydro-2H-pyridazin-3-one;
6-{4-[3-((R)-2-methyl-pyrrolidin-1-yl)-propoxy]-phenyl}-5-pyridin-2-yl-2H-pyridazin-3-one;
6-[4-(piperidin-4-yloxy)-phenyl]-5-pyridin-2-yl-4,5-dihydro-2H-pyridazin-3-one;
6-[4-(1-cyclobutyl-piperidin-4-yloxy)-phenyl]-5-pyridin-2-yl-4,5-dihydro-2H-pyridazin-3-one;
6-[4-(1-cyclobutyl-piperidin-4-yloxy)-phenyl]-5-pyridin-2-yl-2H-pyridazin-3-one;
6-[4-(1-cyclobutyl-piperidin-4-yloxy)-phenyl]-4-methyl-4,5-dihydro-2H-pyridazin-3-one;
5-[6-(1-cyclobutyl-piperidin-4-yloxy)-pyridin-3-yl]-2H-pyridazin-3-one;
2-(2-fluoro-ethyl)-6-{4-[3-((R)-2-methyl-pyrrolidin-1-yl)-propoxy]-phenyl}-2H-pyridazin-3-one;
6-{3-fluoro-4-[3-((R)-2-methyl-pyrrolidin-1-yl)-propoxy]-phenyl}-2H-pyridazin-3-one;
6-[3-fluoro-4-(3-piperidin-1-yl-propoxy)-phenyl]-2H-pyridazin-3-one;
4-methyl-6-{4-[3-((R)-2-methyl-pyrrolidin-1-yl)-propoxy]-phenyl}-4,5-dihydro-2H-pyridazin-3-one;
4-methyl-6-{4-[3-((R)-2-methyl-pyrrolidin-1-yl)-propoxy]-phenyl}-2H-pyridazin-3-one;
4-methyl-6-[4-(3-piperidin-1-yl-propoxy)-phenyl]-2H-pyridazin-3-one;
4-{4-[3-((S)-2-hydroxymethyl-pyrrolidin-1-yl)-propoxy]-phenyl}-2-methyl-5,6,7,8-tetrahydro-2H-phthalazin-1-one;
2-methyl-4-{3-[3-((R)-2-methyl-pyrrolidin-1-yl)-propoxy]-phenyl}-2,5,6,7-tetrahydro-cyclopenta[d]pyridazin-1-one;
2-methyl-4-[3-(3-piperidin-1-yl-propoxy)-phenyl]-2,5,6,7-tetrahydro-cyclopenta[d]pyridazin-1-one;
4-{3-[3-((S)-2-hydroxymethyl-pyrrolidin-1-yl)-propoxy]-phenyl}-2-methyl-2,5,6,7-tetrahydro-cyclopenta[d]pyridazin-1-one;
2-isopropyl-5-{4-[3-((R)-2-methyl-pyrrolidin-1-yl)-propoxy]-phenyl}-2H-pyridazin-3-one;
2-[3-((R)-2-methyl-pyrrolidin-1-yl)-propoxy]-5-(6-oxo-1,6-dihydro-pyridazin-3-yl)-benzonitrile;
2-[3-(piperidin-1-yl)-propoxy]-5-(6-oxo-1,6-dihydro-pyridazin-3-yl)-benzonitrile;
2-(2-hydroxyethyl)-6-{4-[3-((R)-2-methyl-pyrrolidin-1-yl)-propoxy]-phenyl}-2H-pyridazin-3-one;
6-{4-[(S)-2-methyl-3-((R)-2-methyl-pyrrolidin-1-yl)-propoxy]-phenyl}-2H-pyridazin-3-one;
4-[4-(3-piperidin-1-yl-propoxy)-phenyl]-2,5,6,7-tetrahydro-cyclopenta[d]pyridazin-1-one;
6-[4-(3-piperidin-1-yl-propoxy)-phenyl]-2H-pyridazin-3-one;
6-[3-methoxy-4-(3-piperidin-1-yl-propoxy)-phenyl]-2H-pyridazin-3-one;
6-{3-methoxy-4-[3-((R)-2-methyl-pyrrolidin-1-yl)-propoxy]-phenyl}-2H-pyridazin-3-one;
6-[2-methyl-4-(3-piperidin-1-yl-propoxy)-phenyl]-2H-pyridazin-3-one;
6-{4-[3-((R)-2-methyl-pyrrolidin-1-yl)-propoxy]-phenyl}-2-pyrimidin-2-yl-2H-pyridazin-3-one;
6-[6-(1-cyclopentyl-piperidin-4-yloxy)-pyridin-3-yl]-2H-pyridazin-3-one;
6-[6-(1-isopropyl-piperidin-4-ylmethoxy)-pyridin-3-yl]-2H-pyridazin-3-one;
6-[6-(1-cyclobutyl-piperidin-4-yloxy)-pyridin-3-yl]-2H-pyridazin-3-one;
6-[6-(1-isopropyl-piperidin-4-yloxy)-pyridin-3-yl]-2H-pyridazin-3-one;
6-[6-(1-cyclopentyl-piperidin-4-yloxy)-pyridin-3-yl]-2-methyl-2H-pyridazin-3-one;
6-[6-(1-cyclobutyl-piperidin-4-yloxy)-pyridin-3-yl]-2-methyl-2H-pyridazin-3-one;
6-[6-(1-cyclobutyl-piperidin-4-yloxy)-pyridin-3-yl]-2-isopropyl-2H-pyridazin-3-one;
6-{6-[3-((R)-2-methyl-pyrrolidin-1-yl)-propoxy]-pyridin-3-yl}-2H-pyridazin-3-one;
6-[6-(3-piperidin-1-yl-propoxy)-pyridin-3-yl]-2H-pyridazin-3-one;
6-[6-(1-cyclobutyl-piperidin-4-yloxy)-pyridin-3-yl]-4,4-dimethyl-4,5-dihydro-2H-pyridazin-3-one;
6-[6-(1-cyclobutyl-piperidin-4-yloxy)-pyridin-3-yl]-2-pyridin-2-yl-2H-pyridazin-3-one;
6-[4-(1-cyclobutyl-piperidin-4-yloxy)-phenyl]-4,5-dihydro-2H-pyridazin-3-one;
6-[4-(1-cyclobutyl-piperidin-4-yloxy)-3-fluoro-phenyl]-4,5-dihydro-2H-pyridazin-3-one;
6-[4-(1-cyclobutyl-piperidin-4-yloxy)-phenyl]-4,4-dimethyl-4,5-dihydro-2H-pyridazin-3-one;
6-[4-(1-cyclobutyl-piperidin-4-yloxy)-3-fluoro-phenyl]-4,4-dimethyl-4,5-dihydro-2H-pyridazin-3-one;
6-[4-(1-cyclopentyl-piperidin-4-yloxy)-phenyl]-2H-pyridazin-3-one;
6-[4-(1-cyclobutyl-piperidin-4-yloxy)-phenyl]-2H-pyridazin-3-one;
6-[4-(1-cyclobutyl-piperidin-4-yloxy)-3-fluoro-phenyl]-2H-pyridazin-3-one;
6-[4-(1-cyclobutyl-piperidin-4-yloxy)-phenyl]-2-pyridin-2-yl-2H-pyridazin-3-one;
6-[4-(piperidin-4-yloxy)-phenyl]-2-pyridin-2-yl-4,5-dihydro-2H-pyridazin-3-one;

6-[4-((R)-1-cyclohexyl-pyrrolidin-3-yloxy)-phenyl]-4,5-dihydro-2H-pyridazin-3-one;

6-[4-((R)-1-cyclohexyl-pyrrolidin-3-yloxy)-phenyl]-2H-pyridazin-3-one;

6-[4-((R)-1-cyclobutyl-pyrrolidin-3-yloxy)-phenyl]-2H-pyridazin-3-one;

6-[4-((R)-1-cyclopentyl-pyrrolidin-3-yloxy)-phenyl]-4,5-dihydro-2H-pyridazin-3-one;

2-cyclobutyl-6-[4-(1-cyclobutyl-piperidin-4-yloxy)-phenyl]-4,5-dihydro-2H-pyridazin-3-one;

2-cyclobutyl-6-[4-(1-cyclopentyl-piperidin-4-yloxy)-phenyl]-4,5-dihydro-2H-pyridazin-3-one;

2-cyclobutyl-6-[4-(piperidin-4-yloxy)-phenyl]-4,5-dihydro-2H-pyridazin-3-one;

6-[4-(1-cyclobutyl-piperidin-4-yloxy)-phenyl]-2-(2,2,2-trifluoro-ethyl)-4,5-dihydro-2H-pyridazin-3-one;

6-[4-(1-cyclopentyl-piperidin-4-yloxy)-phenyl]-2-(2,2,2-trifluoro-ethyl)-4,5-dihydro-2H-pyridazin-3-one;

6-{4-[3-((R)-2-methyl-pyrrolidin-1-yl)-propoxy]-phenyl}-2-(2,2,2-trifluoro-ethyl)-4,5-dihydro-2H-pyridazin-3-one;

6-{-4-[3-piperidin-1-yl-propoxy]-phenyl}-2-(2,2,2-trifluoro-ethyl)-4,5-dihydro-2H-pyridazin-3-one;

6-{4-[3-((R)-2-methyl-pyrrolidin-1-yl)-propoxy]-phenyl}-2-(2,2,2-trifluoro-ethyl)-2H-pyridazin-3-one;

6-[4-(3-piperidin-1-yl-propoxy)-phenyl]-2-(2,2,2-trifluoro-ethyl)-2H-pyridazin-3-one;

5-[4-(1-cyclobutyl-piperidin-4-yloxy)-phenyl]-3,4-diaza-bicyclo[4.2.0]oct-4-en-2-one;

5-{4-[3-((R)-2-methyl-pyrrolidin-1-yl)-propoxy]-phenyl}-3,4-diaza-bicyclo[4.2.0]oct-4-en-2-one;

4-[4-(1-cyclobutyl-piperidin-4-yloxy)-phenyl]-2,4-a,5,6,7,7a-hexahydro-cyclopenta[d]pyridazin-1-one;

4-{4-[3-((R)-2-methyl-pyrrolidin-1-yl)-propoxy]-phenyl}-2,4-a,5,6,7,7a-hexahydro-cyclopenta[d]pyridazin-1-one;

4-[4-(1-cyclobutyl-piperidin-4-yloxy)-phenyl]-2,5,6,7-tetrahydro-cyclopenta[d]pyridazin-1-one;

2-cyclobutyl-6-[6-(1-cyclobutyl-piperidin-4-yloxy)-pyridin-3-yl]-4,5-dihydro-2H-pyridazin-3-one;

6-{4-[3-((R)-2-methyl-pyrrolidin-1-yl)-propoxy]-phenyl}-4,5-dihydro-2H-pyridazin-3-one;

4,4-dimethyl-6-{4-[3-((R)-2-methyl-pyrrolidin-1-yl)-propoxy]-phenyl}-4,5-dihydro-2H-pyridazin-3-one;

6-{3-fluoro-4-[3-((R)-2-methyl-pyrrolidin-1-yl)-propoxy]-phenyl}-4,5-dihydro-2H-pyridazin-3-one;

6-[3-fluoro-4-(3-piperidin-1-yl-propoxy)-phenyl]-4,5-dihydro-2H-pyridazin-3-one;

5,5-dimethyl-6-{4-[3-((R)-2-methyl-pyrrolidin-1-yl)-propoxy]-phenyl}-4,5-dihydro-2H-pyridazin-3-one;

6-{4-[3-((R)-2-methyl-pyrrolidin-1-yl)-propoxy]-phenyl}-2-pyridin-2-yl-4,5-dihydro-2H-pyridazin-3-one;

6-{3,5-difluoro-4-[3-((R)-2-methyl-pyrrolidin-1-yl)-propoxy]-phenyl}-2H-pyridazin-3-one;

6-{3,5-dibromo-4-[3-((R)-2-methyl-pyrrolidin-1-yl)-propoxy]-phenyl}-2H-pyridazin-3-one;

6-{3,5-difluoro-4-[3-((R)-2-methyl-pyrrolidin-1-yl)-propoxy]-phenyl}-4,5-dihydro-2H-pyridazin-3-one;

6-[4-(1-cyclobutyl-piperidin-4-yloxy)-3,5-difluoro-phenyl]-4,5-dihydro-2H-pyridazin-3-one;

6-[4-(1-cyclobutyl-piperidin-4-yloxy)-3,5-difluoro-phenyl]-2H-pyridazin-3-one;

6-[4-(1-cyclobutyl-piperidin-4-yloxy)-phenyl]-5-methyl-4,5-dihydro-2H-pyridazin-3-one;

(R)-6-[4-(1-cyclobutyl-piperidin-4-yloxy)-phenyl]-5-methyl-4,5-dihydro-2H-pyridazin-3-one;

(S)-6-[4-(1-cyclobutyl-piperidin-4-yloxy)-phenyl]-5-methyl-4,5-dihydro-2H-pyridazin-3-one;

6-[4-(1-cyclobutyl-piperidin-4-yloxy)-phenyl]-5-ethyl-4,5-dihydro-2H-pyridazin-3-one;

6-[4-(1-cyclobutyl-piperidin-4-yloxy)-phenyl]-5-methyl-2-pyridin-2-yl-4,5-dihydro-2H-pyridazin-3-one;

5-methyl-6-{4-[3-((R)-2-methyl-pyrrolidin-1-yl)-propoxy]-phenyl}-4,5-dihydro-2H-pyridazin-3-one racemate;

5-methyl-6-{4-[3-((R)-2-methyl-pyrrolidin-1-yl)-propoxy]-phenyl}-4,5-dihydro-2H-pyridazin-3-one diastereomer;

5-methyl-6-{4-[3-((R)-2-methyl-pyrrolidin-1-yl)-propoxy]-phenyl}-4,5-dihydro-2H-pyridazin-3-one diastereomer;

5-methyl-6-[4-(3-piperidin-1-yl-propoxy)-phenyl]-4,5-dihydro-2H-pyridazin-3-one;

5-methyl-6-[4-(3-pyrrolidin-1-yl-propoxy)-phenyl]-4,5-dihydro-2H-pyridazin-3-one;

6-{(R)-2-methyl-4-[3-(2-methyl-pyrrolidin-1-yl)-propoxy]-phenyl}-4,5-dihydro-2H-pyridazin-3-one;

2-{4-[3-((R)-2-methyl-pyrrolidin-1-yl)-propoxy]-phenyl}-6-phenyl-2H-pyridazin-3-one;

6-methyl-2-{4-[3-((R)-2-methyl-pyrrolidin-1-yl)-propoxy]-phenyl}-2H-pyridazin-3-one;

2-{4-[3-((R)-2-methyl-pyrrolidin-1-yl)-propoxy]-phenyl}-2H-phthalazin-1-one;

2-[6-(1-cyclobutyl-piperidin-4-yloxy)-pyridin-3-yl]-6-phenyl-2H-pyridazin-3-one;

2-{4-[3-((R)-2-methyl-pyrrolidin-1-yl)-propoxy]-phenyl}-6-pyridin-3-yl-2H-pyridazin-3-one;

4-[4-(1-cyclobutyl-piperidin-4-yloxy)-phenyl]-3-methyl-6H-isoxazolo[3,4-d]pyridazin-7-one;

3-methyl-4-[4-(piperidin-4-yloxy)-phenyl]-6H-isoxazolo[3,4-d]pyridazin-7-one;

3-methyl-4-[4-(3-piperidin-1-yl-propoxy)-phenyl]-6H-isoxazolo[3,4-d]pyridazin-7-one;

3-methyl-4-{4-[3-((R)-2-methyl-pyrrolidin-1-yl)-propoxy]-phenyl}-6H-isoxazolo[3,4-d]pyridazin-7-one;

8-[3-((R)-2-methyl-pyrrolidin-1-yl)-propoxy]-5,6-dihydro-2H-benzo[h]cinnolin-3-one;

5-methyl-6-{4-[3-((R)-2-methyl-pyrrolidin-1-yl)-propoxy]-phenyl}-2H-pyridazin-3-one;

5-ethyl-6-{4-[3-((R)-2-methyl-pyrrolidin-1-yl)-propoxy]-phenyl}-2H-pyridazin-3-one;

8-[3-(2-methyl-pyrrolidin-1-yl)-propoxy]-4,4-a,5,6-tetrahydro-2H-benzo[h]cinnolin-3-one;

6-{2-methoxy-4-[3-((R)-2-methyl-pyrrolidin-1-yl)-propoxy]-phenyl}-4,5-dihydro-2H-pyridazin-3-one;

6-{2-fluoro-4-[3-((R)-2-methyl-pyrrolidin-1-yl)-propoxy]-phenyl}-2H-pyridazin-3-one;

6-{4-[3-((R)-2-methyl-pyrrolidin-1-yl)-propoxy]-phenyl}-2-pyridin-2-yl-2H-pyridazin-3-one;

6-{4-[3-((R)-2-methyl-pyrrolidin-1-yl)-propoxy]-phenyl}-4-pyridin-2-yl-4,5-dihydro-2H-pyridazin-3-one;

6-{4-[3-((R)-2-methyl-pyrrolidin-1-yl)-propoxy]-phenyl}-4-pyridin-2-yl-2H-pyridazin-3-one;

8-[3-((R)-2-methyl-pyrrolidin-1-yl)-propoxy]-5,6-dihydro-3H-benzo[h]cinnolin-2-one;

6-[4-(1-cyclobutyl-piperidin-4-yloxy)-2-fluoro-phenyl]-4,5-dihydro-2H-pyridazin-3-one;

8-(1-cyclobutyl-piperidin-4-yloxy)-4,4-a,5,6-tetrahydro-2H-benzo[h]cinnolin-3-one;

6-[4-(1-cyclobutyl-piperidin-4-yloxy)-2-fluoro-phenyl]-2H-pyridazin-3-one;

6-[4-(1-cyclobutyl-piperidin-4-yloxy)-phenyl]-5-methyl-2H-pyridazin-3-one;

5-{4-[3-((R)-2-methyl-pyrrolidin-1-yl)-propoxy]-phenyl}-2H-pyridazin-3-one;

2-methoxymethyl-5-{4-[3-((R)-2-methyl-pyrrolidin-1-yl)-propoxy]-phenyl}-2H-pyridazin-3-one;

5-{4-[(S)-2-methyl-3-((R)-2-methyl-pyrrolidin-1-yl)-propoxy]-phenyl}-2H-pyridazin-3-one;
5-{4-[(R)-2-methyl-3-((R)-2-methyl-pyrrolidin-1-yl)-propoxy]-phenyl}-2H-pyridazin-3-one;
5-[4-((S)-2-methyl-3-piperidin-1-yl-propoxy)-phenyl]-2H-pyridazin-3-one;
5-[4-((R)-2-methyl-3-piperidin-1-yl-propoxy)-phenyl]-2H-pyridazin-3-one;
5-{3,5-dibromo-4-[3-((R)-2-methyl-pyrrolidin-1-yl)-propoxy]-phenyl}-2H-pyridazin-3-one;
2-methoxymethyl-5-{2-methyl-4-[3-((R)-2-methyl-pyrrolidin-1-yl)-propoxy]-phenyl}-2H-pyridazin-3-one;
5-{2-methyl-4-[3-((R)-2-methyl-pyrrolidin-1-yl)-propoxy]-phenyl}-2H-pyridazin-3-one;
2-methoxymethyl-5-[2-methyl-4-(3-piperidin-1-yl-propoxy)-phenyl]-2H-pyridazin-3-one;
5-[2-methyl-4-(3-piperidin-1-yl-propoxy)-phenyl]-2H-pyridazin-3-one;
5-[4-(1-cyclobutyl-piperidin-4-yloxy)-2-methyl-phenyl]-2-methoxymethyl-2H-pyridazin-3-one;
4-methoxy-2-methoxymethyl-5-{4-[3-((R)-2-methyl-pyrrolidin-1-yl)-propoxy]-phenyl}-2H-pyridazin-3-one;
5-methoxy-2-methoxymethyl-4-{4-[3-((R)-2-methyl-pyrrolidin-1-yl)-propoxy]-phenyl}-2H-pyridazin-3-one;
5-methoxy-4-{4-[3-((R)-2-methyl-pyrrolidin-1-yl)-propoxy]-phenyl}-2H-pyridazin-3-one;
6-[4-(3-morpholin-4-yl-propoxy)-phenyl]-2H-pyridazin-3-one;
6-{4-[3-((S)-2-methyl-pyrrolidin-1-yl)-propoxy]-phenyl}-2H-pyridazin-3-one;
6-[4-(3-pyrrolidin-1-yl-propoxy)-phenyl]-2H-pyridazin-3-one;
6-{4-[3-(cyclobutyl-methyl-amino)-propoxy]-phenyl}-2H-pyridazin-3-one;
6-{4-[3-(cyclopentyl-methyl-amino)-propoxy]-phenyl}-2H-pyridazin-3-one;
5-{4-[3-((R)-2-methyl-pyrrolidin-1-yl)-propoxy]-phenyl}-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-{4-[(S)-2-methyl-3-((R)-2-methyl-pyrrolidin-1-yl)-propoxy]-phenyl}-3,4-diaza-bicyclo[4.1.0]hept-4-en-2-one;
5-{4-[3-((R)-2-methyl-pyrrolidin-1-yl)-propoxy]-phenyl}-3,4-diaza-bicyclo[4.1.0]hept-4-en-2-one single isomer;
5-{4-[3-((R)-2-methyl-pyrrolidin-1-yl)-propoxy]-phenyl}-3,4-diaza-bicyclo[4.1.0]hept-4-en-2-one single isomer;
5-[4-(1-cyclobutyl-piperidin-4-yloxy)-phenyl]-3,4-diaza-bicyclo[4.1.0]hept-4-en-2-one single isomer;
5-[4-(1-cyclobutyl-piperidin-4-yloxy)-phenyl]-3,4-diaza-bicyclo[4.1.0]hept-4-en-2-one single isomer;
5-[4-(1-cyclobutyl-piperidin-4-yloxy)-phenyl]-3-ethyl-3,4-diaza-bicyclo[4.1.0]hept-4-en-2-one;
5-[4-(1-cyclobutyl-piperidin-4-yloxy)-phenyl]-3-isopropyl-3,4-diaza-bicyclo[4.1.0]hept-4-en-2-one;
5-[4-(1-cyclobutyl-piperidin-4-yloxy)-phenyl]-3-methyl-3,4-diaza-bicyclo[4.1.0]hept-4-en-2-one;
5-[4-(1-cyclobutyl-piperidin-4-yloxy)-phenyl]-3-(4-fluoro-phenyl)-3,4-diaza-bicyclo[4.1.0]hept-4-en-2-one;
5-[4-(1-cyclobutyl-piperidin-4-yloxy)-phenyl]-3-(2,2,2-trifluoro-ethyl)-3,4-diaza-bicyclo[4.1.0]hept-4-en-2-one;
6-[4-(2-hydroxy-3-piperidin-1-yl-propoxy)-phenyl]-2H-pyridazin-3-one;
6-{4-[2-hydroxy-3-((R)-2-methyl-pyrrolidin-1-yl)-propoxy]-phenyl}-2H-pyridazin-3-one;
6-{4-[(S)-2-hydroxy-3-((R)-2-methyl-pyrrolidin-1-yl)-propoxy]-phenyl}-2H-pyridazin-3-one;
6-{4-[(R)-2-hydroxy-3-((R)-2-methyl-pyrrolidin-1-yl)-propoxy]-phenyl}-2H-pyridazin-3-one;
6-[4-((R)-2-hydroxy-3-piperidin-1-yl-propoxy)-phenyl]-2H-pyridazin-3-one;
5-[4-(1-cyclopentyl-piperidin-4-yloxy)-phenyl]-3-methyl-3,4-diaza-bicyclo[4.1.0]hept-4-en-2-one;
5-[4-(1-cyclopentyl-piperidin-4-yloxy)-phenyl]-3,4-diaza-bicyclo[4.1.0]hept-4-en-2-one; and
6-cyclopropyl-2-{4-[3-((R)-2-methyl-pyrrolidin-1-yl)-propoxy]-phenyl}-2H-pyridazin-3-one;
or a stereoisomeric form, mixture of stereoisomeric forms, or a pharmaceutically acceptable salt thereof.

More preferably, they are selected from the group consisting of:
5-[4-(1-cyclobutyl-piperidin-4-yloxy)-phenyl]-6-methyl-2H-pyridazin-3-one;
6-[4-(3-piperidin-1-yl-propoxy)-phenyl]-2H-pyridazin-3-one;
6-{4-[3-((R)-2-methyl-pyrrolidin-1-yl)-propoxy]-phenyl}-4,5-dihydro-2H-pyridazin-3-one;
6-[4-(1-cyclobutyl-piperidin-4-yloxy)-phenyl]-4,4-dimethyl-4,5-dihydro-2H-pyridazin-3-one;
6-[4-(1-cyclobutyl-piperidin-4-yloxy)-3-fluoro-phenyl]-4,4-dimethyl-4,5-dihydro-2H-pyridazin-3-one;
6-[6-(1-cyclobutyl-piperidin-4-yloxy)-pyridin-3-yl]-4,4-dimethyl-4,5-dihydro-2H-pyridazin-3-one;
5-{4-[3-((R)-2-methyl-pyrrolidin-1-yl)-propoxy]-phenyl}-2-pyridin-2-yl-2H-pyridazin-3-one;
5-[4-(3-piperidin-1-yl-propoxy)-phenyl]-2-pyridin-2-yl-2H-pyridazin-3-one;
6-{4-[(S)-2-Methyl-3-((R)-2-methyl-pyrrolidin-1-yl)-propoxy]-phenyl}-2H-pyridazin-3-one;
4,4-dimethyl-6-{4-[3-((R)-2-methyl-pyrrolidin-1-yl)-propoxy]-phenyl}-4,5-dihydro-2H-pyridazin-3-one;
5-{4-[3-((R)-2-methyl-pyrrolidin-1-yl)-propoxy]-phenyl}-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-{4-[(S)-2-methyl-3-((R)-2-methyl-pyrrolidin-1-yl)-propoxy]-phenyl}-3,4-diaza-bicyclo[4.1.0]hept-4-en-2-one;
5-{4-[3-((R)-2-methyl-pyrrolidin-1-yl)-propoxy]-phenyl}-3,4-diaza-bicyclo[4.1.0]hept-4-en-2-one;
5-{4-[3-((R)-2-methyl-pyrrolidin-1-yl)-propoxy]-phenyl}-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-[4-(1-cyclobutyl-piperidin-4-yloxy)-phenyl]-3,4-diaza-bicyclo[4.2.0]oct-4-en-2-one;
5-methyl-6-{4-[3-((R)-2-methyl-pyrrolidin-1-yl)-propoxy]-phenyl}-4,5-dihydro-2H-pyridazin-3-one one diastereomer;
5-methyl-6-{4-[3-((R)-2-methyl-pyrrolidin-1-yl)-propoxy]-phenyl}-4,5-dihydro-2H-pyridazin-3-one one diastereomer;
5-methyl-6-{4-[3-((R)-2-methyl-pyrrolidin-1-yl)-propoxy]-phenyl}-4,5-dihydro-2H-pyridazin-3-one; and
6-{4-[3-((R)-2-methyl-pyrrolidin-1-yl)-propoxy]-phenyl}-2H-pyridazin-3-one;
or a stereoisomeric form, mixture of stereoisomeric forms, or a pharmaceutically acceptable salt thereof.

Still more preferably, they are selected from the group consisting of:
5-{4-[3-((R)-2-methyl-pyrrolidin-1-yl)-propoxy]-phenyl}-2-pyridin-2-yl-2H-pyridazin-3-one;

5-[4-(3-piperidin-1-yl-propoxy)-phenyl]-2-pyridin-2-yl-2H-pyridazin-3-one;
6-{4-[(S)-2-methyl-3-((R)-2-methyl-pyrrolidin-1-yl)-propoxy]-phenyl}-2H-pyridazin-3-one;
4,4-dimethyl-6-{4-[3-((R)-2-methyl-pyrrolidin-1-yl)-propoxy]-phenyl}-4,5-dihydro-2H-pyridazin-3-one;
5-{4-[3-((R)-2-methyl-pyrrolidin-1-yl)-propoxy]-phenyl}-3,4-diaza-bicyclo[4.1.0]hept-4-en-2-one;
5-;[4-(1-cyclobutyl-piperidin-4-yloxy)-phenyl]-3,4-diaza-bicyclo[4.1.0]hept-4-en-2-one;
5-{4-[(S)-2-methyl-3-((R)-2-methyl-pyrrolidin-1-yl)-propoxy]-phenyl}-3,4-diaza-bicyclo[4.1.0]hept-4-en-2-one;
5-{4-[3-((R)-2-methyl-pyrrolidin-1-yl)-propoxy]-phenyl}-3,4-diaza-bicyclo[4.1.0]hept-4-en-2-one;
5-{4-[3-((R)-2-methyl-pyrrolidin-1-yl)-propoxy]-phenyl}-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-[4-(1-cyclobutyl-piperidin-4-yloxy)-phenyl]-3,4-diaza-bicyclo[4.2.0]oct-4-en-2-one;
5-methyl-6-{4-[3-(R)-2-methyl-pyrrolidin-1-yl)-propoxy]-phenyl}-4,5-dihydro-2H-pyridazin-3-one one diastereomer;
5-methyl-6-{4-[3-((R)-2-methyl-pyrrolidin-1-yl)-propoxy]-phenyl}-4,5-dihydro-2H-pyridazin-3-one one diastereomer;
5-methyl-6-{4-[3-((R)-2-methyl-pyrrolidin-1-yl)-propoxy]-phenyl}-4,5-dihydro-2H-pyridazin-3-one; and
6-{4-[3-((R)-2-methyl-pyrrolidin-1-yl)-propoxy]-phenyl}-2H-pyridazin-3-one;
or a stereoisomeric form, mixture of stereoisomeric forms, or a pharmaceutically acceptable salt thereof.

Even more preferably, they are selected from the group consisting of:
4,4-dimethyl-6-{4-[3-((R)-2-methyl-pyrrolidin-1-yl)-propoxy]-phenyl}-4,5-dihydro-2H-pyridazin-3-one;
5-{4-[3-((R)-2-methyl-pyrrolidin-1-yl)-propoxy]-phenyl}-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-{4-[(S)-2-methyl-3-((R)-2-methyl-pyrrolidin-1-yl)-propoxy]-phenyl}-3,4-diaza-bicyclo[4.1.0]hept-4-en-2-one;
5-{4-[3-((R)-2-methyl-pyrrolidin-1-yl)-propoxy]-phenyl}-3,4-diaza-bicyclo[4.1.0]hept-4-en-2-one;
5-{4-[3-((R)-2-methyl-pyrrolidin-1-yl)-propoxy]-phenyl}-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-[4-(1-cyclobutyl-piperidin-4-yloxy)-phenyl]-3,4-diaza-bicyclo[4.1.0]hept-4-en-2-one;
5-[4-(1-cyclobutyl-piperidin-4-yloxy)-phenyl]-3,4-diaza-bicyclo[4.2.0]oct-4-en-2-one;
5-methyl-6-{4-[3-((R)-2-methyl-pyrrolidin-1-yl)-propoxy]-phenyl}-4,5-dihydro-2H-pyridazin-3-one one diastereomer;
5-methyl-6-{4-[3-((R)-2-methyl-pyrrolidin-1-yl)-propoxy]-phenyl}-4,5-dihydro-2H-pyridazin-3-one one diastereomer;
5-methyl-6-{4-[3-((R)-2-methyl-pyrrolidin-1-yl)-propoxy]-phenyl}-4,5-dihydro-2H-pyridazin-3-one; and
6-{4-[3-((R)-2-methyl-pyrrolidin-1-yl)-propoxy]-phenyl}-2H-pyridazin-3-one;
or a stereoisomeric form, mixture of stereoisomeric forms, or a pharmaceutically acceptable salt thereof; with the compound 6-{4-[3-((R)-2-methyl-pyrrolidin-1-yl)-propoxy]-phenyl}-2H-pyridazin-3-one, or a stereoisomeric form, mixture of stereoisomeric forms, or a pharmaceutically acceptable salt thereof being most preferred.

In certain alternatively preferred embodiments, the compounds of formula I are selected from the group consisting of:
2-methyl-6-{4-[3-((R)-2-methyl-pyrrolidin-1-yl)-propoxy]-phenyl}-2H-pyridazin-3-one;
2-methyl-6-[4-(3-piperidin-1-yl-propoxy)-phenyl]-2H-pyridazin-3-one;
2-isopropyl-6-[4-(3-piperidin-1-yl-propoxy)-phenyl]-2H-pyridazin-3-one;
2-isopropyl-6-[4-(3-piperidin-1-yl-propoxy)-phenyl]-4,5-dihydro-2H-pyridazin-3-one;
2-isopropyl-6-{4-[3-((R)-2-methyl-pyrrolidin-1-yl)-propoxy]-phenyl}-2H-pyridazin-3-one;
2-ethyl-6-{4-[3-((R)-2-methyl-pyrrolidin-1-yl)-propoxy]-phenyl}-2H-pyridazin-3-one;
6-{3-fluoro-4-[3-((R)-2-methyl-pyrrolidin-1-yl)-propoxy]-phenyl}-2-methyl-2H-pyridazin-3-one;
2-(2,4-dichloro-benzyl)-6-{4-[3-((R)-2-methyl-pyrrolidin-1-yl)-propoxy]-phenyl}-4,5-dihydro-2H-pyridazin-3-one;
2-(3,5-dichloro-phenyl)-6-{4-[3-((R)-2-methyl-pyrrolidin-1-yl)-propoxy]-phenyl}-2H-pyridazin-3-one;
6-[3-fluoro-4-(3-piperidin-1-yl-propoxy)-phenyl]-2-phenyl-2H-pyridazin-3-one;
6-{4-[3-((R)-2-methyl-pyrrolidin-1-yl)-propoxy]-phenyl}-2H-pyridazin-3-one;
4-{4-[3-((R)-2-methyl-pyrrolidin-1-yl)-propoxy]-phenyl}-2,5,6,7-tetrahydro-cyclopenta[d]pyridazin-1-one;
2-methyl-6-{4-[(S)-2-methyl-3-((R)-2-methyl-pyrrolidin-1-yl)-propoxy]-phenyl}-2H-pyridazin-3-one;
6-{4-[3-((S)-2-hydroxymethyl-pyrrolidin-1-yl)-propoxy]-phenyl}-2-methyl-2H-pyridazin-3-one;
6-{4-[3-((R)-2-hydroxymethyl-pyrrolidin-1-yl)-propoxy]-phenyl}-2-methyl-2H-pyridazin-3-one;
2-methyl-6-{4-[3-((R)-2-methyl-pyrrolidin-1-yl)-propoxy]-phenyl}-4,5-dihydro-2H-pyridazin-3-one;
2-benzyl-6-{4-[3-((R)-2-methyl-pyrrolidin-1-yl)-propoxy]-phenyl}-4,5-dihydro-2H-pyridazin-3-one;
2-benzyl-6-{4-[3-((R)-2-methyl-pyrrolidin-1-yl)-propoxy]-phenyl}-2H-pyridazin-3-one;
6-{4-[3-((R)-2-methyl-pyrrolidin-1-yl)-propoxy]-phenyl}-2-phenyl-2H-pyridazin-3-one;
6-{4-[3-((R)-2-methyl-pyrrolidin-1-yl)-propoxy]-phenyl}-2-phenyl-2H-pyridazin-3-one;
2-{4-[3-((R)-2-methyl-pyrrolidin-1-yl)-propoxy]-phenyl}-2H-pyridazin-3-one;
5-Isopropyl-7-{4-[3-((R)-2-methyl-pyrrolidin-1-yl)-propoxy]-phenyl}-5H-thieno[2,3-d]pyridazin-4-one;
7-{4-[3-(2,5-dimethyl-pyrrolidin-1-yl)-propoxy]-phenyl}-5-isopropyl-5H-thieno[2,3-d]pyridazin-4-one;
5-isopropyl-7-{4-(3-piperidin-1-yl-propoxy)-phenyl}-5H-thieno[2,3-d]pyridazin-4-one;
7-{4-[3-(3,3-dimethyl-piperidin-1-yl)-propoxy]-phenyl}-5-isopropyl-5H-thieno[2,3-d]pyridazin-4-one;
5-isopropyl-7-{4-[3-((S)-2-methoxymethyl-pyrrolidin-1-yl)-propoxy]-phenyl}-5H-thieno[2,3-d]pyridazin-4-one;
5-isopropyl-7-{4-[3-((R)-2-methoxymethyl-pyrrolidin-1-yl)-propoxy]-phenyl}-5H-thieno[2,3-d]pyridazin-4-one;
7-[4-(3-diethylamino-propoxy)-phenyl]-5-isopropyl-5H-thieno[2,3-d]pyridazin-4-one;
5-isopropyl-7-[4-(3-pyrrolidin-1-yl-propoxy)-phenyl]-5H-thieno[2,3-d]pyridazin-4-one;
5-isopropyl-7-{4-[3-(4-pyrrolidin-1-yl-piperidin-1-yl)-propoxy]-phenyl}-5H-thieno[2,3-d]pyridazin-4-one;

7-{4-[3-((2R,5R)-2,5-dimethyl-pyrrolidin-1-yl)-propoxy]-phenyl}-5-isopropyl-5H-thieno[2,3-d]pyridazin-4-one;
7-{4-[3-((R)-2-methyl-pyrrolidin-1-yl)-propoxy]-phenyl}-5-propyl-5H-thieno[2,3-d]pyridazin-4-one;
7-{4-[3-((2R,5R)-2,5-dimethyl-pyrrolidin-1-yl)-propoxy]-phenyl}-5-propyl-5H-thieno[2,3-d]pyridazin-4-one;
7-{4-[3-(4-methyl-piperidin-1-yl)-propoxy]-phenyl}-5-propyl-5H-thieno[2,3-d]pyridazin-4-one;
7-{4-[3-(4-dimethylamino-piperidin-1-yl)-propoxy]-phenyl}-5-propyl-5H-thieno[2,3-d]pyridazin-4-one;
5-propyl-7-{4-[3-((S)-2-pyrrolidin-1-ylmethyl-pyrrolidin-1-yl)-propoxy]-phenyl}-5H-thieno[2,3-d]pyridazin-4-one;
5-(4-chloro-benzyl)-7-[4-(3-piperidin-1-yl-propoxy)-phenyl]-5H-thieno[2,3-d]pyridazin-4-one;
5-(4-chloro-benzyl)-7-{4-[3-((R)-2-methyl-pyrrolidin-1-yl)-propoxy]-phenyl}-5H-thieno[2,3-d]pyridazin-4-one;
2,4-dimethyl-6-[4-(3-piperidin-1-yl-propoxy)-phenyl]-2H-pyridazin-3-one;
2,4-dimethyl-6-{4-[3-((R)-2-methyl-pyrrolidin-1-yl)-propoxy]-phenyl}-2H-pyridazin-3-one;
2-isopropyl-4-methyl-6-{4-[3-((R)-2-methyl-pyrrolidin-1-yl)-propoxy]-phenyl}-2H-pyridazin-3-one;
2-isopropyl-4-methyl-6-[4-(3-piperidin-1-yl-propoxy)-phenyl]-2H-pyridazin-3-one;
2-benzyl-4-methyl-6-{4-[3-((R)-2-methyl-pyrrolidin-1-yl)-propoxy]-phenyl}-2H-pyridazin-3-one;
2-benzyl-4-methyl-6-{4-(3-piperidin-1-yl-propoxy)-phenyl}-2H-pyridazin-3-one;
4-benzyl-2-methyl-6-{4-[3-((R)-2-methyl-pyrrolidin-1-yl)-propoxy]-phenyl}-2H-pyridazin-3-one;
4-benzyl-2-methyl-6-[4-(3-piperidin-1-yl-propoxy)-phenyl]-2H-pyridazin-3-one;
2-methyl-6-{4-[3-((R)-2-methyl-pyrrolidin-1-yl)-propoxy]-phenyl}-5-phenyl-2H-pyridazin-3-one;
2-methyl-5-phenyl-6-[4-(3-piperidin-1-yl-propoxy)-phenyl]-2H-pyridazin-3-one;
2-methyl-4-{4-[3-((R)-2-methyl-pyrrolidin-1-yl)-propoxy]-phenyl}-2H-phthalazin-1-one;
2-methyl-4-[4-(3-piperidin-1-yl-propoxy)-phenyl]-2H-phthalazin-1-one;
2-methyl-4-[4-(2-piperidin-1-yl-ethoxy)-phenyl]-2H-phthalazin-1-one;
2-methyl-4-[4-(3-pyrrolidin-1-yl-propoxy)-phenyl]-2H-phthalazin-1-one;
4-[4-(3-azepan-1-yl-propoxy)-phenyl]-2-methyl-2H-phthalazin-1-one;
2-(4-chloro-benzyl)-4-{4-[3-((R)-2-methyl-pyrrolidin-1-yl)-propoxy]-phenyl}-2H-phthalazin-1-one;
2-(4-chloro-benzyl)-4-[4-(3-piperidin-1-yl-propoxy)-phenyl]-2H-phthalazin-1-one;
2-methyl-4-{4-[3-((R)-2-methyl-pyrrolidin-1-yl)-propoxy]-phenyl}-2,5,6,7-tetrahydro-cyclopenta[d]pyridazin-1-one;
2-methyl-4-[4-(3-piperidin-1-yl-propoxy)-phenyl]-2,5,6,7-tetrahydro-cyclopenta[d]pyridazin-1-one;
2-methyl-4-{4-[3-((R)-2-methyl-pyrrolidin-1-yl)-propoxy]-phenyl}-2,4-a,5,6,7,7a-hexahydro-cyclopenta[d]pyridazin-1-one;
2-methyl-4-[4-(3-piperidin-1-yl-propoxy)-phenyl]-2,4-a,5,6,7,7a-hexahydro-cyclopenta[d]pyridazin-1-one;
2-methyl-4-{4-[3-((R)-2-methyl-pyrrolidin-1-yl)-propoxy]-phenyl}-5,6,7,8-tetrahydro-2H-phthalazin-1-one;
4-{4-[3-(butyl-ethyl-amino)-propoxy]-phenyl}-2-methyl-5,6,7,8-tetrahydro-2H-phthalazin-1-one;
4-[4-(3-methyl-4-oxo-3,4-dihydro-phthalazin-1-yl)-phenoxymethyl]-piperidine-1-carboxylic acid tert-butyl ester;
2-methyl-4-[4-(piperidin-4-ylmethoxy)-phenyl]-2H-phthalazin-1-one;
4-[4-(1-cyclobutyl-piperidin-4-ylmethoxy)-phenyl]-2-methyl-2H-phthalazin-1-one;
4-[4-(1-methyl-6-oxo-1,6-dihydro-pyridazin-3-yl)-phenoxymethyl]-piperidine-1-carboxylic acid tert-butyl ester;
2-methyl-6-[4-(piperidin-4-ylmethoxy)-phenyl]-2H-pyridazin-3-one;
6-[4-(1-cyclobutyl-piperidin-4-ylmethoxy)-phenyl]-2-methyl-2H-pyridazin-3-one;
6-[4-(1-isopropyl-piperidin-4-ylmethoxy)-phenyl]-2-methyl-2H-pyridazin-3-one;
6-[4-(1-cyclopropylmethyl-piperidin-4-ylmethoxy)-phenyl]-2-methyl-2H-pyridazin-3-one;
6-[4-(1-cyclopentyl-piperidin-4-ylmethoxy)-phenyl]-2-methyl-2H-pyridazin-3-one;
2-methyl-6-[4-(1-methyl-piperidin-4-ylmethoxy)-phenyl]-2H-pyridazin-3-one;
6-[4-(1-isopropyl-piperidin-4-yloxy)-phenyl]-2-methyl-2H-pyridazin-3-one;
2-methyl-6-[4-(piperidin-4-yloxy)-phenyl]-2H-pyridazin-3-one;
2-methyl-6-[4-(piperidin-4-yloxy)-phenyl]-2H-pyridazin-3-one;
2-methyl-8-[3-((R)-2-methyl-pyrrolidin-1-yl)-propoxy]-5,6-dihydro-2H-benzo[h]cinnolin-3-one;
8-[3-((R)-2-methyl-pyrrolidin-1-yl)-propoxy]-2-phenyl-5,6-dihydro-2H-benzo[h]cinnolin-3-one;
2-benzyl-8-(3-piperidin-1-yl-propoxy)-5,6-dihydro-2H-benzo[h]cinnolin-3-one;
2-isopropyl-8-(3-piperidin-1-yl-propoxy)-5,6-dihydro-2H-benzo[h]cinnolin-3-one;
2-methyl-7-[3-((R)-2-methyl-pyrrolidin-1-yl)-propoxy]-2H-phthalazin-1-one;
2-methyl-7-(3-piperidin-1-yl-propoxy)-2H-phthalazin-1-one; and
6-{3-fluoro-4-[3-((R)-2-methyl-pyrrolidin-1-yl)-propoxy]-phenyl}-2-phenyl-2H-pyridazin-3-one;
and stereoisomeric forms, mixtures of stereoisomeric forms or pharmaceutically acceptable salt forms thereof; with the compound 6-{4-[3-((R)-2-methyl-pyrrolidin-1-yl)-propoxy]-phenyl}-2H-pyridazin-3-one, or a stereoisomeric form, mixture of stereoisomeric forms, or a pharmaceutically acceptable salt thereof being more preferred.

In a second embodiment, the compounds of formula I are selected from Examples 22 to 38, 49 to 50 and 52 to 55. In a third embodiment, the compounds are selected from Examples 12, and 56 to 61. In a fourth embodiment, the compounds are selected from Examples 1 to 3, 5 to 7, 9 to 11, 13 to 15, 18, 20, 39 to 48, and 81. In a fifth embodiment, the compounds are selected from Examples 51, and 62 to 74. In a sixth embodiment, the compounds are selected from Examples 4, 8, 16 to 17, and 19. In a seventh embodiment, the compounds are selected from Examples 75 to 78. In a eighth embodiment, the compounds are Examples 79 and 80.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker New York, 1992, incorporated by reference herein in its entirety It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

For therapeutic purposes, the compounds of the present invention can be administered by any means that results in the contact of the active agent with the agent's site of action in the body of the subject. The compounds may be administered by any conventional means available for use in conjunction with pharmaceuticals, either as individual therapeutic agents or in combination with other therapeutic agents, such as, for example, analgesics. The compounds employed in the methods of the present invention including, for example, the compounds of Formula I, I*, I**, I(a-i), and/or II, may be administered by any means that results in the contact of the active agents with the agents' site or site(s) of action in the body of a patient. The compounds of the present invention are preferably administered in therapeutically effective amounts for the treatment of the diseases and disorders described herein to a subject in need thereof.

A therapeutically effective amount can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A preferred daily dose for adult humans includes about 25, 50, 100 and 200 mg, and an equivalent dose in a human child. The compounds may be administered in one or more unit dose forms. The unit dose ranges from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

Although the compounds of the present invention may be administered as the pure chemicals, it is preferable to present the active ingredient as a pharmaceutical composition.

Generally speaking, therapeutic compounds of this invention may be administered to a patient alone or in combination with a pharmaceutically acceptable carrier. Accordingly, the compounds of the invention, for example, compounds of Formula I, I*, I**, I(a-i), and/or II, are preferably combined with a pharmaceutical carrier selected on the basis of the chosen route of administration and standard pharmaceutical practice as described, for example, in *Remington's Pharma-* ceutical Sciences (Mack Publishing Co., Easton, Pa., 1980), the disclosures of which are hereby incorporated herein by reference, in their entireties. The carrier(s) must be acceptable in the sense of being compatible with the other ingredients of the composition and not deleterious to the recipient thereof. The relative proportions of active ingredient and carrier may be determined, for example, by the solubility and chemical nature of the compounds, chosen route of administration and standard pharmaceutical practice.

The compounds of the present invention may be formulated into pharmaceutical compositions by admixture with one or more pharmaceutically acceptable excipients. The excipients are selected on the basis of the chosen route of administration and standard pharmaceutical practice, as described, for example, in *Remington: The Science and Practice of Pharmacy*, 20$^{th}$ ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations. Such controlled-release, or extended-release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the afore listed excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

Pharmaceutical kits useful in, for example, the treatment of pain, which comprise a therapeutically effective amount of a compound of the invention and/or other therapeutic compounds described herein, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compound of the invention and/or other therapeutic compound as described herein may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The compounds of the present invention may be used in methods to bind histamine receptors, more preferably histamine $H_3$ receptors. Such binding may be accomplished by contacting the receptor with an effective amount of a compound of Formula I, I*, I**, I(a-i), and/or II. The histamine receptors may be located in the central nervous system or located peripherally to the central nervous system or in both locations. Preferably, the contacting step conducted in an aqueous medium, preferably at physiologically relevant ionic strength, pH, and the like.

In yet another aspect, the invention is directed to methods of binding histamine receptors, more preferably histamine $H_3$ receptors, comprising the step of administering to a patient in need thereof, an effective amount of a compound of the invention including, for example, a compound of Formula I, I*, I**, I(a-i), and/or II, or any combination thereof.

In certain preferred aspects, the methods comprise the step of administering to said patient an therapeutically effective amount of a compound of Formula I, I*, I**, I(a-i), and/or II, or any combination thereof.

In some preferred embodiments, the histamine receptors are $H^3$ histamine receptors. In certain more preferred embodiments, the compound selectively binds $H^3$ histamine receptors relative to $H_1$, $H_2$ and/or $H_4$ receptors. In certain preferred embodiments, the $H^3$ histamine receptors are located in the central nervous system. In some other preferred embodiments, the compound of Formula I, I*, I**, I(a-i), and/or II, or any combination thereof exhibits activity toward the histamine receptors. In certain preferred embodiments, the binding agonizes the activity of the cannabinoid receptors. In other preferred embodiments, the binding antagonizes the activity of the cannabinoid receptors, more preferably as a neutral antagonist. In still other preferred embodiments, the binding inversely agonizes the activity of the cannabinoid receptors.

In yet other preferred embodiments, the compounds of Formula I, I*, I**, I(a-i), and/or II, or any combination thereof exhibit activity toward the histamine receptors in vivo. In alternatively preferred embodiments, the compounds of Formula I, I*, I**, I(a-i), and/or II, or any combination thereof, exhibit activity toward the histamine receptors in vitro.

In certain other preferred aspects of the invention, there are provided methods of treating a disease, disorder or condition that may be affected, modulated or controlled through the binding of histamine, preferably $H_3$ histamine receptors. More preferably these diseases, disorders, and/or conditions selected from the group consisting of narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders, inflammation, and myocardial infarction. The methods herein provided comprise administering to a subject in need of such treatment a therapeutically effective amount of a compound of the invention, preferably a compound of formula:

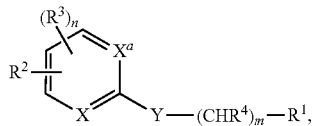

more preferably a compound of formula I, I*, I**, I(a-i), and/or II, or any combination thereof.

In certain preferred embodiments, the disorder is narcolepsy or sleep/wake disorders. Alternatively the disorder treated is attention deficit hyperactivity disorder.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

Synthesis

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

The general routes to prepare the examples shown herein are shown in the Schemes 1 and 2. The reagents and starting materials are commercially available, or readily synthesized by well-known techniques by one of ordinary skill in the arts. All substituents in the synthetic Schemes, unless otherwise indicated, are as previously defined.

Condensation of 4-(4-methoxyphenyl)-4-oxobutyric acid or ester, or a derivative thereof, with hydrazine or an N-substituted hydrazine derivative in a solvent such as ethanol or 2-propanol provided a route to 4,5-dihydropyridazinone intermediates. Keto-acid intermediates with substitution at the 4- and 5-position (Examples with $R^{13/13a}$ and $R^{14/14a}$) may be readily prepared (Heterocycles, 2002, 57, 39; Indian J. Chem, 1977, 16B, 631; Chem Pharm Bull, 1980, 42, 1850; J. Med. Chem. 2003, 46, 2008). Pyridazinones with $R^{13/13a}$ and $R^{14/14a}$ fused with heteroaryl or cycloalkyl were readily prepared from the corresponding anhydrides. NH(N2) pyridazinones were alkylated with alkyl or substituted alkyl groups using an $R^{12}$-halide, a base, for example $K_2CO_3$, $Cs_2CO_3$ or NaH, in an inert solvent such as DMF or $CH_3CN$.

In cases where $R^{13}$ or $R^{14}$ substituted 4,5-dihydropyridazinone formed a mixture of isomers, the isomers were separated by standard methods known in the art. Intermediates wherein $R^{12}$ is H may be converted to analogs wherein $R^{12}$ is aryl or heteroaryl by standard palladium or copper coupling reactions using the appropriate aryl or heteroaryl halide. The 4,5-dihydropyridazinone may be oxidized to an aromatic pyridazinone using $MnO_2$, $CuCl_2$, DDQ, selenium oxide, DMSO/base or sodium 3-nitrobenzenesulfonate in the presence of sodium hydroxide.

Scheme 1. General synthesis of N2 H and substituted examples

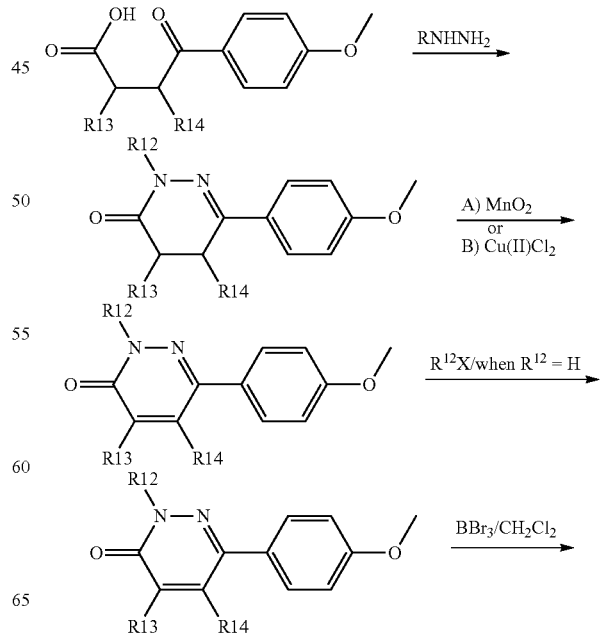

-continued

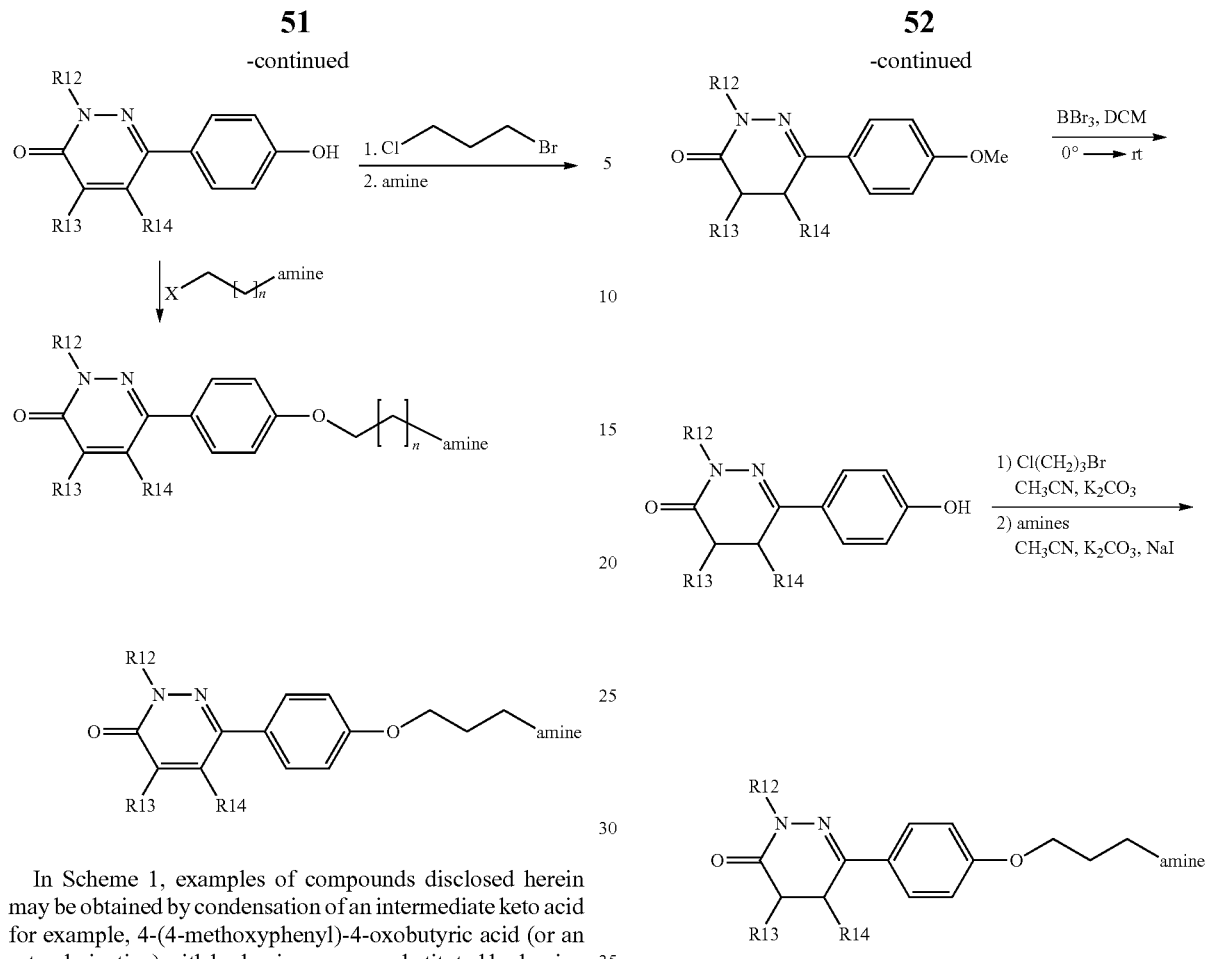

In Scheme 1, examples of compounds disclosed herein may be obtained by condensation of an intermediate keto acid for example, 4-(4-methoxyphenyl)-4-oxobutyric acid (or an ester derivative) with hydrazine or an n-substituted hydrazine derivative in a solvent such as ethanol or 2-propanol to produce a dihydropyridazinone intermediate. The keto-acid intermediates not commercially available are readily prepared and described using literature methods. Keto-acid intermediates with $R^{13}$ or $R^{14}$ groups in the 4 or 5-positions or fused aryl or heteroaryl groups are described (Heterocycles, 2002, 57, 39; Indian J. Chem, 1977, 16B, 631; Chem Pharm Bull, 1980, 42, 1850; J. Med. Chem. 2003, 46, 2008). The N2 position may be substituted with alkyl or substituted alkyl groups using a base, for example $K_2CO_3$, $Cs_2CO_3$ or NaH in an inert solvent such as DMF or $CH_3CN$. In cases where $R^{13}$ or $R^{14}$ substituted dihydropyridazinone form isomers, the individual isomers may be separated using conventional methods known to the art. $R^{13}$ aryl or heteroaryl groups may be introduced by standard palladium or copper coupling reactions using the appropriate aryl or heteroaryl halide. Alternatively, the 4,5-position may be oxidized to the pyridazinone intermediate using for example $MnO_2$, $CuCl_2$, DDQ or selenium oxide as the oxidizing agent. The N2 nitrogen may be H, or further substituted using methods outlined previously.

Scheme 2. General synthesis of 4,5-dihydro examples

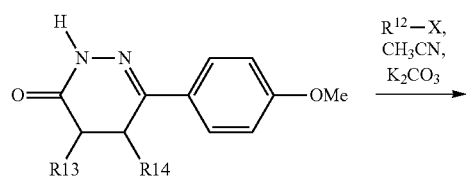

As outlined in Scheme 1 and 2, the pyridazinone or dihydro pyridazinone methoxy intermediate is demethylated using $BBr_3$ in dichloromethane to produce the phenol. Alkylation of the phenol with bromochloropropane or a dibromoalkane intermediate in a suitable solvent such as DMF, acetone, butanone or $CH_3CN$ with $K_2CO_3$ produces the halogen intermediate. Alkylation of the halide intermediate with an amine gives the target dihydropyridazinone examples of the invention. Other suitable leaving groups may be used such as mesylates as precursors to amines Mitsunobo reactions with cyclic amino-ethers such as 4-hydroxypiperidine, 3-hydroxypyrrolidine or substituted amino alcohols produce the corresponding examples. Alkyl bridged analogs or linker group with hetero atoms can readily be prepared for example from methoxy indanones, tetralones, benzocycloheptanones, dihydro-2H-benzo[b]oxepinones, dihydro-2H-benzo[b]thiepinones, chromanones, or thiochromanones.

As outlined in Schemes 3 and 4, the pyridazinone or 4,5-dihydropyridazinone was demethylated using $BBr_3$ in dichloromethane to produce phenol intermediates III and IIIa. Alkylation of the phenol intermediates with 3-bromo-1-chloropropane or a dibromo intermediate in a suitable solvent such as DMF, acetone, butanone or $CH_3CN$ with $K_2CO_3$ produced the corresponding alkylated intermediate. Displacement of the halide with an amine gave the target dihydropyridazinone examples of general structures V and Va.

Scheme 3. General synthesis of R12 H and substituted examples
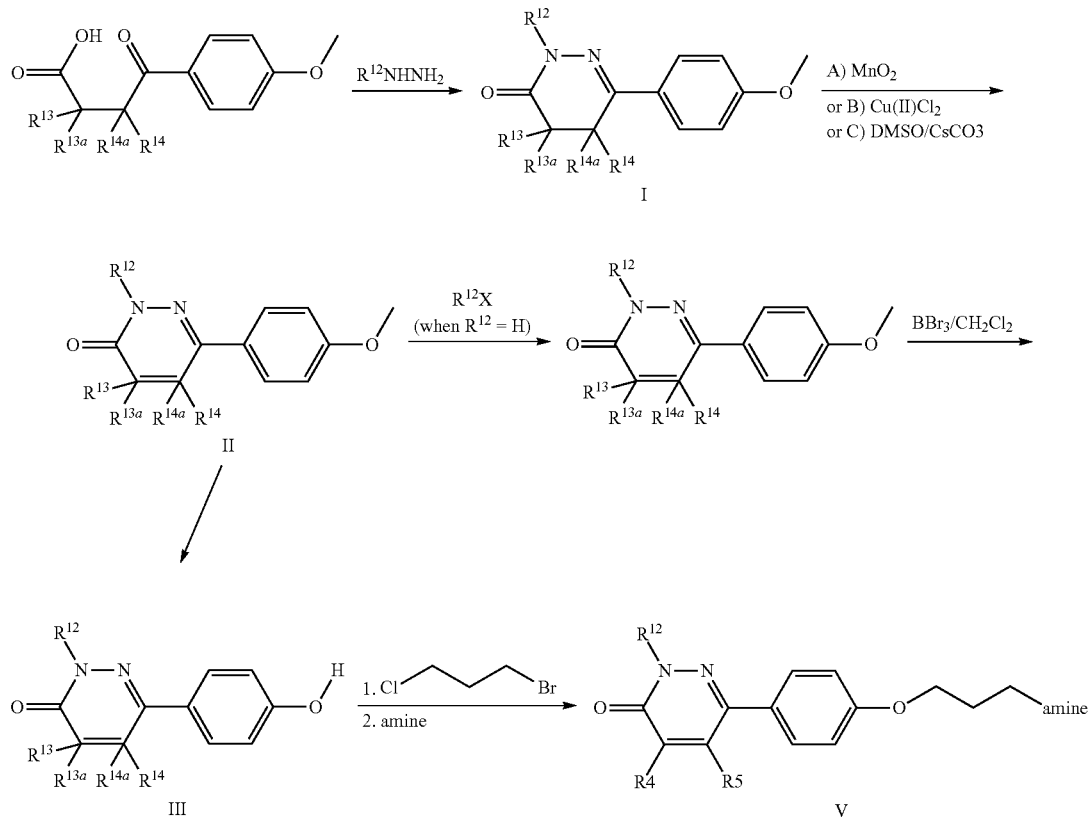
Scheme 4. General synthesis of 4,5-dihydro examples
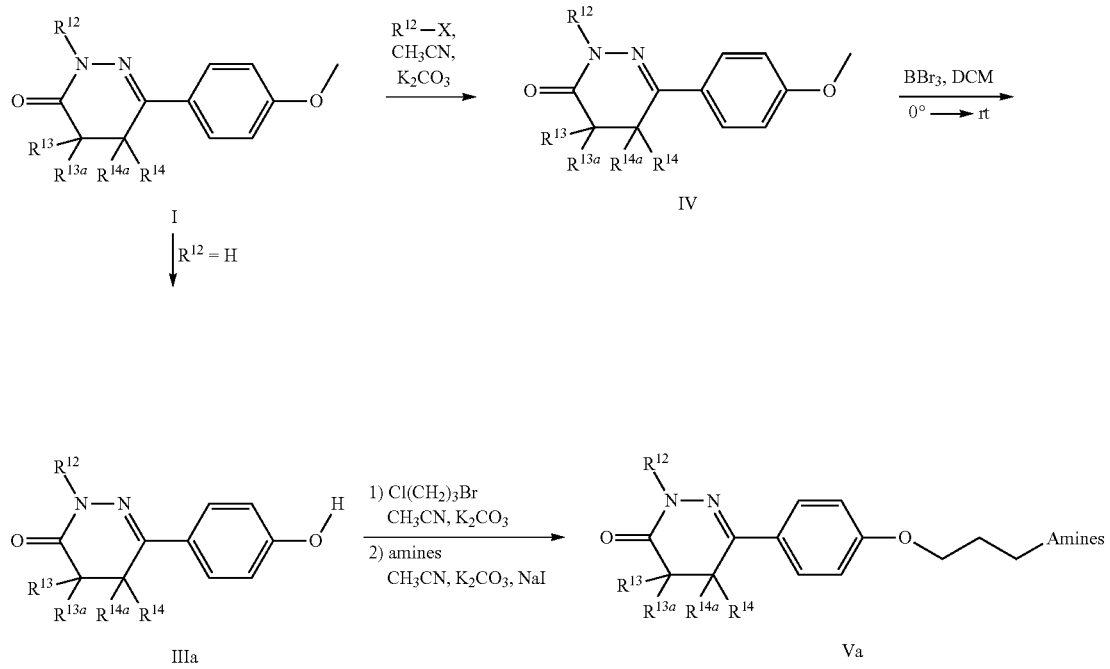

As outlined in Scheme 5, the phenol intermediate was coupled under Mitsunobo conditions with hydroxypiperidines, pyrrolidines or azepines to give the piperidine or cyclic amine derivatives of general structure VI. Using reaction conditions described previously, examples of general structure VII was prepared.

Scheme 5. General synthesis of 4,5-dihydro examples

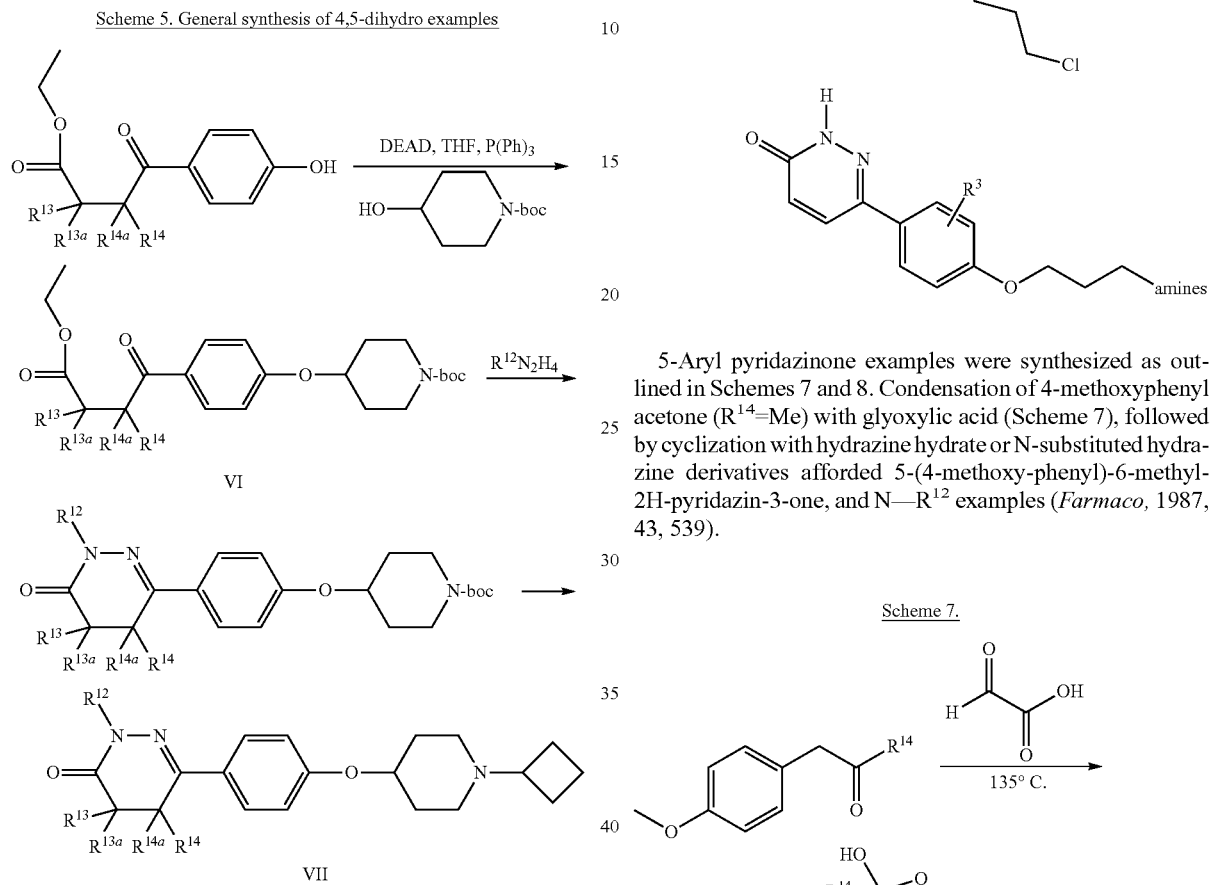

Scheme 6 discloses an Aldol condensation route to examples wherein $R^{12}$ is H. 4-Hydroxy-acetophenone or a derivative thereof was condensed with a keto-acid, for example glycolic acid in acetic acid, and cyclized with hydrazine to give an aromatic pyridazinone (*J. Med. Chem.*, 1987, 30, 239).

Scheme 6.

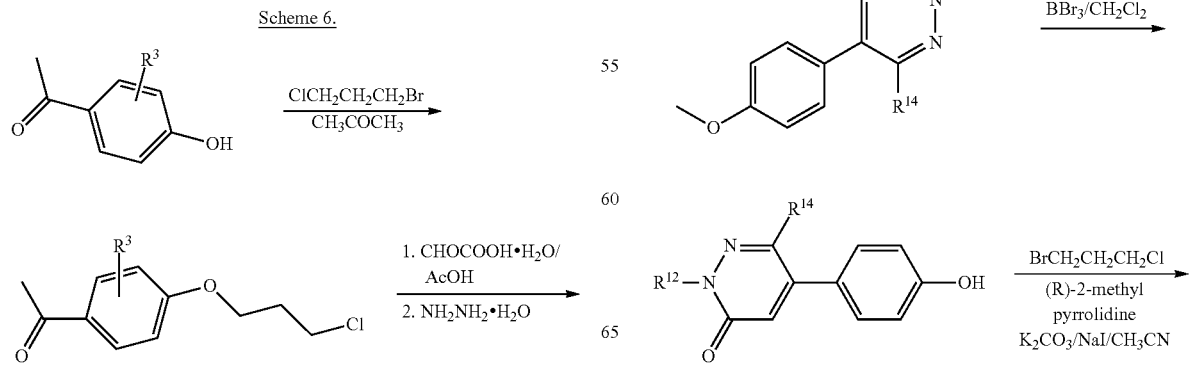

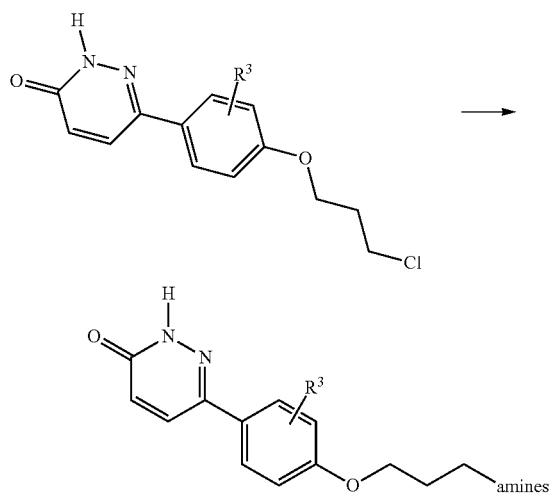

5-Aryl pyridazinone examples were synthesized as outlined in Schemes 7 and 8. Condensation of 4-methoxyphenyl acetone ($R^{14}$=Me) with glyoxylic acid (Scheme 7), followed by cyclization with hydrazine hydrate or N-substituted hydrazine derivatives afforded 5-(4-methoxy-phenyl)-6-methyl-2H-pyridazin-3-one, and N—$R^{12}$ examples (*Farmaco*, 1987, 43, 539).

Scheme 7.

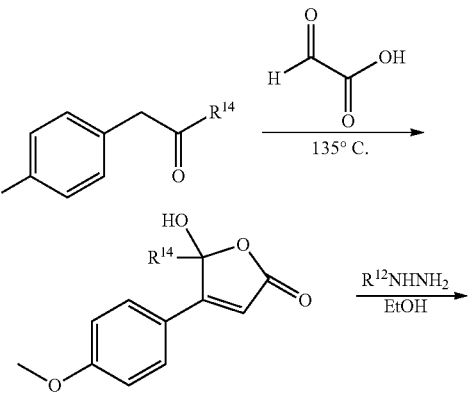

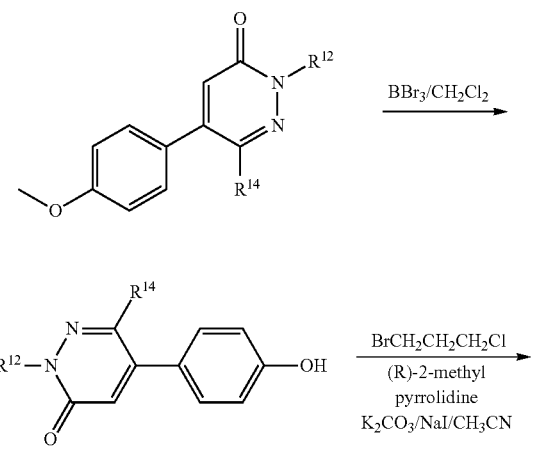

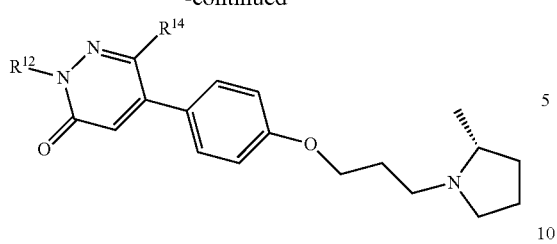
5-Aryl examples where $R^{14}$ is H were prepared as outlined in Scheme 8 starting from 4-methoxyphenylacetaldehyde using conditions shown in Scheme 7.
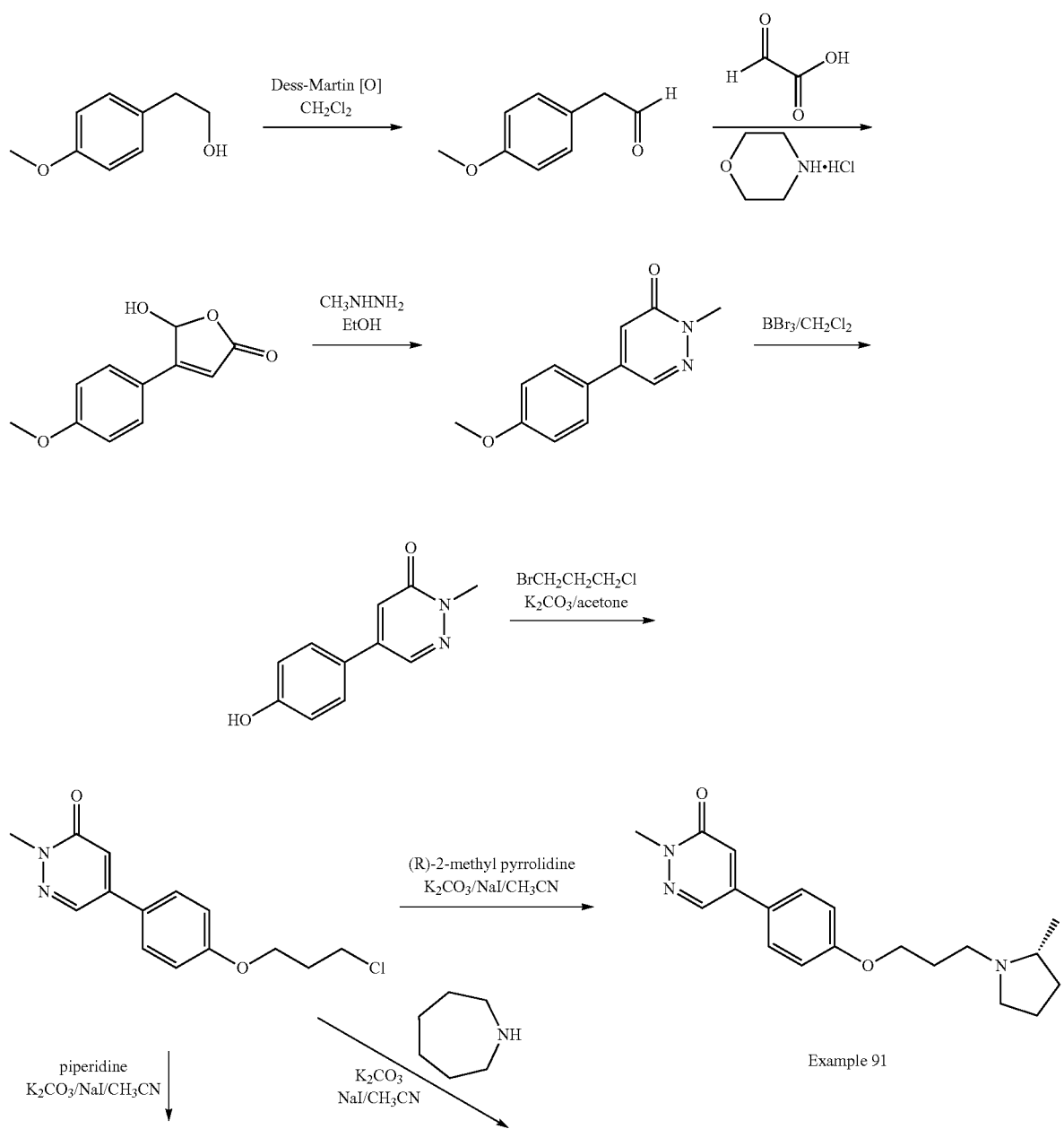

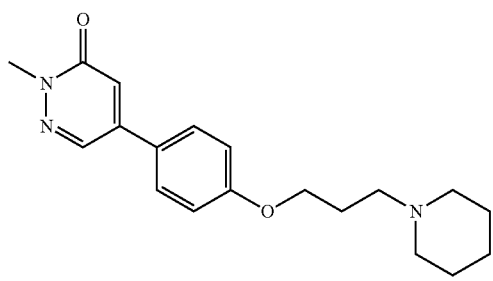

Example 92

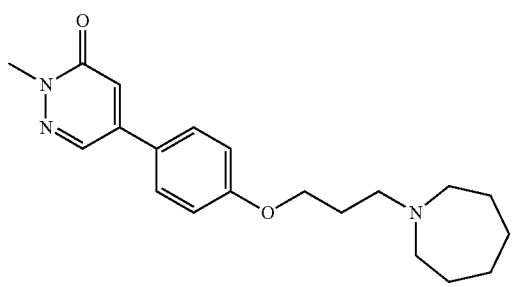

Example 93

Aza examples (X=N) where $R^{13}$ and $R^{13a}$ are each methyl were prepared as outlined in Scheme 9 by alkylation of 1-(6-chloropyridin-3-yl)ethanone with 4-hydroxy-N-Boc-piperidine and a base such as NaH, potassium tertiary butoxide, or KHMDS in DMSO, DMF or THF. A second alkylation step using potassium bis(trimethylsilyl)amide in toluene and, for example 2-bromo-2-methyl-propionic acid ethyl ester, produced the keto-ester intermediates VIII. Example 148 was produced as shown in Scheme 9 using conditions described previously.

Scheme 9.

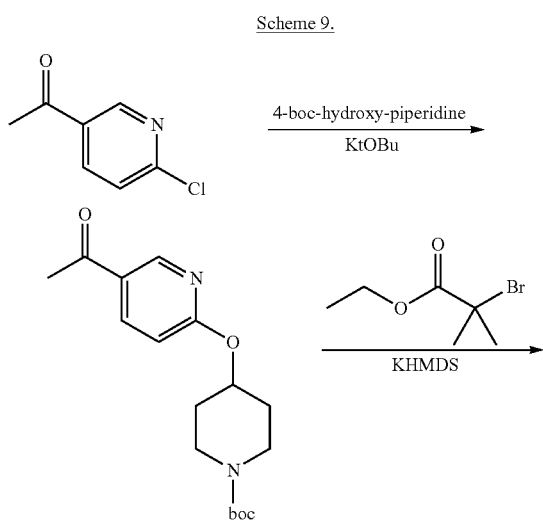

-continued

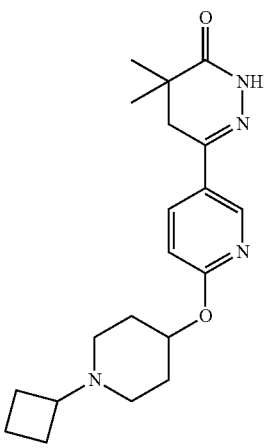

Example 148

Scheme 10 shows the route to aza (X=N) examples where $R^{12}$ is heteroaryl(For example, Example 149 (6-[6-(1-Cyclobutyl-piperidin-4-yloxy)-pyridin-3-yl]-2-pyridin-2-yl-2H-pyridazin-3-one). 6-(6-Chloropyridin-3-yl)-4,5-dihydro-2H-pyridazin-3-one intermediate IX, prepared from ethyl-4-(4-chloro-3-pyridyl)-4-oxobutyrate and hydrazine in ethanol was alkylated with 4-hydroxy-boc-piperidine and a base (KHMDS, DMSO) to intermediate X and converted to example 141 using methods described previously. Treatment of Example 141 with 2-bromopyridine in the presence of copper(I) iodide gives Example 149. Using aryl halides or heteroaryl halides gave examples where $R^{12}$ is aryl or heteroaryl.

Scheme 10.

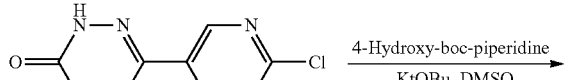

IX

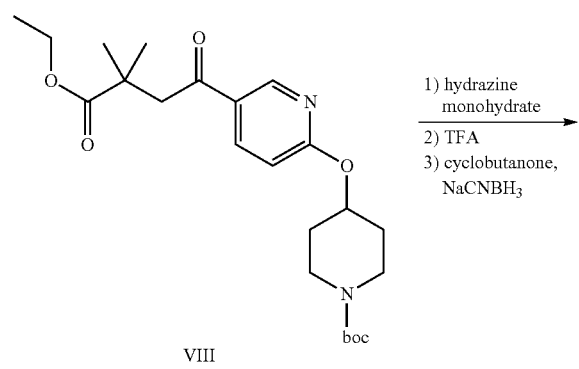

VIII

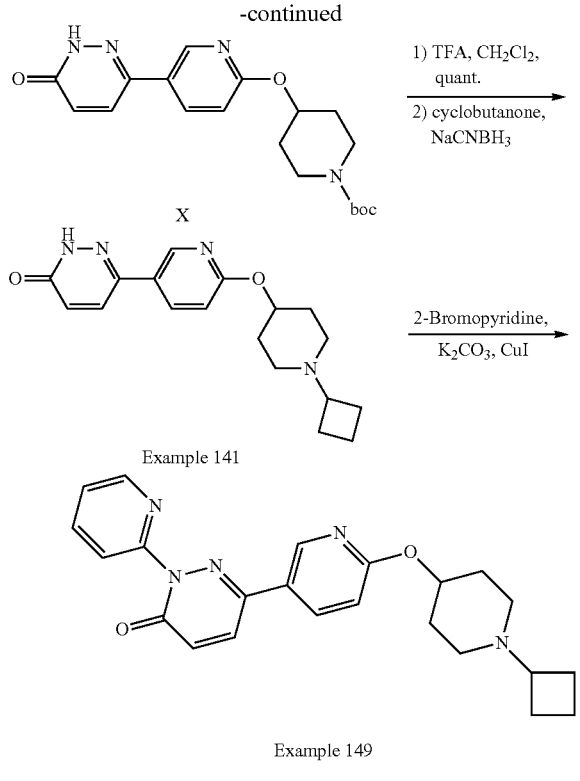

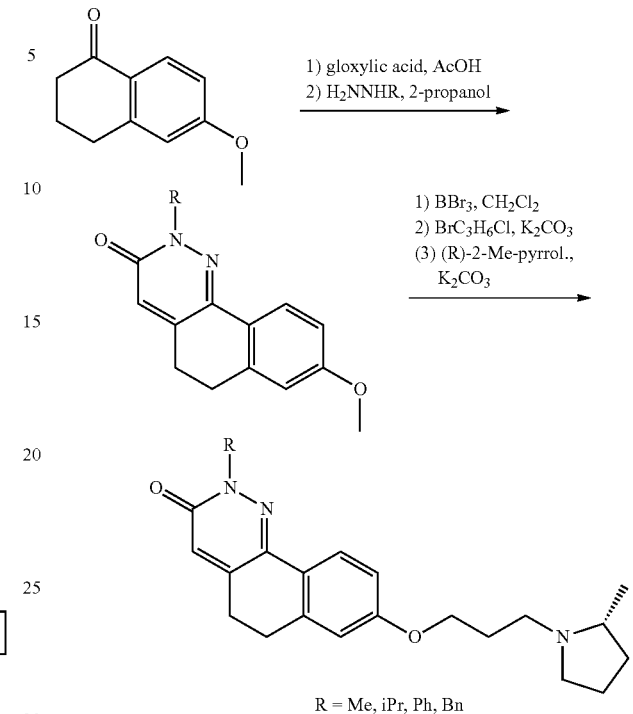

Bridged examples (Scheme 11) were prepared using methoxy tetralones and glycolic acid in an aldol synthesis. Phenol formation and alkylations as described previously produced the N-substituted examples. Alternatively, the use of β-tetralones provided a route to pyridazinone regioisomers.

Scheme 12 shows bridged analogs where $R^{12}$ is H, prepared by varying the order of the reactions. Addition of Zn dust to the aldol/ring closure procedure gave a one-pot synthesis of the dihydropyridazinone.

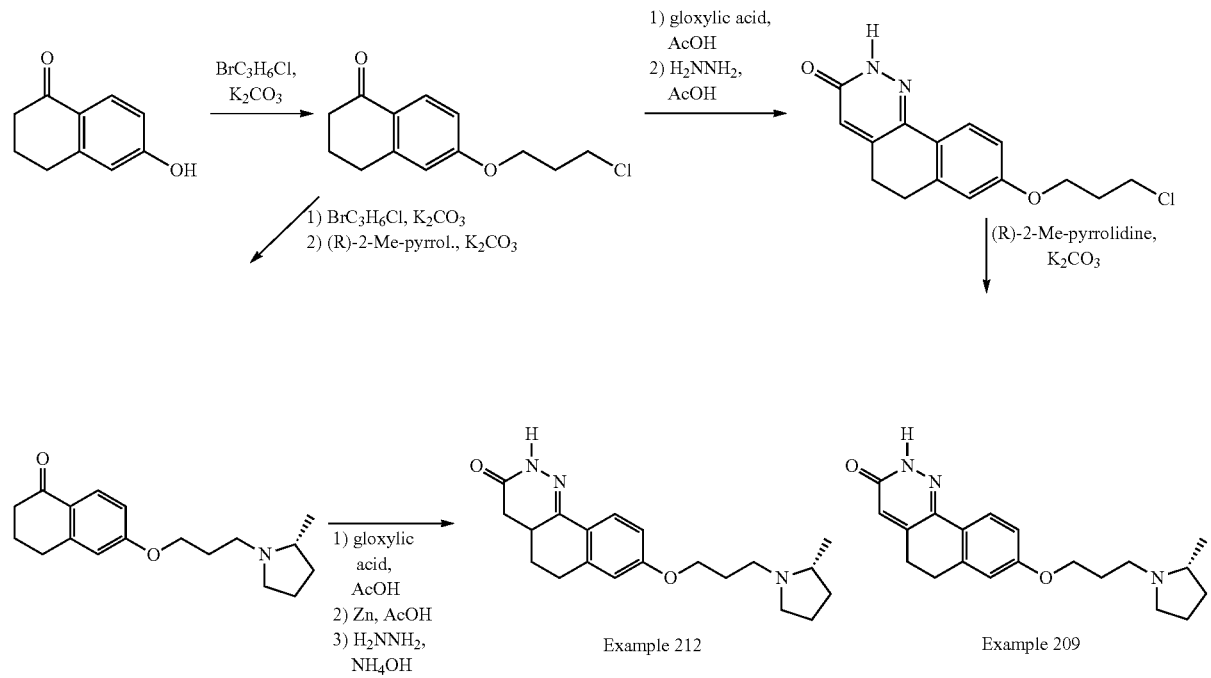

The present invention will now be illustrated by reference to the following specific, non-limiting examples. Those skilled in the art of organic synthesis may be aware of still other synthetic routes to the invention compounds. The reagents and intermediates used herein are commercially available or may be prepared according to standard literature procedures.

EXAMPLES

Other features of the invention will become apparent in the course of the following descriptions of exemplary embodiments as shown below. The compounds shown herein have activity in the targets described herein at concentrations ranging from 0.1 nM to 10 µM. These examples are given for illustration of the invention and are not intended to be limiting thereof.

Example 1

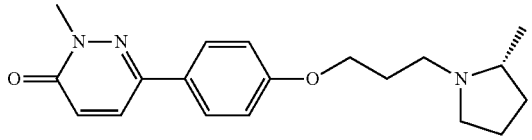

2-Methyl-6-{4-[3-((R)-2-methyl-pyrrolidin-1-yl)-propoxy]-phenyl}-2H-pyridazin-3-one Step 1

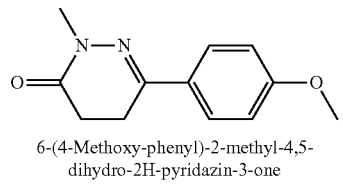

6-(4-Methoxy-phenyl)-2-methyl-4,5-dihydro-2H-pyridazin-3-one

In a 500 mL round bottom flask, 4-(4-methoxyphenyl)-4-oxobutyric acid (27 g, 132 mmol) and methylhydrazine (7.3 g, 8.5 mL, 159 mmol) in 2-propanol (150 mL) were stirred at reflux 12 h. The solvent was concentrated to about 50 mL, ether was added (~50 mL) and the product collected by filtration, washed 1× with ether and dried under house vacuum. Yield 27 g (94%, purity >95%), mp 133-135° C. $^1$H NMR (CDCl$_3$) δ 2.57 (m, 2H), 2.9 (m, 2H), 3.4 (s, 3H), 3.8 (s, 3H), 6.9 (d, 2H), 7.6 (d, 2H). MS m/z=218 (M+H).

Step 2

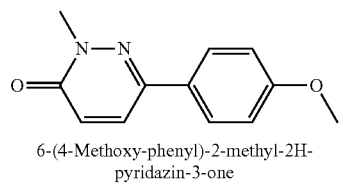 [SMILES: COc1ccc(-c2ccc(=O)n(C)n2)cc1]

6-(4-Methoxy-phenyl)-2-methyl-2H-pyridazin-3-one

Method A:

In a 1 L round bottom flask, 6-(4-methoxyphenyl)-2-methyl-4,5-dihyrdo-2H-pyridazin-3-one (27 g, 124 mmol) and MnO$_2$ (30 g, 345 mmol) in xylene (250 mL) was stirred at vigorous reflux 14 h. The reaction was cooled to rt and filtered through a pad of celite. The xylene was concentrated and the resulting yellow solid was triturated with ether/hexane (1:2) and collected to produce 20 g (75%, HPLC 98% purity) of product. The celite/MnO$_2$ pad was washed with CHCl$_3$:MeOH 9:1 (2×~100 mL), filtered and concentrated. The residue was triturated with ether/hexane (1:2) and collected to give a second crop (4 g, 15%, 96% purity) total yield 24 g (90%). mp 109-110° C. $^1$H NMR (DMSO-d$_6$) δ 3.75 (s, 3H), 3.85 (s, 3H), 7.0-7.05 (d, 2H, d, 1H), 7.82 (d, 2H), 8.01 (d, 1H); MS m/z=216 (M+H).

Method B:

A mixture of 6-(4-methoxyphenyl)-2-methyl-4,5-dihyrdo-2H-pyridazin-3-one (3.27 g, 15 mmol) and Cu(II) Cl$_2$ (3.96 g, 2 eq., anhydrous, Acros) in 45 ml of anhydrous acetonitrile was refluxed for 2 hr. HPLC indicated the completion of the reaction (rt (product)=7.66 min, rt (SM)=7.88 min) The reaction was cooled to rt and poured into ice-water (~100 ml) and the acetonitrile removed at reduced pressure. The resulting off-white solid was filtered off, washed with water, and then crystallized from EtOH:Et$_2$O to give the product (2.47 g, 76%).

Step 3

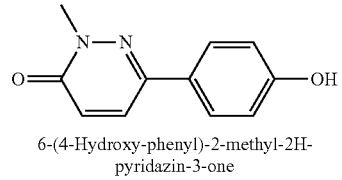

6-(4-Hydroxy-phenyl)-2-methyl-2H-pyridazin-3-one

To 6-(4-methoxyphenyl)-2-methyl-2H-pyridazin-3-one (10 g, 46.3 mmol) in 15 mL DCM cooled on an ice-water bath to ~5° C. was added 93 mL of BBr$_3$ (1M soln in DCM) over 5 min. The ice bath was removed and the solution stirred at rt for 4 h. The reaction was cooled on an ice-bath and saturated NH$_4$Cl solution (100 mL) added slowly. After the addition was complete, the DCM was removed under reduced pressure, excess water added and the product collected, washed 1× with MeOH (~20 mL) and dried to give 9.2 g (98%): Mp 242-245° C. $^1$H NMR (DMSO-d$_6$) δ 3.8 (s, 3H), 6.85 (d, 2H), 7.0 (d, 1H), 7.7 (d, 2H), 7.95 (d, 1H), 9.8 (s, 1H); MS m/z=203 (M+H).

Step 4

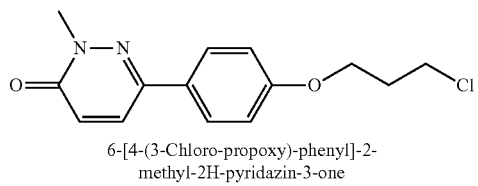 [SMILES: Cn1nc(-c2ccc(OCCCCl)cc2)ccc1=O]

6-[4-(3-Chloro-propoxy)-phenyl]-2-methyl-2H-pyridazin-3-one

Phenol from step 3 (500 mg, 2.3 mmol), 3-bromo-1-chloropropane (720 mg, 4.6 mmol) and K$_2$CO$_3$ (950 mg) in CH₃CN (25 mL) was stirred at reflux 20 h. The reaction was filtered and concentrated. The resulting oil was dissolved in Et₂O, and washed with water, NaCl solution, dried (MgSO₄) and concentrated. The product was triturated with Et₂O-hexanes to yield 580 mg (91%) mp 186-187° C. ¹H NMR (DMSO-d₆) δ 2.2 (t, 2H), 3.7 (s, 3H), 3.8 (t, 2H), 4.15 (t, 2H), 7.0-7.1 (m, 3H), 7.8 (d, 2H), 8.0 (d, 1H). MS m/z=279 (M+H).

Example 1

Step 5

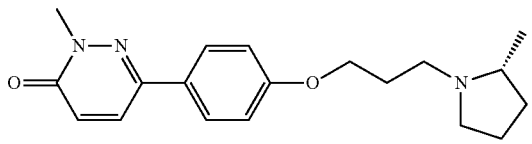

2-Methyl-6-{4-[3-((R)-2-methyl-pyrrolidin-1-yl)-propoxy]-phenyl}-2H-pyridazin-3-one 6-[4-(3-Chloropropoxy)phenyl]-2-methyl-2H-pyridazin-3-one (1.5 g, 5.4 mmol), K₂CO₃ (2.2 g 16.2 mmol), NaI (805 mg, 5.4 mmol) R-methylpyrrolidine HCl (1.3 g, 10.8 mmol) in CH₃CN (30 mL) was heated under N₂ at 90° C. for 2 days. The reaction was filtered and concentrated. The residue was dissolved in EtOAc and washed with 2N Na₂CO₃ (1×), NaCl solution (1×) dried (MgSO₄) and concentrated. The product was purified by ISCO chromatography (80 g silica gel column, 95:5 DCM: MeOH). The fractions were combined and concentrated to yield 850 mg (48%) of free base. The HCl was prepared by adding a 1N HCl-ether solution to the based in ether. The product was collected, and recrystallized from CH₃CN-ether. mp 183-185° C. ¹H NMR (DMSO-d₆) δ 1.38 (d, 3H), 1.62 (m, 1H), 1.92-1.3.1 (m, 3H), 3.4 (m, 3H), 3.7 (m, 1H), 3.7 (s, 3H), 4.15 (m, 2H), 7.0-7.17 (m, 3H), 7.8 (d, 2H), 8.0 (d, 1H), 10.1 (s, 1H). MS m/z=328 (M+H).

Example 11

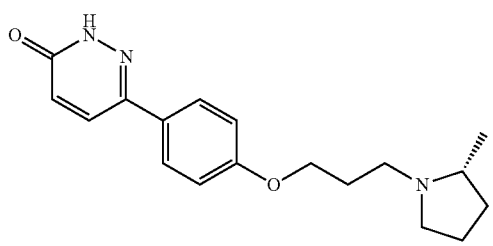

6-{4-[3-((R)-2-Methyl-pyrrolidin-1-yl)-propoxy]-phenyl}-2H-pyridazin-3-one

Step 1

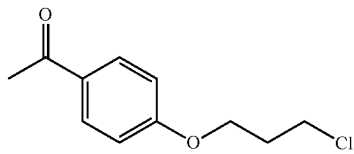

1-[4-(3-Chloro-propoxy)-phenyl]-ethanone

A mixture of 1-(4-hydroxyphenyl)ethanone (20.4 g, 150 mmol), K₂CO₃ (62.1 g, 3.0 eq.), and 3-bromo-1-chloropropane (29.6 mL, 2.0 eq.) in CH₃COCH₃ (200 mL) was heated to 65° C. overnight. The mixture was filtered, washed with acetone, and concentrated to dryness. The crude product was dissolved in 150 mL of CH₂Cl₂, and washed with saturated NaHCO₃, NaCl solution and dried over Na₂SO₄. Concentration to dryness under vacuum afforded product (31.5 g, 99% yield): MS m/z 213 (M+H).

Step 2

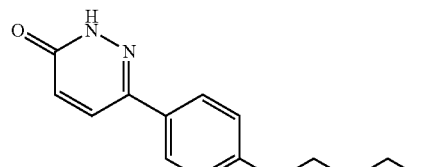

6-[4-(3-Chloro-propoxy)-phenyl]-2H-pyridazin-3-one

A mixture of the product from step 11 (4.6 g, 1.0 eq.) and glyoxalic acid monohydrate (4.6 g, 1.0 eq.) was stirred in 15 mL of acetic acid at 100° C. for 2 h. The solvent was evaporated and to the residue was added 25 mL of water, and cooled to 0° C. while conc. aqueous NH₄OH was added to pH 8. To this mixture, hydrazine hydrate (4.76 mL, 2 eq.) was added and heated to 100° C. for 1 h. The resulting solid was filtered, washed with water. The crude material was dissolved in CH₂Cl₂/MeOH and purified by column chromatography with CH₂Cl₂ to 10% MeOH in CH₂Cl₂; Mp 191-3° C.; MS m/z 265 (M+H).

Step 3

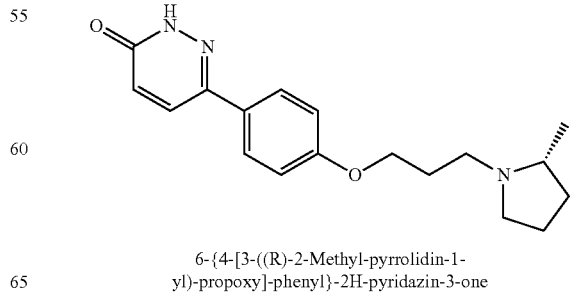

6-{4-[3-((R)-2-Methyl-pyrrolidin-1-yl)-propoxy]-phenyl}-2H-pyridazin-3-one

A mixture of the product from step 2 (5.5 g, 21 mmol), K$_2$CO$_3$ (3.5 eq, 10.1 g), 100 mg of NaI, and R-2-methylpyrrolidine hydrochloride (2 eq., 5.1 g) in 250 mL of acetonitrile was heated to 80° C. for 2 days. The reaction mixture was then filtered, washed with CH$_2$Cl$_2$ (2×50 mL), and concentrated. The residue was dissolved in 200 mL of CH$_2$Cl$_2$, and washed with saturated NaHCO$_3$, saturated NaCl, dried with Na$_2$SO$_4$ and concentrated. The residue was purified by ISCO graduate chromatography with 100% CH$_2$Cl$_2$ to 5% MeOH: 95% CH$_2$Cl$_2$:0.5 mL of 2-aminopropane and then to 10% MeOH: 90% CH$_2$Cl$_2$:0.5 mL of 2-aminopropane to give the product. The product was dissolved in 15 mL of MeOH and then added 30 mL of 0.5 N HCl in EtOH. Evaporation of the solvent, and crystallization from MeOH: Et$_2$O afforded the example 11 as the HCl salt (2.65 g, 41%): Mp 240-2° C.; MS m/z 314 (M+H).

The following examples were prepared as HCl salts unless noted using methods for example 1 and example 11. The 4,5-dihydro examples were prepared using the method for step 3 on the product from step 1.

| Example | Structure | Mp (° C.) | MS m/z |
|---|---|---|---|
| 2 | 2-Methyl-6-[4-(3-piperidin-1-yl-propoxy)-phenyl]-2H-pyridazin-3-one | 200-201 | 328 (M + H) |
| 3 | 2-Isopropyl-6-[4-(3-piperidin-1-yl-propoxy)-phenyl]-2H-pyridazin-3-one | 118-122 | 356 (M + H) |
| 4 | 2-Isopropyl-6-[4-(3-piperidin-1-yl-propoxy)-phenyl]-4,5-dihydro-2H-pyridazin-3-one | 76-77 | 358 (M + H) |
| 5 | 2-Isopropyl-6-{4-[3-((R)-2-methyl-pyrrolidin-1-yl)-propoxy]-phenyl}-2H-pyridazin-3-one | 60-64 (tartrate) | 356 (M + H) |
| 6 | 2-Ethyl-6-{4-[3-((R)-2-methyl-pyrrolidin-1-yl)-propoxy]-phenyl}-2H-pyridazin-3-one | 58-62 (tartrate) | 342 (M + H) |

-continued

| Example | Structure | Mp (° C.) | MS m/z |
|---|---|---|---|
| 7 | 6-{3-Fluoro-4-[3-((R)-2-methyl-pyrrolidin-1-yl)-propoxy]-phenyl}-2-methyl-2H-pyridazin-3-one | 140-142 | 346 (M + H) |
| 8 | 2-(2,4-Dichloro-benzyl)-6-{4-[3-((R)-2-methyl-pyrrolidin-1-yl)-propoxy]-phenyl}-4,5-dihydro-2H-pyridazin-3-one | 140-146 | 375 (M + H) |
| 9 | 2-(3,5-Dichloro-phenyl)-6-{4-[3-((R)-2-methyl-pyrrolidin-1-yl)-propoxy]-phenyl}-2H-pyridazin-3-one | 214-222 | 450 (M + H) |
| 10 | 6-[3-Fluoro-4-(3-piperidin-1-yl-propoxy)-phenyl]-2-phenyl-2H-pyridazin-3-one | 230-232 | 408 (M + H) |

-continued

| Example | Structure | Mp (° C.) | MS m/z |
|---|---|---|---|
| 81 | 6-{3-Fluoro-4-[3-((R)-2-methyl-pyrrolidin-1-yl)-propoxy]-phenyl}-2-phenyl-2H-pyridazin-3-one | 190-191 | 408 (M + H) |
| 11 | 6-{4-[3-((R)-2-Methyl-pyrrolidin-1-yl)-propoxy]-phenyl}-2H-pyridazin-3-one | 240-2 | 314 (M + H) |
| 12 | 4-{4-[3-((R)-2-Methyl-pyrrolidin-1-yl)-propoxy]-phenyl}-2,5,6,7-tetra-hydro-cyclopenta[d]pyridazin-1-one | 147 | 354 (M + H) |
| 13 | 2-Methyl-6-{4-[(S)-2-methyl-3-((R)-2-methyl-pyrrolidin-1-yl)-propoxy]-phenyl}-2H-pyridazin-3-one | 188-190 | 342 (M + H) |
| 82 | 2-Methyl-6-{4-[(R)-2-methyl-3-((R)-2-methyl-pyrrolidin-1-yl)-propoxy]-phenyl}-2H-pyridazin-3-one | 76-78 | 342 (M + H) |
| 14 | 6-{4-[3-((S)-2-Hydroxymethyl-pyrrolidin-1-yl)-propoxy]-phenyl}-2-methyl-2H-pyridazin-3-one | 169 | 344 (M + H) |

-continued

| Example | Structure | Mp (° C.) | MS m/z |
|---|---|---|---|
| 15 | 6-{4-[3-((R)-2-Hydroxymethyl-pyrrolidin-1-yl)-propoxy]-phenyl}-2-methyl-2H-pyridazin-3-one | 166-7 | 344 (M + H) |
| 16 | 2-Methyl-6-{4-[3-((R)-2-methyl-pyrrolidin-1-yl)-propoxy]-phenyl}-4,5-dihydro-2H-pyridazin-3-one | 145-147 | 330 (M + H) |
| 17 | 2-Benzyl-6-{4-[3-((R)-2-methyl-pyrrolidin-1-yl)-propoxy]-phenyl}-4,5-dihydro-2H-pyridazin-3-one | 56-58 | 406 (M + H) |
| 18 | 2-Benzyl-6-{4-[3-((R)-2-methyl-pyrrolidin-1-yl)-propoxy]-phenyl}-2H-pyridazin-3-one | 228-230 | 404 (M + H) |
| 19 | 6-{4-[3-((R)-2-Methyl-pyrrolidin-1-yl)-propoxy]-phenyl}-2-phenyl-2H-pyridazin-3-one | 213-215 | 392 (M + H) |

-continued

| Example | Structure | Mp (° C.) | MS m/z |
|---|---|---|---|
| 20 | 6-{4-[3-((R)-2-Methyl-pyrrolidin-1-yl)-propoxy]-phenyl}-2-phenyl-2H-pyridazin-3-one | 82-86 | 390 ( M + H) |
| 84 | 6-{3,5-Difluoro-4-[3-((R)-2-methyl-pyrrolidin-1-yl)-propoxy]-phenyl}-2-methyl-2H-pyridazin-3-one | 175-178 base | 364 ( M + H) |
| 85 | 6-{3-Chloro-4-[3-((R)-2-methyl-pyrrolidin-1-yl)-propoxy]-phenyl}-2-methyl-2H-pyridazin-3-one | 178 dec. | 362 ( M + H) |

Example 21

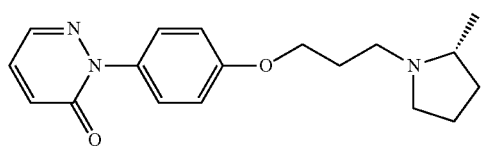

2-{4-[3-((R)-2-Methyl-pyrrolidin-1-yl)-propoxy]-phenyl}-2H-pyridazin-3-one

A mixture of R-1-[3-(4-bromo-phenoxy)-propyl]-2-methyl-pyrrolidine (560 mg, 1.87 mmol), 2H-pyridazin-3-one (180 mg, 1.87 mmol), $K_2CO_3$ (775 mg, 5.61 mmol), copper powder (120 mg, 1.87 mmol) in pyridine (75 mL) was stirred at reflux under nitrogen for 18 h. The reaction was cooled to rt and concentrated at reduced pressure. The residue was dissolved onto fluorsil for elution and purification by ISCO silica gel chromatography (95:5:1/DCM, MeOH, isopropyl amine) The fractions containing pure product were collected and concentrated. The solid was recrystallized from $Et_2O$-hexanes to give 210 mg of Example 21 as a white solid; Mp 106-107° C. The HCl salt was prepared by dissolving the base in MeOH and adding 1N $Et_2O$—HCl: Mp 175-177° C. (MeOH-$Et_2O$); MS m/z 314 (M+H).

Example 22

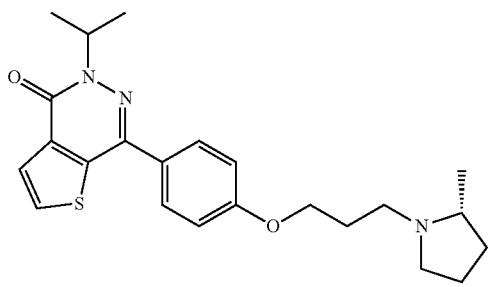

5-Isopropyl-7-{4-[3-((R)-2-methyl-pyrrolidin-1-yl)-propoxy]-phenyl}-5H-thieno[2,3-d]pyridazin-4-one

Step 1

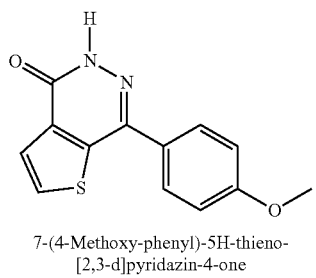 [SMILES: COc1ccc(-c2n[nH]c(=O)c3ccsc23)cc1]

7-(4-Methoxy-phenyl)-5H-thieno-
[2,3-d]pyridazin-4-one

A solution of 3-thiophenecarboxylic acid (10 g, 78 mmol) in 250 mL of THF at 0° C. under $N_2$ was added 2.0 M LDA (2.2 eq., 86 mL) dropwise. After 10 min at 0° C., p-anisaldehyde (10.6 mL, 1.12 eq.) was added and the mixture was slowly warmed to room temperature overnight. The reaction was stirred for ~14 h, after which 100 mL of ice-water was added, and the solvent was evaporated. The aqueous solution was washed with EtOAc (2×40 mL), and then added $KMnO_4$ (2 eq., 12.4 g) dropwise at 0° C. The ice-bath was removed and the reaction was heated to 60° C. for 3 h. The solid was collected and washed with hot water. The aqueous layer was acidified to pH~3, extracted with EtOAc (3×50 mL). The combined EtOAc was dried and evaporated. The crude solid was dissolved in 50 mL of EtOH, and $NH_2NH_2 \cdot H_2O$ (1.5 eq., 1.5 mL) was added dropwise. The reaction was heated to 80° C. for 3 h, and the resulting solid was collected and washed with EtOH to give 3.6 g (36%): MS m/z 259 (M+H).

Step 2

5-Isopropyl-7-(4-methoxy-phenyl)-5H-
thieno[2,3-d]pyridazin-4-one

A solution of the product from step 1 in 10 mL of DMF was added $Cs_2CO_3$ (2 eq. 1.95 g) and 2-iodopropane (1.2 eq., 360 uL). The reaction was heated to 80° C. for 2 h, and then filtered through celite, washed with MeOH: $CH_2Cl_2$ (95:5). The filtrate was concentrated and purified by silica gel flash chromatography (MeOH: $CH_2Cl_2$, 97:3) to afford 585 mg (65%) of the product: Mp 124-6° C.; MS m/z 301 (M+H).

Step 3

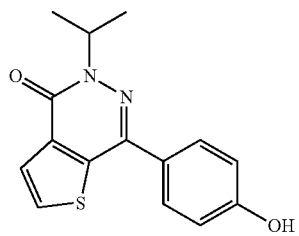

7-(4-Hydroxy-phenyl)-5-isopropyl-5H-
thieno[2,3-d]pyridazin-4-one

A solution of the product from step 2 (1.0 g, 3.3 mmol) in 25 mL of $CH_2Cl_2$ was cooled to 0° C. and $BBr_3$ (1M in DCM, 16.7 mL) was added dropwise. The ice-bath was removed and the reaction was stirred at rt for 1 h. The reaction mixture was then poured into 50 mL of ice cold saturated $NH_4Cl$ solution with stirring. The resulting solid was collected, washed with water (3×15 mL), and $Et_2O$ (2×15 mL) to give the product of step 3 (868 mg, 92%): Mp 256-257° C.; MS m/z 287 (M+H).

Step 4

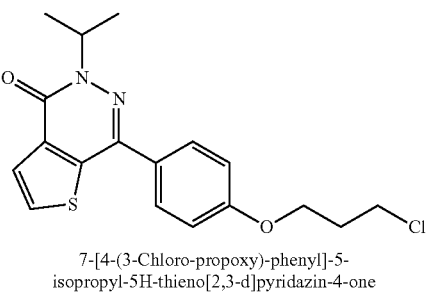 [SMILES: CC(C)n1nc(-c2ccc(OCCCCl)cc2)c2sccc2c1=O]

7-[4-(3-Chloro-propoxy)-phenyl]-5-
isopropyl-5H-thieno[2,3-d]pyridazin-4-one

A solution of the product of step 3 (858 mg, 3 mmol), $K_2CO_3$ (1.24 g, 3.0 eq.), and 3-bromo-1-chloropropane (0.3 mL, 1.05 eq.) in acetone:DMF (25 mL:3 mL) was heated to 80° C. overnight. The mixture was then filtered, washed with acetone, and concentrated to dryness to afford the product of step 4 (1.17 mg, 98% yield): Mp 92-4° C.; MS m/z 363 (M+H).

Step 5

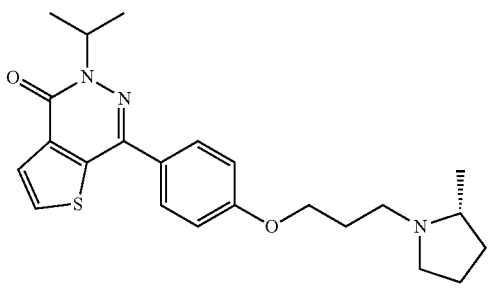

5-Isopropyl-7-{4-[3-((R)-2-methyl-pyrrolidin-1-yl)-propoxy]-phenyl}-5H-thieno[2,3-d]pyridazin-4-one A mixture of the product of step 4 (109 mg, 0.3 mmol), $K_2CO_3$ (3.5 eq, 145 mg), 50 mg of NaI, and R-2-methylpyrrolidine hydrochloride (1.2 eq., 44 mg) in 10 mL of acetonitrile was heated to 80° C. for 2 days. The reaction mixture was then filtered, washed with $CH_2Cl_2$ (2×20 mL) and concentrated. The residue was dissolved in 20 mL of $CH_2Cl_2$, and washed with saturated $NaHCO_3$ solution, saturated NaCl solution, dried with $Na_2SO_4$, and concentrated. The residue was purified by preparative TLC or ISCO graduate silica gel chromatography (MeOH: $CH_2Cl_2$:2-aminopropane; 5:95:0.5) to give the product. The product was dissolved in 5 mL of MeOH, and added 0.5 mL of 1N HCl in EtOH. Evaporation of the solvent, and crystallization from MeOH: $Et_2O$ afforded the HCl salt of example 22 (5-isopropyl-7-(4-(3-((R)-2-methyl-pyrrolidin-1yl)propoxy)phenyl)-5H-thieno[2,3-d]pyridazin-4-one) (52 mg, 42%): Mp 123-4° C.; MS m/z 412 (M+H).

The following examples were prepared as HCl salts using methods of example 22.

| Example | Structure | Mp (° C.) | MS m/z |
|---|---|---|---|
| 23 | 7-{4-[3-(2,5-Dimethyl-pyrrolidin-1-yl)-propoxy]-phenyl}-5-isopropyl-5H-thieno[2,3-d]pyridazin-4-one | 158-159 | 426 (M + H) |
| 24 | 5-Isopropyl-7-[4-(3-piperidin-1-yl-propoxy)-phenyl]-5H-thieno[2,3-d]pyridazin-4-one | 195-196 | 412 (M + H) |

-continued

| Example | Structure | Mp (° C.) | MS m/z |
|---|---|---|---|
| 25 | 7-{4-[3-(3,3-Dimethyl-piperidin-1-yl)-propoxy]-phenyl}-5-isopropyl-5H-thieno[2,3-d]pyridazin-4-one | 100-102 | 440 (M + H) |
| 26 | 5-Isopropyl-7-{4-[3-((S)-2-methoxy-methyl-pyrrolidin-1-yl)-propoxy]-phenyl}-5H-thieno[2,3-d]pyridazin-4-one | 83 dec. | 442 (M + H) |
| 27 | 5-Isopropyl-7-{4-[3-((R)-2-methoxy-methyl-pyrrolidin-1-yl)-propoxy]-phenyl}-5H-thieno[2,3-d]pyridazin-4-one | 9-96 | 442 (M + H) |
| 28 | 7-[4-(3-Diethylamino-propoxy)-phenyl]-5-isopropyl-5H-thieno[2,3-d]pyridazin-4-one | 188-190 | 400 (M + H) |

| Example | Structure | Mp (° C.) | MS m/z |
| --- | --- | --- | --- |
| 29 | 5-Isopropyl-7-[4-[3-pyrrolidin-1-yl-propoxy)-phenyl]-5H-thieno[2,3-d]-pyridazin-4-one | 144 | 398 (M + H) |
| 30 | 5-Isopropyl-7-{4-[3-(4-pyrrolidin-1-yl-piperidin-1-yl)-propoxy]-phenyl}-5H-thieno[2,3-d]pyridazin-4-one | 283 dec. | 481 (M + H) |
| 31 | 7-{4-[3-((2R,5R)-2,5-Dimethyl-pyrrolidin-1-yl)-propoxy]-phenyl}-5-isopropyl-5H-thieno[2,3-d]pyridazin-4-one | 106 dec. | 426 (M + H) |
| 32 | 7-{4-[3-((R)-2-Methyl-pyrrolidin-1-yl)-propoxy]-phenyl}-5-propyl-5H-thieno[2,3-d]pyridazin-4-one | 151-153 | 412 (M + H) |

-continued
| Example | Structure | Mp (° C.) | MS m/z |
|---------|-----------|-----------|--------|
| 33 | 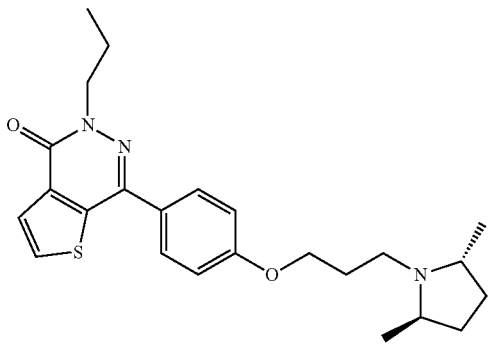<br>7-{4-[3-((2R,5R)-2,5-Dimethyl-pyrrolidin-1-yl)-propoxy]-phenyl}-5-propyl-5H-thieno[2,3-d]pyridazin-4-one | 84 dec. | 426 (M + H) |
| 34 | 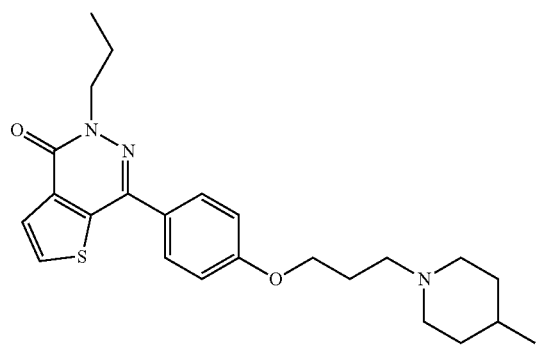<br>7-{4-[3-(4-Methyl-piperidin-1-yl)-propoxy]-phenyl}-5-propyl-5H-thieno[2,3-d]pyridazin-4-one | 168-170 | 426 (M + H) |
| 35 | 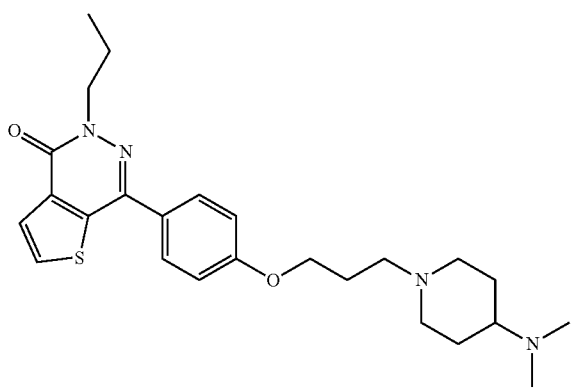<br>7-{4-[3-(4-Dimethylamino-piperidin-1-yl)-propoxy]-phenyl}-5-propyl-5H-thieno[2,3-d]pyridazin-4-one | 207-209 | 455 (M + H) |

-continued

| Example | Structure | Mp (° C.) | MS m/z |
|---|---|---|---|
| 36 | 5-Propyl-7-{4-[3-((S)-2-pyrrolidin-1-ylmethyl-pyrrolidin-1-yl)-propoxy]-phenyl}-5H-thieno[2,3-d]pyridazin-4-one | 123 dec. | 481 (M + H) |
| 37 | 5-(4-Chloro-benzyl)-7-[4-(3-piperidin-1-yl-propoxy)-phenyl]-5H-thieno[2,3-d]pyridazin-4-one | 227-229 | 494 (M + H) |
| 38 | 5-(4-Chloro-benzyl)-7-{4-[3-((R)-2-methyl-pyrrolidin-1-yl)-propoxy]-phenyl}-5H-thieno[2,3-d]pyridazin-4-one | 223-224 | 494 (M + H) |

Example 39

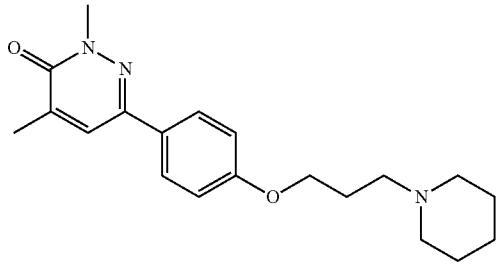

2,4-Dimethyl-6-[4-(3-piperidin-1-yl-propoxy)-phenyl]-2H-pyridazin-3-one

Step 1. A solution of 2-methoxy-4-oxo-4-(4'-methoxyphenyl) butyric acid (2.22 g, 10 mmol) and hydrazine hydrate (1.5 eq., 688 μL) in 20 mL of EtOH was stirred at 80° C. overnight. The solvent was removed and the solid was collected and washed with cold EtOH to give 6-(4-methoxyphenyl)-4-methyl-4,5-dihydro-2H-pyridazin-3-one (2.05 g, 94%): Mp 203-6° C.

Step 2. A mixture of the product from step 1 (6-(4-methoxy-phenyl)-4-methyl-4,5-dihydro-2H-pyridazin-3-one; 1.96 g, 9 mmol) and Cu(II) Cl$_2$ (2.48 g, 2 eq.) in of acetonitrile (15 mL) was heated to 70° C. for 2 h. The reaction was quenched with ice-water (~100 mL), the resulting solid was collected and crystallized from isopropanol to give 1.42 g (73%) of 6-(4-methoxy-phenyl)-4-methyl-2H-pyridazin-3-one: Mp 265-7° C.; MS m/z 217 (M+H).

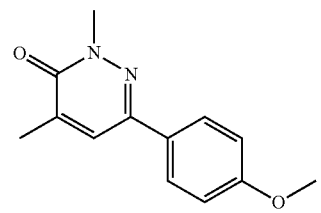

6-(4-Methoxy-phenyl)-2,4-dimethyl-2H-pyridazin-3-one

Step 3. The product of step 2 (6-(4-methoxy-phenyl)-2,4-dimethyl-2H-pyridazin-3-one) was prepared as described for example 22 step 2 using 6-(4-methoxy-phenyl)-4-methyl-4,5-dihydro-2H-pyridazin-3-one, MeI and Cs$_2$CO$_3$.

Example 39

6-(4-(3-Chloropropoxy)-phenyl)-2,4-dimethyl-2H-pyridazin-3-one was prepared from the product of step 3 and 3-bromo-1-chloropropane using the procedure described for Example 22 step 4. Example 39 (2,4-dimethyl-6-[4-(3-piperidin-1-yl-propoxy)-phenyl]-2H-pyridazin-3-one) was prepared using 6-(4-(3-chloropropoxy)-phenyl)-2,4-dimethyl-2H-pyridazin-3-one and piperidine by the methods described for example 22 step 5. The hydrochloride salt was prepared; Mp 222-3° C.; MS m/z 342 (M+H).

The following examples as HCl salts were prepared using methods described for example 1 and example 22.

| Example | Structure | Mp (° C.) | MS m/z |
|---|---|---|---|
| 40 | 2,4-Dimethyl-6-{4-[3-((R)-2-methyl-pyrrolidin-1-yl)-propoxy]-phenyl}-2H-pyridazin-3-one | 175-176 | 342 (M + H) |
| 41 | 2-Isopropyl-4-methyl-6-{4-[3-((R)-2-methyl-pyrrolidin-1-yl)-propoxy]-phenyl}-2H-pyridazin-3-one | 54-155 | 370 (M + H) |

-continued

| Example | Structure | Mp (° C.) | MS m/z |
|---|---|---|---|
| 42 | 2-Isopropyl-4-methyl-6-[4-(3-piperidin-1-yl-propoxy)-phenyl]-2H-pyridazin-3-one | 197-198 | 370 (M + H) |
| 43 | 2-Benzyl-4-methyl-6-{4-[3-((R)-2-methyl-pyrrolidin-1-yl)-propoxy]-phenyl}-2H-pyridazin-3-one | 190-192 | 418 (M + H) |
| 44 | 2-Benzyl-4-methyl-6-[4-(3-piperidin-1-yl-propoxy)-phenyl]-2H-pyridazin-3-one | 232-233 | 418 (M + H) |
| 45 | 4-Benzyl-2-methyl-6-{4-[3-((R)-2-methyl-pyrrolidin-1-yl)-propoxy]-phenyl}-2H-pyridazin-3-one | 232-233 | 418 (M + H) |

-continued

| Example | Structure | Mp (° C.) | MS m/z |
|---|---|---|---|
| 46 | 4-Benzyl-2-methyl-6-[4-(3-piperidin-1-yl-propoxy)-phenyl]-2H-pyridazin-3-one | 186-187 | 418 (M + H) |
| 47 | 2-Methyl-6-{4-[3-((R)-2-methyl-pyrrolidin-1-yl)-propoxy]-phenyl}-5-phenyl-2H-pyridazin-3-one | 207-209 | 404 (M + H) |
| 48 | 2-Methyl-5-phenyl-6-[4-(3-piperidin-1-yl-propoxy)-phenyl]-2H-pyridazin-3-one | 212-214 | 404 (M + H) |
| 49 | 2-Methyl-4-{4-[3-((R)-2-methyl-pyrrolidin-1-yl)-propoxy]-phenyl}-2H-phthalazin-1-one | 216-217 | 378 (M + H) |

| Example | Structure | Mp (° C.) | MS m/z |
|---|---|---|---|
| 50 | 2-Methyl-4-[4-(3-piperidin-1-yl-propoxy)-phenyl]-2H-phthalazin-1-one | 241-242 | 378 (M + H) |
| 51 | 2-Methyl-4-[4-(2-piperidin-1-yl-ethoxy)-phenyl]-2H-phthalazin-1-one | 253-254 | 364 (M + H) |
| 52 | 2-Methyl-4-[4-(3-pyrrolidin-1-yl-propoxy)-phenyl]-2H-phthalazin-1-one | 201-203 | 364 (M + H) |
| 53 | 4-[4-(3-Azepan-1-yl-propoxy)-phenyl]-2-methyl-2H-phthalazin-1-one | 238-240 | 392 (M + H) |

-continued

| Example | Structure | Mp (° C.) | MS m/z |
|---|---|---|---|
| 54 | 2-(4-Chloro-benzyl)-4-{4-[3-((R)-2-methyl-pyrrolidin-1-yl)-propoxy]-phenyl}-2H-phthalazin-1-one | 217-218 | 489 (M + H) |
| 55 | 2-(4-Chloro-benzyl)-4-[4-(3-piperidin-1-yl-propoxy)-phenyl]-2H-phthalazin-1-one | 216-217 | 489 (M + H) |
| 56 | 2-Methyl-4-{4-[3-((R)-2-methyl-pyrrolidin-1-yl)-propoxy]-phenyl}-2,5,6,7-tetrahydro-cyclopenta[d]pyridazin-1-one | 212-214 | 368 (M + H) |
| 57 | 2-Methyl-4-[4-(3-piperidin-1-yl-propoxy)-phenyl]-2,5,6,7-tetrahydro-cyclopenta[d]pyridazin-1-one | 214-216 | 368 (M + H) |

-continued

| Example | Structure | Mp (° C.) | MS m/z |
|---|---|---|---|
| 58 | 2-Methyl-4-{4-[3-((R)-2-methyl-pyrrolidin-1-yl)-propoxy]-phenyl}-2,4a,5,6,7,7a-hexahydro-cyclopenta[d]pyridazin-1-one | <50 | 370 (M + H) |
| 59 | 2-Methyl-4-[4-(3-piperidin-1-yl-propoxy)-phenyl]-2,4a,5,6,7,7a-hexahydro-cyclopenta[d]pyridazin-1-one | <50 | 370 (M + H) |
| 60 | 2-Methyl-4-{4-[3-((R)-2-methyl-pyrrolidin-1-yl)-propoxy]-phenyl}-5,6,7,8-tetrahydro-2H-phthalazin-1-one | 156-158 | 382 (M + H) |
| 61 | 4-{4-[3-(Butyl-ethyl-amino)-propoxy]-phenyl}-2-methyl-5,6,7,8-tetrahydro-2H-phthalazin-1-one | 196-198 | 382 (M + H) |

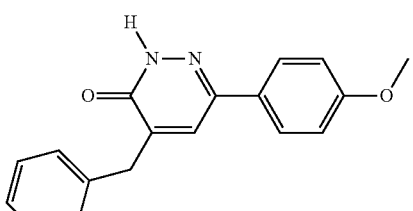

4-Benzyl-6-(4-methoxy-phenyl)-2H-
pyridazin-3-one 6-(4-methoxy-phenyl)-4,5-dihydro-2H-pyridazin-3-one (1.65 g, 7.5 mmol) in 15 mL of EtOH was heated to 80° C. as 20 mL of 4% of KOH/EtOH solution was added dropwise. After 5 min., benzaldehyde (1.0 eq. 0.76 mL) was added and the mixture stirred at 80° C. for 2 h. The reaction was cooled to rt., poured into ice-$H_2O$ (75 mL) and the resulting solid was collected and crystallized from EtOH to give 1.67 g (76%) of intermediate 4-benzyl-6-(4-methoxy-phenyl)-2H-pyridazin-3-one: MS m/z 293 (M+H). This intermediate was used to prepare examples 45 and example 46.

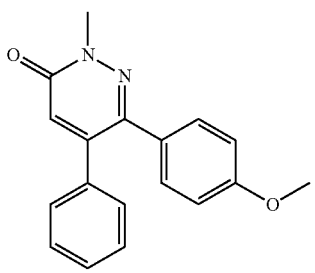

6-(4-Methoxy-phenyl)-2-methyl-5-
phenyl-2H-pyridazin-3-one

Step 1. A suspension of NaH (12.8 mmol, 512 mg) in DMSO (23 mL) was added 4'-methoxy-2-phenylacetophenone (12.8 mmol, 2.89 g) in 10 ml toluene dropwise under argon. After 30 minutes of stirring, ethyl bromoacetate (1.4 mL, 1 eq.) in 10 mL of toluene was added and the mixture was stirred at rt overnight. The reaction was quenched by addition of 2N HCl (4 mL), and then 60 mL of water. The mixture was extracted with $CH_2Cl_2$ (3×30 mL), dried over $MgSO_4$ and concentrated under vacuum overnight to afforded 4.0 g (99%) of 4-(4-methoxy-phenyl)-4-oxo-3-phenyl-butyric acid ethyl ester.

Step 2. A solution of 4-(4-methoxy-phenyl)-4-oxo-3-phenyl-butyric acid ethyl ester (5.0 g, 16 mmol) in EtOH:$H_2O$ (60 mL 1:1) was stirred as 10N NaOH (16 mL) was added dropwise. The reaction was stirred at rt for 1 hr. The solvent was evaporated and the residue was diluted with water (50 mL) and extracted with $CH_2Cl_2$ (2×20 mL). The aqueous layer was then acidified with 3N HCl to pH ~2-3, extracted with $CH_2Cl_2$ (3×30 mL). The $CH_2Cl_2$ extracts were dried over $MgSO_4$, and the oil was crystallized from $Et_2O$/MeOH to give 4.5 g (99%) of 4-(4-methoxy-phenyl)-4-oxo-3-phenyl-butyric acid: mp 157-9° C.; MS m/z 283 (M−H).

Step 3. A solution of 4-(4-methoxy-phenyl)-4-oxo-3-phenyl-butyric acid (1.5 g, 5.28 mmol) and hydrazine hydrate (1.5 eq., 363 μL) in 20 mL of EtOH was stirred at 80° C. overnight. The solvent was reduced and the solid was filtered and then washed with cold EtOH to give 6-(4-methoxy-phenyl)-5-phenyl-4,5-dihydro-2H-pyridazin-3-one (1.46 g, 99%): mp 176-7° C.; MS m/z 281 (M+H).

Examples 47 and 48 were prepared from 6-(4-methoxy-phenyl)-5-phenyl-4,5-dihydro-2H-pyridazin-3-one as described in Example 39.

Example 62

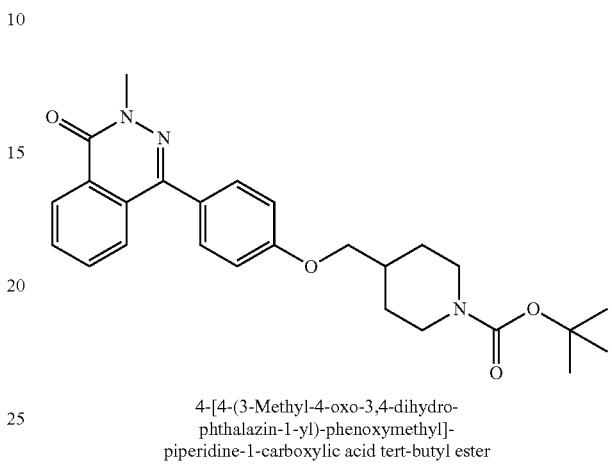

4-[4-(3-Methyl-4-oxo-3,4-dihydro-
phthalazin-1-yl)-phenoxymethyl]-
piperidine-1-carboxylic acid tert-butyl ester A suspension of 4-(4-hydroxy-phenyl)-2-methyl-2H-phthalazin-1-one (252 mg, 1.0 mmol) and of 4-bromomethyl) piperidine-1-carboxylic acid t-butyl ester (786 mg, 3 eq) in 1 mL of 4N NaOH and 8 mL of DMSO was stirred at rt for 24 h. The reaction was diluted with water (20 mL), extracted with EtOAc (3×10 mL), and the combined extracts were washed with $NaHCO_3$ solution, NaCl solution and dried over $MgSO_4$. The product was purified by ISCO graduate chromatography (100% $CH_2Cl_2$ to 95:5 $CH_2Cl_2$: MeOH) to afford 198 mg (50%) of 4-(4-(1(3-methyl-4-oxo-3,4-dihydro-phthalazin-1-yl)-phenoxymethyl)-piperidine-1-carboxylic acid t-butyl ester: Mp 167-9° C.; MS m/z 450 (M+H).

Example 63

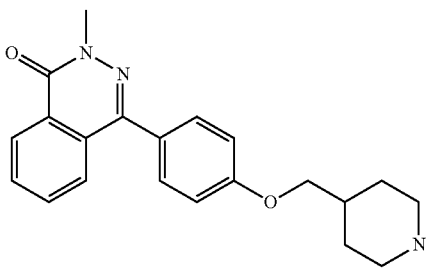

2-Methyl-4-[4-(piperidin-4-ylmethoxy)-
phenyl]-2H-phthalazin-1-one

A solution of example 62 (4-(4-(1(3,-methyl-4-oxo-3,4-dihydro-phthalazin-1-yl)-phenoxymethyl)-piperidine-1-carboxylic acid tert-butyl ester) (180 mg, 0.4 mmol) and 4N HCl (2 mL) in dioxane (5 mL) and water (0.5 mL) was heated to 50° C. for 2 h. The solvent was evaporated, and the product was triturated with $Et_2O$ to give 117 mg (84%) of example 63

(2-methyl-4-(4-(piperidin-4-ylmethoxy)-phenyl)-2H-phthalazin-1-one) HCl: Mp 207-9° C.; MS m/z 350 (M+H).

Example 64

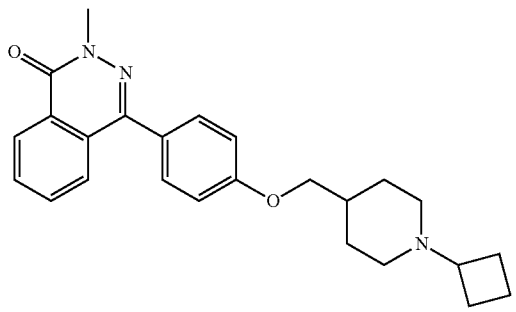

4-[4-(1-Cyclobutyl-piperidin-4-ylmethoxy)-
phenyl]-2-methyl-2H-phthalazin-1-one

A solution of example 63 (2-methyl-4-(4-(piperidin-4-yl-methoxy)-phenyl)-2H-phthalazin-1-one) (90 mg, 0.23 mg) and NaCNBH$_3$ in DMF: MeOH:AcOH (3:6 mL: 0.25 mL) was stirred under N$_2$ as cyclobutanone (81.7 mg, 5 eq.) was added. The reaction was stirred at 60° C. for 1.5 h, quenched with 3 mL of water, extracted with CH$_2$Cl$_2$ (3×10 mL), washed with NaHCO$_3$, NaCl solution, dried and concentrated. The crude product was purified by silica gel chromatography using 5% MeOH: 95% CH$_2$Cl$_2$: 0.5 mL of isopropyl amine The fractions were collected, concentrated and the product dissolved in 5 mL of MeOH, and added 0.5 mL of 1N HCl in EtOH. The solvent was evaporated, and the HCl product crystallized from MeOH-Et$_2$O to give example 64 (4-(4-(1-cyclobutyl-piperidin-4-ylmethoxy)-phenyl)-2-methyl-2H-phthalazin-1-one HCl) (53 mg, 57%): Mp 256-7° C.; MS m/z 404 (M+H).

The following examples as HCl salts were prepared from 6-(4-hydroxy-phenyl)-2-methyl-2H-pyridazin-3-one using the procedures for examples 62-64. Example 65 is the base.

| Example | Structure | Mp (° C.) | MS m/z |
|---|---|---|---|
| 65 | 4-[4-(1-Methyl-6-oxo-1,6-dihydro-pyridazin-3-yl)-phenoxymethyl]-piperidine-1-carboxylic acid tert-butyl ester | 164-166 | 400 (M + H) |
| 66 | 2-Methyl-6-[4-(piperidin-4-ylmethoxy)-phenyl]-2H-pyridazin-3-one | 249-251 | 300 (M + H) |

-continued

| Example | Structure | Mp (° C.) | MS m/z |
|---|---|---|---|
| 67 | 6-[4-(1-Cyclobutyl-piperidin-4-ylmethoxy)-phenyl]-2-methyl-2H-pyridazin-3-one | 250-252 | 354 (M + H) |
| 68 | 6-[4-(1-Isopropyl-piperidin-4-ylmethoxy)-phenyl]-2-methyl-2H-pyridazin-3-one | 187-189 | 342 (M + H) |
| 69 | 6-[4-(1-Cyclopropylmethyl-piperidin-4-ylmethoxy)-phenyl]-2-methyl-2H-pyridazin-3-one | 230-231 | 354 (M + H) |
| 70 | 6-[4-(1-Cyclopentyl-piperidin-4-ylmethoxy)-phenyl]-2-methyl-2H-pyridazin-3-one | 250-251 | 368 (M + H) |

| Example | Structure | Mp (° C.) | MS m/z |
|---|---|---|---|
| 71 | 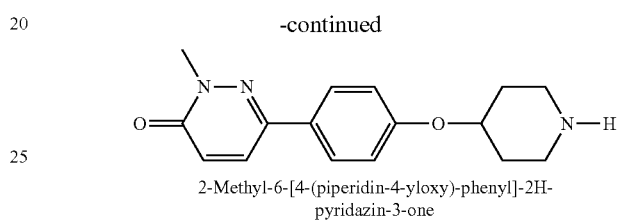<br>2-Methyl-6-[4-(1-methyl-piperidin-4-ylmethoxy)-phenyl]-2H-pyridazin-3-one | 257-258 | 314 (M + H) |

Example 72

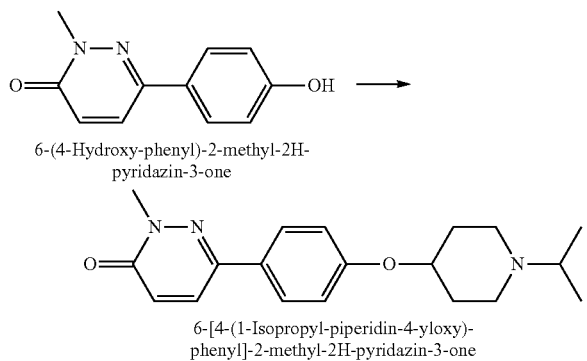

6-(4-Hydroxy-phenyl)-2-methyl-2H-pyridazin-3-one

6-[4-(1-Isopropyl-piperidin-4-yloxy)-phenyl]-2-methyl-2H-pyridazin-3-one

A mixture of 6-(4-hydroxy-phenyl)-2-methyl-2H-pyridazin-3-one (500 mg, 2.6 mmol), triphenylphosphine (1.35 g, 5.2 mmol), 4-hydroxy-N-iPr-piperidine (745 mg, 10.4 mmol) in THF (50 mL) was added DEAD (1.1 g, 6.5 mmol) dropwise. The reaction was stirred at rt overnight, then concentrated. The product was purified by ISCO silica gel chromatography (95:5. DCM: MeOH). The HCl salt was prepared by addition of 1M Et$_2$O HCl to a methanol solution of the base. mp 108-110° C. MS m/z 328 (M+H).

Example 73

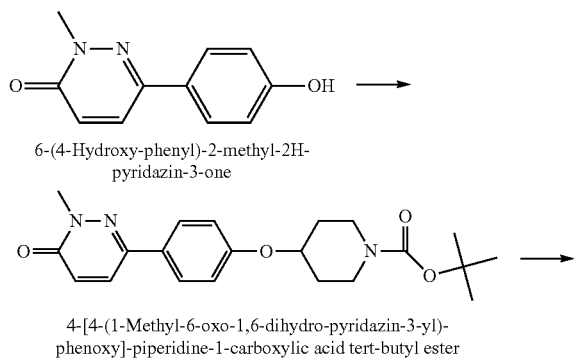

6-(4-Hydroxy-phenyl)-2-methyl-2H-pyridazin-3-one

4-[4-(1-Methyl-6-oxo-1,6-dihydro-pyridazin-3-yl)-phenoxy]-piperidine-1-carboxylic acid tert-butyl ester 2-Methyl-6-[4-(piperidin-4-yloxy)-phenyl]-2H-pyridazin-3-one A solution of 6-(4-hydroxy-phenyl)-2-methyl-2H-pyridazin-3-one (1.0 mg, 4.6 mmol), triphenylphosphine (1.44 g, 5.5 mmol), 4-hydroxy-N—BOC-piperidine (1.1 mg, 5.5 mmol), in THF (40 mL) was added DEAD (0.96 g, 5.5 mmol) dropwise on an ice-batch. The batch was removed and the reaction was stirred at rt 2-days. The reaction was concentrated at reduced pressure and Et$_2$O (40 mL) was added and stirred 2 h and the solids removed by filtration. The solution was concentrate and the product was purified by ISCO silica gel chromatography (95:5. DCM: MeOH). The resulting 4-[4-(1-methyl-6-oxo-1,6-dihydro-pyridazin-3-yl)-phenoxy]-piperidine-1-carboxylic acid t-butyl ester was dissolved in dioxane (5 mL) and 4N HCl in dioxane (4 mL) as added and stirred 2 h. The solution was concentrated and 2N Na$_2$CO$_3$ added to pH 9. The aqueous solution was added solid sodium chloride until saturated, then extracted with EtOAc (2×50 mL), dried (MgSO$_4$) and concentrated. The HCl salt was prepared by addition of 1M HCl Et$_2$O solution to a methanol solution of the base. Mp>210° C. MS m/z 386 (M+H).

Example 74

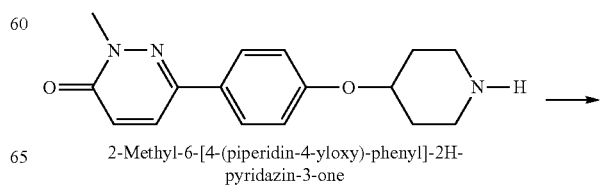

2-Methyl-6-[4-(piperidin-4-yloxy)-phenyl]-2H-pyridazin-3-one

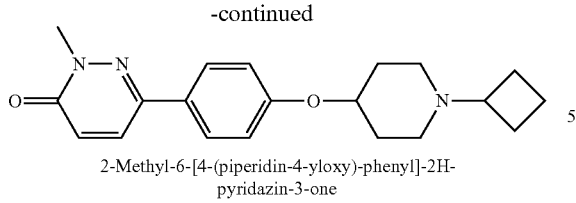

2-Methyl-6-[4-(piperidin-4-yloxy)-phenyl]-2H-pyridazin-3-one

To a solution of example 73 (0.25 g, 0.9 mmol) and cyclobutanone in MeOH (10 mL) was added HOAc (0.5 mL) then solid sodium cyanoborohydride (560 mg, 62.8 mmol). The reaction was stirred 4 h then concentrated. $Na_2CO_3$ solution was added, and extracted with EtOAc (2×50 mL), dried over $MgSO_4$, filtered and concentrated. To the residue in $CH_3CN$ (3 mL) was added a 1N $HCl/Et_2O$ solution and concentrated. Example 74 was recrystallized from $CH_3CN$-$Et_2O$ to give 180 mg of a white solid. Mp 250-252° C. MS m/z 340 (M+H).

Example 75

Step 1

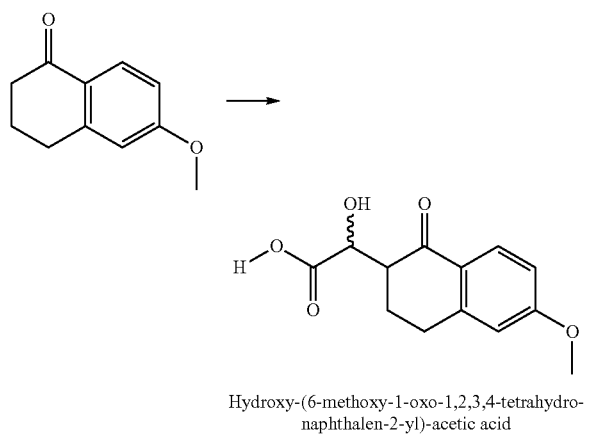

Hydroxy-(6-methoxy-1-oxo-1,2,3,4-tetrahydro-naphthalen-2-yl)-acetic acid

A mixture of 6-methoxy-1-tetralone (20 g, 114 mmol) and glyoxylic acid monohydrate (10.5 g, 114 mmol) was heated at 120° C. in a melt for 5 min. After slight cooling, EtOAc (100 mL) was carefully added. The solid which precipitated was collected to afford 8.5 g (30%) of hydroxyl-(6-methoxy-1-oxo-1,2,3,4-tetrahydro-naphthalen-2-yl)-acetic acid; Mp 212-214° C., MS m/z 251 (M+H).

Step 2

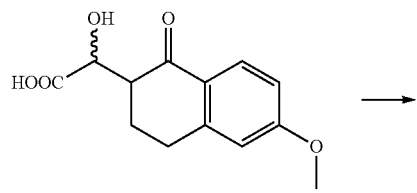

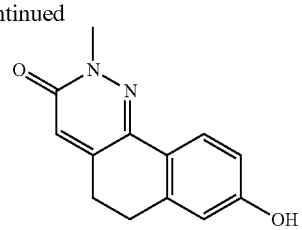

8-Hydroxy-2-methyl-5,6-dihydro-2H-benzo[h]cinnolin-3-one

A solution of the product from step 1 (700 mg, 2.8 mmol) and N-methylhydrazine (0.3 mL) in 2-propanol (10 mL) was heated to reflux 18 h. The solvent was removed under vacuum and the solid was triturated with methanol (2 mL), collected and then suspended in methylene chloride (2 mL) at 0° C. $BBr_3$ (10 mL of 1M solution in DCM, 10 mmol) was slowly added dropwise and the ice bath removed. After 3 h at ambient temperature, saturated $NH_4Cl$ solution (10 mL) was added. The DCM was removed under vacuum and the resulting slurry was carefully neutralized with saturated $NaHCO_3$ solution and washed with water. The solids were collected to afford 8-hydroxy-2-methyl-5,6-dihydro-2H-benzo[h]cinnolin-3-one (175 mg, 27%) as a white solid; m p>300° C. MS m/z 229 (M+H).

Step 3

2-Methyl-8-[3-((R)-2-methyl-pyrrolidin-1-yl)-propoxy]-5,6-dihydro-2H-benzo[h]cinnolin-3-one To a slurry of the product from step 2 (166 mg, 0.7 mmol) 1-bromo-3-chloro-propane (126 mg, 0.9 mmol) and $K_2CO_3$ (110 mg, 0.8 mmol) in acetonitrile (5 mL) was stirred 18 h at 100° C. The solvent was removed under vacuum and the solids were partitioned between EtOAc (10 mL) and water (10 mL). The organics were washed with EtOAc (2×10 mL), dried over $MgSO_4$ and the solvent was removed under vacuum. Silica gel chromatography with EtOAc/hexanes as eluent afforded 196 mg of the intermediate 3-chloropropyl-ether (88%) as a white solid. The chloro intermediate was slurried (196 mg, 0.6 mmol) in acetonitrile (4 mL) and added R-2-methyl-pyrrolidine tartrate (227 mg, 0.9 mmol), KI (20 mg, 0.1 mmol) and $K_2CO_3$ (355 mg, 2.4 mmol). The reaction was stirred 18 h at 100° C., and the solvent was removed under vacuum. The solids were partitioned between $CH_2Cl_2$ (10 mL) and water (10 mL). The water layer was washed with $CH_2Cl_2$ (3×10 mL). The combined organic layers were dried over $Na_2SO_4$ and concentrated under vacuum. Silica gel chromatography using $CH_2Cl_2$/MeOH (95:5) as eluent gave the product as an oil. The HCl salt was prepared from EtOH and 1M HCl in $Et_2O$ to give 130 mg (52%) of example 75 as a white solid; Mp 192-194° C.; MS m/z 354 (M+H).

The following examples were prepared as HCl salts using the methods described for example 75.
| Example | Structure | Mp (° C.) | MS m/z |
|---|---|---|---|
| 76 | 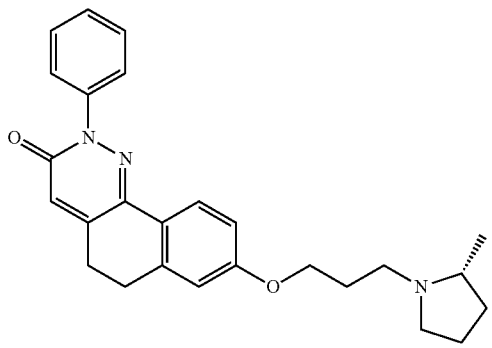 8-[3-((R)-2-Methyl-pyrrolidin-1-yl)-propoxy]-2-phenyl-5,6-dihydro-2H-benzo[h]cinnolin-3-one | 140-142 | 416 (M + H) |
| 77 | 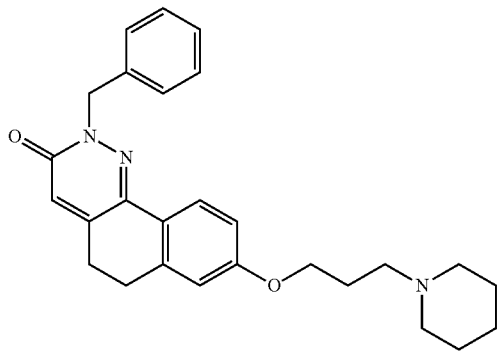 2-Benzyl-8-(3-piperidin-1-yl-propoxy)-5,6-dihydro-2H-benzo[h]cinnolin-3-one | 206-208 | 438 (M + H) |
| 78 | 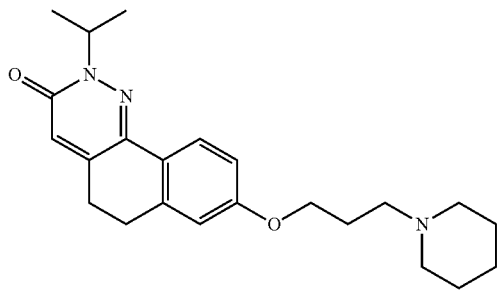 2-Isopropyl-8-(3-piperidin-1-yl-propoxy)-5,6-dihydro-2H-benzo[h]cinnolin-3-one | 250-252 | 354 (M + H) |

Example 79

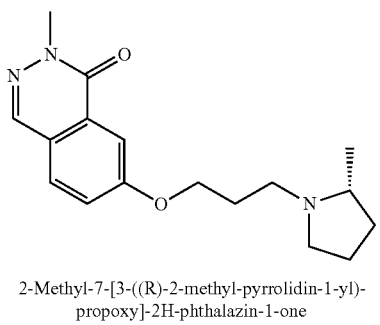 [SMILES: C[C@@H]1CCCN1CCCOc1ccc2cnn(C)c(=O)c2c1]

2-Methyl-7-[3-((R)-2-methyl-pyrrolidin-1-yl)-
propoxy]-2H-phthalazin-1-one

Step 1. A solution of 2-formyl-5-methoxy-benzoic acid (1.0 g, 6.10 mmol) and methyl hydrazine (0.481 mL, 1.5 eq.) in ethanol (15 mL) was stirred at 85° C. for 1.5 days. The solvent was removed and the solid was collected and washed with cold EtOH to give 7-methyl-2-methyl-2H-phthalazin-1-one (780 mg): MS m/z 191 (M+H).

Step 2-3. 7-(3-Chloro-propoxy)-2-methyl-2H-phthalazin-1-one was prepared from 7-methyl-2-methyl-2H-phthalazin-1-one using the procedure described in Example 22 Step 3, and Step 4.

The hydrochloride salt of example 79 (2-methyl-7-(3-(R)-2-methyl-pyrrolidin-1-yl)-propoxy)-2H-phthalazin-1-one) was prepared using the procedure as described in Example 22 Step 5: Mp 252-3° C.; MS m/z 302 (M+H).

The following examples were prepared as HCl salts using methods of example 79.

| Example | Structure | Mp (° C.) | MS m/z |
|---|---|---|---|
| 79 | 2-Methyl-7-[3-((R)-2-methyl-pyrrolidin-1-yl)-propoxy]-2H-phthalazin-1-one | 252-253 | 302 (M + H) |
| 80 | 2-Methyl-7-(3-piperidin-1-yl-propoxy)-2H-phthalazin-1-one | 251-252 | 302 (M + H) |

Example 83

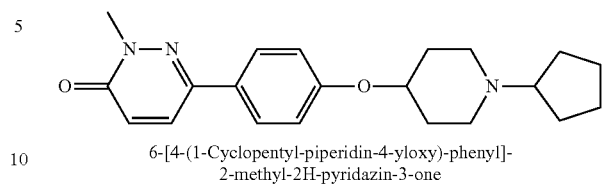

6-[4-(1-Cyclopentyl-piperidin-4-yloxy)-phenyl]-
2-methyl-2H-pyridazin-3-one

This compound was prepared using the same method as example 74 using example 73 and cyclopentanone in MeOH (10 mL)/HOAc (0.5 mL) followed by solid sodium cyanoborohydride. The reaction was stirred 4 h then concentrated. Na$_2$CO$_3$ solution was added, and extracted with EtOAc (2×50 mL), dried over MgSO$_4$, filtered and concentrated. Example 83 was recrystallized from CH$_3$CN-Et$_2$O to give a white solid. Mp 129-132° C. MS m/z 354 (M+H).

Example 86

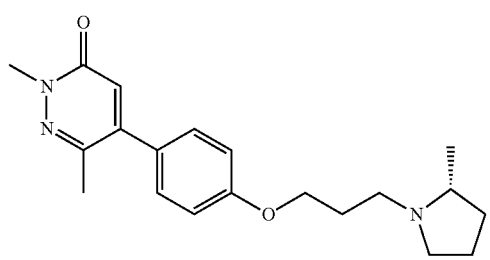

2,6-Dimethyl-5-{4-[3-((R)-2-methyl-pyrrolidin-
1-yl)-propoxy]-phenyl}-2H-pyridazin-3-one Step 1

5-(4-Methoxy-phenyl)-2,6-dimethyl-2H-
pyridazin-3-one

A mixture of 1-(4-methoxyphenyl)propan-2-one (16.4 g, 100 mmol) and glyoxalic acid hydrate (9.20 g, 100 mmol) were heated to 135° C. overnight, then the water was distilled off at 120° C. for 2 h. The residue was taken up in 40 mL of ethanol with stirring as methylhydrazine (10.5 mL, 200 mmol) was added dropwise. The reaction was heated to 85° C. overnight. The solvent was evaporated and the residue was dissolved in 200 mL of methylene chloride and washed with 5% NaHCO$_3$ solution (2×20 mL), saturated NaCl solution, then dried over Na$_2$SO$_4$ and concentrated. The residue was purified by silica gel chromatography (2% MeOH in CH$_2$Cl$_2$) to give 5-(4-methoxyphenyl)-2,6-dimethyl-2H-pyridazin-3-one (4.2 g) MS m/z 231 (M+H).

Step 2

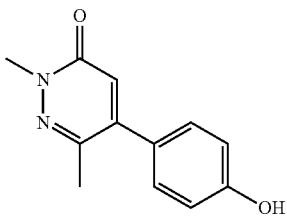

5-(4-Hydroxy-phenyl)-2,6-dimethyl-
2H-pyridazin-3-one

A solution of the product from step 1 (3.2 g, 14 mmol) in CH$_2$Cl$_2$ (40 mL) was cooled to 0° C. and BBr$_3$ (6.6 mL, 5.0 eq.) was added dropwise. The ice-bath was removed and the reaction was stirred at rt for 1 h, after which the reaction mixture was poured into 50 mL of ice cold saturated NH$_4$Cl solution with stirring. The resulting solid was filtered, and washed with water (3×15 mL) then Et$_2$O (2×15 mL) to give the product of step 2 (0.66 g, 22%): MS m/z 217 (M+H).

Step 3

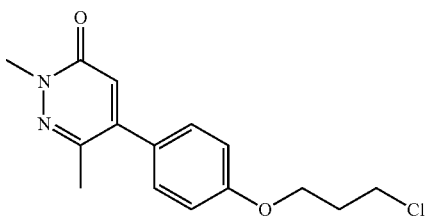

5-[4-(3-Chloro-propoxy)-phenyl]-
2,6-dimethyl-2H-pyridazin-3-one

A solution of the product from step 2 (710 mg, 3.29 mmol), K$_2$CO$_3$ (1.36 g, 3.0 eq.) and 3-bromo-1-chloropropane (0.39 mL, 1.2 eq.) in CH$_3$COCH$_3$ (30 mL) was heated to 80° C. overnight. The mixture was then filtered, washed with acetone and concentrated to dryness to afford the product of step 3 (950 mg, 98%): MS m/z 293 (M+H).

Step 4

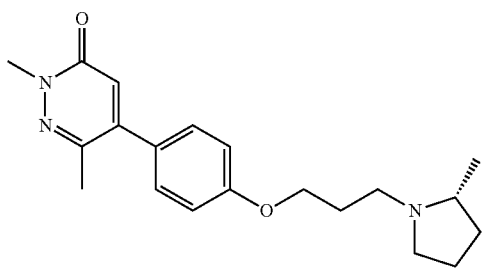

2,6-Dimethyl-5-{4-[3-((R)-2-methyl-pyrrolidin-
1-yl)-propoxy]-phenyl}-2H-pyridazin-3-one A mixture of the product of step 3 (481 mg, 1.65 mmol), K$_2$CO$_3$ (3.5 eq, 795 mg), 50 mg of NaI, and R-2-methylpyr-rolidine hydrochloride (2.0 eq., 773 mg) in acetonitrile (10 mL) was heated to 80° C. for 2 days. The reaction was then filtered, washed with CH$_2$Cl$_2$ (2×20 mL) and concentrated. The residue was dissolved in 30 mL of CH$_2$Cl$_2$ and washed with saturated NaHCO$_3$, saturated NaCl solution, dried with Na$_2$SO$_4$ and then concentrated. The residue was purified by preparative TLC (10% MeOH: 90% CH$_2$Cl$_2$:0.5 mL 2-aminopropane) to give the product. The product was dissolved in 10 mL of MeOH, and was added 2.5 mL of 1N HCl in EtOH. The solvents were evaporated and the product crystallized from MeOH:Et$_2$O to give example 86 as the HCl salt (231 mg, 41%): Mp 176-8° C.; MS m/z 342 (M+H).

Example 87

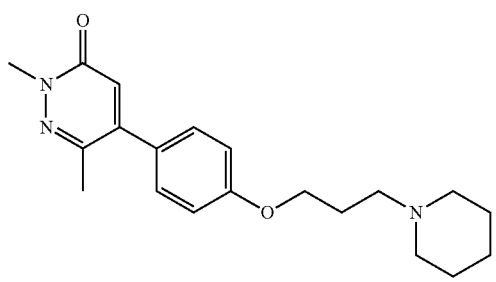

2,6-Dimethyl-5-[4-(3-piperidin-1-
yl-propoxy)-phenyl]-2H-pyridazin-3-one

This compounds was prepared using the procedure for example 86 using the product of step 3 and piperidine to give the hydrochloride salt; Mp 210-211° C.; MS m/z 342 (M+H).

Example 88

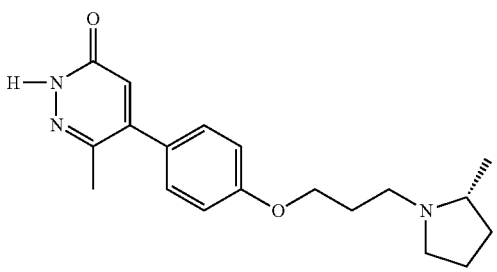

6-Methyl-5-{4-[3-((R)-2-methyl-pyrrolidin-
1-yl)-propoxy]-phenyl}-2H-pyridazin-3-one Step 1

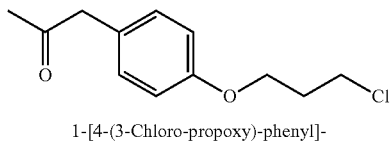

1-[4-(3-Chloro-propoxy)-phenyl]-
propan-2-one

A solution of 4-hydroxyphenylacetone (4.5 g, 30 mmol) and potassium carbonate (4.14 g, 3.0 eq.) in 50 mL of acetone was stirred under N$_2$ as 1-bromo-3-chloro-propane was added dropwise. The reaction was heated to 80° C. overnight. The mixture was then filtered through celite, washed with acetone and concentrated to afford 1-[4-(3-chloro-propoxy)phenyl]propan-2-one (6.3 g, 93% yield): MS m/z 227 (M+H).

Step 2

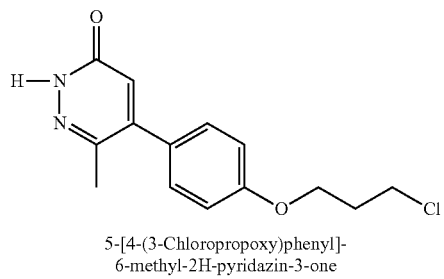 [SMILES: Cc1n[nH]c(=O)cc1-c1ccc(OCCCCl)cc1]

5-[4-(3-Chloropropoxy)phenyl]-
6-methyl-2H-pyridazin-3-one

5-[4-(3-Chloropropoxy)phenyl]-6-methyl-2H-pyridazin-3-one was prepared from the product from step 1 using the procedure described in Example 86 step 1.

Step 3

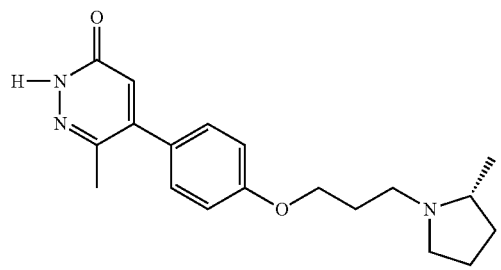

6-Methyl-5-{4-[3-((R)-2-methyl-pyrrolidin-
1-yl)-propoxy]-phenyl}-2H-pyridazin-3-one 6-Methyl-5-{4-[3-(®-2-methyl-pyrrolidin-1-yl)-propoxy]-phenyl}-2(-1-pyridazin-3-one) hydrochloride salt was prepared from 5-[4-(3-chloropropoxy)phenyl]-6-methyl-2H-pyridazin-3-one and R-2-methylpyrrolidine hydrochloride using the procedure described in Example 86. Step 4; Mp 115° C. (dec), MS m/z 329 (M+H).

Example 89

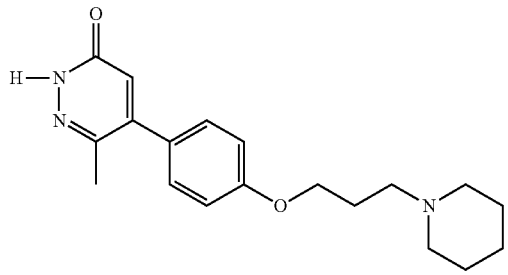

6-Methyl-5-[4-(3-piperidin-1-yl-
propoxy)-phenyl]-2H-pyridazin-3-one

This compound was prepared using the procedure for example 88 using the product of step 2 and piperidine to give the hydrochloride salt Mp dec 123 (dec.)° C.; MS m/z 328 (M+H).

Example 90

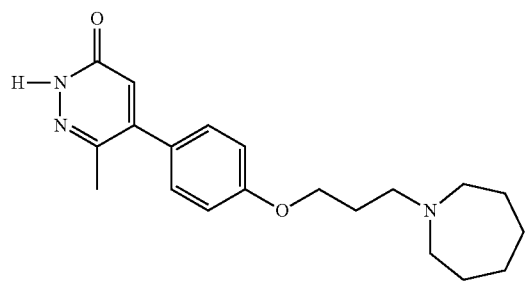

5-[4-(3-Azepan-1-yl-propoxy)-phenyl]-6-
methyl-2H-pyridazin-3-one

This compound was prepared using the procedure for example 88 to give the hydrochloride salt Mp 204-6° C.; MS m/z 342 (M+H).

Example 91

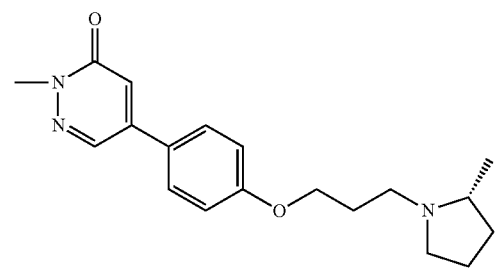

2-Methyl-5-{4-[3-((R)-2-methyl-pyrrolidin-
1-yl)-propoxy]-phenyl}-2H-pyridazin-3-one Step 1

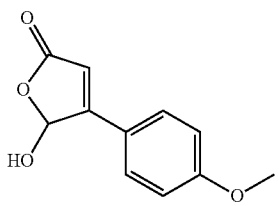

5-Hydroxy-4-(4-methoxy-phenyl)-5H-
furan-2-one

A solution of 4-methoxyphenyl ethanol (15.0 g, 98.2 mmol) in 150 mL of methylene chloride was stirred at 0° C. while Dess-Martin periodinane (50 g, 1.2 eq.) was added in small portions. The ice-bath was removed and the reaction was stirred at rt for 1 h. The reaction mixture was then diluted with methylene chloride (100 mL), washed with 10% sodium thiosulfate, saturated NaHCO₃ solution, water, saturated NaCl solution, and dried over Na₂SO₄. The product was purified using silica gel chromatography (100% hexanes to 20% EtOAC/hexanes) to afford 5.3 g (34%) of 4-methoxyphenyl acetaldehyde.

A suspension of glyoxalic acid hydrate (2.45 g, 26.6 mmol) and morpholine hydrochloride (3.28 g, 26.35 mmol) in dioxane (25 mL) was stirred as water (2 mL) was added. The homogeneous solution and 4-methoxyphenyl acetaldehyde (3.8 g, 25.3 mmol) was then added and the solution was stirred at reflux for 24 h. The solvent was evaporated and a solid was formed after addition of 20 mL of water. The solid was collected and washed with water to give 5.1 g (98%) of the product: MS m/z 189 (M-17+H).

Step 2

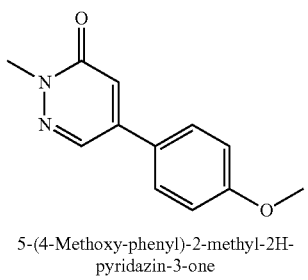

5-(4-Methoxy-phenyl)-2-methyl-2H-pyridazin-3-one

A suspension of 5-hydroxy-4-(4-methoxyphenyl)-5H-furan-2-one (2.06 g, 10 mmol) in 30 mL of ethanol was stirred as methylhydrazine (0.78 mL, 1.5 eq) was added dropwise. The reaction was heated to reflux at 85° C. for 2 h, then the solvent was reduced at reduced pressure to give a solid, which was collected and washed with cold EtOH to give 1.0 g (46%) of 5-(4-methoxy-phenyl)-2-methyl-2H-pyridazin-3-one: MS m/z 217 (M+H).

Step 3

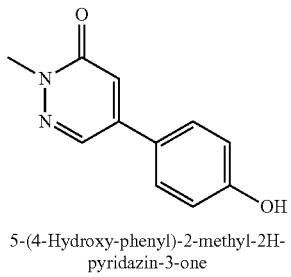

5-(4-Hydroxy-phenyl)-2-methyl-2H-pyridazin-3-one 5-(4-Hydroxyphenyl)-2-methyl-2H-pyridazin-3-one was prepared from 5-(4-methoxy-phenyl)-2-methyl-2H-pyridazin-3-one with BBr₃ using the procedure described in Example 86. Step 2; Mp 296-8° C.; MS m/z 203 (M+H).

Step 4

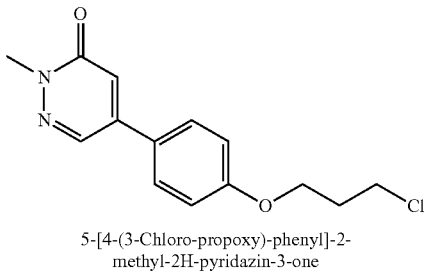 [SMILES: Cn1ncc(-c2ccc(OCCCCl)cc2)cc1=O]

5-[4-(3-Chloro-propoxy)-phenyl]-2-methyl-2H-pyridazin-3-one

5-[4-(3-Chloro-propoxy)-phenyl]-2-methyl-2H-pyridazin-3-one was prepared from 5-(4-hydroxy-phenyl)-2-methyl-2H-pyridazin-3-one with 1-bromo-3-chloro-propane using the procedure described in Example 86 Step 3; Mp 90-91° C.; MS m/z 279 (M+H).

Step 5

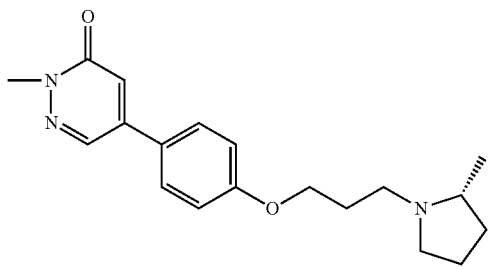

2-Methyl-5-{4-[3-((R)-2-methyl-pyrrolidin-1-yl)-propoxy]-phenyl}-2H-pyridazin-3-one This compound was prepared as the hydrochloride salt from 5-[4-(3-chloropropoxy)-phenyl]-2-methyl-2H-pyridazin-3-one and R-2-methylpyrrolidine using the procedure described in Example 86 Step 4; Mp 222-3° C.; MS m/z 328 (M+H).

Example 92

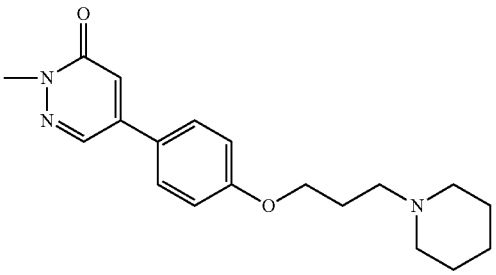

2-Methyl-5-[4-(3-piperidin-1-yl-propoxy)-phenyl]-2H-pyridazin-3-one

This compound was prepared as the hydrochloride salt using 5-[4-(3-chloropropoxy)-phenyl]-2-methyl-2H-pyridazin-3-one and piperidine using the procedure described in Example 91 Step 5; Mp 253-4° C.; MS m/z 328 (M+H).

Example 93

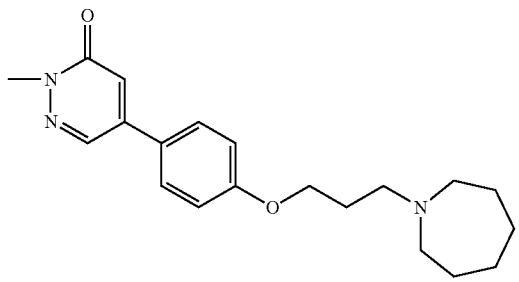

5-[4-(3-Azepan-1-yl-propoxy)-phenyl]-
2-methyl-2H-pyridazin-3-one

This compound was prepared as the hydrochloride salt using 5-[4-(3-chloropropoxy)-phenyl]-2-methyl-2H-pyridazin-3-one and azepine using the procedure described in Example 91 Step 5; Mp 247-8° C.; MS m/z 342 (M+H).

Example 94

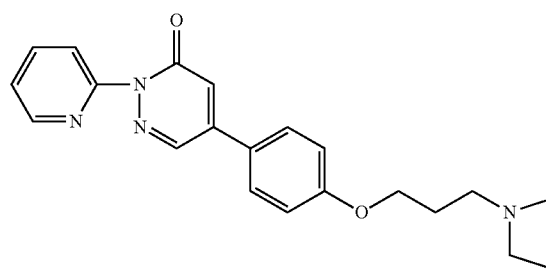

5-{4-[3-((R)-2-Methyl-pyrrolidin-1-yl)-
propoxy]-phenyl}-2-pyridin-2-yl-2H-
pyridazin-3-one Step 1

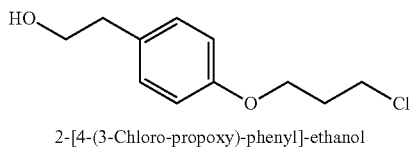 [SMILES: OCCc1ccc(OCCCCl)cc1]

2-[4-(3-Chloro-propoxy)-phenyl]-ethanol

A mixture of 2-(4-hydroxyphenyl)ethanol (13.82 g, 100.0 mmol) and potassium carbonate (34.0 g, 250.0 mmol) in 125.0 mL of acetone was stirred as 1-bromo-3-chloropropane (24.0 g, 150.0 mmol) was added dropwise. The reaction was stirred at 60° C. overnight, and then filtered through celite, washed with acetone and concentrated. The residue was dissolved in EtOAc (250 mL) and washed with 2N $Na_2CO_3$, water, and saturated NaCl solution. After drying over $Na_2SO_4$ the solution was concentrated to give 21 g (98%): Mp 49-50° C.; MS m/z 197 (M−H).

Step 2

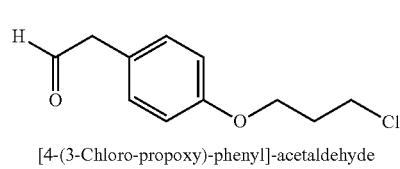 [SMILES: O=CCc1ccc(OCCCCl)cc1]

[4-(3-Chloro-propoxy)-phenyl]-acetaldehyde

A solution of Dess-Martin periodinane (20.4 g, 48.0 mmol) in 200 mL of methylene chloride was stirred as 2-[4-(3-chloropropoxy)ethanol (8.59 g, 40.0 mmol) in 60.0 mL of methylene chloride was added dropwise via addition funnel The reaction was stirred at rt for 1 h, diluted with ether (400 mL) and poured into 200 mL of 1.3 M NaOH solution. The ether layer was separated and washed with 1.3 M NaOH solution (100 mL), water until pH 7, and dried over $Na_2SO_4$. The product was purified using silica gel flash chromatography with 20% $Et_2O$ in hexane to give 6.75 g (79.3%) of [4-(3-chloro-propoxy)phenyl]acetaldehyde: MS m/z 213 (M+H).

Step 3

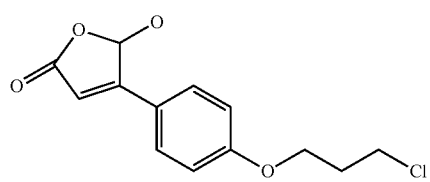

4-[4-(3-Chloro-propoxy)-phenyl]-5-
hydroxy-5H-furan-2-one

A suspension of glyoxalic acid hydrate (3.04 g, 33.1 mmol) and morpholine hydrochloride (4.09 g, 33.1 mmol) in dioxane (48 mL) was stirred at 4.5 mL of water was added. To the homogeneous solution [4-(3-chloropropoxy)phenyl]acetaldehyde (6.70 g, 31.5 mmol) was then added and the solution was stirred at reflux for 24 h. The solvent was evaporated and 50 mL of water was added. The solid was collected and washed with water to give 8.3 g (98%): MS m/z 251 (M-17+H).

Step 4

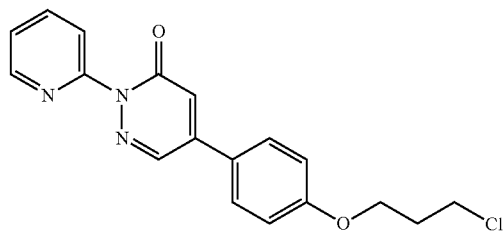

5-[4-(3-Chloro-propoxy)-phenyl]-2-pyridin-2-yl-2H-pyridazin-3-one

A solution of the product from step 3 (8.0 g, 29.8 mmol) and 2-hydrazinopyridine (9.75 g, 3.0 mmol) in 80 mL of acetic acid was stirred at 110° C. for 24 h. The solvent was evaporated and the residue was purified with ISCO Combiflash chromatography with 2% MeOH in methylene chloride. The product was crystallized from EtOH and ether to give 5.88 g (58%) of 5-[4-(3-chloropropoxy)-phenyl)-5-hydroxy-5H-furan-2-one: Mp 219-220° C.; MS m/z 391 (M+H).

Step 5

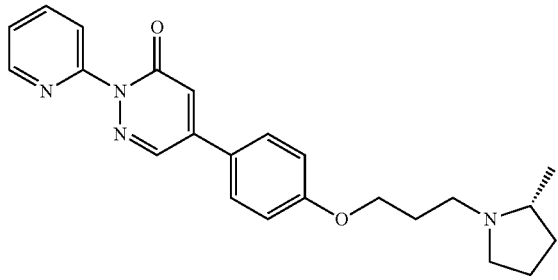

5-{4-[3-((R)-2-Methyl-pyrrolidin-1-yl)-propoxy]-pheny}-2-pyridin-2-yl-2H-pyridazin-3-one A mixture of the product from step 4, R-2-methyl-pyrrolidine benzenesulfonic acid salt (12.0 g, 51.0 mmol), potassium carbonate (8.2 g, 59.0 mmol) and sodium iodide (50 mg, 0.334 mmol) in 150.0 mL of acetonitrile was heated to 80° C. for 24 h. The reaction mixture was then filtered, washed with methylene chloride (2×20 mL) and concentrated. The residue was dissolved in 100 mL of methylene chloride and washed with saturated NaHCO$_3$, saturated NaCl solution, dried over Na$_2$SO$_4$ and concentrated. The residue was purified by ISCO graduate silica gel chromatography with 10% MeOH in CH$_2$Cl$_2$ with 0.5% of iPrNH$_2$ to give the product. The product was dissolved in MeOH and added 40.0 mL of 1N HCl in EtOH and concentrated to dryness. Crystallization using MeOH and CH$_3$CN afforded the HCl salt (5.45 g, 75%) Mp 219-220° C.; MS m/z 391 (M+H).

Example 95

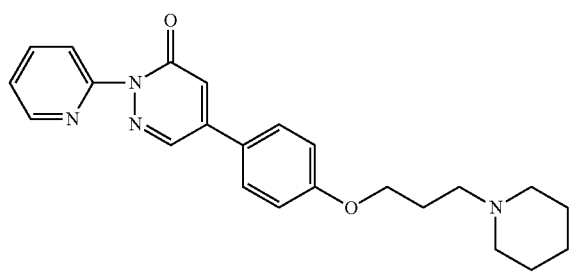

5-[4-(3-Piperidin-1-yl-propoxy)-phenyl]-2-pyridin-2-yl-2H-pyridazin-3-one

This compound was prepared using the procedure for example 94 to give the HCl salt; Mp 266-8° C.; MS m/z 391 (M+H).

Example 96

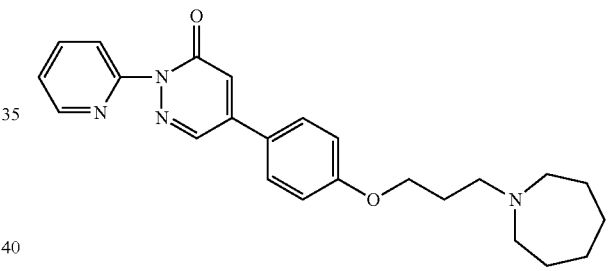

5-[4-(3-Azepan-1-yl-propoxy)-phenyl]-2-pyridin-2-yl-2H-pyridazin-3-one

This compound was prepared using the procedure for example 94 to give the HCl salt; Mp 230-2° C.; MS m/z 405 (M+H).

Example 97

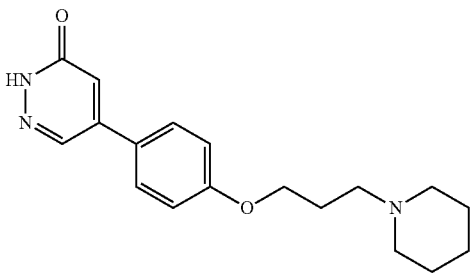

2-Methyl-5-[4-(3-piperidin-1-yl-propoxy)-phenyl]-2H-pyridazin-3-one

Step 1

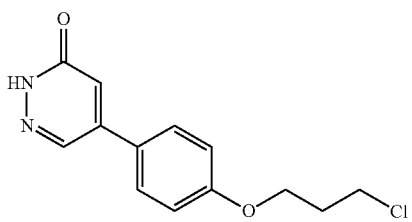

5-[4-(3-Chloro-propoxy)-phenyl]-2H-pyridazin-3-one

A solution of the product from example 94 step 3 (2.0 g, 7.45 mmol) and hydrazine hydrate (0.59 g, 1.5 eq.) in 20 mL of EtOH was stirred at 85° C. for 2 h. The solvent was reduced and the solid was collected and washed with cold EtOH to give 1.2 g (61%) of 5-[4-(3-chloropropoxy)phenyl]-2H-pyridazin-3-one: Mp 197-9° C.; MS m/z 265 (M+H).

Step 2

This compound was prepared from the product of step 1 (5.8 g, 17.0 mmol) and piperidine using the procedure for example 88. The hydrochloride salt of the product was prepared; Mp 249-250° C.; MS m/z 314 (M+H).

Example 98

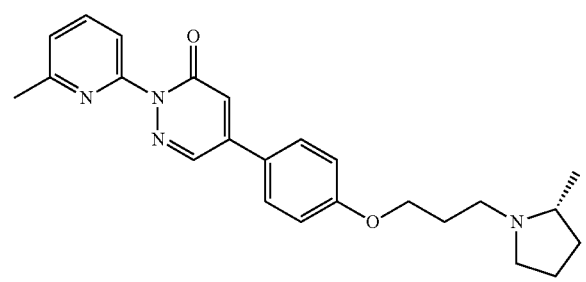

2-(6-Methyl-pyridin-2-yl)-5-{4-[3-((R)-2-methyl-pyrrolidin-1-yl)-propoxy]-phenyl}-2H-pyridazin-3-one Step 1

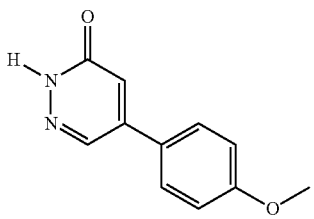

5-(4-Methoxy-phenyl)-2H-pyridazin-3-one

A suspension of 5-hydroxy-4-(4-methoxyphenyl)-5H-furan-2-one (2.00 g, 9.7 mmol) in 15 mL of ethanol was stirred as hydrazine hydrate (0.97 g, 2.0 eq) was added in dropwise. The reaction was stirred at 85° C. overnight, and then the solvent was reduced. The solid was collected and washed with cold EtOH to give 1.7 g (87%) of 5-(4-methoxy-phenyl)-2H-pyridazin-3-one: MS m/z 203 (M+H).

Step 2

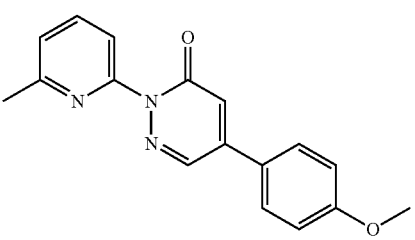

5-(4-Methoxy-phenyl)-2-(6-methyl-pyridin-2-yl)-2H-pyridazin-3-one

A mixture of the product from step 1 (1.34 g, 6.62 mmol), copper (I) iodide (0.4 g, 2.0 mmol) and potassium carbonate (1.4 g, 9.9 mmol) in DMF (15 mL) was stirred and degassed with N₂ for 3 min. Then 2-bromo-6-methylpyridine was added dropwise. After stirred at 120° C. overnight, the mixture was filtered through celite, washed with 50 mL of CH₂Cl₂, 15% of NH₄OH solution (3×15 mL), water, saturated NaCl solution, and dried over Na₂SO₄. The residue was purified by ISCO graduate chromatography (5% MeOH in CH₂Cl₂) to give 5-(4-methoxyphenyl)-2-(6-methylpyridin-2-yl)-2H-pyridazin-3-one (0.30 g, 15%): Mp 167-8° C.; MS m/z 294 (M+H).

Step 3

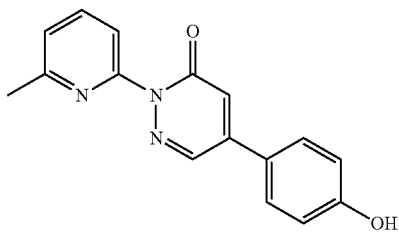

5-(4-Hydroxy-phenyl)-2-(6-methyl-pyridin-2-yl)-2H-pyridazin-3-one

This compound was prepared using the procedure described for Example 91 step 3; MS m/z=280 (M+H).

Step 4

Example 98 was prepared from the product of step 3 using procedures described in Example 91. Step 4 and Step 5; Mp 118-120° C.; MS m/z 405 (M+H).

Example 99

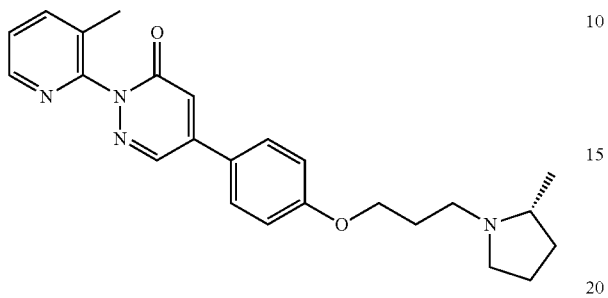

2-(3-Methyl-pyridin-2-yl)-5-{4-[3-((R)-2-methylpyrrolidin-1-yl)-propoxy]-phenyl}-2H-pyridazin-3-one Example 99 was prepared as the hydrochloride salt using procedures described for Example 98; Mp 98-100° C.; MS m/z 405 (M+H).

Example 100

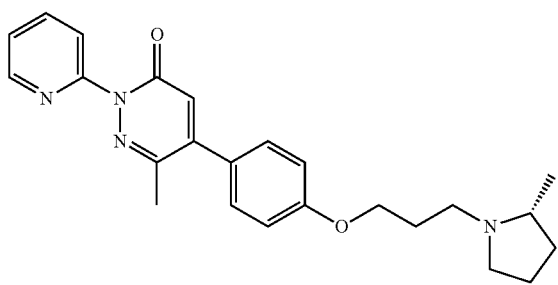

6-Methyl-5-{4-[3-((R)-2-methyl-pyrrolidin-1-yl)-propoxy]-phenyl}-2H-pyridazin-3-one Example 100 was prepared as the hydrochloride salt using procedures described for Example 98; Mp 155-7° C.; MS m/z 405 (M+H).

Example 101

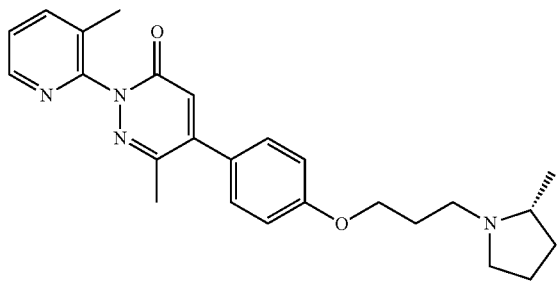

6-Methyl-2-(3-methyl-pyridin-2-yl)-5-{4-[3-((R)-2-methyl-pyrrolidin-1-yl)-propoxy]-phenyl}-2H-pyridazin-3-one Example 101 was prepared as the hydrochloride salt using procedures described for Example 98; Mp 106° C. (dec.); MS m/z 419(M+H).

Example 102

Step 1

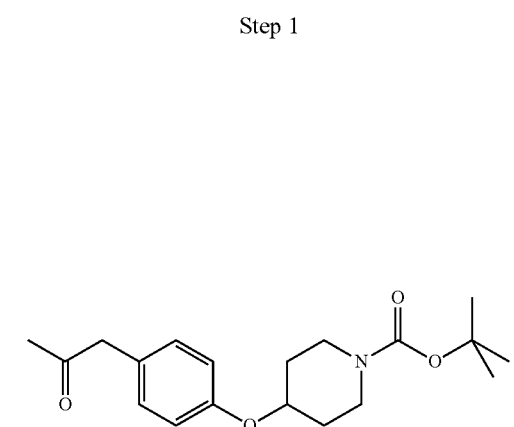

4-[4-(2-Oxo-propyl)-phenoxy]-piperidine-1-carboxylic acid tert-butyl ester

A solution of triphenylphosphine (18.5 g, 70.6 mmol) and 40% DEAD in toluene (12.3 g, 70.6 mmol) in 125.0 mL of tetrahydrofuran was cooled to 0° C. under $N_2$ as a solution of 1-(4-hydroxy-phenyl)-propan-2-one (6.54 g, 43.6 mmol) and 4-hydroxy-piperidine-1-carboxylic acid tert-butyl ester (10.7 g, 53.2 mmol) in 125.0 mL of tetrahydrofuran was added dropwise via addition funnel After stirred at rt overnight, the solvent was evaporated. The residue was stirred in hexane/EtOAc, the solid formed was filtered. The hexane/EtOAC solution was concentrated and purified by ISCO graduate chromatography (hexane-20% EtOAc in hexane) to give 4-[4-2-oxo-propyl)-phenoxy]-piperidine-1-carboxylic acid tert-butyl ester (8.52 g, 59%).

Step 2

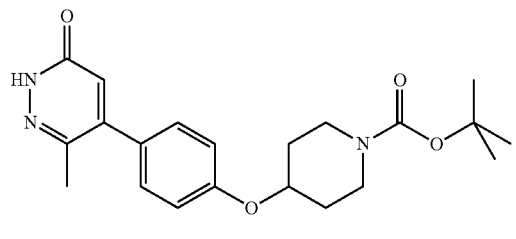

4-[4-(3-Methyl-6-oxo1,6-dihydro-pyridazin-4-yl)-phenoxy]-piperidine-1-carboxylic acid tert-butyl ester A mixture of 4-[4-(2-oxo-propyl)-phenoxy]-piperidine-1-carboxylic acid tert-butyl ester (7.01 g, 21.03 mmol) and glyoxalic acid hydrate (1.9 g, 21 mmol) was heated to 100° C. for 5 h. The resulting dark thick oil was stirred in 30 mL of EtOH as hydrazine hydrate (2.1 g, 42 mmol) was added. After stirred at 90° C. for 5 hr, the reaction was cooled to rt, and the solvent was evaporated. The crude product was purified by flash chromatography (10% MeOH in CH$_2$Cl$_2$), followed by trituration with ether to give 4-[4-(3-methyl-6-oxo-1,6-dihydro-pyridazin-4-yl)-phenoxy]-piperidine-1-carboxylic acid tert-butyl ester (3.25 g, 46%): Mp 184-6° C.; MS m/z 386 (M+H).

Example 102

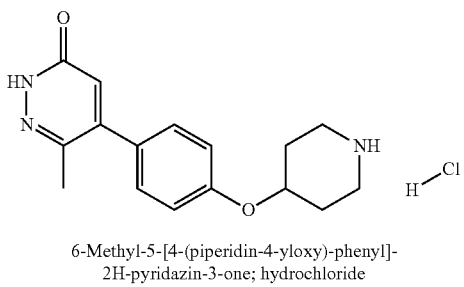

6-Methyl-5-[4-(piperidin-4-yloxy)-phenyl]-2H-pyridazin-3-one; hydrochloride

A solution of the product from step 2 (4-[4-(3-methyl-6-oxo-1,6-dihydro-pyridazin-4-yl)-phenoxy]-piperidine-1-carboxylic acid tert-butyl ester) (7.6 g, 20 mmol) in 30 mL of dioxane and 3.0 mL of water was cooled to 0° C. as 24 mL of 4M HCl in dioxane was added dropwise. After stirring at 50° C. for 1 h, the solvent was evaporated. The white solid was triturated with ether to give 6-methyl-5-[4-(piperidin-4-yloxy)-phenyl]-2H-pyridazin-3-one HCl (6.2 g, 92%): Mp 225-7° C.; MS m/z 286 (M+H).

Example 103

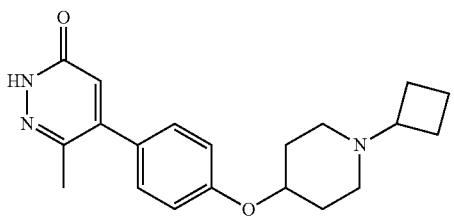

5-[4-(1-Cyclobutyl-piperidin-4-yloxy)-phenyl]-6-methyl-2H-pyridazin-3-one

A solution of example 102 (5.4 g, 18.9 mmol), sodium cyanoborohydride (2.4 g, 38 mmol) and cyclobutanone (6.6 g, 95 mmol) in 40.0 mL of DMF, 80.0 mL of MeOH and 5.0 mL of acetic acid was stirred at 60° C. for 1 h. The reaction was cooled to rt, quenched with ice-water and the solvent evaporated. The residue was diluted with 100 mL of CH$_2$Cl$_2$, washed with saturated NaHCO$_3$ solution (3×30 mL), water (2×20 mL), NaCl solution (30 mL) and dried over Na$_2$SO$_4$. The crude product was purified by Combiflash chromatography (CH$_2$Cl$_2$ to 10% MeOH in CH$_2$Cl$_2$ with 0.5% of iPrNH$_2$) to give the free base of the product. The product was then dissolved in MeOH and filtered. Then 30 mL of 1N HCl was added and the solution evaporated. The hydrochloride salt was crystallized from MeOH and Et$_2$O to give example 103 HCl (6.03 g, 90%): Mp 296-7° C.; MS m/z 340 (M+H).

Example 104

Step 1

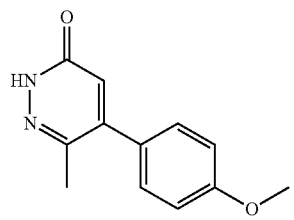

5-(4-Methoxy-phenyl)-6-methyl-2H-pyridazin-3-one 5-(4-methoxyphenyl)-6-methyl-2H-pyridazin-3-one was prepared from 1-(4-methoxy-phenyl)propan-2-one and glyoxalic acid and hydrazine hydrate using the procedure described in Example 86 Step 1; Mp 255-256° C.; MS m/z 203 (M+H).

Step 2

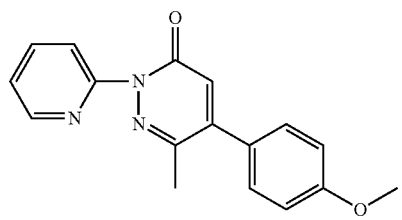

5-(4-Methoxy-phenyl)-6-methyl-2-pyridin-2-yl-2H-pyridazin-3-one 5-(4-Methoxy-phenyl)-6-methyl-2-pyridin-2-yl-2H-pyridazin-3-one was prepared from 5-(4-methoxy-phenyl)-6-methyl-2H-pyridazin-3-one and 2-bromopyridine in the presence of copper iodide using the procedure described in Example 98 Step 2; Mp 156-7° C.; MS m/z 294 (M+H).

Step 3

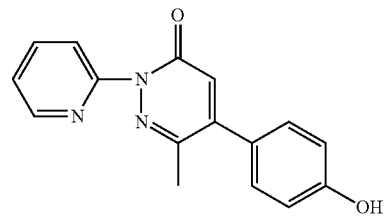

5-(4-Hydroxy-phenyl)-6-methyl-2-pyridin-2-yl-2H-pyridazin-3-one 5-(4-Hydroxy-phenyl)-6-methyl-2-pyridin-2-yl-2H-pyridazin-3-one was prepared from 5-(4-Methoxy-phenyl)-6- methyl-2-pyridin-2-yl-2H-pyridazin-3-one and BBr₃ in CH₂Cl₂ using the procedure described in Example 91 Step 3; Mp 252-4° C.; MS m/z 280 (M+H).

Step 4

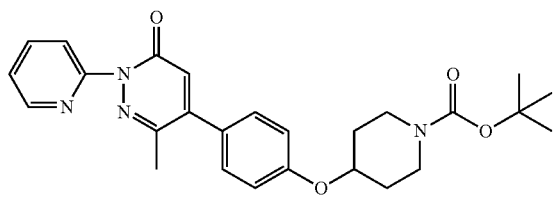

4-[4-(3-Methyl-6-oxo-1-pyridin-2-yl-1,6-dihydro-pyridazin-4-yl)-phenoxy]-piperidine-1-carboxylic acid tert-butyl ester A mixture of 5-(4-hydroxyphenyl)-6-methyl-2-pyridin-2-yl-2H-pyridazin-3-one (97.7 g, 28 mmol), t-butyl 4-methanesulfonyloxypiperidine-1-carboxylic acid ester (15 g, 55 mmol) and cesium carbonate (18 g, 55 mmol) in 75 mL of DMF was stirred at 100° C. overnight. The reaction mixture was cooled to rt, filtered through celite, and concentrated. The crude product was diluted with 100 mL of CH₂Cl₂, washed with 2N NaCO₃, water, NaCl solution, then dried over Na₂SO₄, and concentrated. The product was purified by flash chromatography (5% MeOH in CH₂Cl₂) and triturated with EtOAc and hexane to give 4-[4-(3-methyl-6-oxo-1-pyridin-2-yl-1,6-dihydropyridazin-4-yl)-phenoxy]-piperidine-1-carboxylic acid tert-butyl ester (6.7 g, 72%): MS m/z 463 (M+H).

Example 104

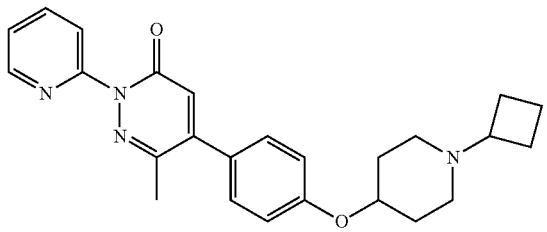

5-[4-(1-Cyclobutyl-piperidin-4-yloxy)-phenyl]-6-methyl-2-pyridin-2-yl-2H-pyridazin-3-one This compound was prepared using the product from step 4 and the procedures described in Example 103 Step 3 and Step 4; HCL salt mp 285-6° C.; MZ m/z 417 (M+H).

Example 105

Step 1

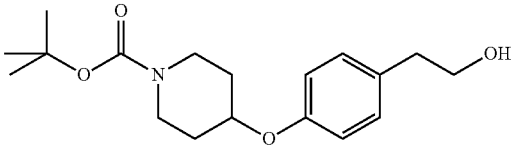

4-[4-(2-Hydroxy-ethyl)-phenoxy]-piperidine-1-carboxylic acid tert-butyl ester

A mixture of 2-(4-hydroxyphenyl)ethanol (4.15 g, 30 mmol), 4-methanesulfonyloxy-piperidine-1-carboxylic acid t-butyl ester (10.51 g, 37.6 mmol) and cesium carbonate (19.6 g, 60 mmol) in 100 mL of DMF was stirred at 100° C. overnight. The reaction mixture was cooled to rt, filtered through celite and concentrated. The crude product was diluted with 100 mL of CH₂Cl₂, washed with 2N Na₂CO₃, water, NaCl solution, dried over Na₂SO₄, and concentrated. The product was purified by flash chromatography (60% EtOAc in hexanes) to give 4-[4-(2-hydroxy-ethyl)-phenoxy]-piperidine-1-carboxylic ester (8.2 g, 59%): MS m/z 222 (M-Boc+H).

Step 2

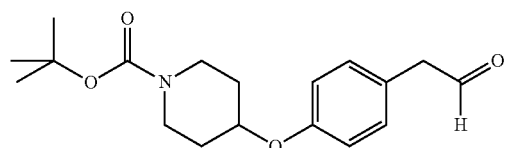

4-[4-(2-Oxo-ethyl)-phenoxy]-piperidine-1-carboxylic acid tert-butyl ester

A solution of 4-[4-(2-hydroxyethyl)-phenoxy]piperidine-1-carboxylic acid tert-butyl ester (8.10 g, 25.2 mmol) in 90 mL of CH₂Cl₂ was cooled to 0° C. as Dess-Martin periodinane (11.2 g, 26.5 mmol) was added in portions. After stirred at rt overnight, the reaction was diluted with 100 mL of CH₂Cl₂, and washed with saturated NaHCO₃ (5×100 mL), water, and dried over Na₂SO₄. Flash chromatography with 60% Et₂O in hexane gave 2.83 g (35%) of 4-[4-(2-oxo-ethyl)-phenoxy]-piperidine-1-carboxylic acid tert-butyl ester: MS m/z 220 (M-Boc+H).

Step 3

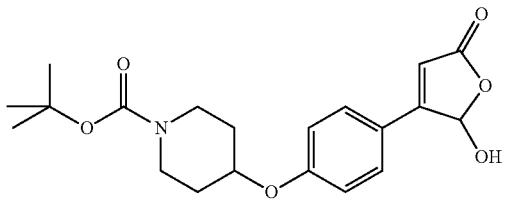

4-[4-(2-Hydroxy-5-oxo-2,5-dihydro-furan-3-yl)-phenoxy]-piperidine-1-carboxylic acid tert-butyl ester 4-[4-(2-hydro-5-oxo-2,5-dihydro-furan-3-yl)-phenoxy]-piperidine-1-carboxylic acid tert-butyl ester was prepared from 4-[4-(2-oxo-ethyl)-phenoxy]-piperidine-1-carboxylic acid tert-butyl ester and glyoxalic acid hydrate using procedure described in Example 94 Step 3; MS m/z 275 (M-Boc+H).

Step 4

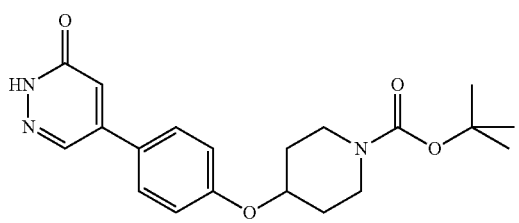

4-[4-(6-Oxo-1,6-dihydro-pyridazin-4-yl)-phenoxy]-piperidine-1-carboxylic acid tert-butyl ester A solution of the product from step 3 (1.0 g, 2.7 mmol) and hydrazine hydrate (0.27 g, 5.3 mmol) in 12 mL of MeOH was stirred at 80° C. overnight. After being cooled to rt, the solvent was reduced and the solid was filtered and washed with cold EtOH to give 0.63 g (57%) of 4-[4-(6-oxo-1,6-dihydro-py-ridazin-4-yl)-phenoxy]piperidine-1-carboxylic acid tert-butyl ester: Mp 222-3° C.; MS m/z 372 (M+H).

Example 105

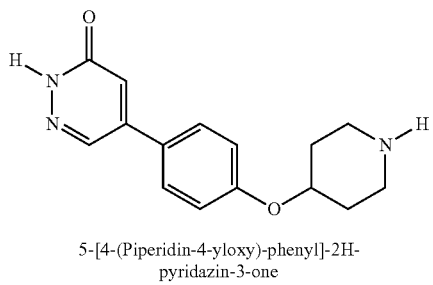 [SMILES: O=c1cc(-c2ccc(OC3CCNCC3)cc2)cn[nH]1]

5-[4-(Piperidin-4-yloxy)-phenyl]-2H-pyridazin-3-one

This compound was prepared using the procedure for example 102; Mp ° C.; MS m/z 272 (M+H).

Example 106

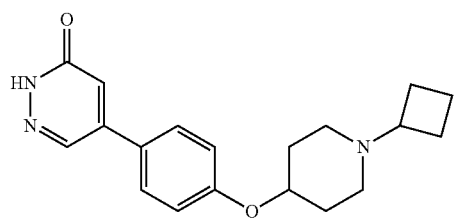

5-[4-(1-Cyclobutyl-piperidin-4-yloxy)-phenyl]2-H-pyridazin-3-one

This compound was prepared as the HCl salt using the procedure for example 103; Mp 296-8° C.; MS m/z 326 (M+H).

Example 107

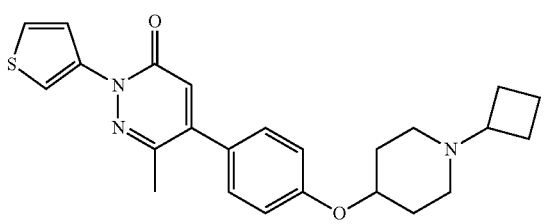

5-[4-(1-Cyclobutyl-piperidin-4-yloxy)-phenyl]-6-methyl-2-thiophen-3-yl-2H-pyridazin-3-one This compound was prepared as the HCl salt using the procedure for example 104; Mp 277-9° C.; MS m/z 422 (M+H).

Example 108

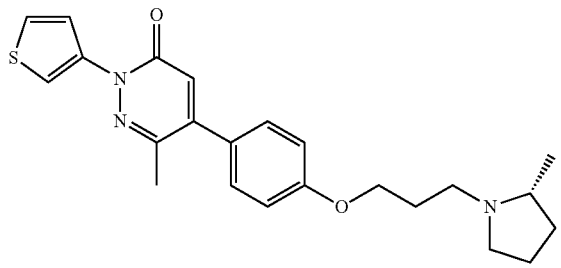

6-Methyl-5-[4-[3-((R)-2-methyl-pyrrolidin-1-yl)-propoxy]-phenyl]-2-thiophen-3-yl-2H-pyridazin-3-one This compound was prepared as the HCl salt using the procedure for example 98; Mp 212-3° C.; MS m/z 410 (M+H).

Example 109

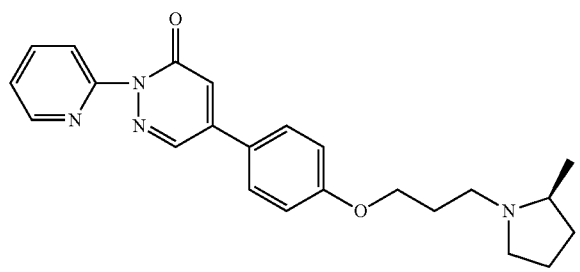

5-{4-[3-((S)-2-Methyl-pyrrolidin-1-yl)-propoxy]-phenyl}-2-pyridin-2-yl-2H-pyridazin-3-one Example 109 was prepared using the same procedure as Example 94 except using 5-2-methylpyrrolidine HCl; Mp 218-220° C.; MS m/z 391 (M+H).

Example 110

Step 1

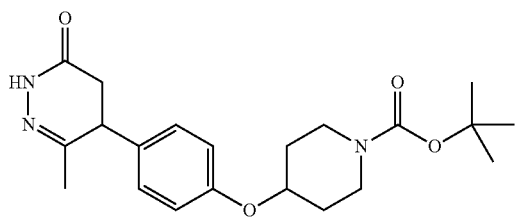

4-[4-(3-Methyl-6-oxo-1,4,5,6-tetrahydro-pyridazin-4-yl)-phenoxy]-piperidine-1-carboxylic acid tert-butyl ester A solution of the intermediate from Example 102 step 1 (1.0 g, 3.0 mmol) in THF (10 mL) at −78° C. under N₂ was added KHMDS (0.5 M in toluene, 9.0 mL) dropwise. After 30 min at −78° C., ethyl bromoacetate (0.75 g, 4.5 mmol) was added drop wise. After 1 hr at −78° C., the reaction was quenched with 1 N HCl (4.0 mL), diluted with 20 mL of EtOAc and the layers separated. The EtOAc layer was washed with 5% NaHCO₃, NaCl solution, then dried over Na₂SO₄ and concentrated. To the crude solid in 10 mL of EtOH was added hydrazine hydrate (0.22 g, 0.45 mmol) and the reaction then stirred at 85° C. for 2 h. The mixture was cooled to rt, the solvent was reduced and the solid was filtered and washed with cold EtOH to give 0.65 g (56%) of 4-[4-(3-methyl-6-oxo-1,4,5,6-tetrahydro-pyridazin-4-yl)-phenoxyl]-piperidine-1-carboxylic acid tert-butyl ester: Mp 165-7° C.; MS m/z 288 (M-Boc+H).

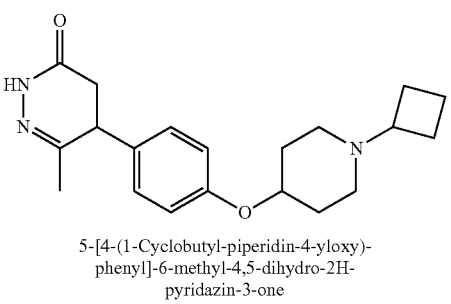 [SMILES: CC1=NNC(=O)CC1c1ccc(OC2CCN(C3CCC3)CC2)cc1]

5-[4-(1-Cyclobutyl-piperidin-4-yloxy)-phenyl]-6-methyl-4,5-dihydro-2H-pyridazin-3-one Example 110 was prepared from the product of step 1 using procedures described in Example 102 and Example 103; Mp 178-9° C.; MS m/z 342 (M+H).

Example 111

Step 1

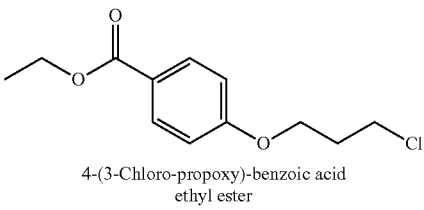 [SMILES: CCOC(=O)c1ccc(OCCCCl)cc1]

4-(3-Chloro-propoxy)-benzoic acid ethyl ester

A suspension of 4-hydroxybenzoic acid ethyl ester (5.0 g, 30 mmol), 1-bromo-3-chloropropane (7.1 g, 45 mmol) and potassium carbonate (14 g, 100 mmol) in 50 mL of acetone using the procedure described in Example 88 Step 1 gave the product as a clear oil.

Step 2

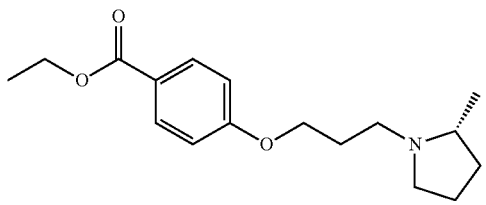

4-[3-((R)-2-Methyl-pyrrolidin-1-yl)-propoxy]-benzoic acid ethyl ester

A mixture of the product from step 1 (6.5 g, 27 mmol), R-2-methylpyrrolidine benzene sulfonic acid (16 g, 67 mmol), potassium carbonate (11 g, 80 mmol) and sodium iodide (50 mg, 0.3 mmol) in 100 mL of acetonitrile was stirred at 80° C. overnight. The reaction mixture was filtered through celite, washed with $CH_2Cl_2$, combined and concentrated. The residue was dissolved in $CH_2Cl_2$, washed with saturated $NaHCO_3$, water, saturated NaCl, then dried over $Na_2SO_4$ to give 7.5 g (96%) of 4-[3-R-2-methylpyrrolidin-1-yl-propoxy]benzoic acid ethyl ester; MS m/z 292 (M+H).

Step 3

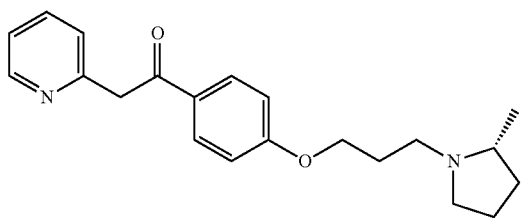

1-{4-[3-((R)-2-Methyl-pyrrolidin-1-yl)-propoxy]-phenyl}-2-pyridin-2-yl-ethanone

A solution of the product from step 2 (4.0 g, 14 mmol) and 2-methylpyridine (2.6 g, 27 mmol) in 60 mL of THF was cooled to 0° C., then LiHMDS (1.0 M, 27 mmol) was added dropwise. After addition, the reaction was stirred at 45° C. overnight. The reaction was quenched with ice-water, extracted with $CH_2Cl_2$ (3×50 mL), combined, washed with saturated $NaHCO_3$, water, then dried over $Na_2SO_4$. Flash chromatography using 10% MeOH in $CH_2Cl_2$ gave the product (3.7 g, 78%); Mp 40-42° C.; MS m/z 339 (M+H).

Step 4

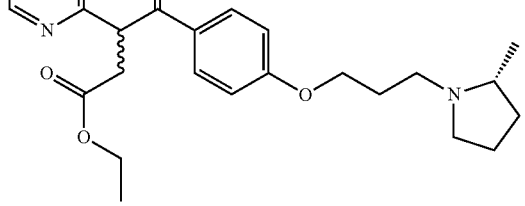

4-{4-[3-((R)-2-Methyl-pyrrolidin-1-yl)-propoxy]-phenyl}-4-oxo-3-pyridin-2-yl-butyric acid ethyl ester A mixture of sodium hydride (0.092 g, 3.8 mmoL) in 10 mL of DMSO was stirred under $N_2$ as the product from step 3 (1.0 g, 3.8 mmol) in 5.0 mL of DMSO was added dropwise. After the reaction was stirred for 30 min, a solution of ethyl bromoacetate (0.64 g, 8.83 mmol) in 6.0 mL of toluene was added dropwise, and the reaction was stirred at rt for 1 h. The reaction was then quenched with $NH_4Cl$ solution and the solvent was evaporated. The residue was extracted with $CH_2Cl_2$ (3×20 mL), combined, washed with saturated $NaHCO_3$, saturated NaCl then dried over $Na_2SO_4$. The crude product was purified by flash chromatography using 10% MeOH in $CH_2Cl_2$ to give the product (0.65 g, 52%).

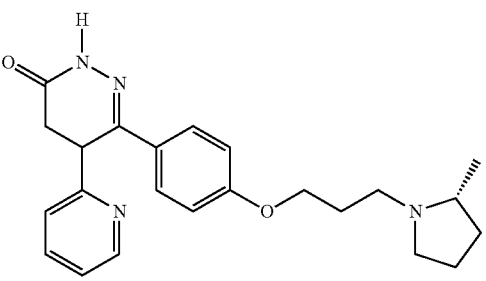

6-{4-[3-((R)-2-Methyl-pyrrolidin-1-yl)-propoxy]-phenyl}-5-pyridin-2-yl-4,5-dihydro-2H-pyridazin-3-one A solution of the ester intermediate (4-{4-[3-R-2-methyl-pyrrolidin-1-yl)-phenyl}-4-oxo-3-pyridin-2-yl-butyric acid ethyl ester) (9.2 g, 22 mmol) and hydrazine hydrate (2.2 g, 43 mmol) in 150 mL of EtOH was stirred at reflux overnight. Flash chromatography using 15% MeOH in $CH_2Cl_2$ with 0.5% of $iPrNH_2$ followed by treatment of the product with 1N HCl in EtOH gave hydrochloride of 6-{4-[3-R-2-methylpyrrolidin-1-yl)-propoxy]-phenyl}-5-pyridin-2-yl-4,5-dihydro-2H-pyridazin-3-one (6.1 g, 71%); Mp 133° C. (dec.); MS m/z 393 (M+H).

Example 112

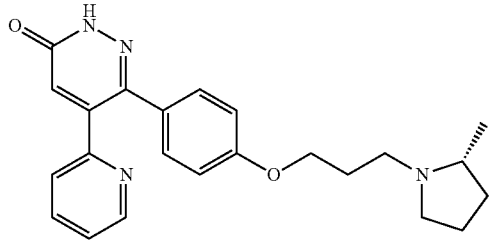

6-{4-[3-((R)-2-Methyl-pyrrolidin-1-yl)-
propoxy]-phenyl}-5-pyridin-2-yl-
2H-pyridazin-3-one A mixture of example 111 (0.39 g, 1.0 mmol) in 4.0 mL of water was added sodium 3-nitrobenzenesulfonate (0.18 g, 0.78 mmol) and NaOH (0.12 g, 3.0 mmol). The reaction was heated to 100° C. as 2.5 mL of EtOH was added to make the reaction homogeneous. After 2 h at 100° C., the reaction was cooled to rt. 2N HCl was added to adjust pH to ~6, then the reaction was extracted with CH$_2$Cl$_2$ (3×20 mL), which was washed with saturated NaHCO$_3$, saturated NaCl, and then dried over Na$_2$SO$_4$. The product was purified by preparative TLC using 10% MeOH in CH$_2$Cl$_2$ and 0.5% of iPrNH$_2$ to give the product. The hydrochloride salt was prepared by treating the free base with 1N HCl in EtOH (0.14 g, 35%); Mp 234° C. (dec.); MS m/z 391 (M+H).

Example 113

Step 1

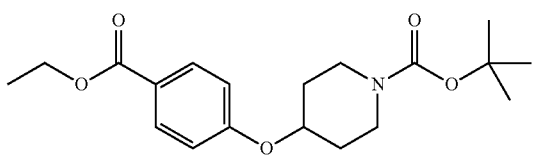

4-(4-Ethoxycarbonyl-phenoxy)-piperidine-
1-carboxylic acid tert-buytyl ester 4-(4-Ethoxycarbonylphenoxy)piperidine-1-carboxylic acid tert-butyl ester was prepared from 4-hydroxybenzoic acid ethyl ester and 4-hydroxypiperidine-1-carboxylic acid tert-butyl ester using the procedure described in Example 103 step 1; Mp 76-78° C.; MS m/z 350 (M+H).

Step 2

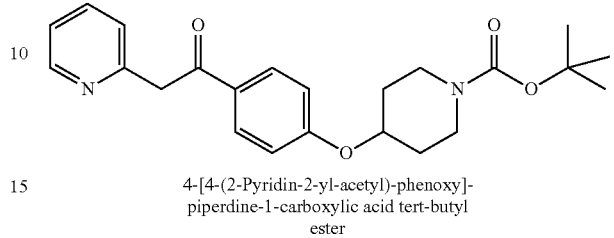

4-[4-(2-Pyridin-2-yl-acetyl)-phenoxy]-
piperdine-1-carboxylic acid tert-butyl
ester A solution of 4-(4-ethoxycarbonylphenoxy)piperidine-1-carboxylic acid tert-butyl ester (3.5 g, 10 mmol) and 2-methylpyridine (1.9 g, 2.0 mmol) in 50 mL of THF was stirred at 0° C. as LiHMDS (1.0M, 22 mL) was added dropwise. The reaction was stirred at 45° C. overnight, then quenched with ice-water and the solvent evaporated. The residue was extracted with CH$_2$Cl$_2$ (3×30 mL), and the combined CH$_2$Cl$_2$ layers were washed with saturated NaHCO$_3$, saturated NaCl solution, dried over Na$_2$SO$_4$, and concentrated to give the product; Mp 138-140° C.; MS m/z 397 (M+H).

Step 3

4-[4-(3-(Ethoxycarbonyl-2-pyridin-2-yl-
propionyl)-phenoxy]-piperidine-1-
carboxylic acid tert-butyl ester A mixture of sodium hydride (0.21 g, 8.8 mmoL) in 10 mL of DMSO was stirred under N$_2$ as 4-[4-(2-pyridine-2-yl-acetyl)-phenoxy]-piperidine-1-carboxylic acid tert-butyl ester (3.50 g, 8.83 mmol) in 15 mL of DMSO was added dropwise. After 30 min, a solution of ethyl bromoacetate (1.47 g, 8.83 mmol) in 8.0 mL of toluene was added dropwise. The reaction was stirred at rt for 2 h and then quenched with saturated NH$_4$Cl solution, and the solvent was evaporated. The residue was extracted with CH$_2$Cl$_2$ (3×20 mL), combined, washed with saturated NaHCO$_3$, saturated NaCl solution and dried over Na$_2$SO$_4$. The crude product was purified by Combiflash chromatography (CH$_2$Cl$_2$ to 1% MeOH in CH$_2$Cl$_2$) to give the product (4.0 g, 94%): Mp 118-120° C.; MS m/z 483 (M+H).

Step 4

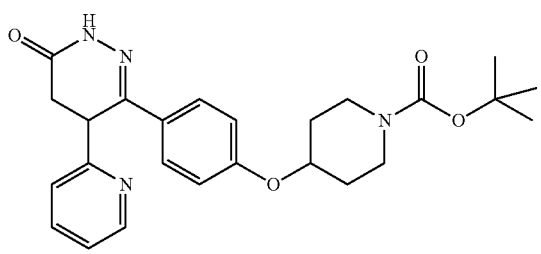

4-[4-(6-Oxo-4-pyridin-2-yl-1,4,5,6-tetrahydro-pyridazine-3-yl)-phenoxy]-piperidine-1-carboxylic acid tert-butyl ester A solution of the product from step 3 (4.0 g, 8.3 mmol) and hydrazine hydrate (0.83 g, 16 mmol) in 30 mL of EtOH was stirred at 90° C. overnight. The yellow suspension was reduced to ~15 mL of EtOH. The solid was collected and washed with cold EtOH to give the product (2.05 g, 55%): Mp 213-214° C.; MS m/z 395 (M-tBu+H).

Example 113

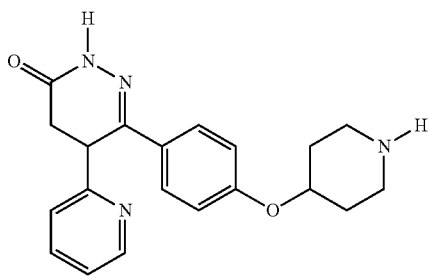

6-[4-(Piperidin-4-yloxy)-phenyl]-5-pyridin-2-yl-4,5-dihydro-2H-pyridazin-3-one

This compound was prepared from the product of step 4 using procedures described in Example 102 Step 3 MS m/z 351 (M+H).

Example 114

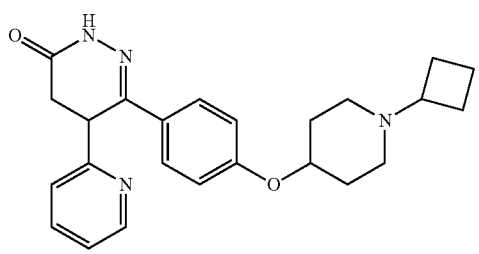

6-[4-(1-Cyclobutyl-piperidin-4-yloxy)-phenyl]-5-pyridin-2-yl-4,5-dihydro-2H-pyridazin-3-one This compound was prepared using the procedure for Example 103; Mp 199° C. (dec); MS m/z 405 (M+H).

Example 115

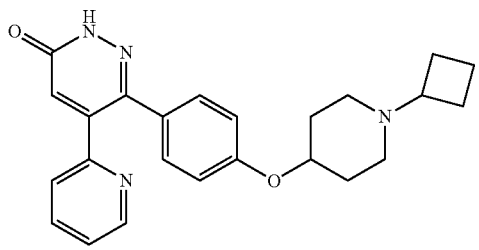

6-[4-(1-Cyclobutyl-piperidin-4-yloxy)-phenyl]-5-pyridin-2-yl-2H-pyridazin-3-one

Step 1

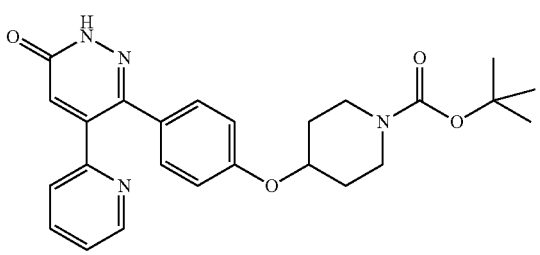

4-[4-(6-Oxo-4-pyridin-2-yl-1,6-dihydro-pyridazin-3-yl)-phenoxy]-piperidine-1-carboxylic acid tert-butyl ester A mixture of the product from Example 113 step 4 (0.3 g, 0.67 mmol) and cesium carbonate (0.65 g, 2 mmol) in 4.0 mL of DMSO was heated under air at 150° C. for 0.5 h. The reaction was cooled to rt, filtered, washed with CH$_2$Cl$_2$ (3×15 mL) and combined. The CH$_2$Cl$_2$ solution was washed with saturated NaHCO$_3$, water and dried over Na$_2$SO$_4$. The crude product was crystallized from MeOH and ether to give the Boc product; Mp 210-2° C.; MS m/z 449 (M+H)

6-[4-(1-cyclobutyl-piperidin-4-yloxy)-phenyl]-5-pyridin-2-yl-2H-pyridazin-3-one was prepared from the product in step 1 using procedures described in Example 102 Step 3 and Example 103; Mp 203° C. (dec.); MS m/z 403(M+H).

Example 116

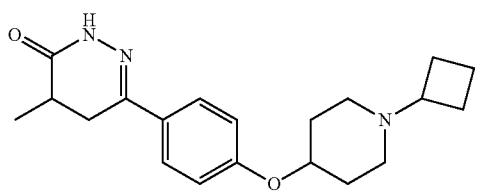

6-[4-(1-Cyclobutyl-piperidin-4-yloxy)-phenyl]-4-methyl-4,5-dihydro-2H-pyridazin-3-one

Step 1

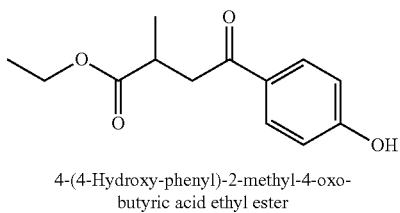 [SMILES: CCOC(=O)C(C)CC(=O)c1ccc(O)cc1]

4-(4-Hydroxy-phenyl)-2-methyl-4-oxo-
butyric acid ethyl ester

A solution of 4-(4-methoxyphenyl)-2-methyl-4-oxobutyric acid (10 g, 45 mmol) and 150 mL of 48% HBr in 20 mL of AcOH was heated to 100° C. for 48 h. The solvent was evaporated and EtOH (3×30 mL) was added and evaporated to give 4-(4-methoxy-phenyl)-2-methyl-4-oxobutyric acid ethyl ester (9.96 g, 93%); MS m/z 259 (M+23).

Step 2

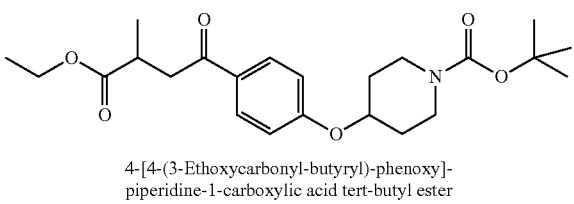 [SMILES: CCOC(=O)C(C)CC(=O)c1ccc(OC2CCN(C(=O)OC(C)(C)C)CC2)cc1]

4-[4-(3-Ethoxycarbonyl-butyryl)-phenoxy]-
piperidine-1-carboxylic acid tert-butyl ester 4-[4-(3-Ethoxycarbonyl-butyryl)-phenoxy]piperidine-1-carboxylic acid tert-butyl ester was prepared using procedure described in Example 102 step 1; MS m/z 442 (M+23).

The final product 6-[4-(1-cyclobutylpiperidin-4-yloxy) phenyl]-4-methyl-4,5-dihydro-2H-pyridazin-3-one HCl was prepared from 4-[4-(3-ethoxycarbonyl-butyryl)phenoxy]-piperidine-1-carboxylic acid tert-butyl ester using procedures described in Example 117. Step 3 and Example 103; Mp 257-9° C.; MS m/z 342 (M+H).

Example 117

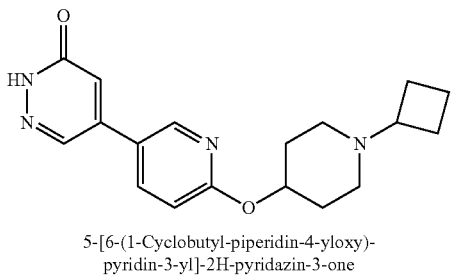 [SMILES: O=c1cc(-c2ccc(OC3CCN(C4CCC4)CC3)nc2)cn[nH]1]

5-[6-(1-Cyclobutyl-piperidin-4-yloxy)-
pyridin-3-yl]-2H-pyridazin-3-one

Step 1

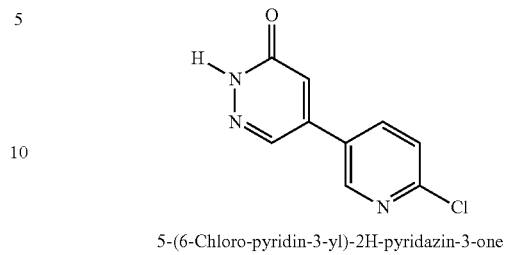

5-(6-Chloro-pyridin-3-yl)-2H-pyridazin-3-one 4,5-Dichloropyridazin-6-one (10 g, 60.6 mmol) and 57 wt. % hydroiodic acid in water (80 mL, 1.0 mmol) was heated to 150° C. for 24 h. The reaction was cooled to rt, the solid was washed with sodium thiosulfate. The crude product was triturated with $CH_2Cl_2$: MeOH (1:1) and filtered to give 5-iodo-2H-pyridazin-3-one (4.64 g, 35%).

A mixture of 5-iodo-2H-pyridazin-3-one (4.64 g, 21 mmol) and 30% formaldehyde in water was heated to reflux for overnight. The reaction was cooled to rt, and the resulting solid was filtered to give 2-hydromethyl-5-iodo-2H-pyridazin-3-one (5.2 g, 99%).

A mixture of 2-hydromethyl-5-iodo-2H-pyridazin-3-one (1.15 g, 4.56 mmol) and 2-chloro-5-pyridineboronic acid (0.72 g, 4.57 mmol), tetrakis(triphenylphosphine)-palladium (0) (0.53 g, 0.46 mmol) and potassium carbonate (1.89 g, 13.7 mmol) in 30 mL of 1,2-dimethoxyethane and 10 mL of water was degassed for 3 min, then heated to 85° C. overnight. The reaction was cooled to rt, filtered and washed with ethyl acetate. The organic layer was separated, concentrated, and triturated with ether to give 5-(6-chloro-pyridin-3-yl)-2H-pyridazin-3-one (0.4 g, 36%); MS m/z 208 (M+H).

Step 2

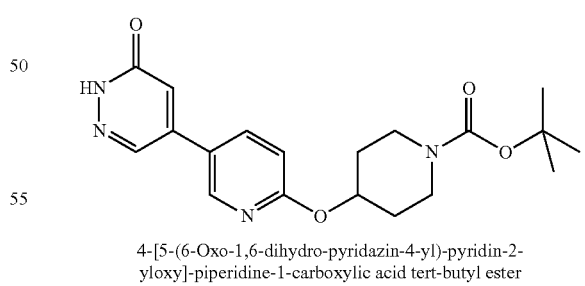

4-[5-(6-Oxo-1,6-dihydro-pyridazin-4-yl)-pyridin-2-
yloxy]-piperidine-1-carboxylic acid tert-butyl ester A solution of 5-(6-chloropyridin-3-yl)-2H-pyridazin-3-one (73 mg, 0.35 mmol) and 4-hydroxypiperidine-1-carboxylic acid tert-butyl ester (140 mg, 0.70 mmol) in 2.7 mL of DMSO was stirred as KOtBu in 2-methyl-2-propanol (1.0 M, 14.4 mL) was added dropwise. After stirring at 110° C. overnight, the reaction was cooled to rt, and 2 mL of water was added. The mixture was extracted with $CH_2Cl_2$ (3×10 mL), the extracts combined and dried over Na₂SO₄. The crude product was purified by prep. TLC with 10% MeOH in CH₂Cl₂ to give 71 mg (54%) of 4-[5-(6-oxo-1,6-dihydropyridazin-4-yl)-pyridin-2-yloxy]piperidine-1-carboxylic acid tert-butyl ester; MS m/z 273 (M-Boc-H).

Example 117 hydrochloride was prepared from the product in step 2 using procedures described in Example 102 Step 3 and Example 103; Mp 232-4° C.; MS m/z 327 (M+H).

Example 118

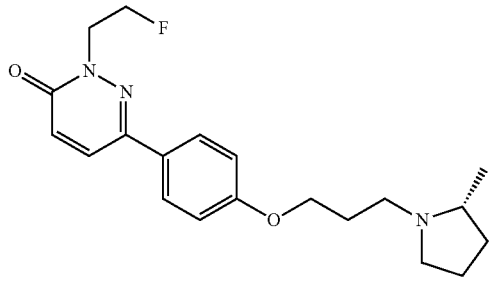

2-(2-Fluoro-ethyl)-6-{4-[3-((R)-2-methyl-pyrrolidin-1-yl)-propoxy]-phenyl}-2H-pyridazin-3-one Step 1

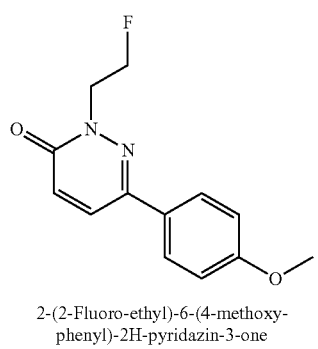 [SMILES: COc1ccc(-c2ccc(=O)n(CCF)n2)cc1]

2-(2-Fluoro-ethyl)-6-(4-methoxy-phenyl)-2H-pyridazin-3-one

A mixture of 6-(4-methoxyphenyl)-2H-pyridazin-3-one (170 mg, 0.83 mmol), 1-bromo-2-fluoroethane (122.5 mg, 1.5 eq.), NaI (20 mg) and cesium carbonate (553 mg, 2.0 eq.) in 5 mL of CH₃CN was heated to 70° C. overnight. The reaction mixture was filtered and concentrated. The product was purified by ISCO combiflash with 50% hexane and EtOAc to give 2-(2-fluoroethyl)-6-(4-methoxyphenyl)-2H-pyridazin-3-one (200 mg, 97%); MS m/z 349 (M+H).

Example 118 hydrochloride was prepared from the product in step 1 using procedures described in Example 1 and example 86; mp 135-6° C.; MS m/z 360 (M+H).

The following compounds were prepared as HCl salts unless noted using methods for example 1, example 11 or example 91.

| Example | Structure | Mp (° C.) | MS m/z |
|---------|-----------|-----------|--------|
| 119 | 6-{3-Fluoro-4-[3-((R)-2-methyl-pyrrolidin-1-yl)-propoxy]-phenyl}-2H-pyridazin-3-one | 252-3 | 332 (M + H) |
| 120 | 6-[3-Fluoro-4-(3-piperidin-1-yl-propoxy)-phenyl]-2H-pyridazin-3-one | 240-2 | 332 (M + H) |
| 121 | 4-Methyl-6-{4-[3-((R)-2-methyl-pyrrolidin-1-yl)-propoxy]-phenyl}-4,5-dihydro-2H-pyridazin-3-one | 201-3 | 330 (M + H) |

-continued

| Example | Structure | Mp (° C.) | MS m/z |
|---|---|---|---|
| 122 | 4-Methyl-6-{4-[3-((R)-2-methyl-pyrrolidin-1-yl)-propoxy]-phenyl}-2H-pyridazin-3-one | 207-8 | 328 (M + H) |
| 123 | 4-Methyl-6-[4-(3-piperidin-1-yl-propoxy)-phenyl]-2H-pyridazin-3-one | 227-9 | 328 (M + H) |
| 124 | 4-{4-[3-((S)-2-Hydroxymethyl-pyrrolidin-1-yl)propoxy]-phenyl}-2-methyl-5,6,7,8-tetrahydro-2H-phthalazin-1-one | 120-2 | 398 (M + H) |
| 125 | 2-Methyl-4-{3-[3-((R)-2-methyl-pyrrolidin-1-yl)-propoxy]-phenyl}-2,5,6,7-tetrahydro-cyclopenta[d]pyridazin-1-one | 172-4 | 368 (M + H) |
| 126 | 2-Methyl-4-[3-(3-piperidin-1-yl-propoxy)-phenyl]-2,5,6,7-tetrahydro-cyclopenta[d]pyridazin-1-one | 189-190 | 368 (M + H) |

-continued

| Example | Structure | Mp (° C.) | MS m/z |
|---|---|---|---|
| 127 | 4-{3-[3-((S)-2-Hydroxymethyl-pyrrolidin-1-yl)-propoxy]-phenyl}-2-methyl-2,5,6,7-tetrahydro-cyclopenta[d]pyridazin-1-one | 193-4 | 384 (M + H) |
| 128 | 2-Isopropyl-5-{4-[3-((R)-2-methyl-pyrrolidin-1-yl)-propoxy]-phenyl}-2H-pyridazin-3-one | 251-3 | 356 (M + H) |
| 129 | 2-[3-((R)-2-Methyl-pyrrolidin-1-yl)-propoxy]-5-(6-oxo-1,6-dihydro-pyridazin-3-yl)-benzonitrile | >200 dec. base | 339 (M + H) |
| 130 | 2-[3-(piperidin-1-yl)-propoxy]-5-(6-oxo-1,6-dihydro-pyridazin-3-yl)-benzonitrile | 207-9 base | 339 (M + H) |
| 131 | 2-(2-Hydroxy-ethyl)-6-{4-[3-((R)-2-methyl-pyrrolidin-1-yl)-propoxy]-phenyl}-2H-pyridazin-3-one | 95-98 base | 358 (M + H) |
| 132 | 6-{4-[(S)-2-Methyl-3-((R)-2-methyl-pyrrolidin-1-yl)-propoxy]-phenyl}-2H-pyridazin-3-one | 163-7 base | 328 (M + H) |

| Example | Structure | Mp (° C.) | MS m/z |
|---|---|---|---|
| 133 | 4-[4-(3-Piperidin-1-yl-propoxy)-phenyl]-2,5,6,7-tetrahydro-cyclopenta[d]pyridazin-1-one | 134 dec. base | 354 (M + H) |
| 134 | 6-[4-(3-Piperidin-1-yl-propoxy)-phenyl]-2H-pyridazin-3-one | 186 dec. base | 314 (M + H) |
| 135 | 6-[3-Methoxy-4-(3-piperidin-1-yl-propoxy)-phenyl]-2H-pyridazin-3-one | 175 dec. base | 344 (M + H) |
| 136 | 6-{3-Methoxy-4-[3-((R)-2-methyl-pyrrolidin-1-yl)-propoxy]-phenyl}-2H-pyridazin-3-one | 148 dec. base | 344 (M + H) |
| 137 | 6-[2-Methyl-4-(3-piperidin-1-yl-propoxy)-phenyl]-2H-pyridazin-3-one | 114 dec. base | 328 (M + H) |
| 138 | 6-{4-[3-((R)-2-Methyl-pyrrolidin-1-yl)-propoxy]-phenyl}-2-pyrimidin-2-yl-2H-pyridazin-3-one | >200 tartrate | 392 (M + H) |

| Example | Structure | Mp (° C.) | MS m/z |
|---|---|---|---|
| 168 | 6-{4-[3-((R)-2-Methyl-pyrrolidin-1-yl)-propoxy]-phenyl}-2-(2,2,2-tri-fluoro-ethyl)-4,5-dihydro-2H-pyridazin-3-one | 76-78 base | 398 (M + H) |
| 169 | 6-{4-[3-piperidin-1-yl-propoxy]-phenyl}-2-(2,2,2-tri-fluoro-ethyl)-4,5-dihydro-2H-pyridazin-3-one | 87-89 base | 398 (M + H) |
| 170 | 6-{4-[3-((R)-2-Methyl-pyrrolidin-1-yl)-propoxy]-phenyl}-2-(2,2,2-tri-fluoro-ethyl)-2H-pyridazin-3-one | 121-123 base | 396 (M + H) |
| 171 | 6-[4-(3-Piperidin-1-yl-propoxy)-phenyl]-2-(2,2,2-trifluoro-ethyl)-2H-pyridazin-3-one | 128-130 base | 396 (M + H) |

Example 139

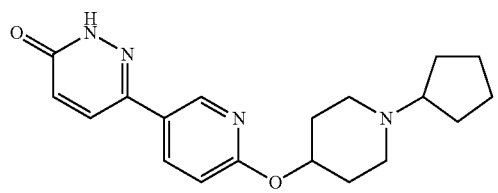

6-[6-(1-Cyclopentyl-piperidin-4-yloxy)-pyridin-3-yl]-2H-pyridazin-3-one

Step 1

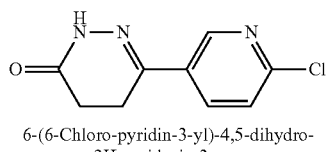

6-(6-Chloro-pyridin-3-yl)-4,5-dihydro-2H-pyridazin-3-one

To ethyl-4-(4-chloro-3-pyridyl)-4-oxobutyrate (5 g, 20.7 mmol) in ethanol (30 mL) was added hydrazine monohydrate (964 µM, 31 mmol). After overnight stirring at 80° C., the reaction was concentrated to half of the volume and the resulting yellow solid was filtered off and dried to give 3.4 g of product (77%); MS m/z 210 (M+H).

Step 2

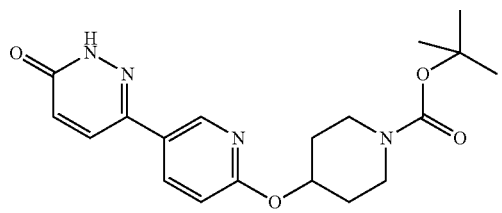

4-[5-(6-Oxo-1,6-dihydro-pyridazin-3-yl)-pyridin-2-yloxy]-piperidine-1-carboxylic acid tert-butyl ester To 6-(6-chloro-pyridin-3-yl)-4,5-dihydro-2H-pyridazin-3-one (3 g, 14.4 mmol) in DMSO (40 mL) was added 4-hydroxy-boc-piperidine (2.9 g, 14.4 mmol), followed by 1M KtOBu (19 mL). After overnight stirring at 100° C. open to air, the reaction was cooled, diluted with dichloromethane and washed several times with water/brine, dried over sodium sulfate, and concentrated under vacuum to obtain 4.9 g crude product (92%); MS m/z 373 (M+H).

Step 3

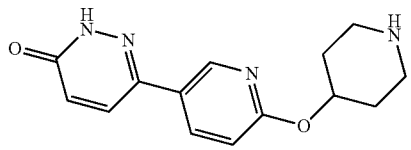

6-[6-(Piperidin-4-yloxy)-pyridin-3-yl]-2H-pyridazin-3-one

To 4-[5-(6-oxo-1,6-dihydro-pyridazin-3-yl)-pyridin-2-yloxy]-piperidine-1-carboxylic acid tert-butyl ester (4.9 g, 13.2 mmol) in dioxane (30 mL) was added 4N HCl/dioxane (6.6 mL, 3 mmol). After overnight stirring at 60° C., the reaction was concentrated under vacuum to obtain 4 g of product as the HCl salt (quantitative); MS m/z 327 (M+H).

Example 139

Step 4

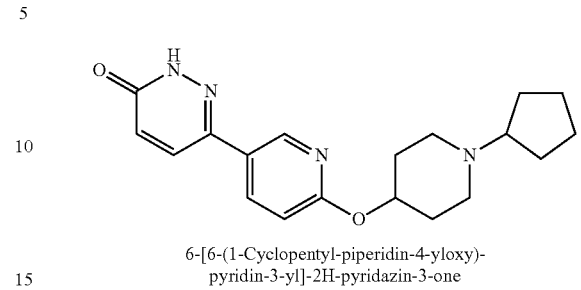

6-[6-(1-Cyclopentyl-piperidin-4-yloxy)-pyridin-3-yl]-2H-pyridazin-3-one

6-[6-(piperidin-4-yloxy)-pyridin-3-yl]-2H-pyridazin-3-one hydrochloride (407 mg, 1.18 mmol) in a mixture of DMF (5 mL), methanol (15 mL), and acetic acid (250 µL) was added cyclopentanone (314 µL, 3.54 mmol), followed by sodium cyanoborohydride (371 mg, 5.9 mmol). After stirring at 60° C. for 2 h, the reaction was concentrated, partitioned between dichloromethane/1N sodium carbonate, washed with water/brine, dried over sodium sulfate, and concentrated. The product was purified using prep TLC plates (9:1 dichloromethane:methanol) (25%); Mp 233-237° C.; MS m/z 341 (M+H).

Example 140

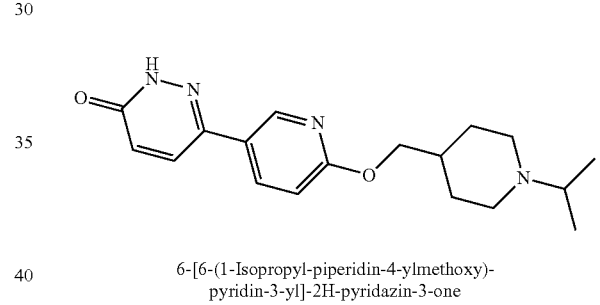

6-[6-(1-Isopropyl-piperidin-4-ylmethoxy)-pyridin-3-yl]-2H-pyridazin-3-one

To the product from step 1 Example 139 (115 mg, 0.55 mmol) in DMSO (5 mL) was added (1-isopropanol-piperidin-4-yl)methanol (130 mg, 0.83 mmol) and 1M KtOBu (1.1 mL, 1.1 mmol). After overnight stirring at 100° C., the reaction was diluted with dichloromethane, washed with water/brine several times, dried over sodium sulfate, and concentrated. The product was purified by prep TLC plates to obtain 64 mg (35%); Mp 188-191° C.; MS m/z 329 (M+H).

The following examples were prepared using methods for example 139

| Example | Structure | Mp (° C.) | MS m/z |
|---|---|---|---|
| 141 | 6-[6-(1-Cyclobutyl-piperidin-4-yloxy)-pyridin-3-yl]-2H-pyridazin-3-one | 217-219 | 327 (M + H) |

| Example | Structure | Mp (° C.) | MS m/z |
|---------|-----------|-----------|--------|
| 142 | 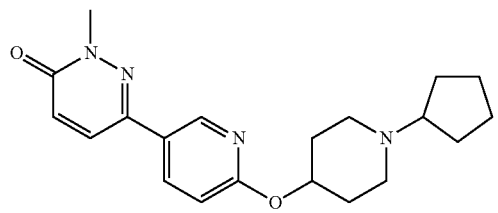<br>6-[6-(1-Isopropyl-piperidin-4-yloxy)-pyridin-3-yl]-2H-pyridazin-3-one | 195-197 | 315 (M + H) |

Example 143

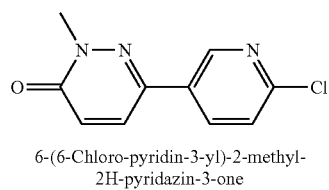

6-[6-(1-Cyclopentyl-piperidin-4-yloxy)-pyridin-3-yl]-2-methyl-2H-pyridazin-3-one

Step 1

6-(6-Chloro-pyridin-3-yl)-2-methyl-2H-pyridazin-3-one

To 6-(6-chloropyridin-3-yl)-4,5-dihydro-2H-pyridazin-3-one (1.03 g, 4.93 mmol) in DMSO (40 mL) was added iodomethane (460 µL, 7.4 mmol) and cesium carbonate (3.2 g, 9.86 mmol). After overnight stirring at 100° C. open to air, the reaction was cooled, diluted with dichloromethane, washed several times with water/brine, dried over sodium sulfate, and concentrated under vacuum to obtain 835 mg product (79%); MS m/z 222 (M+H).

Step 2

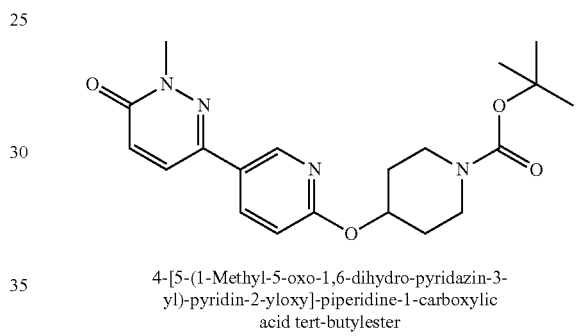

4-[5-(1-Methyl-5-oxo-1,6-dihydro-pyridazin-3-yl)-pyridin-2-yloxy]-piperidine-1-carboxylic acid tert-butylester To 6-(6-chloro-pyridin-3-yl)-2-methyl-2H-pyridazin-3-one (3 g, 13.6 mmol) in toluene (50 mL) was added 4-hydroxy-boc-piperidine (2.7 g, 13.6 mmol) and 1M KtOBu (16.3 mL, 16.3 mmol). After overnight stirring at 80° C., the reaction was concentrated, partitioned between dichloromethane/1N sodium carbonate, washed with water/brine, dried over sodium sulfate, and concentrated. The product was purified by column chromatography (99:1 dichloromethane:methanol) to obtain 2.7 g (51%); MS m/z 387 (M+H).

Example 143-145 were synthesized using Example 139 step 3 and step 4 (deprotection and reductive amination) and Example 143 Step 1 alkylation.

| Example | Structure | Mp (° C.) | MS m/z |
|---------|-----------|-----------|--------|
| 143 | 6-[6-(1-Cyclopentyl-piperidin-4-yloxy)-pyridin-3-yl]-2-methyl-2H-pyridazin-3-one | 154-157 | 355 (M + H) |

-continued

| Example | Structure | Mp (° C.) | MS m/z |
|---|---|---|---|
| 144 | 6-[6-(1-Cyclobutyl-piperidin-4-yloxy)-pyridin-3-yl]-2-methyl-2H-pyridazin-3-one | 175-180 | 341 (M + H) |
| 145 | 6-[6-(1-Cyclobutyl-piperidin-4-yloxy)-pyridin-3-yl]-2H-isopropyl-2H-pyridazin-3-one | 113-115 | 369 (M + H) |

Example 146

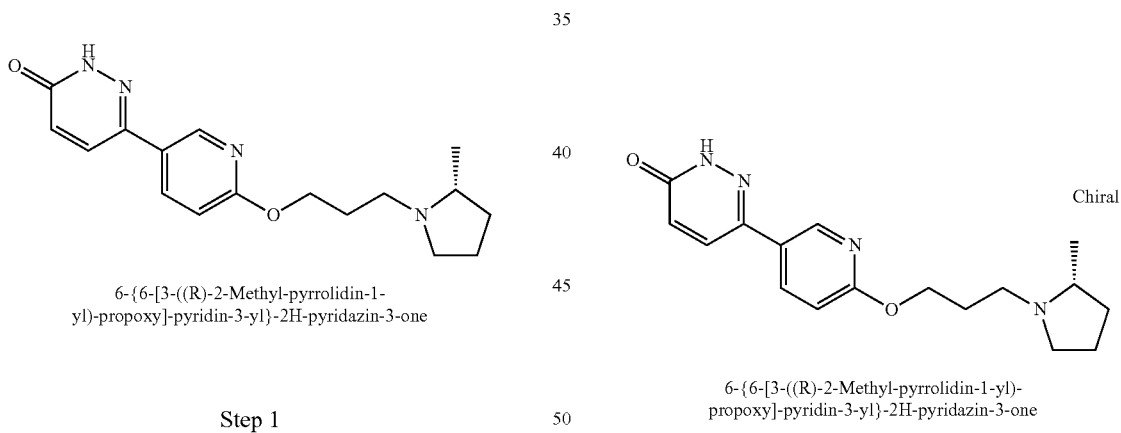

6-{6-[3-((R)-2-Methyl-pyrrolidin-1-yl)-propoxy]-pyridin-3-yl}-2H-pyridazin-3-one

Step 1

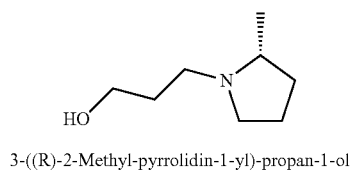

3-((R)-2-Methyl-pyrrolidin-1-yl)-propan-1-ol

To 3-chloro-1-propanol (1.00 g, 10.6 mmol) in 2-butanone (10.00 mL) was added R-2-methyl-pyrrolidine hydrochloride (1.93 g, 15.9 mmol), potassium carbonate (3.65 g, 26.44 mmol), and potassium iodide (1.76 g, 10.6 mmol). After overnight stirring at 100° C., the reaction was filtered, partitioned between dichloromethane/water, washed with brine, dried over sodium sulfate, and concentrated under vacuum to obtain 495 mg product (33%); MS m/z 144 (M+H).

Step 2

To 6-(6-chloro-pyridin-3-yl)-4,5-dihydro-2H-pyridazin-3-one (599 mg, 2.86 mmol) (step 1 example 139) in DMSO (15 mL) was added 3-(R)-2-methylpyrrolidin-1-yl)-propan-1-ol (495 mg, 3.46 mmol) and 1M KOtBu (5.72 mL). After overnight stirring at 110° C. open to air, the reaction mixture was cooled and poured into water, extracted with dichloromethane, washed with brine, dried over sodium sulfate, and concentrated. The product was purified using prep TLC plates (9:1 dichloromethane:methanol) to obtain 68 mg; Mp 178-181° C.; MS m/z 315 (M+H).

Example 147

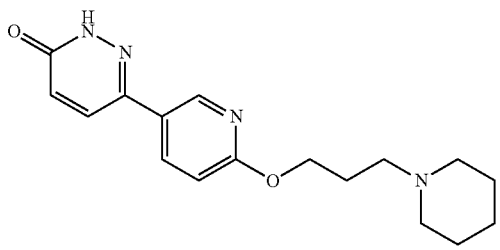

6-[6-(3-Piperidin-1-yl-propoxy)-pyridin-3-yl]-2H-pyridazin-3-one

This compound was prepared using the intermediate from step 1 example 139 and 3-piperidin-1-yl-propanol using methods described for example 146; Mp 155-158° C. MS m/z 315 (M+H).

Example 148

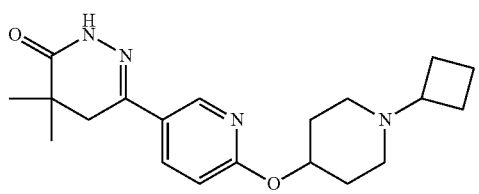

6-[6-(1-Cyclobutyl-piperidin-4-yloxy)-pyridin-3-yl]-4,4-dimethyl-4,5-dihydro-2H-pyridazin-3-one

Step 1

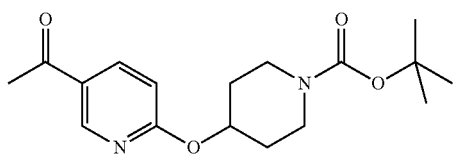

4-(5-Acetyl-pyridin-2-yloxy)-piperidine-1-carboxylic acid tert-butyl ester

To 4-hydroxy-boc-piperidine (1.55 g, 7.71 mmol) in DMSO (12 mL) was added 1M KtOBu (8.36 mL), followed by 1-(6-chloropyridin-3-yl)ethanone (1.00 g, 6.43 mmol). After overnight stirring at 100° C., the reaction was poured into water, extracted with dichloromethane, washed with brine, dried over sodium sulfate, and concentrated. The product was purified using a Single Step column (7:3 hexanes:ethyl acetate) to obtain 0.5 g (25%); MS m/z 321 (M+H).

Step 2

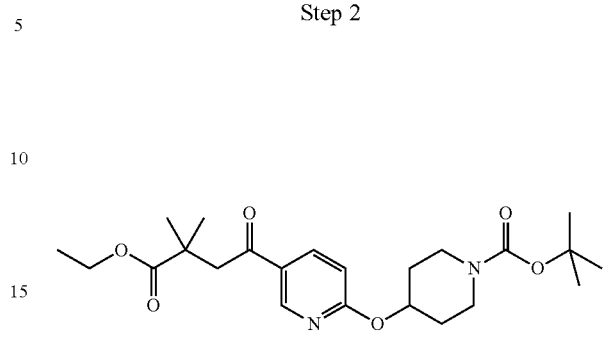

4-[5-(3-Ethoxycarbonyl-3-methyl-butyryl)-pyridin-2-yloxy]-piperidine-1-carboxylic acid tert-butyl ester To 4-(5-acetyl-pyridin-2-yloxy)-piperidine-1-carboxylic acid tert-butyl ester (1.36 g, 4.24 mmol) in THF (15 mL) at −78° C. was added 0.5M potassium bis(trimethylsilyl)amide in toluene (17 mL) and stirred for 30 min before adding 2-bromo-2-methyl-propionic acid ethyl ester (1.25 mL, 8.49 mmol) at −78° C. After overnight stirring at r.t., the reaction was quenched with 1N HCl, extracted with dichloromethane, washed with water/brine, dried over sodium sulfate, and concentrated. The product was purified using a Single Step column (7:3 hexanes:ethyl acetate) to obtain 0.458 g (25%); MS m/z 435 (M+H).

Step 3

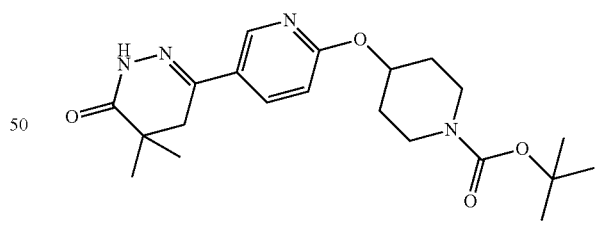

4-[5-(5,5-Dimethyl-6-oxo-1,4,5,6-tetrahydro-pyridazin-3-yl)-pyridin-2-yloxy]-piperidine-1-carboxylic acid tert-butyl ester To 4-[5-(3-ethoxycarbonyl-3-methyl-butyryl-pyridin-2-yloxy]piperidine-1-carboxylic acid tert-butyl ester (0.318 g, 0.732 mmol) in 2-propanol (8 mL) was added hydrazine monohydrate (2 mL). After overnight stirring at 120° C., the reaction was partitioned between dichloromethane/water, washed with brine, dried over sodium sulfate, and concentrated under vacuum to obtain 0.235 mg product (80%); MS m/z 403 (M+H).

Step 4

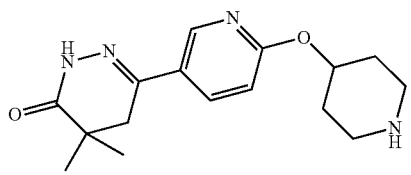

4,4-Dimethyl-6-[6-(piperidin-4-yloxy)-
pyridin-3-yl]-4,5-dihydro-2H-pyridazin-3-one To 4-[5-(5,5-dimethyl-6-oxo-1,4,5,6-tetrahydro-pyridazin-3-yl)-pyridin-2-yloxy]-piperidine-1-carboxylic acid tert-butyl ester (0.340 g, 0.845 mmol) in dichloromethane (5 mL) was added TFA (0.700 mL). After stirring at r.t. for ~3 h, the reaction was concentrated under vacuum to obtain product as the TFA salt (quantitative); MS m/z 303 (M+H).

Example 148 was prepared using the product from step 4 and cyclobutanone using the procedure for example 139 step 4; m 240-245; MS m/z 357 (M+H).

Example 149

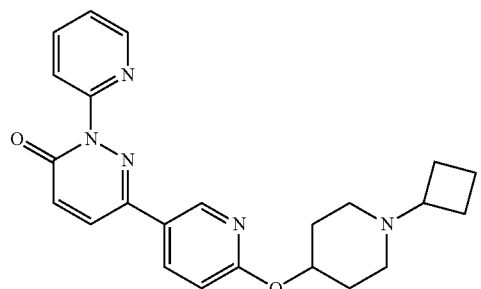

6-[6-(1-Cyclobutyl-piperidin-4-yloxy)-
pyridin-3-yl]-2-pyridin-2-yl-2H-
pyridazin-3-one Step 1

To example 141 (0.509 g, 1.56 mmol) in DMF (8 mL) was added potassium carbonate (0.431 g, 3.12 mmol), 2-bromopyridine (0.223 mL, 2.34 mmol), and copper(I) iodide (0.0297 g, 0.156 mmol). After stirring at 150° C. for 4 h, the reaction was cooled, diluted with dichloromethane, washed with water/brine, dried over sodium sulfate, and concentrated. The product was purified using Prep. TLC plates (9:1 dichloromethane:methanol), dissolved in methanol with 1N HCl/ether (~2 mL) added, concentrated, and recrystallized from methanol/ether as the HCl salt to give 0.223 mg (33%); Mp 261-262° C.; MS m/z 404 (M+H).

Example 150

Step 1

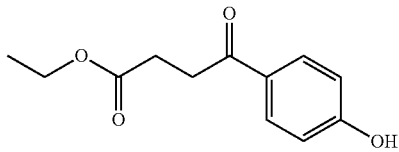

4-(4-Hydroxy-phenyl)-4-oxo-butyric
acid ethyl ester

To 4-(4-methoxy-phenyl)-4-oxo-butyric acid ethyl ester (4.5 g, 19.0 mmol) was added 48% HBr (50 mL). After overnight stirring at 120° C., the reaction was concentrated and ethanol was added several times and concentrated to obtain 4.18 g product (94%); MS m/z 223 (M+H).

Step 2

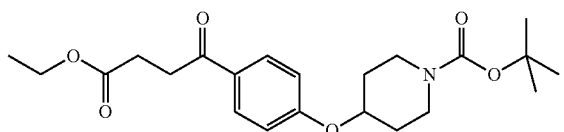

4-[4-(3-Ethoxycarbonyl-propionyl)-
phenoxy]-piperidine-1-carboxylic acid
tert-butyl ester To triphenylphosphine (2.48 g, 9.48 mmol) in THF (25 mL) was added 40% w/w DEAD in toluene (4.00 mL, 8.95 mmol) and the reaction was cooled at 0° C. before adding a mixture of 4-hydroxy-boc-piperidine (1.44, 7.14 mmol) and 4-(4-hydroxyphenyl)-oxo-butyric acid ethyl ester (1.3 g, 5.8 mmol) in THF (25 mL). After overnight stirring at r.t., the reaction was concentrated and the product was purified using a Single Step column (7:3 hexanes:ethyl acetate) to obtain 2.17 g (91%); MS m/z 406 (M+H).

Step 3

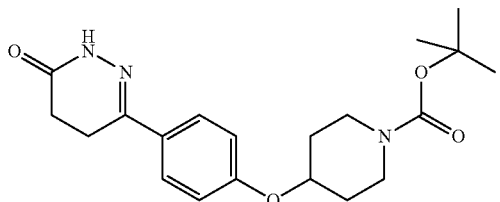

4-[4-(6-Oxo-1,4,5,6-tetrahydro-pyridazin-
3-yl)-pheonoxy]-piperidine-1-carboxylic
acid tert-butyl ester To 4-[4-(3-ethoxycarbonyl-propionyl)-phenoxy]-piperidine-1-carboxylic acid tert-butyl ester (2.68 g, 6.61 mmol) in 2-propanol (25 mL) was added hydrazine monohydrate (0.662 g, 13.2 mmol). After overnight stirring at 120° C., the reaction was concentrated down, partitioned between dichloromethane/water, washed with brine, dried over sodium sulfate, and concentrated under vacuum to obtain 2.18 g product (88%); MS m/z 374 (M+H).

Example 150

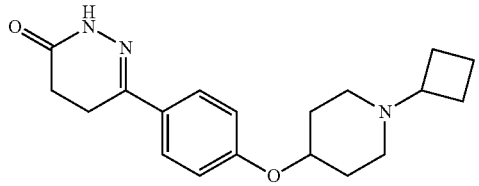

6-[4-(1-Cyclobutyl-piperidin-4-yloxy)-phenyl]-4,5-dihydro-2H-pyridazin-3-one

6-[4-(piperidin-4-yloxy)-phenyl]-4,5-dihydro-2H-pyridazin-3-one trifluoroacetate was prepared using conditions for Example 148 step 4.

To 6-[4-(piperidin-4-yloxy)-phenyl]-4,5-dihydro-2H-pyridazin-3-one trifluoroacetate (6.50 g, 23.8 mmol) in DMF (10 mL), methanol (50 mL), and acetic acid (2 mL) was added cyclobutanone (5.33 mL, 71.3 mmol) and sodium cyanoborohydride (7.47 g, 119 mmol) in portions. After stirring at 60° C. for 4 h, the reaction was concentrated, diluted with dichloromethane, washed with water/brine, dried over sodium sulfate, and concentrated. The product was purified using a Single Step column (9:1 dichloromethane:methanol) and recrystallized from chloroform/ether to obtain 2.2 g (40%); Mp=196-198° C.; MS m/z 328 (M+H).

Examples 151-153 were synthesized using procedures for Example 150.

| Example | Structure | Mp (° C.) | MS m/z |
|---|---|---|---|
| 150 | 6-[4-(1-Cyclobutyl-piperidin-4-yloxy)-phenyl]-4,5-dihydro-2H-pyridazin-3-one | 196-198 | 328 (M + H) |
| 151 | 6-[4-(1-Cyclobutyl-piperidin-4-yloxy)-3-fluoro-phenyl]-4,5-dihydro-2H-pyridazin-3-one | 195-197 | 346 (M + H) |
| 152 | 6-[4-(1-Cyclobutyl-piperidin-4-yloxy)-phenyl]-4,4-dimethyl-4,5-dihydro-2H-pyridazin-3-one | 157-158 | 356 (M + H) |

-continued

| Example | Structure | Mp (° C.) | MS m/z |
|---|---|---|---|
| 153 | 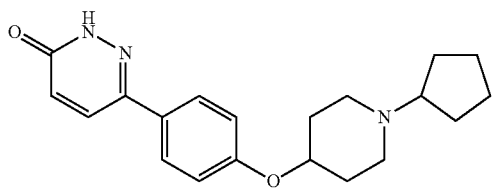  6-[4-(1-Cyclobutyl-piperidin-4-yloxy)-3-fluoro-phenyl]-4,4-dimethyl-4,5-dihydro-2H-pyridazin-3-one | 147-149 | 374 (M + H) |

Example 154

6-[4-(1-Cyclopentyl-piperidin-4-yloxy)-phenyl]-2H-pyridazin-3-one

To example 150 (130 mg, 3.81 mmol) in DMSO (3 mL) was added cesium carbonate (248 mg, 7.61 mmol). After stirring at 130° C. for 2 h open to air, the reaction was filtered, diluted with dichloromethane, washed with water/brine, dried over sodium sulfate, and concentrated. The product was purified using Prep. TLC plates (9:1 dichloromethane:methanol) to obtain 48 mg (37%); Mp 211-213° C.; MS m/z 340 (M+H).

Examples 155-156 were synthesized using methods for example 154.

| Example | Structure | Mp (° C.) | MS m/z |
|---|---|---|---|
| 154 | 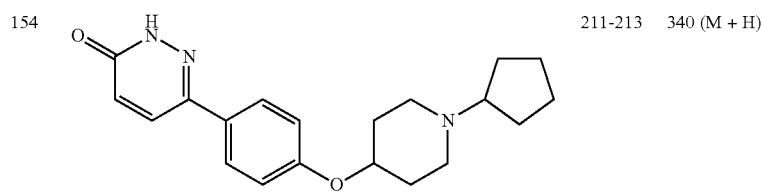  6-[4-(1-Cyclopentyl-piperidin-4-yloxy)-phenyl]-2H-pyridazin-3-one | 211-213 | 340 (M + H) |
| 155 | 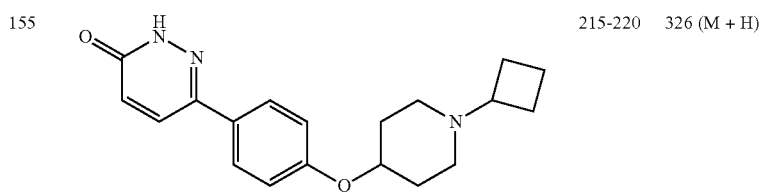  6-[4-(1-Cyclobutyl-piperidin-4-yloxy)-phenyl]-2H-pyridazin-3-one | 215-220 | 326 (M + H) |

| Example | Structure | Mp (° C.) | MS m/z |
|---|---|---|---|
| 156 | 6-[4-(1-Cyclobutyl-piperidin-4-yloxy)-3-fluoro-phenyl]-2H-pyridazin-3-one | 236-238 | 344 (M + H) |

Example 157

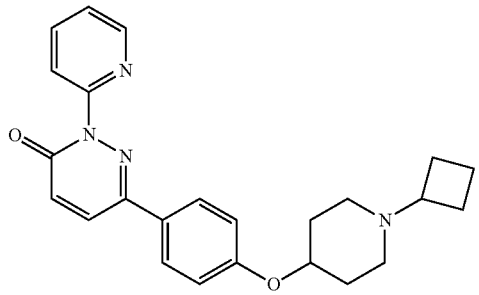

To example 150 (1.50 g, 4.58 mmol) in DMSO (20 mL) was added potassium carbonate (1.90 g, 13.7 mmol), 2-bromopyridine (0.872 mL, 9.16 mmol), and copper(I) iodide (0.0872 g, 0.458 mmol). After overnight stirring at 150° C. open to air, the reaction was filtered, diluted with dichloromethane, washed with water/brine, dried over sodium sulfate, and concentrated. The product was purified using a single step column (9:1 dichloromethane:methanol), dissolved in methanol and 1N HCl/ether (~2 mL) was added, concentrated, and the product was recrystallized from methanol/ether as the HCl salt to obtain 53 mg; Mp>240° C. (dec.); MS m/z 403 (M+H).

Example 158

Step 1

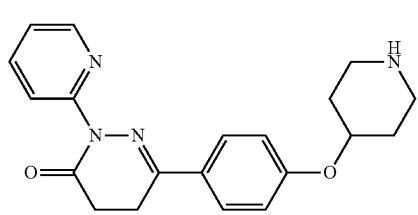

6-[4-(Piperidin-4-yloxy)-phenyl]-2-pyridin-2-yl-4,5-dihydro-2H-pyridazin-3-one

To 4-[4-(3-carboxy-propionyl)-phenoxy]-piperidine-1-carboxylic acid tert-butyl ester (1.34 g, 3.55 mmol) in acetic acid (20 mL) was added 2-hydrazinopyridine (1.94 g, 17.8 mmol). After overnight stirring at 120° C., the reaction was concentrated under vacuum and the product was purified using a Single Step column (9:1 dichloromethane:methanol) to obtain 295 mg; MS m/z 351 (M+H).

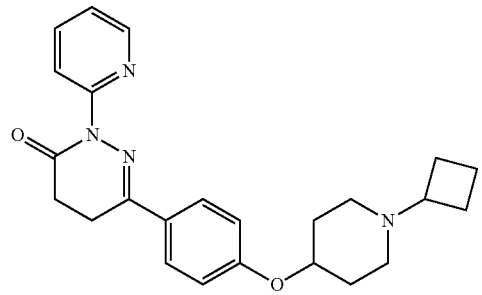 [SMILES: O=c1ccc(-c2ccc(OC3CCN(C4CCC4)CC3)cc2)nn1-c1ccccn1]

6-[4-(1-Cyclobutyl-piperidin-4-yloxy)-phenyl]-2-pyridin-2-yl-4,5-dihydro-2H-pyridazin-3-one Example 158 was synthesized from the product in step 1 by reductive amination described for example 150 and forming the HCl salt; Mp 263-265 MS m/z 405 (M+H).

Examples 159-167 were prepared using methods described for examples 150-157.

| Example | Structure | Mp (° C.) | MS m/z |
|---|---|---|---|
| 159 | 6-[4-((R)-1-Cyclohexyl-pyrrolidin-3-yloxy)-phenyl]-4,5-dihydro-2H-pyridazin-3-one | 184-6 | 342 (M + H) |
| 160 | 6-[4-((R)-1-Cyclobutyl-pyrrolidin-3-yloxy)-phenyl]-2H-pyridazin-3-one | 200-2 | 340 (M + H) |
| 161 | 6-[4-((R)-1-Cyclobutyl-pyrrolidin-3-yloxy)-phenyl]-2H-pyridazin-3-one | — | 311 (M + H) |
| 162 | 6-[4-((R)-1-Cyclopentyl-pyrrolidin-3-yloxy)-phenyl]-4,5-dihydro-2H-pyridazin-3-one | — | 328 (M + H) |

-continued

| Example | Structure | Mp (° C.) | MS m/z |
|---|---|---|---|
| 163 | 2-Cyclobutyl-6-[4-(1-cyclobutyl-piperidin-4-yloxy)-phenyl]-4,5-dihydro-2H-pyridazin-3-one | 120-123 | 382 (M + H) |
| 164 | 2-Cyclobutyl-6-[4-(1-cyclopentyl-piperidin-4-yloxy)-phenyl]-4,5-dihydro-2H-pyridazin-3-one | 100-104 | 396 (M + H) |
| 165 | 2-Cyclobutyl-6-[4-(1-piperidin-4-yloxy)-phenyl]-4,5-dihydro-2H-pyridazin-3-one | 168-170 | 328 (M + H) |
| 166 | 6-[4-(1-Cyclobutyl-piperidin-4-yloxy)-phenyl]-2-(2,2,2-trifluoro-ethyl)-4,5-dihydro-2H-pyridazin-3-one | 146-147 | 410 (M + H) |

| Example | Structure | Mp (° C.) | MS m/z |
|---|---|---|---|
| 167 | 6-[4-(1-Cyclopentyl-piperidin-4-yloxy)-phenyl]-2-(2,2,2-trifluoro-ethyl)-4,5-dihydro-2H-pyridazin-3-one | 225-227 | 424 (M + H) |

Example 172

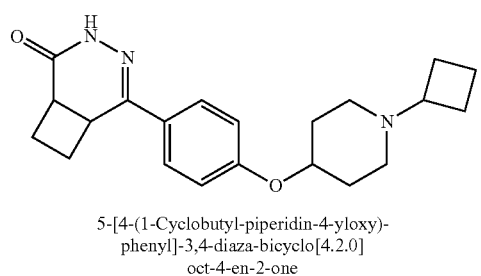 [SMILES: O=C1NN=C(c2ccc(OC3CCN(C4CCC4)CC3)cc2)C2CCC12]

5-[4-(1-Cyclobutyl-piperidin-4-yloxy)-phenyl]-3,4-diaza-bicyclo[4.2.0]oct-4-en-2-one

Step 1

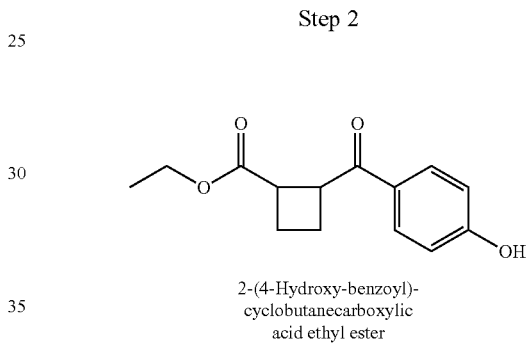

2-(4-Methoxy-benzoyl)-cyclobutanecarboxylic acid

To 3-oxabicyclo[3.2.0]heptane-2,4-dione (8.00 g, 63.4 mmol) in THF (90.00 mL) at −78° C. was added 0.500 M of p-anisyl magnesium bromide (133 mL, 66.6 mmol) in THF (90 mL) dropwise. After stirring at −78° C. for 2 h, the reaction was quenched with ice cold water and concentrated. The aqueous layer was acidified and the white solid was filtered off and dried to obtain 9.72 g product (65%); MS m/z 233 (M−H).

Step 2

2-(4-Hydroxy-benzoyl)-cyclobutanecarboxylic acid ethyl ester

To 2-(4-methoxy-benzoyl)-cyclobutanecarboxylic acid (10.28 g, 43.88 mmol) was added 48% hydrogen bromide in water (50 mL) and acetic acid (50 mL). After overnight stirring at 120° C., the reaction was concentrated, stirred with ethanol a few times, and the product was purified using a Single Step column (7:3 hexanes:ethyl acetate) to obtain 7.70 g (71%); MS m/z 247 (M−H).

Example 172 HCl was synthesized from the product in step 2 using procedures described for example 150; Mp 285-288° C.; MS m/z 354 (M+H)

Example 173

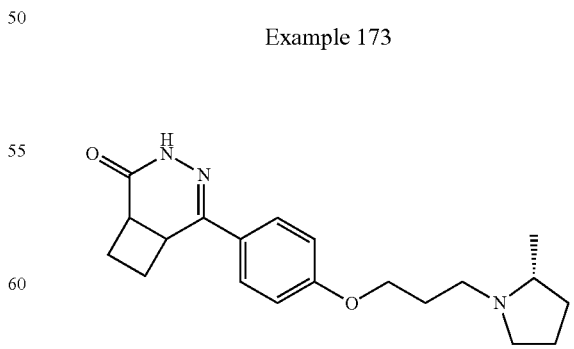

5-{4-[3-((R-2-Methyl-pyrrolidin-1-yl)-propoxy]-phenyl}-3,4-diaza-bicyclo[4.2.0]oct-4-en-2-one

Step 1

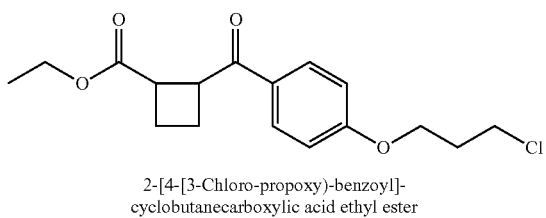 [SMILES: CCOC(=O)C1CCC1C(=O)c1ccc(OCCCCl)cc1]

2-[4-[3-Chloro-propoxy)-benzoyl]-
cyclobutanecarboxylic acid ethyl ester

To 2-(4-hydroxy-benzoyl)-cyclobutanecarboxylic acid ethyl ester (0.55 g, 2.20 mmol) in acetone (10 mL) was added potassium carbonate (0.91 g, 6.58 mmol) and 1-bromo-chloropropane (0.26 mL, 2.63 mmol). After overnight stirring at 70° C., the reaction was filtered, partitioned between dichloromethane/water, washed with brine, dried over sodium sulfate, and concentrated. The product was purified using a Single Step column (9:1 hexanes:ethyl acetate) to obtain 0.30 g (42%); MS m/z 325 (M+H).

Step 2

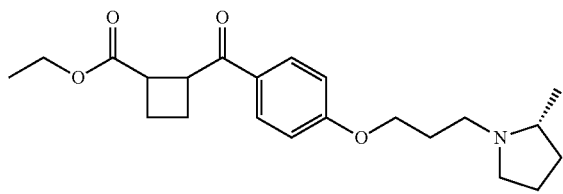

2-{4-[3-((R)-2-Methyl-pyrrolidin-1-
yl)-propoxy]-benzoyl}-cyclobutanecarboxylic
acid ethyl ester To 2-[4-(3-chloro-propoxy)-benzoyl]-cyclobutanecarboxylic acid ethyl ester (0.300 g, 0.924 mmol) in acetonitrile (15 mL) was added (R)-2-methyl-pyrrolidine, benzenesulfonic acid salt (0.337 g, 1.38 mmol), potassium carbonate (0.383 g, 2.77 mmol), and potassium iodide (0.153 g, 0.924 mmol). After overnight stirring at 80° C., the reaction was filtered, diluted with dichloromethane, washed with water/brine, dried over sodium sulfate, and concentrated. The product was purified using a Single Step column (5% methanol/dichloromethane) to obtain 0.213 g (62%); MS m/z 374 (M+H).

Example 173 was synthesized using methods described for example 1 and example 11.

Example 176

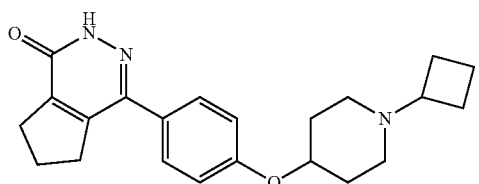

4-[4-[1-Cyclobutyl-piperidin-4-yloxy)-
phenyl]-2,5,6,7-tetrahydro-cyclopenta
[d]pyridazin-1-one To example 174 (0.500 g, 1.36 mmol) in DMSO (5 mL) was added cesium carbonate (0.887 g, 2.72 mmol). After overnight stirring at 140° C. open to air, the reaction was poured into water, extracted with dichloromethane, washed with water/brine, dried over sodium sulfate, and concentrated. The product was purified using Prep. TLC plates (9:1 dichloromethane:methanol); Mp=210-213° C.; MS m/z 366 (M+H).

| Example | Structure | Mp (° C.) | MS m/z |
|---|---|---|---|
| 172 | 5-[4-(1-Cyclobutyl-piperidin-4-yloxy)-phenyl]-3,4-diaza-bicyclo[4.2.0]oct-4-en-2-one | 285-288 | 354 (M + H) |

-continued

| Example | Structure | Mp (° C.) | MS m/z |
|---|---|---|---|
| 173 | 5-{4-[3-((R)-2-Methyl-pyrrolidin-1-yl)-propoxy]-phenyl}-3,4-diaza-bicyclo[4.2.0]oct-4-en-2-one | 218-220 | 342 (M + H) |
| 174 | 4-[4-(1-Cyclobutyl-piperidin-4-yloxy)-phenyl]-2,4a,5,6,7,7a-hexahydro-cyclopenta[d]pyridazin-1-one | dec. >255 | 368 (M + H) |
| 175 | 4-{4-[3-((R)-2-Methyl-pyrrolidin-1-yl)-propoxy]-phenyl}-2,4a,5,6,7,7a-hexahydro-cyclopenta[d]pyridazin-1-one | 218-219 | 356 (M + H) |
| 176 | 4-[4-(1-Cyclobutyl-piperidin-4-yloxy)-phenyl]-2,5,6,7-tetrahydro-cyclopenta[d]pyridazin-1-one | 210-213 | 366 (M + H) |

Example 177

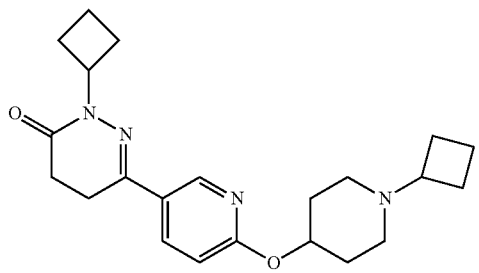

2-Cyclobutyl-6-[6-(1-cyclobutyl-piperidin-4-yloxy)-pyridin-3-yl]-4,5-dihydro-2H-pyridazin-3-one This compound was prepared using ethyl-4-(4-chloro-3-pyridyl)-4-oxobutyrate and cyclobutyl hydrazine using methods described for examples 139 and 143; Mp 146-49 MS m/z 384 (M+H).

Example 178

Method A

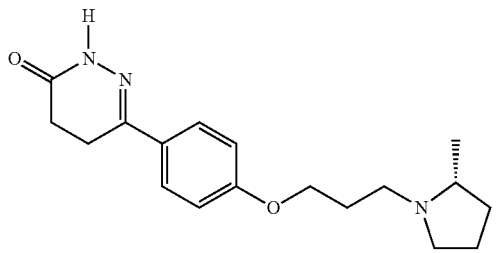

6-{4-[3-((R)-2-Methyl-pyrrolidin-1-yl)-propoxy]-phenyl}-4,5-dihydro-2H-pyridazin-3-one Step 1 4-(4-Hydroxy-phenyl)-4-oxo-butyric acid ethyl ester (3.0 g, 13.5 mmol), 1-bromo-3-chloropropane (4.2 g, 27 mmol) and K$_2$CO$_3$ (5.6 g, 41 mmol) in acetonitrile (50 mL) was stirred at reflux for 12 h. The reaction was filtered, concentrated and purified by silica gel chromatography to give 3.2 g (80%).

Step 2

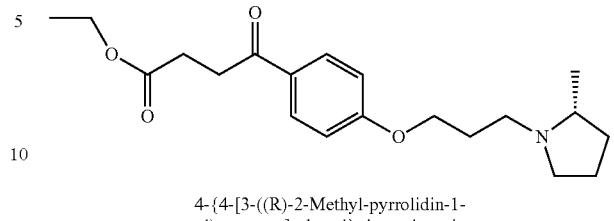

4-{4-[3-((R)-2-Methyl-pyrrolidin-1-yl)-propoxy]-phenyl}-4-oxo-butyric acid ethyl ester The product from step 1 (3.1 g, 10.4 mmol), R-2-methylpyrrolidine HCl (2.5 g, 21 mmol), KI (0.9 g) and K$_2$CO$_3$ (4.1 g, 2.9 mmol) in acetonitrile (75 mL) was stirred at 90° C. for 2 days. The reaction was cooled, filtered and concentrated. The residue was dissolved in Et2O (75 mL) and washed with water and NaCL solution, dried (MgSO$_4$) and concentrated to an oil; MS m/e 348 (M+H).

Step 3

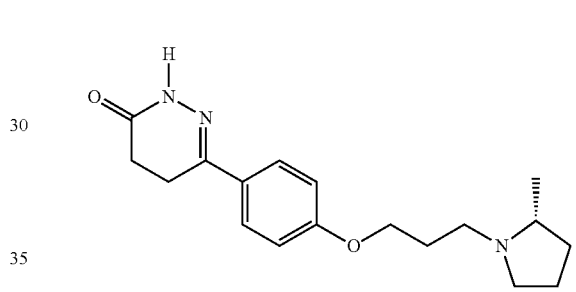

6-{4-[3-((R)-2-Methyl-pyrrolidin-1-yl)-propoxy]-phenyl}-4,5-dihydro-2H-pyridazin-3-one The product from step 2 (3.0 g, 8.6 mmol) and hydrazine hydrate (0.33 g, 10 mmol) in isopropanol (50 mL) was stirred at 95° C. for 24 h. The reaction was cooled to rt, concentrated and the product recrystallized from EtOAc—hexane; Mp 142-45; MS m/z 316 (M+H).

The examples in the following table were synthesized using conditions for example 178 starting with 4-(4-hydroxy-phenyl)-2,2-dimethyl-4-oxo-butyric acid ethyl ester or 4-(3-fluoro-4-hydroxy-phenyl)-4-oxo-butyric acid ethyl ester.

| Example | Structure | Mp (° C.) | MS m/z |
|---|---|---|---|
| 179 | 4,4-Dimethyl-6-{4-[3-((R)-2-methyl-pyrrolidin-1-yl)-propoxy]-phenyl}-4,5-dihydro-2H-pyridazin-3-one | 140-2 base | 344 (M + H) |

| Example | Structure | Mp (° C.) | MS m/z |
|---|---|---|---|
| 180 | 6-{3-Fluoro-4-[3-((R)-2-methyl-pyrrolidin-1-yl)-propoxy]-phenyl}-4,5-dihydro-2H-pyridazin-3-one | 132-3 base | 334 (M + H) |
| 181 | 6-[3-Fluoro-4-(3-piperidin-1-yl-propoxy)-phenyl]-4,5-dihydro-2H-pyridazin-3-one | 164-166 base | 334 (M + H) |

Example 182

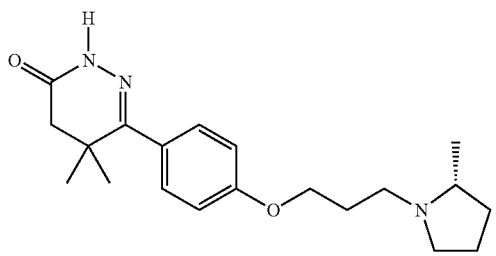

5,5-Dimethyl-6-{4-[3-((R)-2-methyl-pyrrolidin-1-yl)-propoxy]-phenyl}-4,5-dihydro-2H-pyridazin-3-one

Step 1

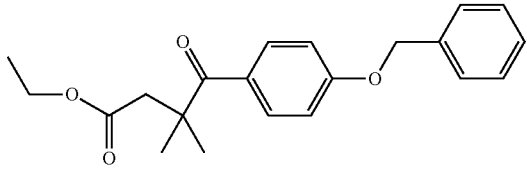

4-(4-Benzyloxy-phenyl)3,3-dimethyl-4-oxo-butyric acid ethyl ester (4-Benzyloxy-phenyl)-trimethylsilanyloxy-acetonitrile (3.0 g, 9.63 mmol) in THF (100 mL) under a nitrogen atmosphere was added LDA (7.2 mL of 2 M in THF) at −72° C. After 0.5 h, methyl 3-methylbut-2-enoate (1.23 mL, 10.1 mmol) in 1 THF (15 mL) was added dropwise. The reaction was stirred at 0° C. for 4 h, and then saturated NH4Cl was added. The THF was removed at reduced pressure; Et2O was added (50 mL) and washed with saturated NH4Cl, water, dried (Na2SO4), and concentrated to give an oil. The oil was dissolved in THF (50 mL) and TBAF (10.1 mL of 1 M THF solution) was added at 0° C. dropwise. After stirring 12 h at rt the reaction was concentrated, dissolved in Et2O and washed with water, NaCl solution and dried (MgSO4). The product was purified by silica gel chromatography (10-20% EtOAc/hexanes) to give 1.5 g; Mp 72-73.

Step 2

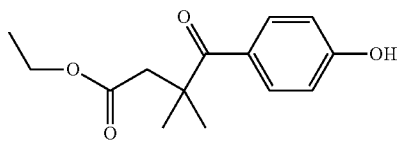

4-(4-Hydroxy-phenyl)-3,3-dimethyl-4-oxo-butyric acid ethyl ester

The product from step 1 (1.25 g, 3.83 mmol) and 10% Pd/C (0.3 g) in MeOH (50 mL) was hydrogenated on a Parr apparatus until TLC indicated completion of the reaction. The mixture was filtered, concentrated to an oil and used directly in the next step; MS m/z 204 (M-OMe).

Step 3

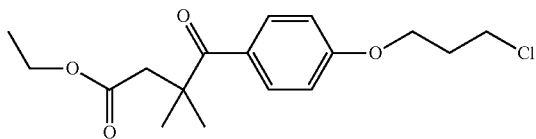

4-[4-(3-Chloro-propoxy)-phenyl]-3,3-dimethyl-4-oxo-butyric acid ethyl ester

The product from step 2 (1.0 g, 4.2 mmol), 1-bromo-3-chloropropane (1.0 g, 8 mmol) and K₂CO₃ in acetonitrile (20 mL) was heated to reflux for 24 h. The reaction was cooled, filtered, concentrated to an oil and purified by ISCO siliga gel chromatography (10% EtOAc/hexanes) to give 0.7 g.

Step 4

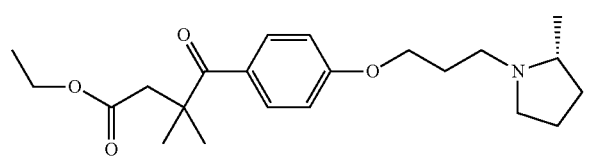

3,3-Dimethyl-4-{4-[3-((R)-2-methyl-pyrrolidin-1-yl)-propoxy]-phenyl}-4-oxo-butyric acid ethyl ester The product from step 3 (0.75 g, 2.4 mmol), R-2-methylpyrrolidine benzene sulfonic acid salt (1.0 g, 5 mmol), K2CO3 (1 g, 7 mmol) and KI (0.1 g) in acetonitrile (25 mL) were heated at 90° C. for 2 days. The reaction was filtered, concentrated, dissolved in Et2O and washed with water, NaCl solution and dried (MgSO₄) to give 0.7 g as an oil; MS m/z 376 (M+H).

Example 182

Step 5

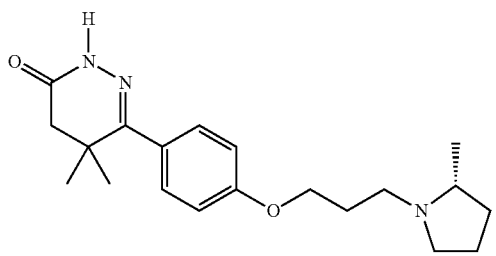

5,5-Dimethyl-6-{4-[3-((R)-2-methyl-pyrrolidin-1-yl)-propoxy]-phenyl}-4,5-dihydro-2H-pyridazin-3-one The product from step 4 (0.75 g, 2.1 mmol) and hydrazine hydrate (2.0 mL) in acetonitrile (25 mL) were heated to reflux for 24 h. The reaction was cooled, concentrated and the product recrystallized using Et₂O-hexanes to give 600 mg (71%); Mp 118-121; MS m/z 344 (M+H).

Example 183

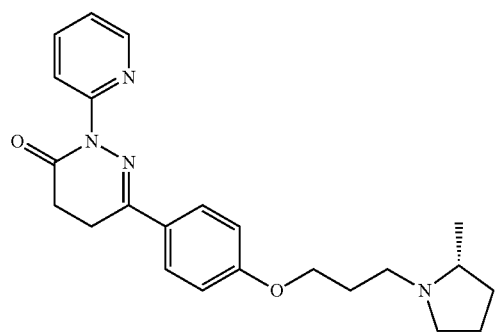

6-{4-[3-((R)-2-Methyl-pyrrolidin-1-yl)-propoxy]-phenyl}-2-pyridin-2-yl-4,5-dihydro-2H-pyridazin-3-one

Step 1

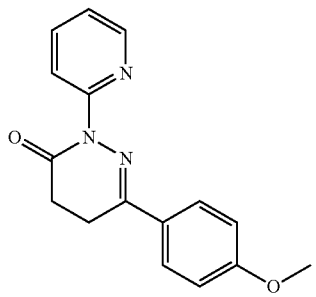

6-(4-Methoxy-phenyl)-2-pyridin-2-yl-4,5-dihydro-2H-pyridazin-3-one

In a 1 neck round bottom flask equipped with a Dean-Stark trap and condenser, 4-(4-methoxyphenyl)-4-oxo-butyric acid (5.0 g, 20 mmol), 2-hydrazinopyridine (3.9 g, 36 mmol) and p-toluene sulfonic acid (0.3 g) in 100 mL benzene were heated to reflux for 2 h while water was removed. The reaction was cooled to rt, an equal volume of Et₂O was added and the product collected; Mp>300° C. This solid was dissolved in HOAc (50 mL) and heated at 100° C. for 6 h. The reaction was concentrated, dissolved in EtOAc and washed with saturated NaHCO₃ solution, water, NaCl solution and dried (MgSO₄). The solvent was concentrated to a thick oil; MS m/z 282 (M+H).

Step 2

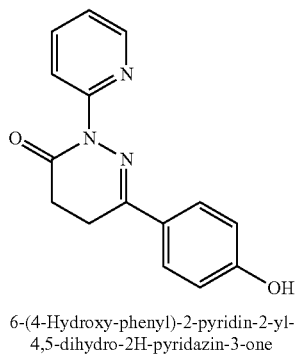 [SMILES: O=C1CCC(c2ccc(O)cc2)=NN1c1ccccn1]

6-(4-Hydroxy-phenyl)-2-pyridin-2-yl-
4,5-dihydro-2H-pyridazin-3-one

The product from step 1 (1.25 g, 4.4 mmol) in DCM (30 mL) was added BBr₃ (30 mL, 1 M in DCM) dropwise at 0° C. After stirring 4 h at rt, the mixture was cooled to 0-5° C. on an ice-bath while saturated NH₄Cl solution (30 mL) was added dropwise. Additional water was added and the DCM was removed at reduced pressure. The solid was collected and dried to give 1.1 g (93%) of a tan solid; Mp>220° C.; MS m/z 268 (M+H).

Step 3

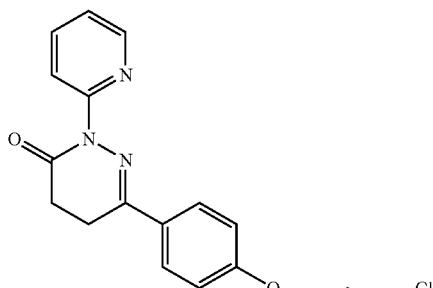

6-[4-(3-Chloro-propoxy)-phenyl]-2-
pyridin-2-yl-4,5-dihydro-2H-pyridazin-3-one

The product from step 3 (5.0 g, 20 mmol), 1-bromo-3-chloropropane (5.9 g, 37.4 mmol) and K₂CO₃ (7.8 g, 56 mmol) in acetonitrile (50 mL) was heated to reflux for 24 h. The reaction was cooled to rt, filtered and concentrated to a thick oil. The product was dissolved in EtOAc and washed with water, NaCl solution and dried (MgSO₄). The product was purified by ISCO silica gel chromatography (95/5/1 DCM/MeOH/1-propylamine) to give 3.7 g of a dark oil; MS m/z 344 (M+H).

Example 183

Step 4

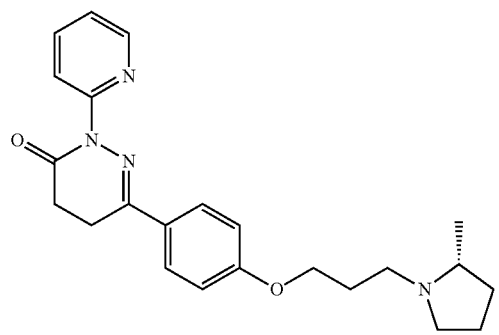

6-{4-[3-((R)-2-Methyl-pyrrolidin-1-
yl)-propoxy]-phenyl}-2-pyridin-2-yl-
4,5-dihydro-2H-pyridazin-3-one The product from step 3 (3.7 g, 10.8 mmol), R-2-methylpyrrolidine benzene sulfonic acid salt (5.24 g, 21.5 mmol), K₂CO₃ (4.46 g, 32.3 mmol) and KI (0.9 g) in acetonitrile (50 mL) were heated to reflux for 2 days. The reaction was cooled, filtered and concentrated. The residue was purified by ISCO silica gel chromatography (95/5/1 DCM/MeOH/1-propylamine) The fractions were concentrated and the HCl salt was prepared using 2M HCl/ether and recrystallized from CH₃CN/ether; Mp 203-205° C.; MS m/z 393 (M+H).

Example 184

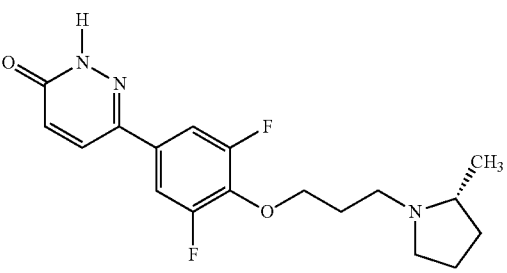

6-{3,5-Difluoro-4-[3-((R)-2-methyl-
pyrrolidin-1-yl)-propoxy]-phenyl}-2H-
pyridazin-3-one

Step 1

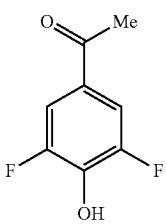

1-(3,5-Difluoro-4-hydroxy-phenyl)-ethanone

A mixture of 1-(3,5-difluoro-4-methoxyphenyl)ethanone (12 g, 64.5 mmol) and 48% aqueous HBr (32 mL) was stirred at reflux for 30 h. The reaction was cooled to rt and diluted with water and the aqueous layer was extracted twice with methylene chloride. The combined organics were dried ($Na_2SO_4$), filtered, and concentrated to give 1-(3,5-difluoro-4-hydroxyphenyl)ethanone (10 g, 91%), mp 141-143° C.; MS m/z 171 (M−H).

Step 2

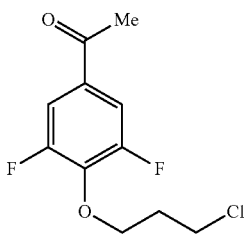

1-[4-(3-Chloro-propoxy)-3,5-difluoro-phenyl]-ethanone

A mixture of 1-(3,5-difluoro-4-hydroxyphenyl)ethanone (8.1 g, 47 mmol), 3-bromo-1-chloropropane (14.7 g, 93 mmol) and $K_2CO_3$ (21.3 g, 154 mmol) in acetone (120 mL) was stirred at reflux for 20 h. The reaction was cooled to rt and concentrated at reduced pressure, then partitioned between water and methylene chloride. The aqueous layer was extracted twice with methylene chloride to obtain 1-[4-(3-chloropropoxy)-3,5-difluoro-phenyl]ethanone (12.9 g, quantitative yield); MS m/z 249 (M+H).

Step 3

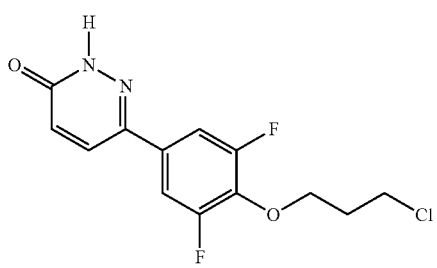

6-[4-(3-Chloro-propoxy)-3,5-difluoro-phenyl]-2H-pyridazin-3-one

A mixture of 1-(4-(3-chloropropoxy)-3,5-difluoro-phenyl]ethanone (11 g, 44.7 mmol) and glyoxalic acid monohydrate (4.2 g, 46.5 mmol) in acetic acid (16 mL) was stirred at 100° C. for 4 h. The acetic acid was evaporated at reduced pressure and diluted with water then cooled to 0° C. and neutralized with ammonium hydroxide to pH 8. To this mixture, hydrazine monohydrate (4.3 mL, 86 mmol) was added and heated at 100° C. for 1 h. The reaction was cooled to rt and the solid was filtered, then dried to give a crude product. The crude product was triturated sequentially with 5% aqueous sodium bicarbonate solution and with a mixture of methylene chloride, methanol, ether and hexane to provide relatively pure product. The product was purified by ISCO (120 g silica gel column) chromatography using 2 to 8% methanol in methylene chloride to furnish 6-[4-(3-chloropropoxy)-3,5-difluorophenyl]-2H-pyridazin-3-one (7.9 g, 59%), MS m/z 301 (M+H).

Step 4

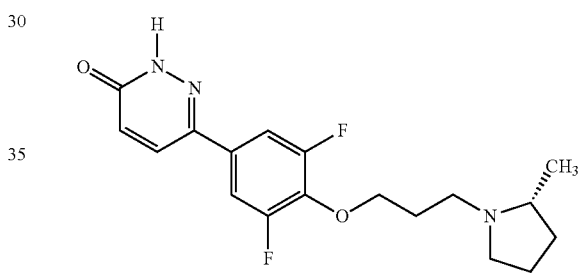

6-{3,5-Difluoro-4-[3-((R)-2-methyl-pyrrolidin-1-yl)-propoxy]-phenyl}-2H-pyridazin-3-one A mixture of 6-[4-(3-chloropropoxy)-3,5-difluorophenyl]-2H-pyridazin-3-one (7.9 g, 26.3 mmol), $K_2CO_3$ (12.7 g 91.9 mmol), NaI (144 mg, 0.96 mmol) and R-methyl-pyrrolidinium benzenesulfonate (13.4 g, 55.3 mmol) in $CH_3CN$ (200 mL) was heated under argon at 80° C. for 35 h. The mixture was filtered over celite and concentrated at reduced pressure and partitioned between saturated aqueous sodium bicarbonate solution and methylene chloride. The aqueous layer was extracted twice with methylene chloride and the combined organics were washed with brine, dried ($Na_2SO_4$), and concentrated. The crude product was purified by ISCO (120 g silica gel column) chromatography using 2 to 5% methanol in methylene chloride to 10% methanol containing 0.25% ammonium hydroxide in methylene chloride to obtain 6-{3,5-difluoro-4-[3-(R)-2-methylpyrrolidin-1-yl)-propoxy]-phenyl}-2H-pyridazin-3-one (4.3 g). The product was

Example 185

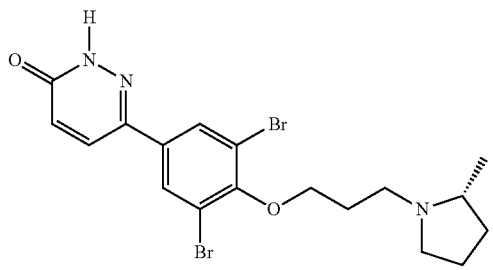

6-{3,5-Dibromo-4-[3-((R)-2-methyl-
pyrrolidin-1-yl)-propoxy]-phenyl}-2H-pyridazin-3-one Example 185 was synthesized using the procedure for example 184; Mp 165-167° C.; MS m/z 472 (M+H).

Example 186

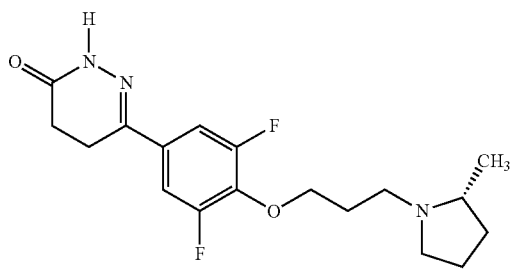

6-{3,5-Difluoro-4-[3-((R)-2-methyl-
pyrrolidin-1-yl)-propoxy]-phenyl}-4,5-
dihydro-2H-pyridazin-3-one

Step 1

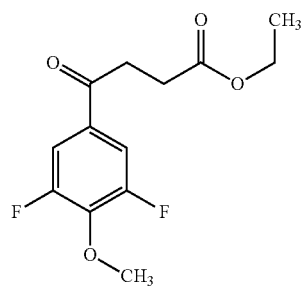

4-(3,5-Difluoro-4-methoxy-phenyl)-4-
oxo-butyric acid ethyl ester

A mixture of 1,3-difluoro-2-methoxybenzene (2.5 g, 17.3 mmol) and ethyl succinyl chloride (4.29 g, 26 mmol) in 1,2-dichloroethane (25 mL) was cooled to 0° C. Aluminum chloride (8 g, 60.1 mmol) was added slowly at 0° C. then stirred at rt for 2 h and quenched with ice and aqueous 2N HCl at 0° C. The aqueous layer was extracted twice with methylene chloride and the combined organics were washed with brine, dried (Na$_2$SO$_4$), filtered, and concentrated to provide a crude product. The crude product was purified by ISCO (80 g silica gel column) chromatography using 8.5% EtOAc in hexane to furnish 4-(3,5-difluoro-4-methoxyphenyl)-4-oxo-butyric acid ethyl ester (2.9 g, 61%).

Step 2

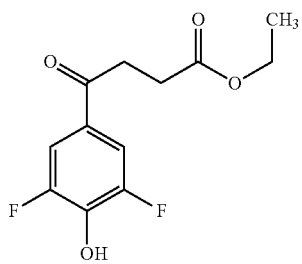

4-(3,5-Difluoro-4-hydroxy-phenyl)-4-
oxo-butyric acid ethyl ester

A mixture of 4-(3,5-difluoro-4-methoxy-phenyl)-4-oxo-butyric acid ethyl ester (2.9 g, 10.6 mmol) and 48% aqueous HBr (15 mL) in acetic acid (30 mL) was stirred at reflux for 8 h. The reaction was cooled to rt and treated three times with ethanol and then concentrated at reduced pressure to provide a crude material. The crude material was dissolved in methylene chloride and washed with water, brine, dried (Na$_2$SO$_4$), filtered, and concentrated to afford 4-(3,5-difluoro-4-hydroxyphenyl-4-oxo-butyric acid ethyl ester (2.5 g, 92%), MS m/z 257 (M+H).

Step 3

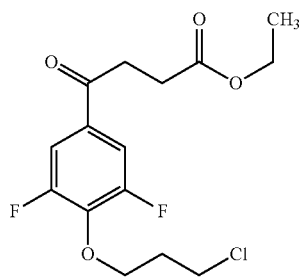

4-[4-(3-Chloro-propoxy)3,5-difluoro-
phenyl]-4-oxo-butyric acid ethyl ester

A mixture of 4-[4-(3-chloropropoxy))-4-oxo-butyric acid ethyl ester (2.5 g, 9.6 mmol), 3-bromo-1-chloropropane (1.9 mL, 18.5 mmol) and K$_2$CO$_3$ (4 g, 28.9 mmol) in acetone (25 mL) was stirred at reflux for 15 h. The reaction was cooled to rt and concentrated at reduced pressure, then partitioned between water and methylene chloride. The aqueous layer was extracted twice with methylene chloride and the combined organics were washed with brine, dried (Na$_2$SO$_4$), filtered, and concentrated to obtain a crude product. The crude product was purified by ISCO (80 g silica gel column) chromatography using 10 to 12.5% EtOAc in hexane to provide 4-[4-(3-chloro-propoxy)-3,5-difluoro-phenyl]-4-oxo-butyric acid ethyl ester (3.1 g, 96%).

Step 4

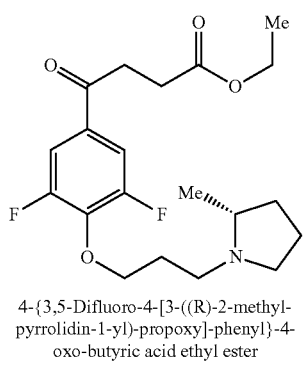 [SMILES: CCOC(=O)CCC(=O)c1cc(F)c(OCCCN2CCC[C@H]2C)c(F)c1]

4-{3,5-Difluoro-4-[3-((R)-2-methyl-pyrrolidin-1-yl)-propoxy]-phenyl}-4-oxo-butyric acid ethyl ester A mixture of 4-[4-(3-chloropropoxy)-3,5-difluorophenyl]-4-oxo-butyric acid ethyl ester (5 g, 14.9 mmol), $K_2CO_3$ (7.2 g, 52.1 mmol), NaI (220 mg, 1.4 mmol), and Benzenesulfonate; (R)-methylpyrrolidinium (8 g, 33 mmol) in $CH_3CN$ (110 mL) was heated under argon at 80° C. for 36 h. The reaction was concentrated and partitioned between saturated aqueous sodium bicarbonate solution and methylene chloride. The aqueous layer was extracted twice with methylene chloride and the combined organics was washed with brine, dried ($Na_2SO_4$), filtered, and concentrated to provide a crude material (96% purity). The crude material was purified by ISCO (80 g silica gel column) chromatography using 2% to 9% methanol in methylene chloride to 10% methanol containing 0.1% ammonium hydroxide in methylene chloride. The isolated material was dissolved in methylene chloride and washed with saturated aqueous sodium bicarbonate solution, brine, dried ($Na_2SO_4$), filtered, and concentrated. The isolated material was crystallized with a mixture of methylene chloride, ether and hexane to obtain 4-{3,5-difluoro-4-[3-(R)-2-methyl-pyrrolidin-1-yl)-propoxy]-phenyl}-4-oxo-butyric acid ethyl ester (3.97 g, 70%, 99% purity), MS m/z=384 (M+H).

Step 5

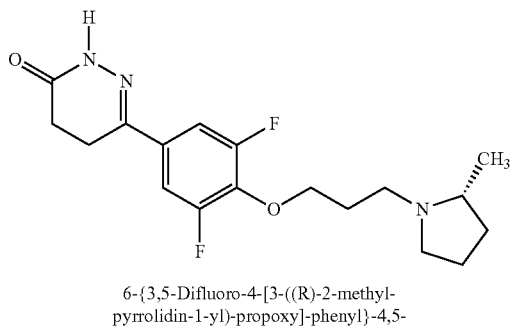

6-{3,5-Difluoro-4-[3-((R)-2-methyl-pyrrolidin-1-yl)-propoxy]-phenyl}-4,5-dihydro-2H-pyridazin-3-one A mixture of 4-{3,5-difluoro-4-[3-(R)-2-methyl-pyrrolidin-1-yl)-propoxy]-phenyl}-4-oxo-butyric acid ethyl ester (3.97 g, 10.4 mmol) and hydrazine monohydrate (1 mL, 20.7 mmol) in isopropanol (25 mL) was heated at 110° C. for 17 h. Isopropanol was evaporated at reduced pressure and partitioned between saturated aqueous sodium bicarbonate solution and methylene chloride. The aqueous layer was extracted twice with methylene chloride and the combined organics was washed with brine, dried ($Na_2SO_4$), filtered, and concentrated to provide a crude material. The crude material was purified by ISCO (80 g) chromatography using 2 to 8% methanol in methylene chloride to 10% methanol containing 0.2% ammonium hydroxide in methylene chloride. The isolated material was dissolved in methylene chloride and washed with saturated aqueous sodium bicarbonate solution, brine, dried ($Na_2SO_4$), filtered, and concentrated. The pure material was crystallized using a mixture of methylene chloride, ether and hexane to obtain 6-{3,5-difluoro-4-[3-(R)-2-methyl-pyrrolidin-1-yl)-propoxy]-phenyl}-4,5-dihydro-2H-pyridazin-3-one (2 g, 55%, 98% purity), mp 102-104° C., MS m/z 352 (M+H).

Example 187

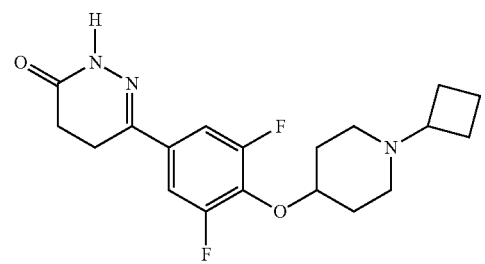

6-[4-(1-Cyclobutyl-piperidin-4-yloxy)-3,5-difluoro-phenyl]-4,5-dihydro-2H-pyridazin-3-one Step 1

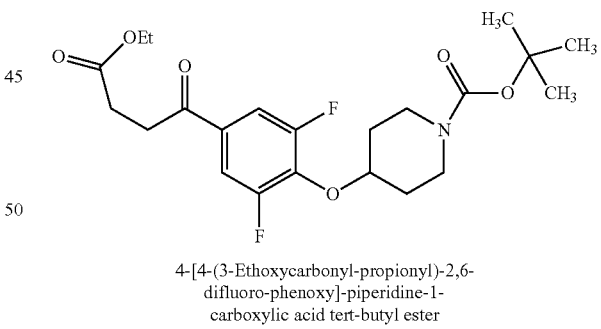

4-[4-(3-Ethoxycarbonyl-propionyl)-2,6-difluoro-phenoxy]-piperidine-1-carboxylic acid tert-butyl ester To a solution of triphenylphosphine (5.79 g, 22.1 mmol) in THF (35 mL) was added 40% w/w DEAD in toluene (10 mL, 15 mmol). The mixture was cooled to 0° C. and a mixture of 4-(3,5-difluoro-4-hydroxy-phenyl)-4-oxo-butyric acid ethyl ester (example 186 step 2) (3.8 g, 14.7 mmol) and 4-hydroxy-piperidine-1-carboxylic acid tert-butyl ester (3.6 g, 18 mmol) in THF (35 mL) was added dropwise under argon. After the addition, the cooling bath was removed and stirred at rt overnight. The reaction mixture was concentrated at reduced pressure and purified by ISCO (120 g) chromatography using 15 to 30% EtOAc in hexane to provide 4-[4-(3-ethoxycarbonylpropionyl)-2,6-difluoro-phenoxy]-piperidine-1-carboxylic acid tert-butyl ester (3.21 g, 49% yield).

Step 2

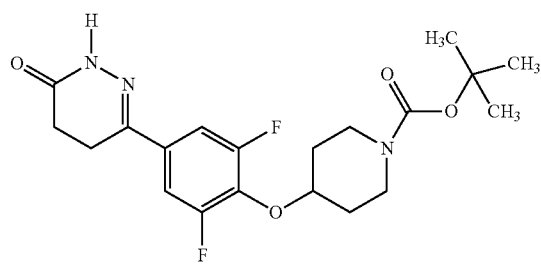

4-[2,6-Difluoro-4-(6-oxo-1,4,5,6-
tetrahydro-pyridazin-3-yl)-phenoxy]-
piperidine-1-carboxylic acid tert-butyl ester A mixture of 4-[4-(3-ethoxycarbonyl-propionyl)-2,6-difluoro-phenoxy]-piperidine-1-carboxylic acid tert-butyl ester (3.21 g, 7.27 mmol) and hydrazine monohydrate (0.7 mL, 14.1 mmol) in isopropanol (20 mL) was stirred at reflux overnight. Isopropanol was concentrated at reduced pressure and partitioned between saturated aqueous sodium bicarbonate solution and methylene chloride. The aqueous layer was extracted twice with methylene chloride and the combined organics was washed with brine, dried ($Na_2SO_4$), filtered, and concentrated to provide a crude material. The crude material was purified by ISCO (80 g silica gel column) chromatography using 15 to 60% EtOAc in hexane to obtain 4-[2,6-difluoro-4-(6-oxo-1,4,5,6-tetrahydro-pyridazin-3-yl)-phenoxy]-piperidine-1-carboxylic acid tert-butyl ester (0.42 g, 14%).

Step 3

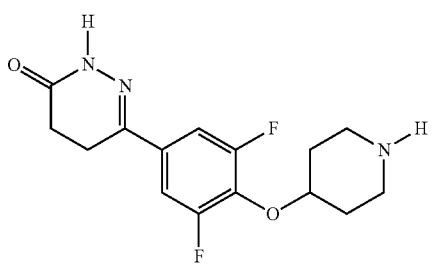

6-[3,5-Difluoro-4-(piperidin-4-yloxy)-
phenyl]-4,5-dihydro-2H-pyridazin-3-one

A solution of 4-[2,6-difluoro-4-(6-oxo-1,4,5,6-tetrahydro-pyridazin-3-yl)-phenoxy]-piperidine-1-carboxylic acid tert-butyl ester (0.42 g, 1 mmol) in methylene chloride (5 mL) was treated with trifluoro acetic acid (10 mL). The mixture was stirred at RT for 3 h and TFA was concentrated at reduced pressure to give 6-[3,5-difluoro-4-(piperidin-4-yloxy)-phenyl]-4,5-dihydro-2H-pyridazin-3-one (0.35 g, quantitative yield), MS m/z 310 (M+H).

Step 4

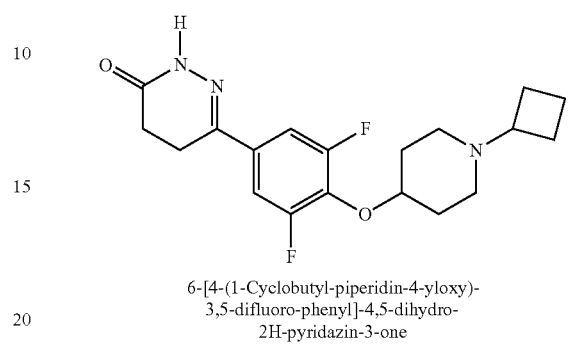

6-[4-(1-Cyclobutyl-piperidin-4-yloxy)-
3,5-difluoro-phenyl]-4,5-dihydro-
2H-pyridazin-3-one A solution of 6-[3,5-difluoro-4-(piperidin-4-yloxy)-phenyl]-4,5-dihydro-2H-pyridazin-3-one (350 mg, 1.1 mmol) in a mixture of DMF (2 mL) and MeOH (9 mL) was stirred under argon. Cyclobutanone (0.38 mL, 5 mmol), sodium cyanoborohydride (0.53 g, 8.45 mmol) and acetic acid (0.4 mL, 7 mmol) were added sequentially and stirred at 60° C. for 3 h. The reaction mixture was concentrated at reduced pressure and partitioned between aqueous 1M sodium carbonate solution and methylene chloride. The aqueous layer was extracted twice with methylene chloride and the combined organics was washed with brine, dried ($Na_2SO_4$), filtered and concentrated to provide a crude product. The crude product was purified by ISCO (40 g) chromatography using 2 to 5% methanol in methylene chloride to 10% methanol containing 0.2% ammonium hydroxide in methylene chloride. The recovered product was dissolved in methylene chloride and washed with saturated aqueous sodium bicarbonate solution, brine, dried ($Na_2SO_4$), filtered, and concentrated to furnish a pure product. The pure product was crystallized with a mixture of methylene chloride, ethanol, ether and hexane to obtain 6-[4-(1-cyclobutyl-piperidin-4-yloxy)-3,5-difluoro-phenyl]-4,5-dihydro-2H-pyridazin-3-one (110 mg, yield), mp 162-164° C.; MS m/z 364 (M+H)

Example 188

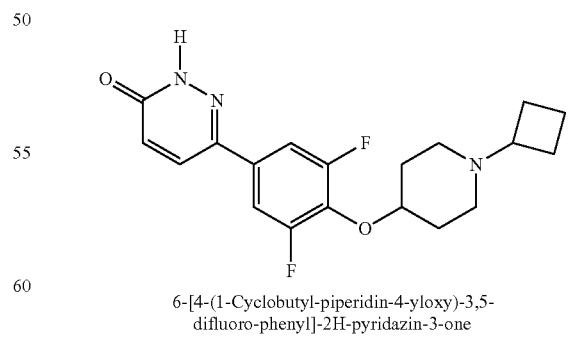

6-[4-(1-Cyclobutyl-piperidin-4-yloxy)-3,5-
difluoro-phenyl]-2H-pyridazin-3-one

A mixture of 6-[4-(1-cyclobutyl-piperidin-4-yloxy)-3,5-difluoro-phenyl]-4,5-dihydro-2H-pyridazin-3-one (137 mg, 0.37 mmol) and cesium carbonate (232 mg, 0.71 mmol) in dimethyl sulfoxide (5 mL) was heated at 130° C. 45 min. The mixture was cooled to rt and partitioned between water and methylene chloride. The aqueous layer was extracted twice with methylene chloride and the combined organics was washed with brine, dried (Na₂SO₄), filtered, and concentrated to provide a crude product. The crude product was purified by ISCO (40 g silica gel column) chromatography using 2% to 8% methanol in methylene chloride to 10% methanol containing 0.2% ammonium hydroxide in methylene chloride. The recovered product was dissolved in methylene chloride and washed with saturated aqueous sodium bicarbonate solution, brine, dried (Na₂SO₄), filtered, and concentrated. The product was crystallized using a mixture of ethanol, ethyl acetate, ether and hexane to give 6-[4-(1-cyclobutyl-piperidin-4-yloxy)-3,5-difluoro-phenyl]-2H-pyridazin-3-one (40 mg, 29%); Mp 195-197° C.; MS m/z 362 (M+H).

Example 189

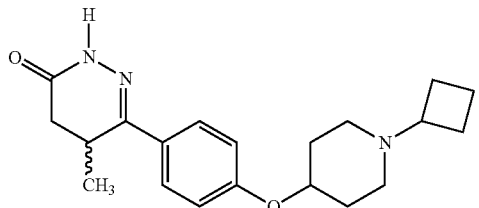

6-[4-(1-Cyclobutyl-piperidin-4-yloxy)-phenyl]-
5-methyl-4,5-dihydro-2H-pyridazin-3-one Step 1

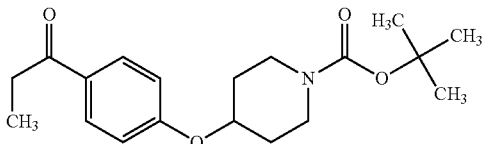

4-(4-Propionyl-phenoxy)-piperidine-
1-carboxylic acid tert-butyl ester

A solution of triphenylphosphine (22.4 g, 85.2 mmol) and 40% w/w DEAD in toluene (12.6 mL, 79.9 mmol) in tetrahydrofuran (100 mL) was cooled to 0° C. A mixture of p-propiophenol (8 g, 53.3 mmol) and 4-hydroxypiperidine-1-carboxylic acid tert-butyl ester (12.9 g, 63.9 mmol) in THF (75 mL) was added dropwise at 0° C. After the addition, the cooling bath was removed and stirred at rt overnight. The reaction mixture was concentrated at reduced pressure and purified by ISCO (120 g silica gel column) chromatography using 5 to 30% EtOAc in hexane to provide an impure product (12 g). The product was again treated with triphenylphosphine and 40% w/w DEAD in toluene, after the completion, the reaction was concentrated at reduced pressure. The crude residue was triturated with a mixture of methylene chloride and hexane and filtered and the filtrate was concentrated at reduced pressure and purified by ISCO (120 g silica gel column) chromatography using 5 to 30% EtOAc in hexane to provide 4-(4-propionylphenoxy)-piperidine-1-carboxylic acid tert-butyl ester (10 g, 56%).

Step 2

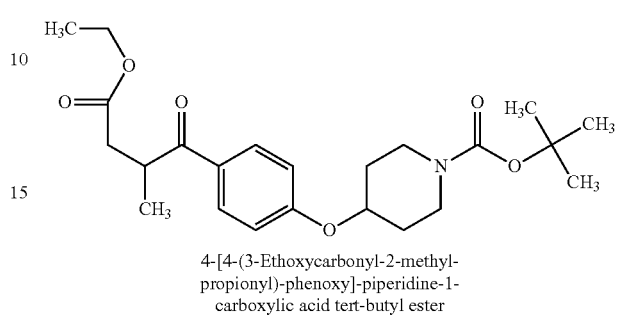

4-[4-(3-Ethoxycarbonyl-2-methyl-
propionyl)-phenoxy]-piperidine-1-
carboxylic acid tert-butyl ester A solution of 4-(4-propionyl-phenoxy)-piperidine-1-carboxylic acid ethyl ester (5 g, 15 mmol) in tetrahydrofuran (40 mL) was cooled to 0° C. Lithium diisopropylamide, (2M solution in THF) (8 mL, 16.4 mmol) was added dropwise and warmed to rt for 30 min. The reaction was cooled again to 0° C. and ethyl bromoacetate (1.8 mL, 16 mmol) was added dropwise and warmed to rt for 30 min and then quenched with aqueous 1M HCl acid at 0° C. The aqueous layer was extracted twice with methylene chloride and the combined organics were washed with brine, dried (Na₂SO₄), filtered, and concentrated to give 4-[4-(3-ethoxycarbonyl-2-methyl-propionyl)-phenoxy]-piperidine-1-carboxylic acid tert-butyl ester (5.8 g, 92%), MS m/z 364 (M-55).

Step 3

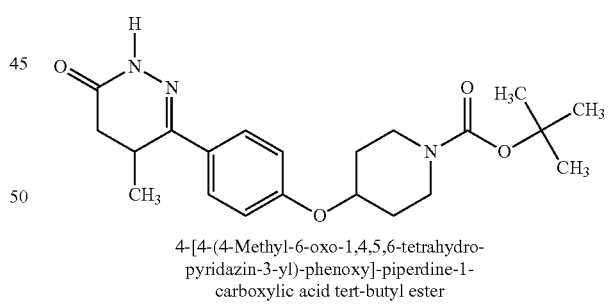

4-[4-(4-Methyl-6-oxo-1,4,5,6-tetrahydro-
pyridazin-3-yl)-phenoxy]-piperdine-1-
carboxylic acid tert-butyl ester A mixture of crude 4-[4-(3-ethoxycarbonyl-2-methyl-propionyl)-phenoxy]-piperidine-1-carboxylic acid tert-butyl ester (9 g, 21.4 mmol) and hydrazine monohydrate (3.58 ml, 71.6 mmol) in isopropanol (70 mL) was heated at 90° C. for 2 days and concentrated at reduced pressure to give a crude residue. The crude reside was dissolved in methylene chloride and washed with saturated aqueous sodium bicarbonate solution, brine, dried (Na₂SO₄), filtered, and concentrated to give a crude product. The crude product was purified by ISCO (120 g silica gel column) chromatography using 2 to 5% methanol in methylene chloride to obtain 4-[4-(4-methyl-6- oxo-1,4,5,6-tetrahydro-pyridazin-3-yl)-phenoxy]-piperidine-1-carboxylic acid tert-butyl ester (4.4 g, 53%), MS m/z 388 (M+H)

tyl-piperidin-4-yloxy)-3,5-difluoro-phenyl]-4,5-dihydro-2H-pyridazin-3-one (640 mg, 17%), mp 163-165° C.; MS m/z 342 (M+H).

Step 4

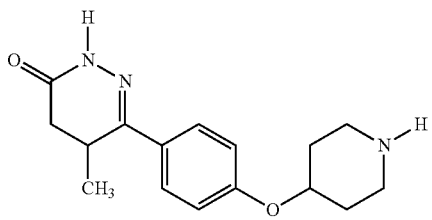

5-Methyl-6-[4-(piperidin-4-yloxy)-phenyl]-4,5-dihydro-2H-pyridazin-3-one

A solution of 4-[4-(4-methyl-6-oxo-1,4,5,6-tetrahydro-pyridazin-3-yl)-phenoxy]-piperidine-1-carboxylic acid tert-butyl ester (1 g, 2.5 mmol) in methylene chloride at RT was treated with trifluoroacetic acid (3 mL, 38.9 mmol) and stirred at RT for 3 h. TFA was evaporated at reduced pressure to obtain 5-methyl-6-[4-(piperidin-4-yloxy)-phenyl]-4,5-dihydro-2H-pyridazin-3-one (0.35 g, 47%), MS m/z 288 (M+H).

Step 5

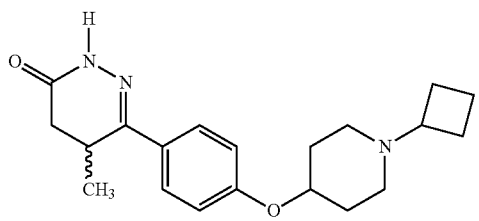

6-[4-(1-Cyclobutyl-piperidin-4-yloxy)-phenyl]-5-methyl-4,5-dihydro-2H-pyridazin-3-one A solution of 5-methyl-6-[4-(piperidin-4-yloxy)-phenyl]-4,5-dihydro-2H-pyridazin-3-one (3.2 mg, 11 mmol) in a mixture of DMF (4 mL) and MeOH (20 mL) was stirred under argon. Cyclobutanone (4.2 mL, 56 mmol), sodium cyanoborohydride (7 g, 111 mmol) and acetic acid (1.5 mL, 26 mmol) were added sequentially and stirred at 60° C. for 20 h. The reaction mixture was concentrated at reduced pressure then quenched with 1M sodium carbonate solution at 0° C. and extracted twice with methylene chloride to provide a crude product. The crude product was purified by ISCO (40 g silica gel column) chromatography using 2 to 5% methanol in methylene chloride to 10% methanol containing 0.2% ammonium hydroxide in methylene chloride. The recovered product was dissolved in methylene chloride and washed with saturated aqueous sodium bicarbonate solution, brine, dried ($Na_2SO_4$), filtered, and concentrated to furnish a pure product. The pure product was crystallized using from a mixture of EtOAc, ethanol, ether and hexane to obtain 6-[4-(1-cyclobu- Example 190

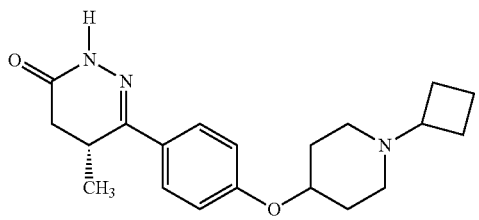

(R)-6-[4-(1-Cyclobutyl-piperidin-4-yloxy)-phenyl]-5-methyl-4,5-dihydro-2H-pyridazin-3-one Example 191

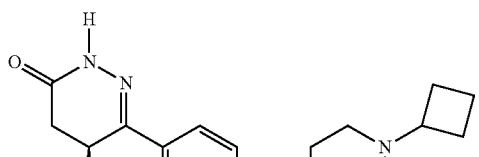

(S)-6-[4-(1-Cyclobutyl-piperidin-4-yloxy)-phenyl]-5-methyl-4,5-dihydro-2H-pyridazin-3-one Racemic Example 189 (660 mg) was separated into two enantiomers by chiral chromatography using chiralPak and 0.1% diethylamine in methanol.

Example 190: R(−)-6-[4-(cyclobutyl-piperidin-4-yloxy)-phenyl-5-methyl-4,5-dihydro-2H-pyradazin-3-one mp 188-190° C., MS m/z 342 (M+H), Hg 365=−29.2, Conc. ~0.1 g/mL Example 191: S(+)-6-[4-(cyclobutyl-piperidin-4-yloxy)-phenyl-5-methyl-4,5-dihydro-2H-pyradazin-3-one one mp 188-190° C., MS m/z 342 (M+H), Hg 365=+30.5, Conc. ~0.1 g/mL).

Example 192

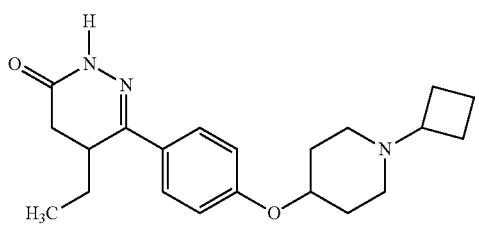 [SMILES: CCC1CC(=O)NN=C1c1ccc(OC2CCN(C3CCC3)CC2)cc1]

Example 192 was synthesized from 1-(4-methoxyphenyl) butan-1-one using procedures for example 189; Mp 152-154° C.; MS m/z 356 (M+H).

Example 193

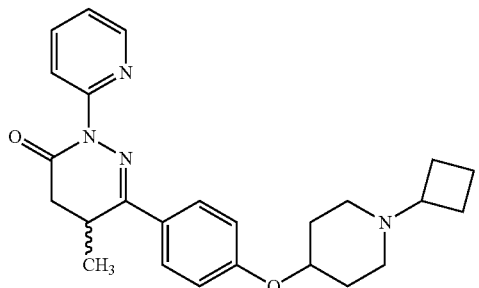

6-[4-(1-Cyclobutyl-piperidin-4-yloxy)-phenyl]-
5-methyl-2-pyridin-2-yl-4,5-dihydro-2H-pyridazin-3-one Step 1

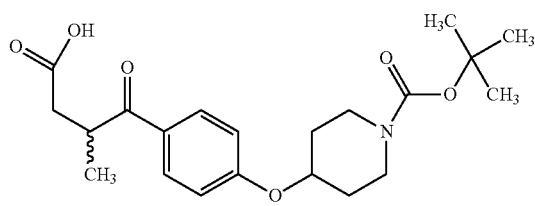

4-[4-(3-Carboxy-2-methyl-propionyl)-
phenoxy]-piperidine-1-carboxylic acid
tert-butyl ester A mixture of 4-[4-(3-ethoxycarbonyl-2-methyl-propionyl)-phenoxy]-piperidine-1-carboxylic acid tert-butyl ester (Example 189 step 2) (5.7 g, 14 mmol) and 1N NaOH (18 mL) in methanol was heated at 65° C. for 1 h. Methanol was evaporated at reduced pressure and diluted with water then cooled to 0° C. The aqueous layer was neutralized carefully with citric acid and extracted twice with methylene chloride to obtain a crude 4-[4-(3-carboxy-2-methyl-propionyl)phenoxy]-piperidine-1-carboxylic acid tert-butyl ester (4.3 g, 81%), MS m/z 390 (M-1)

Step 2

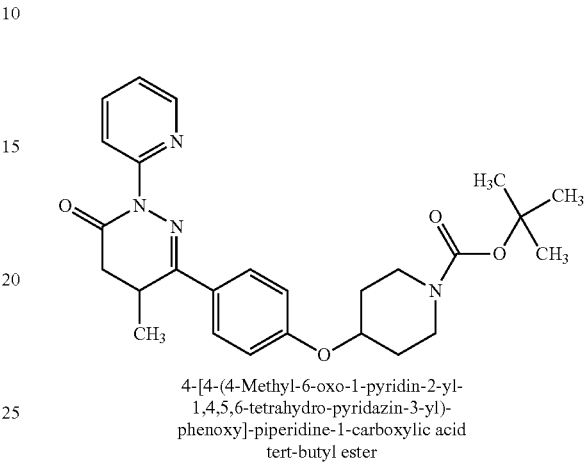

4-[4-(4-Methyl-6-oxo-1-pyridin-2-yl-
1,4,5,6-tetrahydro-pyridazin-3-yl)-
phenoxy]-piperidine-1-carboxylic acid
tert-butyl ester A mixture of 4-[4-(3-carboxy-2-methyl-propionyl)-phenoxy]-piperidine-1-carboxylic acid tert-butyl ester (4.3 g, 11 mmol) and 2-hydrazinopyridine (1.5 g, 14 mmol) in isopropanol (45 mL) was heated in a microwave reactor (300 Watts) at 160° C. for 150 min. Isopropanol was evaporated at reduced pressure and triturated with ether (150 mL) to obtain an orange solid (3 g). The filtrate was concentrated and purified by ISCO (80 g silica gel column) chromatography using 1.5 to 3.5% methanol in methylene chloride to obtain 4-[4-(4-methyl-6-oxo-1-pyridin-2-yl-1,4,5,6-tetrahydropyridazin-3-yl)phenoxy]-piperidine-1-carboxylic acid tert-butyl ester (0.3 g), mp 164-166° C., MS m/z 465 (M+H).

Example 193 was synthesized using the product from step 2 and methods described for example 189 step 4 and step 5.

| Example | Structure | Mp (° C.) | MS m/z |
|---------|-----------|-----------|--------|
| 193 | 6-[4-(1-Cyclobutyl-piperidin-4-yloxy)-phenyl]-5-methyl-2-pyridin-2-yl-4,5-dihydro-2H-pyridazin-3-one | 143-5 HCl | 419 (M + H) |

Example 194

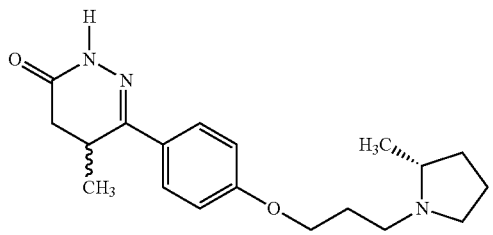

5-Methyl-6-{4-[3-((R)-2-methyl-pyrrolidin-1-yl)-propoxyl]-phenyl}-4,5-dihydro-2H-pyridazin-3-one Step 1

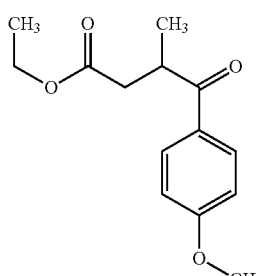

4-(4-Methoxy-phenyl)-3-methyl-4-oxo-butyric acid ethyl ester

A solution of 4-methoxypropiophenone (24 g, 140 mmol) in tetrahydrofuran (220 mL) was cooled to 0° C. Lithium diisopropylamide, (2M solution in THF) (126 mL, 248 mmol) was added dropwise and warmed to rt for 30 min. The reaction was cooled again to 0° C. and ethyl bromoacetate (18 mL, 161 mmol) was added dropwise and warmed to rt for 30 min and then quenched with aqueous 1M HCl acid at 0° C. The aqueous layer was extracted twice with methylene chloride and the combined organics were washed with brine, dried (Na$_2$SO$_4$), filtered, and concentrated to give 4-(4-methoxyphenyl)-3-methyl-4-oxobutyric acid ethyl ester (44 g), MS m/z 205 (M-45).

Step 2

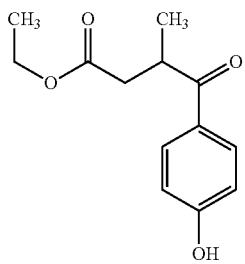

4-(4-Hydroxy-phenyl)-3-methyl-4-oxo-butyric acid ethyl ester

A mixture of crude 4-(4-methoxy-phenyl)-3-methyl-4-oxo-butyric acid ethyl ester (44 g, 175.8 mmol), acetic acid (300 mL) and 48% aqueous HBr (150 mL) was stirred at reflux for 10 h. The reaction was cooled to rt, concentrated at reduced pressure then partitioned between methylene chloride and water and the aqueous layer was extracted three times with methylene chloride and concentrated to provide a crude material. The crude material was dissolved in ethanol (125 mL) and added amberlyst then heated at 85° C. for 15 h. The reaction mixture was filtered over celite at rt and the filtrate was concentrated at reduced pressure and then partitioned between water and methylene chloride. The aqueous layer was extracted twice with methylene chloride to furnish a crude product and the crude product was purified by ISCO (330 g silica gel column) chromatography using 20 to 30% EtOAc in hexane to obtain a mixture (19 g) of 4-(4-hydroxyphenyl)-3-methyl-4-oxo-butyric acid ethyl ester (MS m/z 235 (M-H) and p-hydroxypropiophenone. The mixture was used for the next reaction without further purification.

Step 3

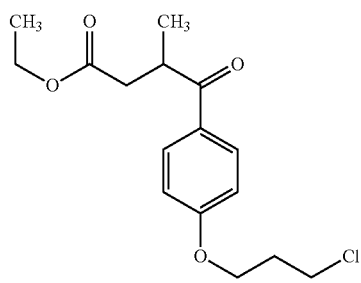

4-[4-(3-Chloro-propoxy)-phenyl]-3-methyl-4-oxo-butyric acid ethyl ester

A mixture of 4-(4-hydroxyphenyl)-3-methyl-4-oxo-butyric acid ethyl ester (12.5 g, 52.9 mmol), 1-bromo-3-chloropropane (11.3 mL, 114.6 mmol) and K$_2$CO$_3$ (21.9 g, 159 mmol) in acetone (200 mL) was stirred at 60° C. for 15 h. The reaction was cooled to RT and filtered over celite and the filtrate was evaporated at reduced pressure to give a crude residue. The crude residue was partitioned between methylene chloride and saturated aqueous sodium bicarbonate solution and the aqueous layer was extracted twice with methylene chloride. The combined organics was washed with brine, dried (Na$_2$SO$_4$), filtered, and concentrated to provide a crude product. The crude product was purified by ISCO (330 g) chromatography using 15% EtOAc in hexane to produce 4-[4-(3-chloro-propoxy)-phenyl]-3-methyl-4-oxo-butyric acid ethyl ester (9.7 g, 56%), MS m/z 267 (M-45).

Step 4

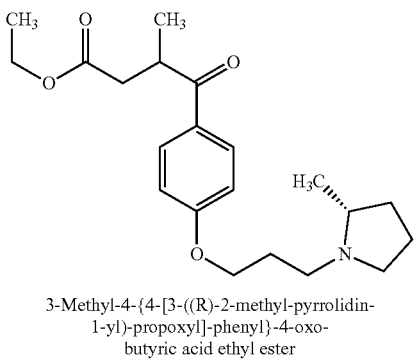 [SMILES: CCOC(=O)CC(C)C(=O)c1ccc(OCCCN2CCC[C@H]2C)cc1]

3-Methyl-4-{4-[3-((R)-2-methyl-pyrrolidin-1-yl)-propoxyl]-phenyl}-4-oxo-butyric acid ethyl ester A mixture of 4-[4-(3-chloro-propoxy)-phenyl]-3-methyl-4-oxo-butyric acid ethyl ester (7 g, 22 mmol), $K_2CO_3$ (9.3 g, 67 mmol), NaI (330 mg, 2.2 mmol), and (R)-methyl-pyrrolidinium benzenesulfonate (11 g, 47 mmol) in $CH_3CN$ (160 mL) was heated under argon at 80° C. for 36 h. The reaction mixture was concentrated at reduced pressure and partitioned between saturated aqueous sodium bicarbonate solution and methylene chloride. The aqueous layer was extracted twice with methylene chloride and the combined organics was washed with brine, dried ($Na_2SO_4$), filtered, and concentrated to provide a crude material. The crude material was purified by ISCO (80 g siliga gel column) chromatography using 2% to 9% methanol in methylene chloride to 10% methanol containing 2.5 mL ammonium hydroxide in methylene chloride to afford a pure product. The pure product was dissolved in methylene chloride and washed with saturated aqueous sodium bicarbonate solution, brine, dried ($Na_2SO_4$), filtered, and concentrated to give 3-methyl-4-{4-R-2-methyl-pyrrolidin-1-yl)-propoxy]-phenyl}-4-oxo-butyric acid ethyl ester (8.39 g, quantitative yield), MS m/z 362 (M+H).

Step 5

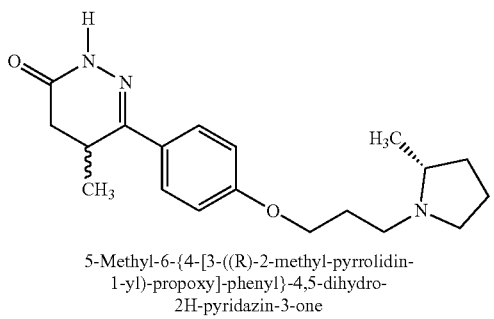 [SMILES: CC1CC(=O)NN=C1c1ccc(OCCCN2CCC[C@H]2C)cc1]

5-Methyl-6-{4-[3-((R)-2-methyl-pyrrolidin-1-yl)-propoxy]-phenyl}-4,5-dihydro-2H-pyridazin-3-one A mixture of 3-methyl-4-{4-R-2-methyl-pyrrolidin-1-yl)-propoxy]-phenyl}-4-oxo-butyric acid ethyl ester (8.39 g, 23.2 mmol) and hydrazine monohydrate (5 mL, 100 mmol) in isopropanol was heated at 100° C. for 36 h. Isopropanol was evaporated at reduced pressure and quenched with saturated aqueous sodium bicarbonate solution and extracted twice with methylene chloride. The combined organics was washed with brine, dried ($Na_2SO_4$), filtered, and concentrated to afford a crude product. The crude product was purified by ISCO (80 g) chromatography using 2 to 10% methanol in methylene chloride to 10% methanol containing 4 mL ammonium hydroxide in methylene chloride to afford a pure product. The pure product was dissolved in methylene chloride and washed with saturated aqueous sodium bicarbonate solution, brine, dried ($Na_2SO_4$), filtered, and concentrated to give 5-methyl-6-{4-[3-R-2-methyl-pyrrolidin-1-yl)propoxy]-phenyl}-4,5-dihydro-2H-pyridazin-3-one (6.1 g, 80%, >95% purity). The product was dissolved in a mixture of ethanol and ethyl acetate and 1M HCl (18 mL) in ether was added and the mixture was concentrated at reduced pressure. Fresh ethanol and ethyl acetate were added and concentrated under vacuum and again dissolved in ethanol and slowly added ethyl acetate, ether and hexane. After stirring for 15 min at RT solid separated, and the solid was filtered, washed with ether and dried at 85° C. in a ChemDry for 15 h to provide example 194 HCl as an off-white solid (5.8 g), mp 169-171° C., MS m/z 330 (M+H).

Example 195

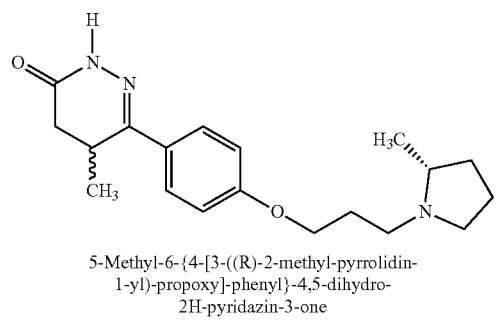 [SMILES: CC1CC(=O)NN=C1c1ccc(OCCCN2CCC[C@H]2C)cc1]

5-Methyl-6-{4-[3-((R)-2-methyl-pyrrolidin-1-yl)-propoxy]-phenyl}-4,5-dihydro-2H-pyridazin-3-one Example 196

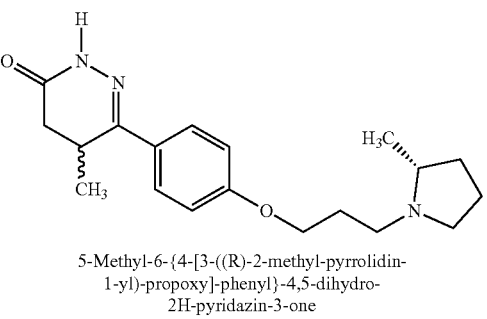 [SMILES: CC1CC(=O)NN=C1c1ccc(OCCCN2CCC[C@H]2C)cc1]

5-Methyl-6-{4-[3-((R)-2-methyl-pyrrolidin-1-yl)-propoxy]-phenyl}-4,5-dihydro-2H-pyridazin-3-one Racemic example 194 (5.8 g) of was separated into two diastereomers using chiralCel and 0.1% diethylamine in methanol.

Example 195: 5-methyl-6-[4-[3-(R)-2-methyl-pyrrolidin-1-yl)-propoxy]-phenyl}-4,5-dihydro-2H-pyridazin-3-one HCl (2.4 g), mp 149-151° C., MS m/z 367 (M+H).

Example 196: 5-methyl-6-[4-[3-(R)-2-methyl-pyrrolidin-1-yl)-propoxy]-phenyl}-4,5-dihydro-2H-pyridazin-3-one HCl (2.6 g), mp 189-191° C., MS m/z 367 (M+H)

Example 197 (racemic) and example 198 (racemic) were synthesized as HCl salts using methods described for example 194.

| Example | Structure | mp (° C.) | MS m/z |
|---|---|---|---|
| 197 | <br>5-Methyl-6-[4-(3-piperidin-1-yl-propoxy)-phenyl]-4,5-dihydro-2H-pyridazin-3-one | 223-225 HCl | 330 (M + H) |
| 198 | 5-Methyl-6-[4-(3-pyrrolidin-1-yl-propoxy)-phenyl]-4,5-dihydro-2H-pyridazin-3-one | 161-163 HCl | 316 (M + H) |

Example 199

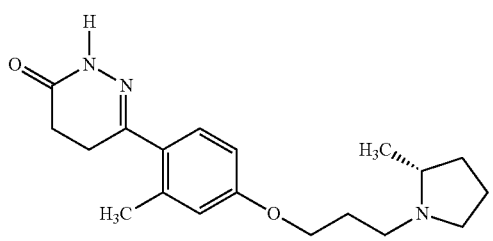

6-{(R)-2-Methyl-4-[3-(2-methyl-pyrrolidin-1-yl)-propoxyl]-phenyl}-4,5-dihydro-2H-pyriazin-3-one Step 1

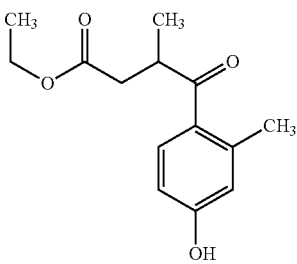

4-(4-Hydroxy-2-methyl-phenyl)-4-oxo-butyric acid ethyl ester

A mixture of 4-(4-methoxy-2-methyl-phenyl)-4-oxo-butyric acid (2 g, 9 mmol), acetic acid (30 mL) and 48% aqueous HBr (10 mL) was heated at 130° C. for 5.5 h. The reaction was cooled to rt and concentrated at reduced pressure and azeotrope twice with benzene to give a crude residue. The crude residue was dissolved in ethanol (25 mL) and added amberlyst then heated at 90° C. for 18 h. The reaction was filtered over celite and evaporated ethanol at reduced pressure then quenched with water and extracted twice with methylene chloride to obtain 4-(4-hydroxy-2-methyl-phenyl)-4-oxo-butyric acid ethyl ester (1.6 g, 75%). The crude material was used for the next reaction without purification.

Step 2

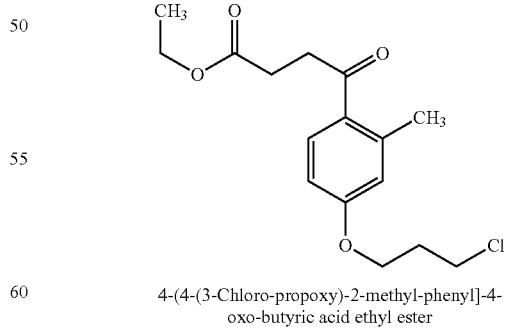

4-(4-(3-Chloro-propoxy)-2-methyl-phenyl]-4-oxo-butyric acid ethyl ester

4-[4-(3-chloro-propoxy)-2-methyl-phenyl]-4-oxo-butyric acid ethyl ester was prepared from 4-(4-hydroxy-2-methylphenyl)-4-oxo-butyric acid ethyl ester according to the procedure in step 3 example 184 MS m/z 267 (M-45).

Step 3

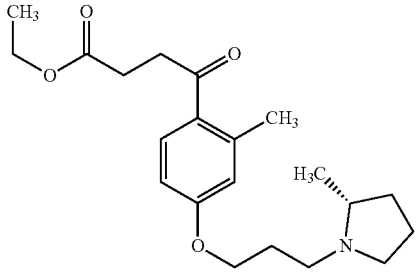

4-{2-Methyl-4-[3-((R)-2-methyl-pyrrolidin-1-yl)-propoxy]phenyl}-4-oxo-butyric acid ethyl ester 4-{2-methyl-4-[3-((R)-2-methyl-pyrrolidin-1-yl)-propoxy]-phenyl}-4-oxo-butyric acid ethyl ester (0.28 g, 67%) was prepared from 4-[4-(3-chloro-propoxy)-2-methyl-phenyl]-4-oxo-butyric acid ethyl ester (0.36 g, 1.15 mmol) according to the procedure in step 4 of example 184; MS m/z 362 (M+H).

Step 4

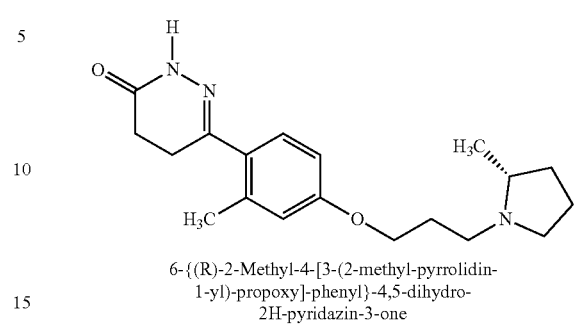

6-{(R)-2-Methyl-4-[3-(2-methyl-pyrrolidin-1-yl)-propoxy]-phenyl}-4,5-dihydro-2H-pyridazin-3-one 6-{(R)-2-methyl-4-[3-(2-methyl-pyrrolidin-1-yl)-propoxy]-phenyl}-4,5-dihydro-2H-pyridazin-3-one was prepared from 4-[4-(3-chloro-propoxy)-2-methyl-phenyl]-4-oxo-butyric acid ethyl ester (0.28 g, 0.77 mmol) according to the procedure in step 5 of example 184 HCl; Mp 121-123° C.; MS m/z=330 (M+H).

Examples 200-204 were synthesized using Cu(0) coupling methods according to Example 21 or CuI/dioxane/1,2-diaminocyclohexane/$Cs_2CO_3$ and starting with R-1-[3-(4-bromo-phenoxy)propyl]-2-methyl-pyrrolidine or 4-(5-bromopyridin-2-yloxy)-piperidine-1-carboxylic acid tert-butyl ester.

| Example | Structure | Mp (° C.) | MS m/z |
|---|---|---|---|
| 200 | 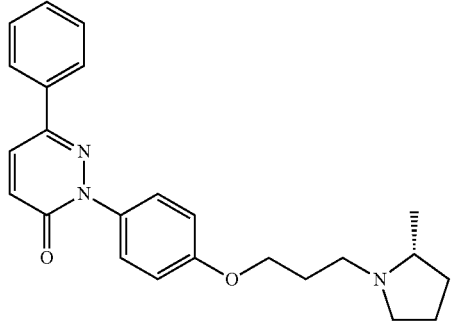<br>2-{4-[3-((R)-2-Methyl-pyrrolidin-1-yl)-propoxy]-phenyl}-6-phenyl-2H-pyridazin-3-one | 86-9 | 390 (M + H) |
| 201 | 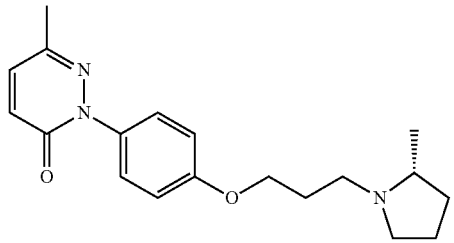<br>6-Methyl-2-{4-[3-((R)-2-methyl-pyrrolidin-1-yl)-propoxy]-phenyl}-2H-pyridazin-3-one | 168-70 | 328 (M + H) fumarate |

| Example | Structure | Mp (° C.) | MS m/z |
|---|---|---|---|
| 202 | 2-{4-[3-((R)-2-Methyl-pyrrolidin-1-yl)-propoxy]-phenyl}-2H-phthalazin-1-one | 70-3 | 364 (M + H) |
| 203 | 2-[6-(1-Cyclobutyl-piperidin-4-yloxy)-pyridin-3-yl]-6-phenyl-2H-pyridazin-3-one | 155-9 fumarate | 403 (M + H) |
| 204 | 2-{4-[3-((R)-2-Methyl-pyrrolidin-1-yl)-propoxy]-phenyl}-6-pyridin-3-yl-2H-pyridazin-3-one | 87-90 | 391 (M + H) |
| 262 | 6-Cyclopropyl-2-{4-[3-((R)-2-methyl-pyrrolidin-1-yl)-propoxy]-phenyl}-2H-pyridazin-3-one | 51-55 fumarate | 354 (M + H) |

Example 205

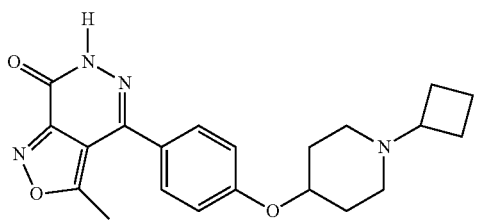

4-[4-(1-cyclobutyl-piperidin-4-yloxy)-phenyl]-
3-methyl-6H-isoxazolo[3,4-d]pyridazin-7-one Step 1

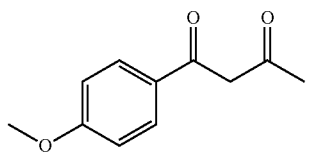

1-(4-Methoxy-phenyl)-butane-1,3-dione

To 9.80 mL of ethyl acetate (100 mmol) in 40 mL dry THF at room temperature was added 2.0 g of 60% sodium hydride (49.9 mmol), 7.50 g of 4'-methoxyacetophenone (49.9 mmol), 100.0 mg of 18-crown-6 (0.40 mmol), and 2 drops of ethanol. After 30 minutes, the reaction was refluxed for 1 h, and then 100 mL of dry THF was added. After an additional 1 h, 30 mL THF was added. After 1 h the reaction was cooled to 0° C. and 25 mL of 10% aqueous sulfuric acid was added. The product was extracted with diethyl ether. The ether extracts were dried with $Na_2SO_4$, filtered, and concentrated in vacuo. The crude material was purified via silica gel chromatography eluting with 4:1 hexane:ethyl acetate to give 5.8 g of 1-(4-methoxyphenyl)butane-1,3-dione containing 30% starting material (via $^1H$ NMR 42% yield).

Step 2

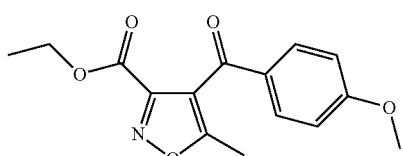

4-(4-Methoxy-benzoyl)-5-methyl-isoxazole-3-
carboxylic acid ethyl ester

To 7.04 mL of 21% sodium ethoxide in ethanol (18.8 mmol) in 60 mL ethanol at 0° C. was added 4.70 g of 1-(4-methoxyphenyl)butane-1,3-dione (17.1 mmol) in 60 mL ethanol dropwise over 24 minutes. After 30 min a solution of 2.59 g of ethyl chloro-(hydroximino)acetate (17.1 mmol) in 30 mL ethanol was added dropwise over 6 minutes. The reaction was warmed to room temperature slowly. When TLC indicated the reaction was complete, the reaction was concentrated in vacuo. Water and saturated $NaHCO_3$ was added and the product extracted with ethyl acetate. The ethyl acetate extracts were dried with $Na_2SO_4$, filtered, and concentrated in vacuo. The crude material was purified via silica gel chromatography eluting with 8:1 hexane:ethyl acetate to give 4-(4-methoxybenzoyl)-5-methylisoxazole-3-carboxylic acid ethyl ester which was dried overnight under high vacuum to give 3.74 g (71.8%).

Step 3

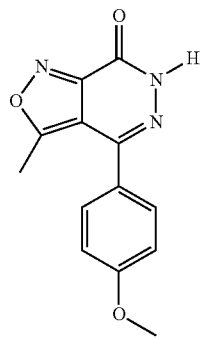

4-(4-Methoxyphenyl)-3-methyl-6H-
isoxazolo[3,4-d]pyridazin-7-one

A solution of 2.47 g of 4-(4-methoxybenzoyl)-5-methyl-isoxazole-3-carboxylic acid ethyl ester (8.54 mmol) and 0.598 mL of hydrazine monohydrate (12.0 mmol) in 18.4 mL ethanol was stirred at room temperature for 19 hours. The heterogeneous reaction was cooled in an ice bath then filtered off the white solid, washing with cold ethanol then diethyl ether. Dried on under high vacuum to give 2.06 g (92%) of 4-(4-methoxyphenyl)-3-methyl-6 h-isoxazolo[3,4-d]pyridazin-7-one.

Step 4

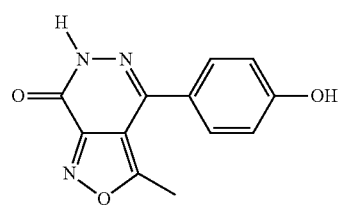

4-(4-Hydroxy-phenyl)-3-methyl-6H-
isoxazolo[3,4-d]pyridazin-7-one

To 1.05 g of 4-(4-methoxyphenyl)-3-methyl-6 h-isoxazolo[3,4-d]pyridazin-7-one (4.08 mmol) in 15 mL dry DMF was added 1.03 g of sodium ethanethiolate in 15 mL dry DMF at room temperature. The reaction was then heated at 100° C. for 2.5 h. Added water and 1M HCl until acidic. Extracted the product with diethyl ether and dried the extracts with $Na_2SO_4$, filtered, and concentrated in vacuo. The product was purified via silica gel chromatography eluting with 95:5 dichloromethane:methanol to give 533 mg of 4-(4-hydroxyphenyl)-3-methyl-6 h-isoxazolo[3,4-d]pyridazin-7-one; Mp 268-276° C.; MS m/z 216 (M—N₂+H).

Step 5

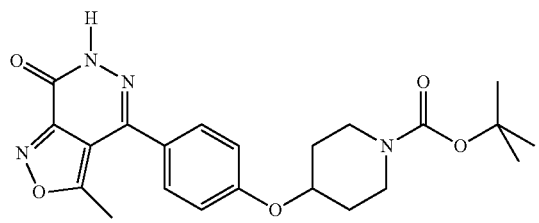

4-[4-(3-Methyl-7-oxo-6,7-dihydro-isoxazolo[3,4-d]
pyridazin-4-yl)-phenoxyl]-piperidine-1-carboxylic
acid tert-butyl ester To a solution of 805 mg of triphenylphosphine (3.07 mmol) in 10 mL dry THF at 0° C. was added 1.30 mL 40% w/w diethylazodicarboxylate in toluene (8.26 mmol). After 15 min, a solution of 524 mg of 4-(4-hydroxyphenyl)-3-methyl-6 h-isoxazolo[3,4-d]pyridazin-7-one (2.05 mmol) and 494 mg of 4-hydroxypiperidine-1-carboxylic acid tert-butyl ester (2.46 mmol) in 18 mL dry THF were added dropwise. The reaction was slowly warmed to room temperature. After 14 h water was added and the product was extracted with ethyl acetate. The extracts were dried with Na₂SO₄, filtered, and concentrated in vacuo. The product was purified via silica gel chromatography eluting with 1:1 hexane:ethyl acetate to give 985 mg of 4-[4-(3-methyl-7-oxo-6,7-dihydroisoxazole[3,4-d]pyridazin-4-yl)phenoxy]piperidine-1-carboxylic acid tert-butyl ester 65.4%.

Step 6

Example 206

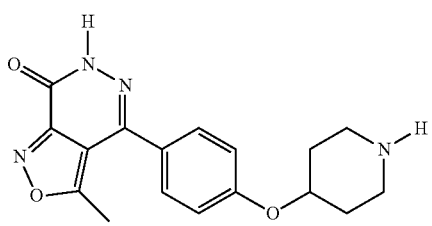

3-Methyl-4-[4-(piperidine-4-yloxy)-phenyl]-6H-
isoxazolo[3,4-d]pyridazin-7-one

To 980 mg of 4-[4-(3-methyl-7-oxo-6,7-dihydroisoxazole[3,4-d]pyridazin-4-yl)phenoxy]-piperidine-1-carboxylic acid tert-butyl ester (1.3 mmol) in 20 mL of dichloromethane was added 1.0 mL of trifluoroacetic acid (13 mmol). After stirring at room temperature for 3 hours, an additional 0.5 mL of trifluoroacetic acid was added. The reaction was concentrated in vacuo as monitored by TLC and concentrated and triturated with diethyl ether to give 375 mg (98% pure) (63% yield) of example 206 as an off-white solid 3-methyl-4-[4-(piperidin-4-yloxy)phenyl]-6 h-isoxazolo-[3,4-d]pyridazin-7-one TFA salt. Mp 283-239° C.; MS m/z 299 (M—N₂+H).

Step 7

Example 205

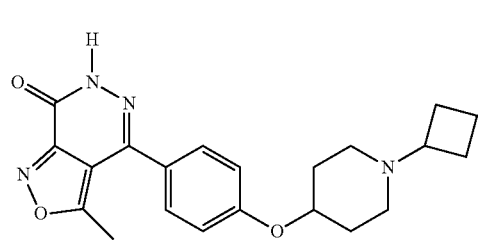

4-[4-(1-Cyclobutyl-piperidin-4-yloxy)-phenyl]-3-
methyl-6H-isoxazolo[3,4-d]pyridazin-7-one To 369 mg of example 206 (3-methyl-4-[4-(piperidin-4-yloxy)phenyl]-6 h-isoxazolo-[3,4-d]pyridazin-7-one trifluoroacetic acid salt) (0.838 mmol) and 84 μL acetic acid (1.5 mmol) in 6 mL dry methanol and 2 mL dry DMF at 0° C. was added 260 mg of sodium cyanoborohydride (4.2 mmol) and then 190 μL, of cyclobutanone (2.5 mmol). The reaction was heated at 60° C. After 1 h, the reaction was complete as determined by LC/MS and was concentrated in vacuo. Water and 2M Na₂CO₃ was added and the product was extracted with dichloromethane. The extracts were dried with Na₂SO₄, filtered, and concentrated in vacuo. The crude product was purified via silica gel chromatography eluting with 500:15:10 dichloromethane:methanol:7N ammonia in methanol to give a colorless oil which was re-concentrated in vacuo with diethyl ether. Added diethyl ether and upon standing, a white solid formed which was triturated with ether to yield 56 mg (17%) of example 205 Mp 182.5-184.0° C.; MS m/z 353 (M—N₂+H).

Example 207

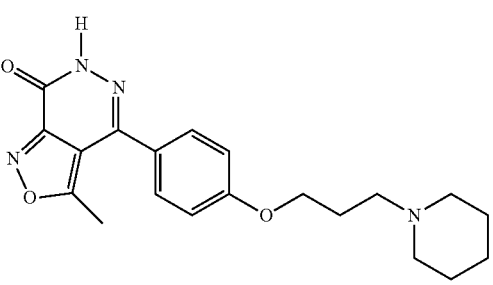

3-Methyl-4-[4-(3-piperidin-1-yl-propoxy)-
phenyl]-6H-isoxazolo[3,4-d]pyridazin-7-one

Step 1

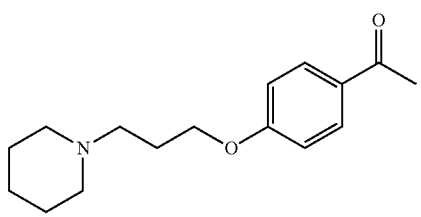 [SMILES: CC(=O)c1ccc(OCCCN2CCCCC2)cc1]

A mixture of 5.97 g of 4'-hydroxyacetophenone (43.8 mmol), 13.0 g of 1-(3-chloropropyl)-piperidine hydrochloride (65.8 mmol), 12.70 g of potassium carbonate (91.89 mmol), and 3.28 g of sodium iodide (21.9 mmol) in 100 mL dry acetone was stirred at reflux. After 1.5 h, the reaction was cooled to room temperature, filtered and concentrated. Ethyl acetate was added and the white solid that remained was filtered off. The filtrate was concentrated in vacuo and the crude residue was purified via silica gel chromatography using a gradient of ethyl acetate then 400:20:10 ethyl acetate: 7N ammonia in methanol:methanol to yield 583 mg of 1-[4-(3-piperidin-1-ylpropoxy)phenyl]ethanone as an oil. MS m/z 265 (M+H).

Step 2

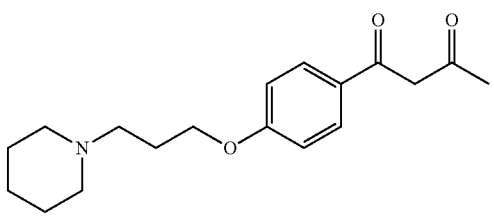

1-[4-(3-Piperidin-1-yl-propoxy)-phenyl]-butane-1,3-dione

To 430 µL of ethyl acetate (4.4 mmol) in 10 mL dry THF at room temperature was added 180 mg of 60% sodium hydride (4.4 mmol), 15.0 mg of 18-crown-6 (0.0568 mmol), 2 drops of ethanol, and then 578 mg (2.212 mmol) of 1-[4-(3-piperidin-1-ylpropoxy)phenyl]ethanone in 10 mL dry THF. After 30 min, the reaction was refluxed. An additional 18 mL of dry THF was added after 1.5 hours to reduce the viscosity of the reaction. After an additional 2 hours, 0.50 mL of 12.1 M aq. HCl was added to the reaction and the reaction was concentrated in vacuo. Water and saturated NaHCO₃ was added and the product extracted with ethyl acetate. The ethyl acetate extracts were dried with Na₂SO₄, filtered, and concentrated in vacuo. The crude material was purified via silica gel chromatography eluting with 500:20:12 dichloromethane:methanol: 7N ammonia in methanol to give a yellow oil which solidified to give 450 mg (66%) of 1-[4-(3-piperidin-1-ylpropoxy)-phenyl]butane-1,3-dione as a yellow solid; Mp 43.0-45.5° C.; MS m/z 304 (M+H).

Step 3

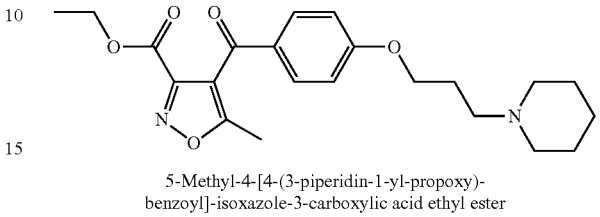

5-Methyl-4-[4-(3-piperidin-1-yl-propoxy)-benzoyl]-isoxazole-3-carboxylic acid ethyl ester To 597 µL of 21% sodium ethoxide in ethanol (1.595 mmol) in 4 mL ethanol at 0° C. was added 440 mg of 1-[4-(3-piperidin-1-ylpropoxy)phenyl]butane-1,3-dione (1.45 mmol) in 5.5 mL ethanol dropwise. After 30 min, a solution of 220 mg of ethyl chloro(hydroximino)acetate (1.45 mmol) in 3 mL ethanol was added dropwise. The reaction was warmed to room temperature slowly. After 19.5 h the reaction was concentrated in vacuo. Water and saturated NaHCO₃ was added and the product extracted with ethyl acetate. The ethyl acetate extracts were dried with Na₂SO₄, filtered, and concentrated in vacuo. The crude material was purified via silica gel chromatography eluting with 500:15:10 dichloromethane:methanol: 7N ammonia in methanol to give 300 mg (50%) of a gold oil determined to be 5-methyl-4-[4-(3-piperidin-1-ylpropoxy)benzoyl]-isoxazole-3-carboxylic acid ethyl ester; MS m/z 401 (M+H)

Step 4

Example 207

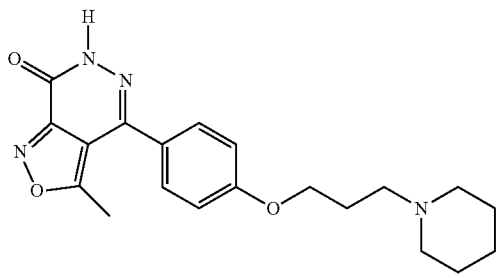

3-Methyl-4-[4-(3-piperidin-1-yl-propoxy)-phenyl]-6H-isoxazolo[3,4-d]pyridazin-7-one To 291.3 mg of 5-methyl-4-[4-(3-piperidin-1-ylpropoxy) benzoyl]isoxazole-3-carboxylic acid ethyl ester (0.7057 mmol) in 1.54 mL of ethanol at room temperature was added 49.4 µL of hydrazine monohydrate (0.988 mmol). After 21 h, the heterogeneous reaction was cooled to 0° C. and filtered. The white solid was washed with cold ethanol then diethyl ether and dried at 65° C. under high vacuum. Yield 120 mg (46%) of a white solid Mp 178-9; MS m/z 369 (M+H).

Example 208

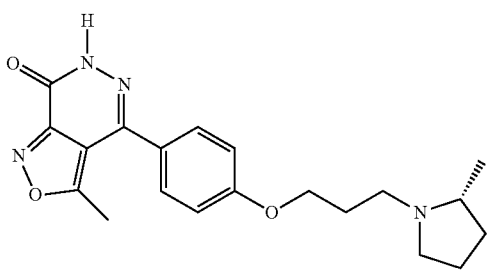

3-Methyl-4-{4-[3-((R)-2-methyl-pyrrolidin-1-yl)-propoxy]-phenyl}-6H-isoxazolo[3,4-d]pyridazin-7-one Example 208 was prepared using methods described for example 207; Mp 169-70° C.; MS m/z 369 (M+H).

Example 178

Method B

Step 1

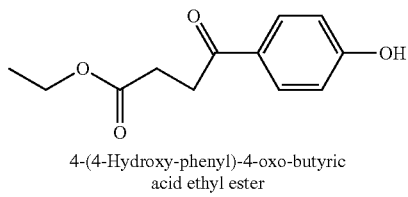 [SMILES: CCOC(=O)CCC(=O)c1ccc(O)cc1]

4-(4-Hydroxy-phenyl)-4-oxo-butyric acid ethyl ester

In a 1 L round bottom flask, 4-(4-methoxyphenyl)-4-oxo-butyric acid (25 g, 106 mmol) in 48% HBr (125 mL) and acetic acid (250 mL) was heated to reflux 18 h. The reaction was cooled slightly and ethanol (250 mL) was added. The solvent was concentrated under vacuum. Additional ethanol (100 mL) was added and solvent concentrated under vacuum again. The resulting oil was crystallized from ethyl acetate/hexanes to produce 8.65 g (37%). MS m/z=223 (M+H).

Step 2

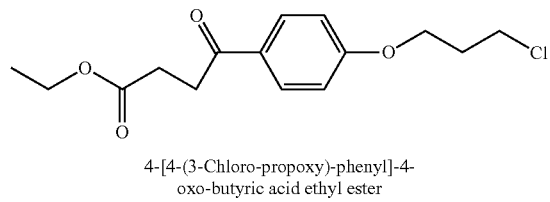 [SMILES: CCOC(=O)CCC(=O)c1ccc(OCCCCl)cc1]

4-[4-(3-Chloro-propoxy)-phenyl]-4-oxo-butyric acid ethyl ester

In a 1 L round bottom flask, 4-(4-hydroxyphenyl)-4-oxo-butyric acid ethyl ester (8.65 g, 39.0 mmol), 1-bromo-3-chloro-propane (6.1 g, 61.0 mmol), and potassium carbonate (9.3 g, 67.1 mmol) in acetonitrile (300 mL) was heated to reflux 14 h. The reaction was cooled and the solvent concentrated under vacuum. The slurry was partitioned between methylene chloride and water, separated and dried over MgSO₄. Purification with silica gel chromatography eluting with hexanes/ethyl acetate (3:1) produced 7.9 g (68%). MS m/z 299 (M+H).

Step 3

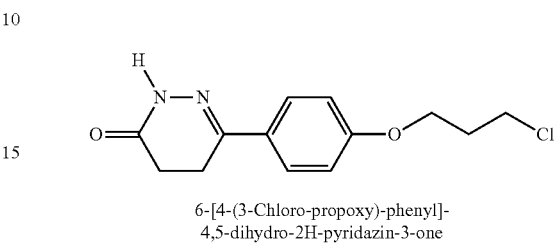

6-[4-(3-Chloro-propoxy)-phenyl]-4,5-dihydro-2H-pyridazin-3-one

In a 500 mL round bottom flask, 4-[4-(3-chloro-propoxy)-phenyl]-4-oxo-butyric acid ethyl ester (7.85 g, 26.3 mmol), and hydrazine monohydrate (2.55 mL, 52.7 mmol), in isopropanol (200 mL) was heated to reflux 14 h. The reaction was cooled and the solvent concentrated under vacuum. Purification with silica gel chromatography eluting with methylene chloride/methanol (95:5) produced 5.2 g (74%). MS m/z 267 (M+H).

Example 178

Step 4

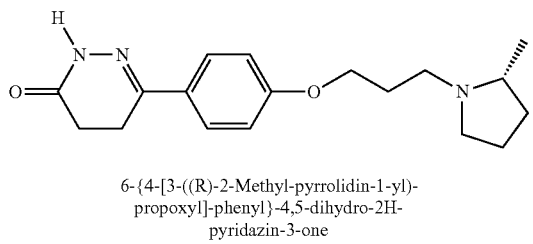 [SMILES: C[C@@H]1CCCN1CCCOc1ccc(C2=NNC(=O)CC2)cc1]

6-{4-[3-((R)-2-Methyl-pyrrolidin-1-yl)-propoxyl]-phenyl}-4,5-dihydro-2H-pyridazin-3-one In a 500 mL round bottom flask, 6-[4-(3-chloro-propoxy)-phenyl]-4,5-dihydro-2H-pyridazin-3-one (5.2 g, 19.5 mmol), benzenesulfonate (R)-2-methyl-pyrrolidinium (9.5 g, 39.0 mmol), potassium carbonate (10.8 g, 78.0 mmol), and potassium iodide (200 mg, 1.2 mmol) in acetonitrile (300 mL) was heated to reflux 14 h. The reaction was cooled and the solvent concentrated under vacuum. The slurry was partitioned between methylene chloride and water, then washed with water three times. The organics were extracted three times with 3% citric acid solution. The combined aqueous layers were basified with sat. NaHCO₃ sol. and extracted with methylene chloride, then dried over MgSO₄. Ethereal HCl was added and the solvents reduced under vacuum. Crystallization from MeOH/Et$_2$O produced 3.17 g (46%). Mp 221-223° C. MS m/z 316 (M+H).

Example 209

Step 1

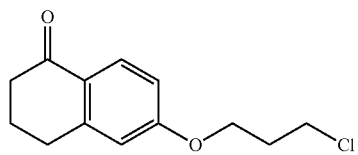

6-(3-Chloro-propoxy)-3,4-dihydro-2H-naphthalen-1-one

In a 500 mL round bottom flask, 6-hydroxy-3,4-dihydro-2H-naphthalen-1-one (10 g, 61.0 mmol), 1-bromo-3-chloropropane (9.6 g, 61.0 mmol), and potassium carbonate (9.3 g, 67.1 mmol) in acetonitrile (300 mL) was heated to reflux 14 h. The reaction was cooled and the solvent concentrated under vacuum. The slurry was partitioned between methylene chloride and water, separated, dried over MgSO$_4$. Purification with silica gel chromatography eluting with hexanes/ethyl acetate (3:1) produced 10.6 g (73%). Mp 85-87° C. MS m/z 239 (M+H).

Step 2

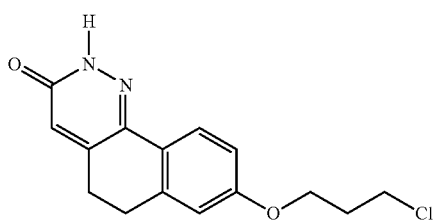

8-(3-Chloro-propoxy)-5,6-dihydro-2H-benzo[h]cinnolin-3-one

In a 100 mL round bottom flask, 6-(3-chloro-propoxy)-3,4-dihydro-2H-naphthalen-1-one (1 g, 4.2 mmol), and glyoxylic acid monohydrate (387 mg, 4.2 mmol), in acetic acid (10 mL) was heated to reflux 6 h. The reaction was cooled and hydrazine monohydrate (0.41 mL, 8.4 mmol) was added and the reaction was heated to reflux 14 h. The reaction was cooled and the solvent concentrated under vacuum. The slurry was partitioned between methylene chloride and water, separated, dried over MgSO$_4$. Purification with silica gel chromatography eluting with methylene chloride/methanol (95:5) produced 620 mg (51%). MS m/z 291 (M+H).

Example 209

Step 3

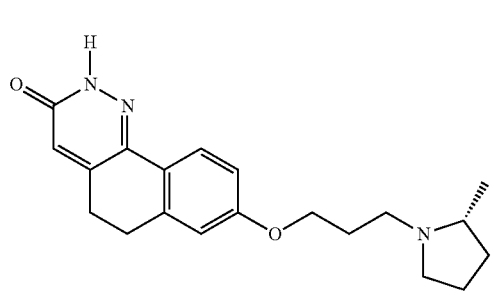

8-[3-((R)-2-Methyl-pyrrolidin-1-yl)-propoxy]-5,6-dihydro-2H-benzo[h]cinnolin-3-one In a 100 mL round bottom flask, 8-(3-chloro-propoxy)-5,6-dihydro-2H-benzo[h]cinnolin-3-one (600 mg, 2.1 mmol), benzenesulfonate (R)-2-methyl-pyrrolidinium (1.02 g, 4.2 mmol), potassium carbonate (1.14 g, 8.3 mmol), and potassium iodide (10 mg, 0.06 mmol) in acetonitrile (60 mL) was heated to reflux 14 h. The reaction was cooled and the solvent concentrated under vacuum. The slurry was partitioned between methylene chloride and water, and then washed with water three times. The organics were extracted three times with 3% citric acid solution. The combined aqueous layers were basified with sat. NaHCO$_3$ sol. and extracted with methylene chloride, then dried over MgSO$_4$. Ethereal HCl was added and the solvents reduced under vacuum. Crystallization from MeOH/Et$_2$O produced 85 mg (11%). Mp 289-292° C. MS m/z 340 (M+H).

Example 210

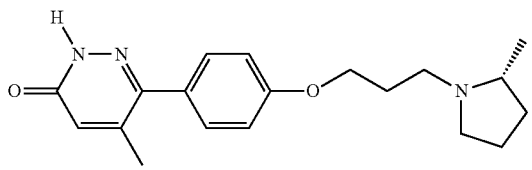

5-Methyl-6-{4-[3-((R)-2-methyl-pyrrolidin-1-yl)-propoxy]-phenyl}-2H-pyridazin-3-one Following the procedure of Example 209: Mp 253-255° C. MS m/z=328 (M+H).

Example 211

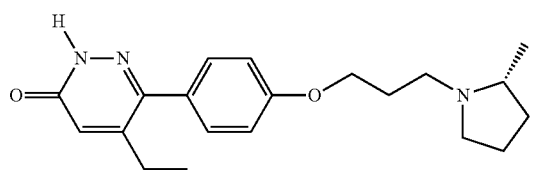

5-Ethyl-6-{4-[3-((R)-2-methyl-pyrrolidin-1-yl)-propoxy]-phenyl}-2H-pyridazin-3-one Following the procedure of Example 209: Mp 272-275° C. MS m/z=342 (M+H).

Example 212

Step 1

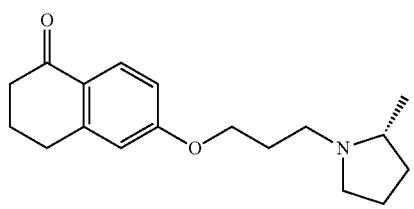

6-[3-((R)-2-Methyl-pyrrolidin-1-yl)-propoxy]-3,4-dihydro-2H-naphthalen-1-one

In a 1 L round bottom flask, 6-(3-chloro-propoxy)-3,4-dihydro-2H-naphthalen-1-one (10.0 g, 41.9 mmol), benzenesulfonate (R)-2-methyl-pyrrolidinium (13.15 g, 84.0 mmol), potassium carbonate (23.15 g, 168 mmol), and potassium iodide (100 mg, 0.6 mmol) in acetonitrile (600 mL) was heated to reflux 14 h. The reaction was cooled and the solvent concentrated under vacuum. The slurry was partitioned between methylene chloride and water, then washed with water three times. The organics were extracted three times with 3% citric acid solution. The combined aqueous layers were basified with sat. NaHCO₃ sol. and extracted with methylene chloride, then dried over MgSO₄. Ethereal HCl was added and the solvents reduced under vacuum. Crystallization from MeOH/Et₂O produced 8.75 g (65%). Mp 183-185° C. MS m/z=288 (M+H).

Example 212

Step 2

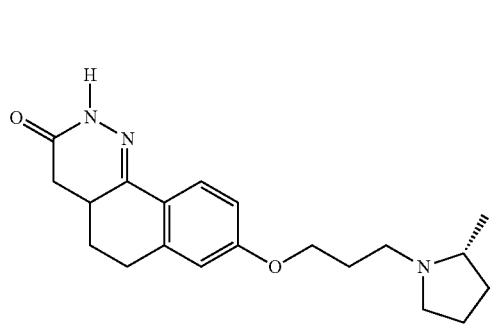

8-[3-(2-Methyl-pyrrolidin-1-yl)-propoxy]-4,4a,5,6-tetrahydro-2H-benzo[h]cinnolin-3-one In a 250 mL round bottom flask, 6-[3-((R)-2-Methyl-pyrrolidin-1-yl)-propoxy]-3,4-dihydro-2H-naphthalen-1-one (3.0 g, 9.3 mmol), and glyoxylic acid monohydrate (1.28 g, 13.9 mmol), in acetic acid (60 mL) was heated to reflux 3 h. The reaction was cooled and zinc dust (1.21 g, 18.5 mmol) was added and the reaction was heated to reflux 14 h. The reaction was cooled and diluted with water (120 mL). The mixture was basified to pH 8 with NH₄OH and then hydrazine monohydrate (0.93 mL, 18.5 mmol) was added. The reaction was heated to reflux 2 h. The reaction was cooled and re-basified with NaHCO₃, then extracted with methylene chloride three times. The organics were dried over MgSO₄, then ethereal HCL was added. The solvents were removed under vacuum and the product was crystallized with MeOH/ether to produce 1.16 g (33%). Mp 193-195° C. MS m/z 342 (M+H).

Example 213

Step 1

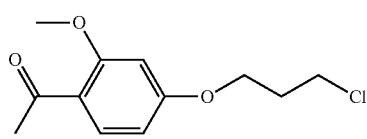

1-[4-(3-Chloro-propoxy)-2-methoxy-phenyl]-ethanone

In a 250 mL round bottom flask, 1-(4-hydroxy-2-methoxyphenyl)ethanone (5.0 g, 30.0 mmol), 1-bromo-3-chloro-propane (3.27 mL, 33.1 mmol), and potassium carbonate (4.75 g, 33.1 mmol) in acetonitrile (100 mL) was heated to reflux 14 h. The reaction was cooled and the solvent concentrated under vacuum. The slurry was partitioned between methylene chloride and water, separated, dried over MgSO₄. Purification with silica gel chromatography eluting with hexanes/ethyl acetate (3:1) produced 6.18 g (85%). Mp 51-53° C. MS m/z 243 (M+H).

Step 2

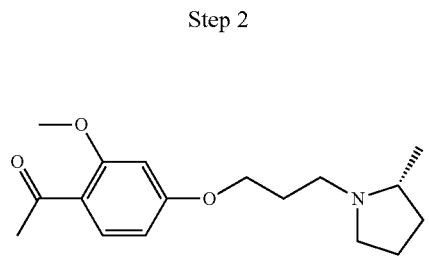

1-{2-Methoxy-4-[3-((R)-2-methyl-pyrrolidin-1-yl)propoxy]-phenyl}ethanone

In a 250 mL round bottom flask, 1-[4-(3-chloro-propoxy)-2-methoxy-phenyl]-ethanone (6.18 g, 25.5 mmol), benzenesulfonate (R)-2-methyl-pyrrolidinium (12.4 g, 50.9 mmol), potassium carbonate (14.1 g, 102 mmol), and potassium iodide (20 mg, 0.12 mmol) in acetonitrile (100 mL) was heated to reflux 14 h. The reaction was cooled and the solvent concentrated under vacuum. The slurry was partitioned between methylene chloride and water, then washed with water three times. The organics were extracted three times with 3% citric acid solution. The combined aqueous layers were basified with sat. NaHCO$_3$ sol. and extracted with methylene chloride, then dried over MgSO$_4$. The solvents were removed under vacuum to produce 4.25 g (57%) of oil. MS m/z 292 (M+H).

Example 213

Step 3

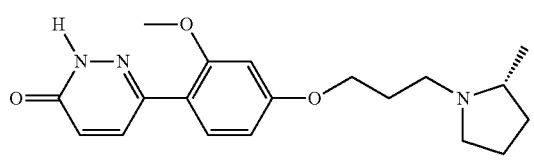

6-{2-Methoxy-4-[3-((R)-2-methyl-pyrrolidin-1-yl)propoxy]-phenyl}-2H-pyridazin-3-one In a 100 mL round bottom flask, 1-{2-methoxy-4-[3-((R)-2-methyl-pyrrolidin-1-yl)-propoxy]-phenyl}-ethanone (4.24 g, 14.5 mmol), and glyoxylic acid monohydrate (2.01 g, 21.8 mmol), in acetic acid (20 mL) was heated to reflux 3 h. The reaction was cooled and diluted with water (40 mL). The mixture was basified to pH 8 with NH$_4$OH and then hydrazine monohydrate (1.41 mL, 29.1 mmol) was added. The reaction was heated to reflux 2 h. The reaction was cooled and re-basified with NaHCO$_3$, then extracted with methylene chloride three times. The organics were dried over MgSO$_4$, then ethereal HCL was added. The solvents were removed under vacuum and the product was crystallized with MeOH/ether to produce 500 mg (9%). Mp 182-186° C. MS m/z 344 (M+H).

Example 214

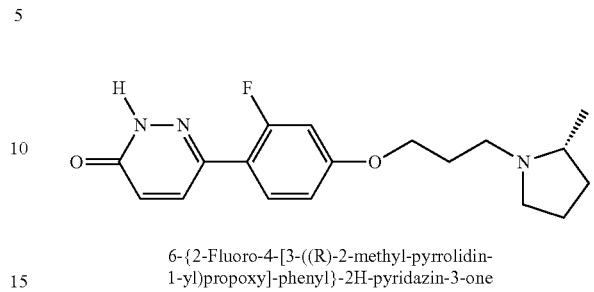

6-{2-Fluoro-4-[3-((R)-2-methyl-pyrrolidin-1-yl)propoxy]-phenyl}-2H-pyridazin-3-one Following the procedure of Example 213: Mp 220-222° C. MS m/z 332 (M+H).

Example 215

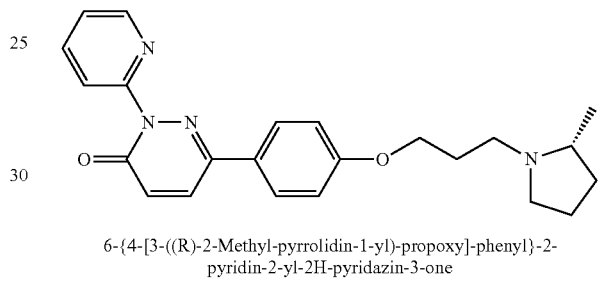

6-{4-[3-((R)-2-Methyl-pyrrolidin-1-yl)-propoxy]-phenyl}-2-pyridin-2-yl-2H-pyridazin-3-one In a 50 mL round bottom flask, 6-{4-[3-((R)-2-methyl-pyrrolidin-1-yl)-propoxy]-phenyl}-2H-pyridazin-3-one (250 mg, 0.71 mmol), 2-bromopyridine (105 mL, 1.07 mmol), copper(I) iodide (13.6 mg, 0.07 mmol), and potassium carbonate (296 mg, 2.14 mmol) in dimethylformamide (10 mL) was heated to reflux 14 h. The reaction was cooled and water (20 mL) was added. The sticky solids were filtered off and then partitioned between methylene chloride and water, separated, and dried over MgSO$_4$. Purification with silica gel chromatography eluting with methylene chloride/methanol (95:5) produced 10 mg (2.4%) oil. MS m/z 391 (M+H).

Example 216

Step 1

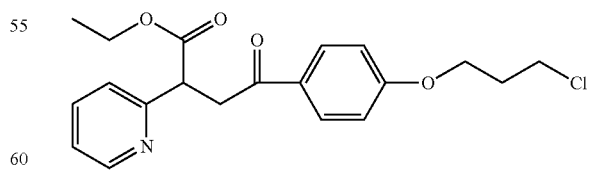

4-[4-(3-Chloro-propoxy)-phenyl]-4-oxo-2-pyridin-2-yl-butyric acid ethyl ester

In a 500 mL round bottom flask ethyl 2-pyridylacetate (2.0 g, 12.1 mmol), and 60% sodium hydride (508 mg, 12.7 mmol) in dimethylformamide (50 mL) was stirred 1 h. 2-Bromo-1-

[4-(3-chloro-propoxy)-phenyl]-ethanone (3.53 g, 12.1 mmol) was then added in dimethylformamide (50 mL) via dropping funnel The reaction was stirred 14 h. Water (300 mL) was added and the organics were extracted three times with ethyl acetate, and then dried over MgSO$_4$. Purification with silica gel chromatography eluting with hexanes/ethyl acetate (3:1) produced 2.8 g (62%). MS m/z 376 (M+H).

Step 2

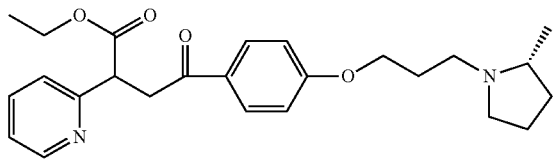

4-{4-[3-((R)-2-Methyl-pyrrolidin-1-yl)-propoxy]-phenyl}-4-oxo-2-pyridin-2-yl-butyric acid ethyl ester In a 100 mL round bottom flask, 4-[4-(3-chloro-propoxy)-phenyl]-4-oxo-2-pyridin-2-yl-butyric acid ethyl ester (2.77 g, 7.4 mmol), benzenesulfonate (R)-2-methyl-pyrrolidinium (3.59 g, 14.7 mmol), potassium carbonate (4.07 g, 29.5 mmol), and potassium iodide (100 mg, 0.6 mmol) in acetonitrile (100 mL) was heated to reflux 14 h. The reaction was cooled and the solvent concentrated under vacuum. The slurry was partitioned between methylene chloride and water, and then washed with water 3 times. The organics were chromatographed through silica gel with methylene chloride/methanol (95:5) eluent. Ethereal HCl was added to make the bis HCl salt and produce 960 mg (28%) of an amorphous solid. MS m/z 425 (M+H).

Example 216

Step 3

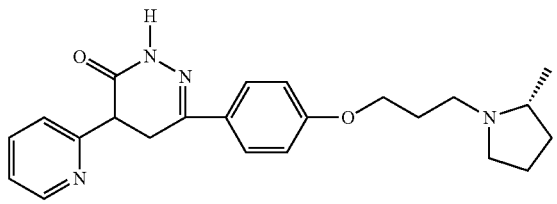

6-{4-[3-((R)-2-Methyl-pyrrolidin-1-yl)-propoxy]-phenyl}-4-pyridin-2-yl-4,5-dihydro-2H-pyridazin-3-one In a 50 mL round bottom flask, 4-{4-[3-((R)-2-methyl-pyrrolidin-1-yl)-propoxy]-phenyl}-4-oxo-2-pyridin-2-yl-butyric acid ethyl ester (950 mg, 1.84 mmol), and hydrazine monohydrate (204 mL, 4.2 mmol), in acetic acid (20 mL) was heated to reflux 14 h. The reaction was cooled and the solvent concentrated under vacuum. The slurry was partitioned between methylene chloride and NaHCO$_3$ sol., extracted three times, and then dried over MgSO$_4$. Purification with silica gel chromatography eluting with methylene chloride/methanol (95:5) produced 250 mg (33%). Ethereal HCl was added to a methanol solution to produce crystals. Mp 231-233° C. MS m/z 393 (M+H).

Example 217

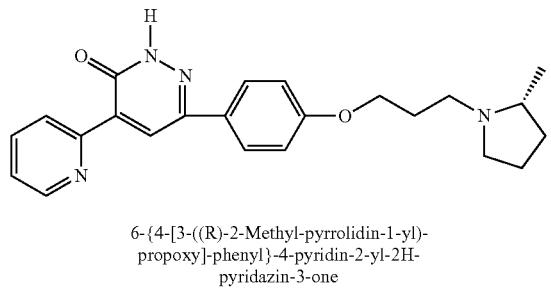 [SMILES: C[C@@H]1CCCN1CCCOc1ccc(-c2cc(-c3ccccn3)c(=O)[nH]n2)cc1]

6-{4-[3-((R)-2-Methyl-pyrrolidin-1-yl)-propoxy]-phenyl}-4-pyridin-2-yl-2H-pyridazin-3-one In a 10 mL round bottom flask, 6-{4-[3-((R)-2-methyl-pyrrolidin-1-yl)-propoxy]-phenyl}-4-pyridin-2-yl-4,5-dihydro-2H-pyridazin-3-one (120 mg, 0.31 mmol), and cesium carbonate (197 mg, 0.62 mmol), in dimethylsulfoxide (3 mL) was heated to 135° C. 3 h. The reaction was cooled and the slurry was partitioned between methylene chloride and water extracted three times, and then dried over MgSO$_4$. Purification with silica gel chromatography eluting with methylene chloride/methanol (95:5), followed by HCl salt formation produced 120 mg (33%). Mp 157-161° C. MS m/z 391 (M+H).

Example 218

Step 1

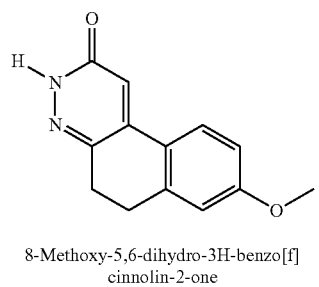 [SMILES: COc1ccc2c(c1)CCc1n[nH]c(=O)cc1-2]

8-Methoxy-5,6-dihydro-3H-benzo[f]cinnolin-2-one

In a 50 mL round bottom flask, 6-methoxy-3,4-dihydro-1H-naphthalen-2-one (1.0 g, 5.68 mmol), and glyoxylic acid monohydrate (523 mg, 5.68 mmol), in acetic acid (10 mL) was heated to reflux 3 h. The reaction was cooled and diluted with water (20 mL). The mixture was basified to pH 8 with NH$_4$OH and then hydrazine monohydrate (0.55 mL, 11.4 mmol) was added. The reaction was heated to reflux 2 h. The reaction was cooled and re-basified with NaHCO$_3$, then extracted with methylene chloride three times. The organics were dried over MgSO$_4$, and the solvents were removed under vacuum to produce 1.1 g (85%). mp dec. 270° C. MS m/z=229 (M+H).

Step 2

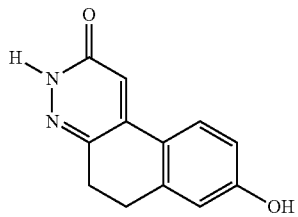

8-Hydroxy-5,6-dihydro-3H-benzo[f]
cinnolin-2-one

In a 100 mL round bottom flask, 8-methoxy-5,6-dihydro-3H-benzo[f]cinnolin-2-one (1.05 g, 4.61 mmol) in methylene chloride (3 mL) was cooled to 0° C. Boron tribromide (23 ml of a 1M sol. in methylene chloride) was added and the reaction warmed to ambient temperature for 4 h. Re-cooled to 0° C. and sat. NH$_4$Cl sol. (23 mL) was added. The solvents were removed under vacuum and water was added. Solids were filtered off and washed with cold methanol to produce 587 mg (59%). Mp>300° C. MS m/z 215 (M+H).

Step 3

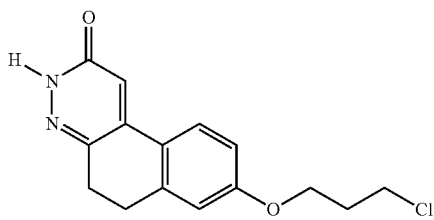

8-(3-Chloro-propoxy)-5,6-dihydro-3H-
benzo[f]cinnolin-2-one

In a 50 mL round bottom flask, 8-hydroxy-5,6-dihydro-3H-benzo[f]cinnolin-2-one (575 mg, 2.69 mmol), 1-bromo-3-chloro-propane (0.27 mL, 2.69 mmol), and potassium carbonate (371 mg, 2.69 mmol) in acetonitrile (20 mL) was heated to reflux 14 h. The reaction was cooled and the solvent concentrated under vacuum. The slurry was partitioned between methylene chloride and water, separated, dried over MgSO$_4$. Purification with silica gel chromatography eluting with methylene chloride/methanol (95:5) produced 106 mg (14%) as an amorphous solid. MS m/z 291 (M+H).

Example 218

Step 4

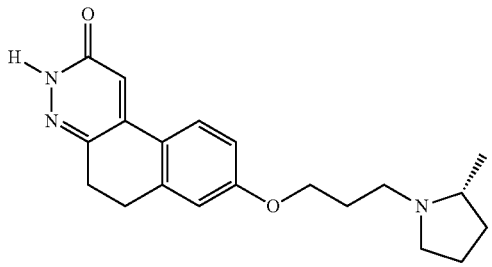

8-(3-((R)-2-Methyl-pyrrolidin-1-yl)-
propoxy]-5,6-dihydro-3H-benzo[f]
cinnolin-2-one In a 25 mL round bottom flask, 8-(3-chloro-propoxy)-5,6-dihydro-3H-benzo[f]cinnolin-2-one (100 mg, 0.34 mmol), benzenesulfonate (R)-2-methyl-pyrrolidinium (168 mg, 0.68 mmol), potassium carbonate (190 mg, 1.36 mmol), and potassium iodide (1 mg, 0.006 mmol) in acetonitrile (10 mL) was heated to reflux 14 h. The reaction was cooled and the solvent concentrated under vacuum. The slurry was partitioned between methylene chloride and water, and then washed with water 3 times. The organics were chromatographed through silica gel with methylene chloride/methanol (95:5) eluent to produce 10 mg (9%). Mp 225° C. (dec.). MS m/z 340 (M+H).

Example 219

Step 1

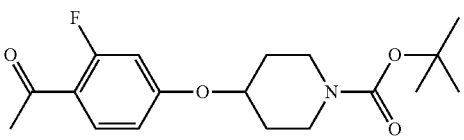

4-(4-Acetyl-3-fluoro-phenoxy)-
piperidine-1-carboxylic acid tert-butyl
ester

In a 500 mL round bottom flask, diethyl azodicarboxylate (16.9 g, 97.3 mmol) and triphenylphosphine (25.5 g, 97.3 mmol) in tetrahydrofuran (200 mL) were cooled to 0° C. 1-(2-Fluoro-4-hydroxy-phenyl)-ethanone (10.0 g, 64.9 mmol) and 4-hydroxy-piperidine-1-carboxylic acid tert-butyl ester (15.67 g, 77.9 mmol) in tetrahydrofuran (100 mL) were added. The reaction was warmed to ambient temperature 14 h. The solvents were concentrated under vacuum and methylene chloride (100 mL) and hexanes (500 mL) were added. The solids were filtered off The mother liquor was concentrated under vacuum and chromatographed through silica gel with hexanes/ethyl acetate (7:3) as eluent to produce 17.5 g (80%). Mp 72-73° C.

Step 2

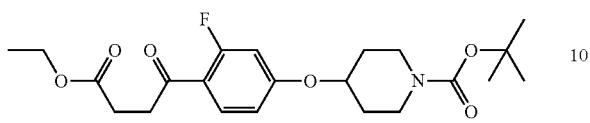

4-[4-(3-Ethoxycarbonyl-propionyl)-3-fluoro-phenoxy]-piperidine-1-carboxylic acid tert-butyl ester In a 250 mL round bottom flask, 4-(4-acetyl-3-fluoro-phenoxy)-piperidine-1-carboxylic acid tert-butyl ester (4.0 g, 12 mmol) in tetrahydrofuran (00 mL) were cooled to −78° C. Lithium diisopropylamide (1.4 g, 13 mmol) was added and stirred 30 min. then warmed to 0° C. Re-cooled to −78° C. and ethyl bromoacetate (1.4 mL, 13 mmol) in tetrahydrofuran (25 mL) was added. The reaction warmed to ambient temperature over 14 h. The reaction was quenched with NH$_4$Cl sol. and the solvents were concentrated under vacuum. The reaction was chromatographed through silica gel with hexanes/ethyl acetate (7:3) as eluent to produce 4.10 g (82%) of oil.

Step 3

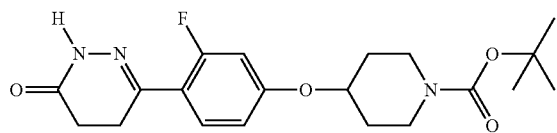

4-[3-Fluoro-4-(6-oxo-1,4,5,6-tetrahydro-pyridazin-3-yl)-phenoxy]-piperidine-1-carboxylic acid tert-butyl ester In a 250 mL round bottom flask, 4-[4-(3-ethoxycarbonyl-propionyl)-3-fluoro-phenoxy]-piperidine-1-carboxylic acid tert-butyl ester (4.1 g, 9.68 mmol), and hydrazine monohydrate (0.97 mL, 19.4 mmol), in isopropanol (100 mL) was heated to reflux 14 h. The reaction was cooled and the solvent concentrated under vacuum. Purification with silica gel chromatography eluting with methylene chloride/methanol (95:5) produced 945 mg (25%). Mp 146-148° C. MS m/z 392 (M+H).

Step 4

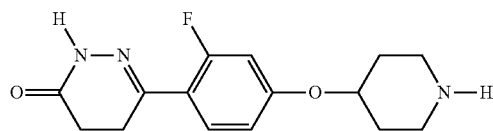

6-[2-Fluoro-4-(piperidin-4-yloxy)-phenyl]-4,5-dihydro-2H-pyridazin-3-one

In a 10 mL round bottom flask, 4-[3-fluoro-4-(6-oxo-1,4,5,6-tetrahydro-pyridazin-3-yl)-phenoxy]-piperidine-1-carboxylic acid tert-butyl ester (410 mg, 1.0 mmol) in trifluoroacetic acid (3 mL) was stirred 2 h. The solvent concentrated under vacuum to produce 420 mg (100%) of the salt as an oil. MS m/z=292 (M+H).

Example 219

Step 5

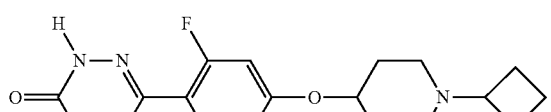

6-[4-(1-Cyclobutyl-piperidin-4-yloxy)-2-fluoro-phenyl]-4,5-dihydro-2H-pyridazin-3-one In a 25 mL round bottom flask, 6-[2-fluoro-4-(piperidin-4-yloxy)-phenyl]-4,5-dihydro-2H-pyridazin-3-one trifluoroacetic acid salt (420 mg, 1.0 mmol) was dissolved in methanol (10 mL), N,N-dimethylformamide (4 mL), and acetic acid (0.4 mL). Cyclobutanone (0.23 mL, 3.0 mmol), and then sodium cyanoborohydride (0.32 g, 5.0 mmol) were added. The reaction was heated to 60° C. for 2 h. The reaction was cooled and diluted with methylene chloride and NaHCO$_3$ sol. to pH 9. The organics were extracted three times and the solvent concentrated under vacuum. Purification with silica gel chromatography eluting with methylene chloride/methanol (95:5) followed by salt formation with ethereal HCl produced 210 mg (54%). Mp>300° C. MS m/z 346 (M+H).

Example 220

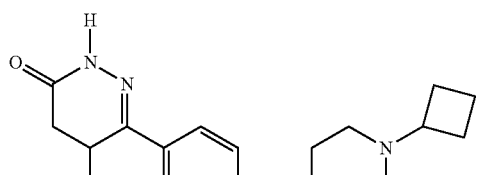

8-(1-Cyclobutyl-piperidin-4-yloxy)-4,4a,5,6-tetrahydro-2H-benzo[h]cinnolin-3-one Following the procedure of Example 219: Mp>300° C. MS m/z=354 (M+H).

Example 221

Step 1

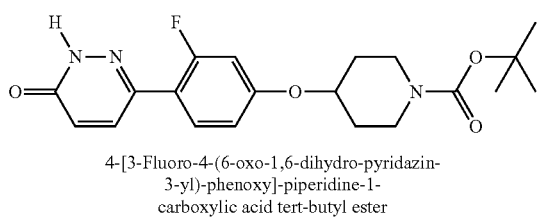 [SMILES: CC(C)(C)OC(=O)N1CCC(Oc2ccc(-c3ccc(=O)[nH]n3)c(F)c2)CC1]

4-[3-Fluoro-4-(6-oxo-1,6-dihydro-pyridazin-3-yl)-phenoxy]-piperidine-1-carboxylic acid tert-butyl ester In a 10 mL round bottom flask, 4-[3-fluoro-4-(6-oxo-1,4,5,6-tetrahydro-pyridazin-3-yl)-phenoxy]-piperidine-1-carboxylic acid tert-butyl ester (525 mg, 1.34 mmol), and cesium carbonate (874 mg, 2.68 mmol), in dimethylsulfoxide (5 mL) was heated to 135° C. 3 h. The reaction was cooled and the slurry was partitioned between methylene chloride and water extracted three times, and then dried over $MgSO_4$. Purification with silica gel chromatography eluting with methylene chloride/methanol (95:5) produced 500 mg (93%). Mp 117-119° C. MS m/z 390 (M+H).

Example 221

Step 2

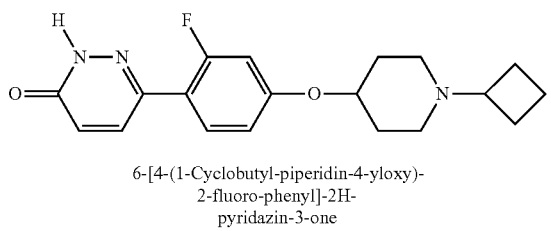 [SMILES: O=c1ccc(-c2ccc(OC3CCN(C4CCC4)CC3)cc2F)n[nH]1]

6-[4-(1-Cyclobutyl-piperidin-4-yloxy)-2-fluoro-phenyl]-2H-pyridazin-3-one

Following the final two steps of Example 219: Mp>300° C. MS m/z 344 (M+H).

Example 222

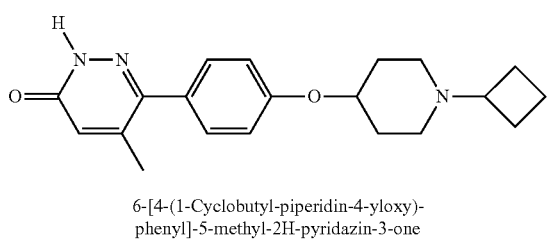 [SMILES: Cc1cc(=O)[nH]nc1-c1ccc(OC2CCN(C3CCC3)CC2)cc1]

6-[4-(1-Cyclobutyl-piperidin-4-yloxy)-phenyl]-5-methyl-2H-pyridazin-3-one

Following the procedure of Example 221: Mp>300° C. MS m/z 340 (M+H).

Example 223

Step 1

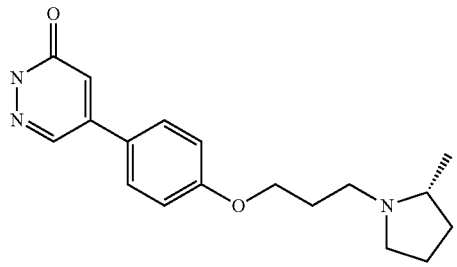

5-{4-[3-((R)-2-Methyl-pyrrolidin-1-yl)-propoxy]-phenyl}-2H-pyridazin-3-one

To a round-bottom flask was added 4-(4,4,5,5-tetramethyl-[1,3,2]dioxaborolan-2-yl)-phenol (11.0 g, 50 mmol), 1-bromo-3-chloropropane (9.88 mL, 100 mmol), potassium carbonate (20.7 g, 150 mmol), and acetonitrile (100 mL). The reaction mixture was heated to reflux for 24 h. The reaction was cooled to room temperature and was filtered. The filtrate was concentrated to give crude 2-[4-(3-chloro-propoxy)-phenyl]-4,4,5,5-tetramethyl-[1,3,2]dioxaborolane. This material was used for next step without purification.

Step 2

To a round-bottom flask was added crude 2-[4-(3-chloro-propoxy)-phenyl]-4,4,5,5-tetramethyl-[1,3,2]dioxaborolane, (R)-2-methyl-pyrrolidine, benzenesulfonic acid salt (24.3 g, 100 mmol), sodium iodide (7.49 g, 50 mmol), potassium carbonate (20.7 g, 150 mmol) and acetonitrile (100 mL). The reaction was heated to reflux for 2.5 days and was cooled to room temperature. The reaction was diluted with methylene chloride (100 mL) and was filtered. The filtrate was concentrated. Purification by column chromatography (5% MeOH in $CH_2Cl_2$) to give 11.3 g (65%, 2 steps) of (R)-2-methyl-1-{3-[4-(4,4,5,5-tetramethyl-[1,3,2]dioxaborolan-2-yl)-phenoxy]-propyl}-pyrrolidine.

Step 3

To a round-bottom flask was added 2-hydroxymethyl-5-iodo-2H-pyridazin-3-one (2.28 g, 9.05 mmol), (R)-2-methyl-1-{3-[4-(4,4,5,5-tetramethyl-[1,3,2]dioxaborolan-2-yl)-phenoxy]-propyl}-pyrrolidine (3.28 g, 9.50 mmol), tetrakis(triphenylphosphine)palladium(0) (2.1 g, 1.8 mmol), potassium carbonate (6.25 g, 45.2 mmol), 1,2-dimethoxyethane (80 mL), and water (40 mL). The reaction mixture was flushed with nitrogen for 30 min and was heated to reflux for 48 h. After cooled to room temperature, the reaction was filtered. The organic layer was separated and concentrated. Purification by column chromatography ($CH_2Cl_2$:MeOH:iPrNH=9:1:0.1) to give 3.31 g (63.5%) of example 223 (5-{4-[3-((R)-2-methyl-pyrrolidin-1-yl)-propoxy]-phenyl}-2H-pyridazin-3-one).

The following examples were prepared using the procedure for example 223.

| Example | Structure | Mp (° C.) | MS m/z |
|---|---|---|---|
| 223 | 5-{4-[3-((R)-2-Methyl-pyrrolidin-1-yl)-propoxy]-phenyl}-2H-pyridazin-3-one | 160-163 | 314 (M + H) |
| 224 | 2-Methoxymethyl-5-{4-[3-((R)-2-methyl-pyrrolidin-1-yl)-propoxy]-phenyl}-2H-pyridazin-3-one | 183-185 | 358 (M + H) |
| 225 | 5-{4-[(S)-2-Methyl-3-((R)-2-methyl-pyrrolidin-1-yl)-propoxy]-phenyl}-2H-pyridazin-3-one | 154-156 | 328 (M + H) |
| 226 | 5-{4-[(R)-2-Methyl-3-((R)-2-methyl-pyrrolidin-1-yl)-propoxy]-phenyl}-2H-pyridazin-3-one | 130-133 | 328 (M + H) |

| Example | Structure | Mp (° C.) | MS m/z |
|---|---|---|---|
| 227 | 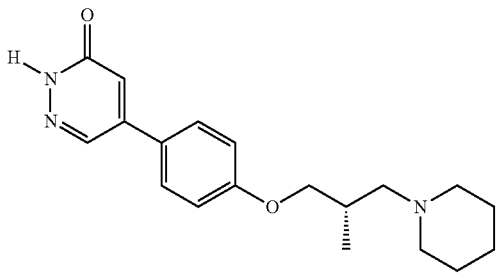<br>5-{4-((S)-2-Methyl-3-piperidin-1-yl-propoxy)-phenyl]-2H-pyridazin-3-o | 145-148 | 328 (M + H) |
| 228 | 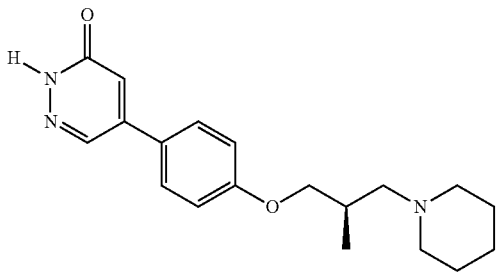<br>5-{4-((R)-2-Methyl-3-piperidin-1-yl-propoxy)-phenyl]-2H-pyridazin-3-one | 160-163 | 328 (M + H) |
| 229 | 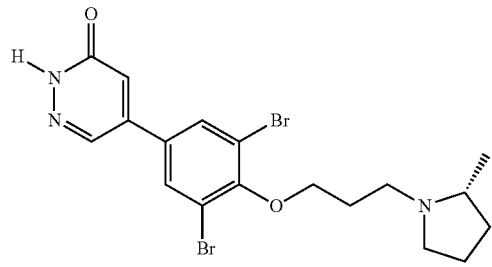<br>5-{3,5-Dibromo-4-[3-((R)-2-methyl-pyrrolidin-1-yl)-propoxy]-phenyl}-2H-pyridazin-3-one | 175-180 | 472 (M + H) |
| 230 | 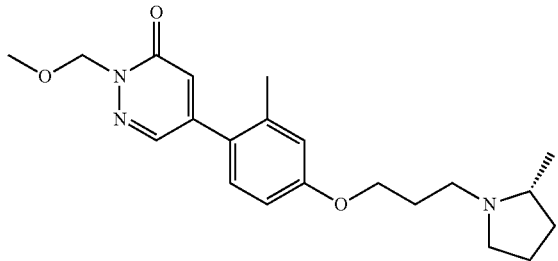<br>2-Methoxymethyl-5-{2-methyl-4-[3-((R)-2-methyl-pyrrolidin-1-yl)-propoxy]-phenyl}-2H-pyridazin-3-one | 139-40.5 HCl | 372 (M + H) |

-continued

| Example | Structure | Mp (° C.) | MS m/z |
|---|---|---|---|
| 231 | 5-{2-methyl-4-[3-((R)-2-methyl-pyrrolidin-1-yl)-propoxy]-phenyl}-2H-pyridazin-3-one | 186-8 HCl | 328 (M + H) |
| 232 | 2-Methoxymethyl-5-[2-methyl-4-(3-piperidin-1-yl-propoxy)-phenyl]-2H-pyridazin-3-one | 185-97 (dec.) HCl | 372 (M + H) |
| 233 | 5-[2-Methyl-4-(3-piperidin-1-yl-propoxy)-phenyl]-2H-pyridazin-3-one | 112-113 | 328 (M + H) |
| 234 | 5-[4-(1-Cyclobutyl-piperidin-4-yloxy)-2-methyl-phenyl]-2-methoxymethyl-2H-pyridazin-3-one | 119.5-123.5 HCl | 384 (M + H) |

Example 235

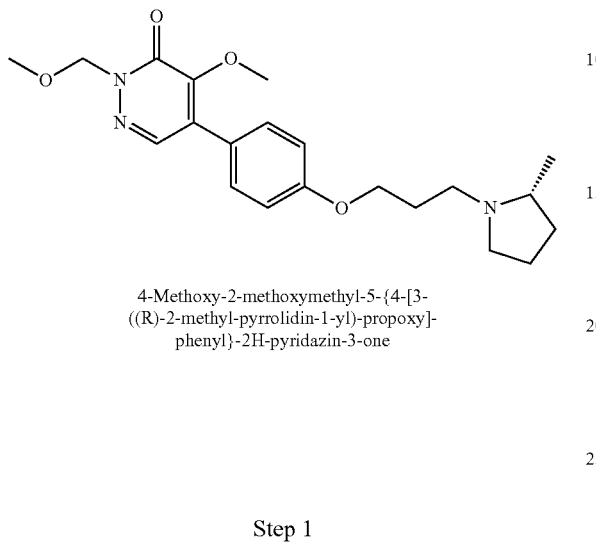

4-Methoxy-2-methoxymethyl-5-{4-[3-
((R)-2-methyl-pyrrolidin-1-yl)-propoxy]-
phenyl}-2H-pyridazin-3-one

Step 1

To a stirred solution of 4,5-dichloropyridazin-6-one (5.00 g, 30.3 mmol) and N,N-diisopropylethylamine (7.92 mL, 45.5 mmol) in methylenechloride (50 mL) was added slowly, bromomethyl methyl ether (4.79 mL, 60.6 mmol) at room temperature (water-bath). The reaction was stirred for 22 h and was then concentrated. Purification by column chromatography (1% MeOH in CH$_2$Cl$_2$) gave 4.74 g (74.8%) of 4,5-dichloro-2-methoxymethyl-2H-pyridazin-3-one.

Step 2

To a stirred solution of 4,5-dichloro-2-methoxymethyl-2H-pyridazin-3one (1.00 g, 4.78 mmol) in 1,4-dioxane (25 mL) at room temperature was added sodium methoxide (271 mg, 5.02 mmol). After 19 h, the reaction was added additional 271 mg of sodium methoxide and was continued to stir for 6 h. The reaction was filtered and the filtrate was concentrated to give 915 mg (93% crude) 5-chloro-4-methoxy-2-methoxymethyl-2H-pyridazin-3-one.

Step 3

To a round-bottom flask was added 5-chloro-4-methoxy-2-methoxymethyl-2H-pyridazin-3-one (902 mg, 4.41 mmol), (R)-2-methyl-1-{3-[4-(4,4,5,5-tetramethyl-[1,3,2]dioxaborolan-2-yl)-phenoxy]-propyl}-pyrrolidine (1.67 g, 4.85 mmol), tetrakis(triphenylphosphine)palladium(0) (510 mg, 0.44 mmol), potassium carbonate (2.34 g, 22.0 mmol), 1,2-dimethoxyethane (15 mL) and water (15 mL). The reaction mixture was flushed with nitrogen for 30 min and was then heated to reflux for 21 h. After cooled to room temperature, the reaction was extracted with CH$_2$Cl$_2$ (100 mL, 50 mL). The combined organic layers were washed with water (50 mL), brine, dried (Na$_2$SO$_4$), and concentrated. Purification by column chromatography (5% MeOH in CH$_2$Cl$_2$) to give 744 mg (43.6%) of example 235 (4-methoxy-2-methoxymethyl-5-{4-[3-((R)-2-methyl-pyrrolidin-1-yl)-propoxy]-phenyl}-2H-pyridazin-3-one) as an oil. MS m/z 388 (M+H).

Example 236

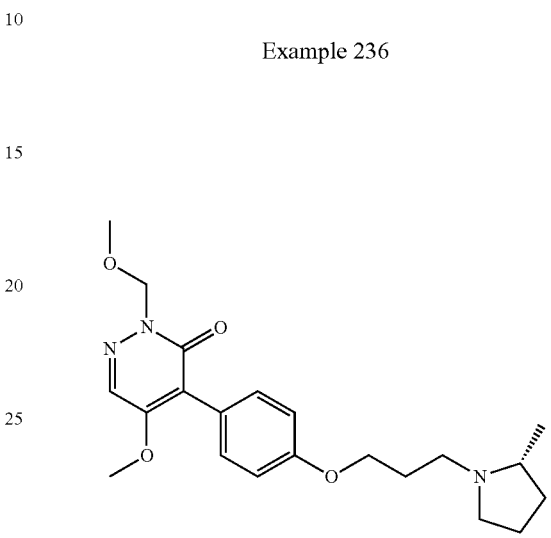

5-Methoxy-2-methoxymethyl-4-{4-[3-
((R)-2-methyl-pyrrolidin-1-yl)-propoxy]-
phenyl}-2H-pyridazin-3-one

Step 1

To a stirred solution of 4,5-dichloro-2-methoxymethyl-2H-pyridazin-3one (500 mg, 2.39 mmol) in methanol (12 mL) at room temperature was added sodium methoxide (258 mg, 4.78 mmol). After stirred for 2 h, the reaction was concentrated. To this residue was added water (20 mL), then extracted with CH$_2$Cl$_2$ (2×50 mL). The combined organic layer was dried (Na$_2$SO$_4$) and concentrated to give 480 mg (98%) 4-chloro-5-methoxy-2-methoxymethyl-2H-pyridazin-3-one.

Step 2

To a round-bottom flask was added 4-chloro-5-methoxy-2-methoxymethyl-2H-pyridazin-3-one (480 mg, 2.34 mmol), (R)-2-methyl-1-{3-[4-(4,4,5,5-tetramethyl-[1,3,2]dioxaborolan-2-yl)-phenoxy]-propyl}-pyrrolidine (890 mg, 2.60 mmol), tetrakis(triphenylphosphine)palladium(0) (270 mg, 0.23 mmol), potassium carbonate (1.24 g, 11.7 mmol), 1,2-dimethoxyethane (15 mL), and water (15 mL). The reaction mixture was flushed with nitrogen for 20 min and was then heated to reflux for 24 h. After cooled to room temperature, the reaction was extracted with CH$_2$Cl$_2$ (2×50 mL). The combined organic layers was washed brine, dried (Na$_2$SO$_4$), and concentrated. Purification by column chromatography (8% MeOH in CH$_2$Cl$_2$) to give 250 mg (26%) example 236 (5-methoxy-2-methoxymethyl-4-{4-[3-((R)-2-methyl-pyrrolidin-1-yl)-propoxy]-phenyl}-2H-pyridazin-3-one). Mp 44-45° C. MS m/z 388 (M+H).

Example 237

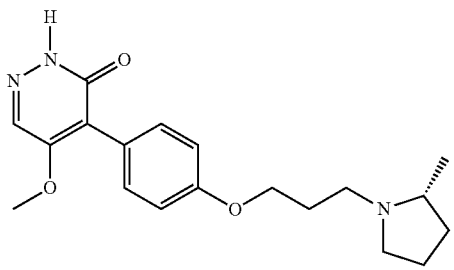

5-Methoxy-4-{4-[3-((R)-2-methyl-pyrrolidin-
1-yl)-propoxy]-phenyl}-2H-
pyridazin-3-one To a round-bottom flask was added example 231 (5-Methoxy-2-methoxymethyl-4-{4-[3-((R)-2-methyl-pyrrolidin-1-yl)-propoxy]-phenyl}-2H-pyridazin-3-one) (1.07 g, 2.76 mmol), methanol (10 mL), and concentrated HCl solution (10 mL). The reaction was heated to reflux for 3 days. After cooled to room temperature, the reaction was neutralized with 10 N NaOH then 5% NaOH solution to pH 7. The reaction was concentrated and the residue was washed with CH$_2$Cl$_2$ (100 mL). The CH$_2$Cl$_2$ layer was concentrated. Purification by column chromatography (15% MeOH in CH$_2$Cl$_2$) to give 350 mg (37%) of 5-methoxy-4-{4-[3-((R)-2-methyl-pyrrolidin-1-yl)-propoxy]-phenyl}-2H-pyridazin-3-one. The product was converted to its hydrochloride salt. Mp 135-140. MS m/z 344 (M+H).

Example 238

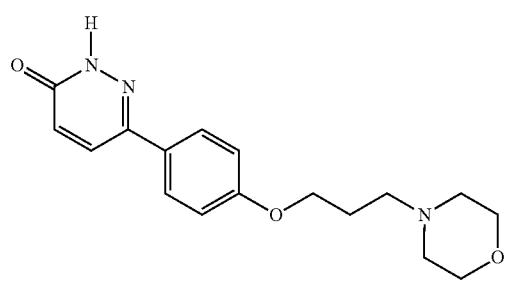

6-[4-(3-Morpholin-4-yl-propoxy)-
phenyl]-2H-pyridazin-3-one

Step 1

To a round-bottom flask was added 1-[4-(3-chloro-propoxy)-phenyl]-ethanone (10.0 g, 47.0 mmol), morpholine (6.15 mL, 70.5 mmol), sodium iodide (7.05 g, 47.0 mmol), potassium carbonate (19.5 g, 141 mmol), and acetonitrile (100 mL). The reaction mixture was heated to reflux for 23 h. The reaction was cooled to room temperature and was diluted with methylene chloride (100 mL). The reaction was filtered and the filtrate was concentrated. Purification by column chromatography (2% MeOH in CH$_2$Cl$_2$) to give 10.5 g (85%) of 6-[4-(3-morpholin-4-yl-propoxy)-phenyl]-2H-pyridazin-3-one.

Step 2

To a round-bottom flask was added 6-[4-(3-morpholin-4-yl-propoxy)-phenyl]-2H-pyridazin-3-one (5.00 g, 19.0 mmol), oxo-acetic acid, hydrate (3.51 g, 38.1 mmol), and acetic acid (15 mL). The reaction was heated to 111° C. for 2.5 h. After cooled to 0° C., the reaction was added water (25 mL) and NH$_4$OH solution until pH-6. To this solution was added hydrazine hydrate (2.76 mL, 57.0 mmol) and was heated to reflux for 20 h (during which additional 3 eq of hydrazine hydrate was added). The reaction was cooled to room temperature and concentrated. Purification by column chromatography (20% MeOH in CH$_2$Cl$_2$) gave 2.53 g (42%) of example 238 6-[4-(3-morpholin-4-yl-propoxy)-phenyl]-2H-pyridazin-3-one.

The following examples were prepared.

| Example | Structure | Mp (° C.) | MS m/z |
|---|---|---|---|
| 238 | 6-[4-(3-Morpholin-4-yl-propoxy)-phenyl]-2H-pyridazin-3-one | 156-159 | 316 (M + H) |

-continued

| Example | Structure | Mp (° C.) | MS m/z |
|---|---|---|---|
| 239 | 6-{4-[3-((S)-2-Methyl-pyrrolidin-1-yl)-propoxy]-phenyl}-2H-pyridazin-3-one | 156-158 | 314 (M + H) |
| 240 | 6-[4-(3-Pyrrolidin-1-yl-propoxy)-phenyl]-2H-pyridazin-3-one | 154-157 | 300 (M + H) |
| 241 | 6-{4-[3-(Cyclobutyl-methyl-amino)-propoxy]-phenyl}-2H-pyridazin-3-one | >50 | 314 (M + H) |
| 242 | 6-{4-[3-(Cyclopentyl-methyl-amino)-propoxy]-phenyl}-2H-pyridazin-3-one | 95-98 | 328 (M + H) |

Example 243

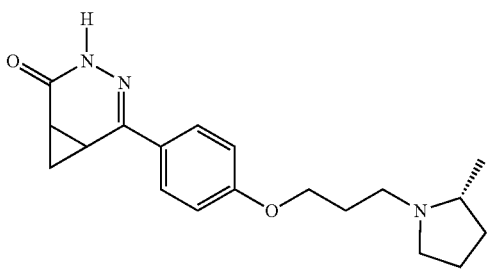

5-{4-[3-((R)-2-Methyl-pyrrolidin-1-yl)-propoxy]-phenyl}-3,4-diaza-bicyclo[4.1.0]hept-4-en-2-one

Step 1

To a round-bottom flask was added phenol (5.0 g, 53.1 mmol), 1-bromo-3-chloropropane (5.52 mL, 55.8 mmol), potassium carbonate (22.0 g, 159 mmol), and acetonitrile (100 mL). The reaction mixture was heated to reflux for 15 h. To this reaction was then added (R)-2-methyl-pyrrolidine hydrochloride (12.9 g, 106 mmol) and sodium iodide (7.96 g, 53.1 mmol) at room temperature. The reaction was continued to reflux for 24 h. After cooled to room temperature, the reaction was filtered through a pad of Celite eluted with $CH_2Cl_2$ (100 mL). The filtrate was concentrated. Purification by column chromatography (5% MeOH in $CH_2Cl_2$) to give 9.02 g (77%) of (R)-2-methyl-1-(3-phenoxy-propyl)-pyrrolidine.

Step 2

To a stirred solution of (R)-2-methyl-1-(3-phenoxy-propyl)-pyrrolidine (1.10 g, 5.02 mmol) and 3-oxa-bicyclo[3.1.0]hexane-2,4-dione (562 mg, 5.02 mmol) in 1,2-dichloroethane (25 mL) at 0° C. was added aluminum trichloride (2.01 g, 15.0 mmol) in small portions. The reaction was heated at 80° C. for 18 h. After cooled to room temperature, the reaction was added crushed ice followed by concentrated HCl solution to break down the complex. The water layer was separated from the organic layer. To this water solution was added hydrazine hydrate (1 mL, 20.6 mmol) and was heated to reflux for 4 h. The reaction was cooled to room temperature and concentrated. Purification by column chromatography (10% MeOH in $CH_2Cl_2$) gave 1.38 g (76%) of example 243 (5-{4-[3-((R)-2-methyl-pyrrolidin-1-yl)-propoxy]-phenyl}-3,4-diaza-bicyclo[4.1.0]hept-4-en-2-one).

The following examples were synthesized. The racemic isomers of example 243 were separated into two enantiomers example 246 and example 247 and example 244 were separated into two enantiomers example 248 and example 249 by chiral chromatography using chiralPak and 0.1% diethylamine in methanol.

| Example | Structure | Mp (° C.) | MS m/z |
|---|---|---|---|
| 243 | 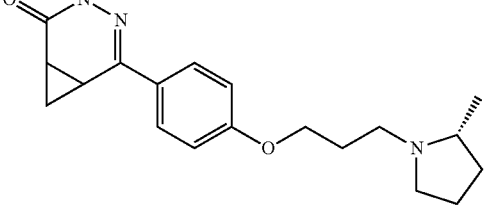<br>5-{4-[3-((R)-2-Methyl-pyrrolidin-1-yl)-propoxy]-phenyl}-3,4-diaza-bicyclo[4.1.0]hept-4-en-2-one | 136-139 HCl | 328 (M + H) |
| 244 | 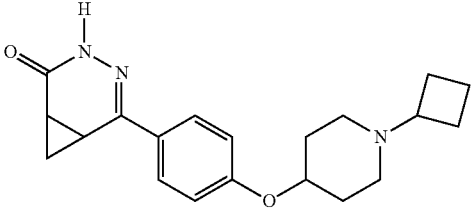<br>5-[4-(1-Cyclobutyl-piperidin-4-yloxy)-phenyl]-3,4-diaza-bicyclo[4.1.0]hept-4-en-2-one | 79-81 | 340 (M + H) |

-continued

| Example | Structure | Mp (° C.) | MS m/z |
|---|---|---|---|
| 245 | 5-{4-[(S)-2-methyl-3-((R)-2-methyl-pyrrolidin-1-yl)-prpoxy]-phenyl}-3,4-diaza-bicyclo[4.1.0]hept-4-en-2-one | 112-115 | 342 (M + H) |
| 246 single isomer | 5-{4-[3-((R)-2-Methyl-pyrrolidin-1-yl)-propoxy]-phenyl}-3,4-diaza-bicyclo[4.1.0]hept-4-en-2-one | 210-211 HCl | 328 (M + H) |
| 247 single isomer | 5-{4-[3-((R)-2-Methyl-pyrrolidin-1-yl)-propoxy]-phenyl}-3,4-diaza-bicyclo[4.1.0]hept-4-en-2-one | 197-198 HCl | 328 (M + H) |
| 248 single isomer | 5-[4-(1-Cyclobutyl-piperidin-4-yloxy)-phenyl]-3,4-diaza-bicyclo[4.1.0]hept-4-en-2-one | 186-187 | 340 (M + H) |

-continued

| Example | Structure | Mp (° C.) | MS m/z |
|---|---|---|---|
| 249 single isomer | 5-[4-(1-Cyclobutyl-piperidin-4-yloxy)-phenyl]-3,4-diaza-bicyclo[4.1.0]hept-4-en-2-one | 185-186 | 340 (M + H) |

Examples 250-254 were prepared as HCl salts following the method of example 243 and example 244.

| Example | Structure | Mp (° C.) | MS m/z |
|---|---|---|---|
| 250 | 5-[4-(1-Cyclobutyl-piperidin-4-yloxy)-phenyl]-3-ethyl-3,4-diaza-bicyclo[4.1.0]hept-4-en-2-one | 246-248 | 368 (M + H) |
| 251 | 5-[4-(1-Cyclobutyl-piperidin-4-yloxy)-phenyl]-3-ethyl-3,4-diaza-bicyclo[4.1.0]hept-4-en-2-one | 110-112 | 382 (M + H) |
| 252 | 5-[4-(1-Cyclobutyl-piperidin-4-yloxy)-phenyl]-3-ethyl-3,4-diaza-bicyclo[4.1.0]hept-4-en-2-one | 243-245 | 354 (M + H) |

-continued

| Example | Structure | Mp (° C.) | MS m/z |
|---|---|---|---|
| 253 | 5-[4-(1-Cyclobutyl-piperidin-4-yloxy)-phenyl]-3-(4-fluoro-phenyl)-3,4-diaza-bicyclo[4.1.0]hept-4-en-2-one | 147-149 | 434 (M + H) |
| 254 | 5-[4-(1-Cyclobutyl-piperidin-4-yloxy)-phenyl]-3-(2,2,2-trifluoro-ethyl)-3,4-diaza-bicyclo[4.1.0]hept-4-en-2-one | 110-121 | 422 (M + H) |
| 260 | 5-[4-(1-Cyclobutyl-piperidin-4-yloxy)-phenyl]-3-methyl-3,4-diaza-bicyclo[4.1.0]hept-4-en-2-one | 264-266 HCl | 368 (M + H) |
| 261 | 5-[4-(1-Cyclopentyl-piperidin-4-yloxy)-phenyl]-3,4-diaza-bicyclo[4.1.0]hept-4-en-2-one | 288-290 HCl | 354 (M + H) |

Example 255

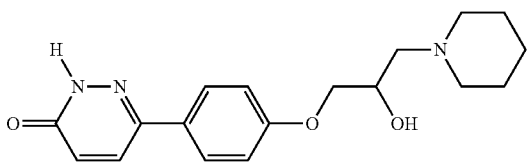

6-[4-(2-Hydroxy-3-piperidin-1-yl-
propoxy)-phenyl]-2H-pyridazin-3-one

Step 1

4-(4,4,5,5-Tetramethyl-1,3,2-dioxaborolan-2-yl)phenol (1.00 g, 4.50 mmol) and anhydrous potassium carbonate (2.20 g, 15.90 mmol) were taken up in racemic epibromohydrin (45 mL).

Reaction mixture was refluxed for 12 h. Potassium carbonate was filtered off and epibromohydrin was evaporated under vacuum. Purification of the product using ISCO silica gel chromatography (hexanes/ethyl acetate 9:1) gave a white solid 1.25 g.

Step 2

The product from step 1 (0.50 g, 1.80 mmol) and piperidine (0.23 g, 2.70 mmol) were dissolved in EtOH and refluxed for 5 h. The solvent was evaporated and the product was purified by ISCO silica gel chromatography eluting with EtOAc/MeOH 9:1 to give product as a white solid 0.49 g (75%).

Step 3

THF anhydrous 15 mL was added to Pd(OAc)$_2$ (0.08 g, 0.35 mmol) and triphenylphosphine (0.38 g, 1.40 mmol) under N$_2$. The reaction was stirred for 5 min and 3,6-dichloropyridazine (1.00 g, 6.70 mmol) was added and reaction mixture was stirred for another 5 min. The product from step 2 (1-piperidin-1-yl-3-[4-(4,4,5,5-tetramethyl-[1,3,2]-dioxaborolan-2-yl)phenoxy]-propan-2-ol) (0.49 g, 1.35 mmol) in 9 mL of anhydrous THF and 5 mL of EtOH was added dropwise, followed by 15 mL of saturated NaHCO$_3$.

The reaction mixture was heated at 82° C. overnight. The solvent was removed and the residue was taken up in methylene chloride and washed with H$_2$O and saturated NaCl, dried over Na$_2$SO$_4$ and was evaporated. The product was purified by ISCO silica gel chromatography eluting with EtOAc/MeOH 9:1 to obtain 0.22 g (46%).

Step 4

The product from step 3 (0.18 g, 0.50 mmol) in 7 mL of glacial acetic acid and NaOAc (0.02 g, 0.25 mmol) was heated to 115° C. for 2 h. The solvent was coevaporated with toluene and the residue was taken up in MeOH and catalytic amount of K$_2$CO$_3$ was added. After 1 h at reflux, the solvent was evaporated and the product was purified by ISCO silica gel chromatography eluting with EtOAc/MeOH 9:1 to give a white solid 0.09 g (82%); Mp 185° C.; MS m/z 330 (M+H).

Example 256

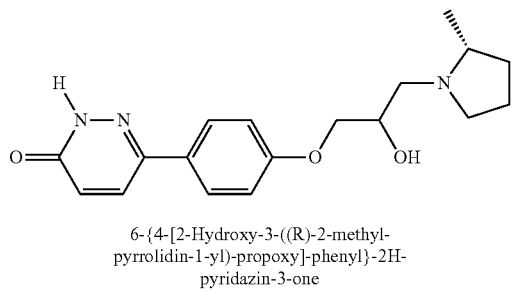 [SMILES: C[C@@H]1CCCN1CC(O)COc1ccc(-c2ccc(=O)[nH]n2)cc1]

6-{4-[2-Hydroxy-3-((R)-2-methyl-
pyrrolidin-1-yl)-propoxy]-phenyl}-2H-
pyridazin-3-one Example 256 was synthesized using the method for example 255 to give a white solid 0.07 g (54%); Mp 153° C.; MS m/z 330 (M+H).

Example 257

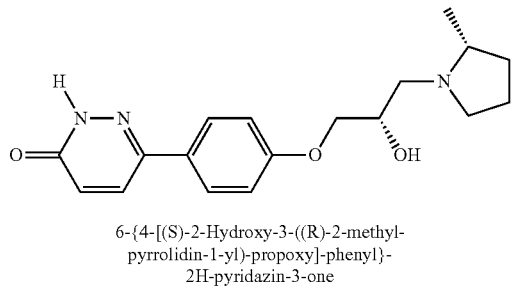 [SMILES: C[C@@H]1CCCN1C[C@H](O)COc1ccc(-c2ccc(=O)[nH]n2)cc1]

6-{4-[(S)-2-Hydroxy-3-((R)-2-methyl-
pyrrolidin-1-yl)-propoxy]-phenyl}-
2H-pyridazin-3-one Example 257 was synthesized using the method for example 256 except using (S)-(+)-epichlorohydrin to give example 257 as a white solid 0.16 g (46%); Mp 156° C.; MS m/z 330 (M+H).

Example 258

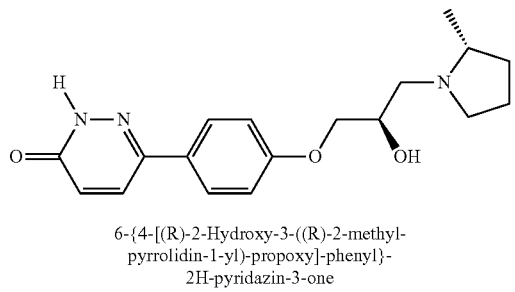 [SMILES: C[C@@H]1CCCN1C[C@@H](O)COc1ccc(-c2ccc(=O)[nH]n2)cc1]

6-{4-[(R)-2-Hydroxy-3-((R)-2-methyl-
pyrrolidin-1-yl)-propoxy]-phenyl}-
2H-pyridazin-3-one Example 258 was synthesized using the method for example 256 except using (R)-(−)-epichlorohydrin to give example 258 as a white solid 0.16 g, (44%); Mp 147° C.; MS m/z 330 (M+H).

Example 259

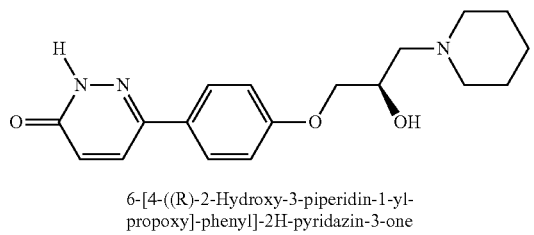 [SMILES: O=c1ccc(-c2ccc(OC[C@H](O)CN3CCCCC3)cc2)n[nH]1]

6-[4-((R)-2-Hydroxy-3-piperidin-1-yl-propoxy]-phenyl]-2H-pyridazin-3-one

Example 259 was synthesized using the method for example 255 using (R)-(−)-epichlorohydrin to give example 259 as a white solid 0.14 g, (48%); Mp 167° C.; MS m/z 330 (M+H).

Utility

The compounds of the present invention are useful, inter alia, as therapeutic agents. Particularly, the compounds are useful for interacting with the $H_3$ receptor. In one embodiment, the present invention provides a method for treating or preventing diseases and disorders, such as those disclosed herein, which comprises administering to a subject in need of such treatment or prevention a therapeutically effective amount of a compound of the present invention.

In an additional embodiment, the present invention provides a method for inhibiting $H_3$ activity comprising providing a compound of the present invention in an amount sufficient to result in effective inhibition. Particularly, the compounds of the present invention can be administered to treat such diseases and disorders such as narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders (such as asthma), inflammation, and myocardial infarction. In certain embodiments, the compounds can be administered to treat narcolepsy or sleep/wake disorders, obesity, cognition, attention deficit hyperactivity disorder (ADHD), and dementia. In other embodiments, the compounds can be administered to treat narcolepsy or sleep/wake disorders, or they can used to treat obesity, or they can used to treat cognition, or they can used to treat attention deficit hyperactivity disorder (ADHD), or they can used to treat dementia.

The inhibition of enzymatic activity by the compounds of the present invention can be determined using, for example, the following assays as set forth below. They are not intended, nor are they to be construed, as limiting the scope of the disclosure.

Rat $H_3$ Assays:

Cell Line Development and Membrane Preparation.

The rat $H_3$ receptor cDNA was PCR amplified from reverse-transcribed RNA pooled from rat thalamus, hypothalamus, striatum and prefrontal cortex with a sequence corresponding to by #338-1672 of Genbank file #NM_053506, encoding the entire 445-amino-acid rat histamine $H_3$ receptor. This was engineered into the pIRES-neo3 mammalian expression vector, which was stably transfected into the CHO-A3 cell line (Euroscreen, Belgium), followed by clonal selection by limiting dilution. Cells were harvested and cell pellets were frozen (−80° C.). Cell pellets were resuspended in 5 mM Tris-HCl, pH 7.5 with 5 nM EDTA and a cocktail of protease inhibitors (Complete Protease Inhibitor Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM $MgCl_2$ and protease inhibitors, recentrifuged as above and the final pellet resuspended in membrane buffer plus 250 mM sucrose and frozen at −80° C.

Radioligand Binding.

Membranes were resuspended in 50 mM Tris HCl (pH 7.4), 5 mM $MgCl_2$, 0.1% BSA. The membrane suspensions (10 μg protein per well) were incubated in a 96 well microtiter plate with [$^3$H]-N-alpha-methylhistamine (approximately 1 nM final concentration), test compounds at various concentrations (0.01 nM-30 μM) and scintillation proximity beads (Perkin Elmer, FlashBlueGPCR Scintillating Beads) in a final volume of 80 μl for 4 hours at room temperature, protected from light. Non-specific binding was determined in the presence of 10 μM clobenpropit. Radioligand bound to receptor, and therefore in proximity to the scintillation beads, was measured using a MicroBeta scintillation counter.

GTPγS Binding.

Membranes were resuspended in 20 mM HEPES pH 7.4 containing: 1 mM EDTA, 0.17 mg/ml dithiothreitol, 100 mM NaCl, 30 μg/ml saponin and 5 mM $MgCl_2$. For measurement of inverse agonist activity, increasing concentrations of test compounds were incubated in a 96 well microtiter plate with 10 μg/well membrane protein, 5 μM GDP, scintillation proximity beads (Perkin Elmer, FlashBlueGPCR Scintillating Beads) and [$^{35}$S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 μM GTP. A decrease in bound [$^{35}$S]-GTPγS is indicative of $H_3$ receptor inverse agonist activity in this assay. Antagonist activity of test compounds was determined in a similar experiment under the following conditions. Membranes were resuspended in 20 mM HEPES pH 7.4 containing: 1 mM EDTA, 0.17 mg/ml dithiothreitol, 200 mM NaCl, 30 μg/ml saponin and 20 mM $MgCl_2$. The membranes were incubated at 10 μg/well membrane protein in a microtiter plate with increasing concentrations of test compounds, 20 μM GDP, scintillation proximity beads and [$^{35}$S]-GTPγS (0.1 nM final concentration) plus 30 nM R-alpha-methylhistamine. The microtiter plates were incubated and processed as described above. A decrease in R-alpha-methylhistamine stimulated [$^{35}$S]-GTPγS binding is indicative of $H_3$ receptor antagonist activity in this assay.

Human $H_3$ Assays:

Methods:

CHO cells stably expressing the human $H_3$ receptor (GenBank: NM_007232) were harvested and cell pellets were frozen (−80° C.). Cell pellets were resuspended in 5 mM Tris-HCl, pH 7.5 with 5 nM EDTA and a cocktail of protease inhibitors (Complete Protease Inhibitor Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM MgCl$_2$ and protease inhibitors, recentrifuged as above and the final pellet resuspended in membrane buffer plus 250 mM sucrose and frozen at −80° C.

Radioligand Binding.

Membranes were resuspended in 50 mM Tris HCl (pH 7.4), 5 mM MgCl$_2$, 0.1% BSA. The membrane suspensions (10 μg protein per well) were incubated in a 96 well microtiter plate with [$^3$H]-N-alpha-methylhistamine (approximately 1 nM final concentration), test compounds at various concentrations (0.01 nM-30 μM) and scintillation proximity beads (Perkin Elmer, FlashBlueGPCR Scintillating Beads) in a final volume of 80 μl for 4 hours at room temperature, protected from light. Non-specific binding was determined in the presence of 10 μM clobenpropit. Radioligand bound to receptor, and therefore in proximity to the scintillation beads, was measured using a MicroBeta scintillation counter.

GTPγS Binding.

Membranes were resuspended in 20 mM HEPES pH 7.4 containing: 1 mM EDTA, 0.17 mg/ml dithiothreitol, 100 mM NaCl, 30 μg/ml saponin and 5 mM MgCl$_2$. For measurement of inverse agonist activity, increasing concentrations of test compounds were incubated in a 96 well microtiter plate with 10 μg/well membrane protein, 5 μM GDP, scintillation proximity beads (Perkin Elmer, FlashBlueGPCR Scintillating Beads) and [$^{35}$S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 μM GTP. A decrease in bound [$^{35}$S]-GTPγS is indicative of H$_3$ receptor inverse agonist activity in this assay. Antagonist activity of test compounds was determined in a similar experiment under the following conditions. Membranes were resuspended in 20 mM HEPES pH 7.4 containing: 1 mM EDTA, 0.17 mg/ml dithiothreitol, 200 mM NaCl, 30 μg/ml saponin and 20 mM MgCl$_2$. The membranes were incubated at 10 μg/well membrane protein in a microtiter plate with increasing concentrations of test compounds, 20 μM GDP, scintillation proximity beads and [$^{35}$S]-GTPγS (0.1 nM final concentration) plus 30 nM R-alpha-methylhistamine. The microtiter plates were incubated and processed as described above. A decrease in R-alpha-methylhistamine stimulated [$^{35}$S]-GTPγS binding is indicative of H$_3$ receptor antagonist activity in this assay.

Other assays that may be used in connection with the present invention are set forth below. Examples of the present invention can be tested in the following in vivo models:

Evaluation of Wake Promoting Activity in Rats

The methodology utilized for evaluating wake promoting activity of test compounds is based on that described by Edgar and Seidel, *Journal of Pharmacology and Experimental Therapeutics*, 283:757-769, 1997, and incorporated herein in its entirety by reference. Compounds of the invention either have demonstrated or are expected to demonstrate utility for wake promoting activity.

Dipsogenia Model:

Inhibition of histamine agonist-induced water drinking in the rat. Histamine, and the H$_3$-selective agonist (R)-α-methylhistamine (RAMH) induce water drinking behavior in the rat when administered either peripherally or centrally (Kraly, F. S., June, K. R. 1982 *Physiol. Behav.* 28: 841; Leibowitz, S. F. 1973 *Brain Res.* 63:440; Ligneau X., Lin, J-S., Vanni-Mercier G., Jouvet M., Muir J. L., Ganellin C. R., Stark H., Elz S., Schunack W., Schwartz, J-C. 1998 *J Pharmcol. Exp. Ther.* 287:658-66; Clapham, J. and Kilpatrick G. J. 1993 *Eur. J. Pharmacol.* 232:99-103) an effect which is blocked by H$_3$ receptor antagonists thioperamide and ciproxifan. Compounds of the invention either have demonstrated or are expected to block RAMH induce water drinking behavior.

Novel Object Discrimination:

Novel object discrimination (NOD; also referred to as novel object recognition) is an assay for short-term visual recognition memory that was first described by Ennaceur and Delacour (Ennaceur, A. and Delacour, J. (1988) *Behav Brain Res* 31: 47-59).

Social Recognition:

Social recognition (SR) is an assay for short-term social (olfactory) memory that was first described by Thor and Holloway (1982). Thor, D. and Holloway, W. (1982) *J Comp Physiolog Psychcol* 96: 1000-1006.

Table A lists the Human and H$_3$ binding data for Examples 1-78 and 81 of the present invention.

TABLE A

| | H3 Pyridazinone Binding data | |
|---|---|---|
| Example | Human H$_3$ Ki nM | Rat H$_3$ Ki nM |
| 1 | A | A |
| 2 | A | B |
| 3 | A | A |
| 4 | A | A |
| 5 | A | A |
| 6 | A | A |
| 7 | A | A |
| 8 | A | A |
| 9 | A | A |
| 10 | A | B |
| 81 | A | A |
| 11 | A | A |
| 12 | A | A |
| 13 | A | A |
| 14 | A | A |
| 15 | B | C |
| 16 | A | A |
| 17 | A | A |
| 18 | A | A |
| 19 | A | A |
| 20 | A | A |
| 21 | A | C |
| 22 | A | A |
| 23 | A | B |
| 24 | A | A |
| 25 | B | D |
| 26 | A | D |
| 27 | D | D |
| 28 | A | B |
| 29 | A | A |
| 30 | A | C |
| 31 | A | B |
| 32 | A | A |
| 33 | A | B |
| 34 | A | A |
| 35 | B | B |
| 36 | B | D |
| 37 | A | B |
| 38 | A | A |
| 39 | A | A |
| 40 | A | A |
| 41 | A | A |
| 42 | B | B |
| 43 | A | A |
| 44 | A | B |
| 45 | A | A |
| 46 | A | B |
| 47 | A | A |
| 48 | A | A |
| 49 | A | A |
| 50 | A | A |
| 51 | A | D |
| 52 | A | A |
| 53 | A | A |

TABLE A-continued

H3 Pyridazinone Binding data

| Example | Human H$_3$ Ki nM | Rat H$_3$ Ki nM |
|---|---|---|
| 54 | A | A |
| 55 | A | A |
| 56 | A | A |
| 57 | A | A |
| 58 | A | A |
| 59 | A | A |
| 60 | A | A |
| 61 | A | A |
| 62 | D | D |
| 63 | D | D |
| 64 | A | B |
| 65 | D | D |
| 66 | D | D |
| 67 | B | D |
| 68 | A | B |
| 69 | B | D |
| 70 | B | B |
| 71 | B | C |
| 72 | A | A |
| 73 | C | D |
| 74 | A | A |
| 75 | A | A |
| 76 | A | A |
| 77 | A | B |
| 78 | A | A |
| 79 | | |
| 80 | | |

Binding constants (K$_i$) for Examples 1 to 78 and 81 in the Human H$_3$ and Rat H$_3$ methods described herein are expressed by letter descriptor to indicate the following ranges: A is 0.1-100 nM; B is 101-500 nM; C is 501-1000 nM; and D is >1000 nM.

Table B lists the Human and Rat H$_3$ binding data for Examples 82-262 of the present invention. The Example numbers in the Table correspond to the Actual Example numbers in the Examples Section.

TABLE B

H3 Pyridazinone Binding data

| Example | human H3 Ki (nM) | rat H3 Ki (nM) |
|---|---|---|
| 81 | A | A |
| 82 | A | A |
| 83 | A | A |
| 84 | A | A |
| 85 | A | A |
| 86 | A | A |
| 87 | A | A |
| 88 | A | A |
| 89 | A | A |
| 90 | A | 5 |
| 91 | A | A |
| 92 | A | A |
| 93 | A | A |
| 94 | A | A |
| 95 | A | A |
| 96 | A | A |
| 97 | A | A |
| 98 | A | A |
| 99 | A | A |
| 100 | A | A |
| 101 | A | A |
| 102 | D | D |
| 103 | A | A |
| 104 | A | A |
| 105 | D | D |
| 106 | A | A |
| 107 | A | A |
| 108 | A | A |
| 109 | A | A |
| 110 | A | A |

TABLE B-continued

H3 Pyridazinone Binding data

| Example | human H3 Ki (nM) | rat H3 Ki (nM) |
|---|---|---|
| 111 | A | A |
| 112 | A | |
| 113 | D | D |
| 114 | A | A |
| 115 | A | A |
| 116 | A | A |
| 117 | A | A |
| 118 | A | A |
| 119 | A | A |
| 120 | A | B |
| 121 | A | A |
| 122 | A | A |
| 123 | A | A |
| 124 | A | A |
| 125 | B | C |
| 126 | B | C |
| 127 | C | C |
| 128 | A | A |
| 129 | A | B |
| 130 | B | B |
| 131 | A | A |
| 132 | A | A |
| 133 | A | A |
| 134 | A | A |
| 135 | B | B |
| 136 | A | B |
| 137 | A | A |
| 138 | A | A |
| 139 | A | A |
| 140 | B | C |
| 141 | A | A |
| 142 | A | B |
| 143 | A | C |
| 143 | A | A |
| 144 | A | A |
| 145 | A | A |
| 146 | A | A |
| 147 | A | B |
| 148 | A | A |
| 149 | A | A |
| 150 | A | A |
| 151 | A | A |
| 152 | A | A |
| 153 | A | A |
| 154 | A | A |
| 155 | A | A |
| 156 | A | A |
| 157 | A | A |
| 158 | A | A |
| 159 | D | D |
| 160 | B | B |
| 161 | D | D |
| 162 | C | D |
| 163 | A | A |
| 164 | A | A |
| 165 | D | D |
| 166 | A | A |
| 167 | A | A |
| 168 | A | A |
| 169 | A | A |
| 170 | A | A |
| 171 | A | A |
| 172 | A | A |
| 173 | A | A |
| 174 | A | A |
| 175 | A | A |
| 176 | A | A |
| 177 | A | A |
| 178 | A | A |
| 179 | A | A |
| 180 | A | A |
| 181 | A | B |
| 182 | A | A |
| 183 | A | A |
| 184 | A | A |

TABLE B-continued

H3 Pyridazinone Binding data

| Example | human H3 Ki (nM) | rat H3 Ki (nM) |
|---|---|---|
| 185 | A | A |
| 186 | A | A |
| 187 | A | A |
| 188 | A | A |
| 189 | A | A |
| 190 | A | A |
| 191 | A | A |
| 192 | A | A |
| 193 | A | A |
| 194 | A | A |
| 195 | A | A |
| 196 | A | A |
| 197 | A | A |
| 198 | A | A |
| 199 | A | A |
| 200 | A | A |
| 201 | A | B |
| 202 | A | A |
| 203 | A | A |
| 204 | A | A |
| 205 | B | B |
| 206 | D | D |
| 207 | A | A |
| 208 | A | A |
| 209 | A | A |
| 210 | A | A |
| 211 | A | A |
| 212 | A | A |
| 213 | B | B |
| 214 | A | A |
| 215 | A | A |
| 216 | A | A |
| 217 | A | A |
| 218 | A | A |
| 219 | A | A |
| 220 | A | A |
| 221 | A | A |
| 222 | A | A |
| 223 | A | A |
| 224 | A | A |
| 225 | A | A |
| 226 | A | A |
| 227 | A | A |
| 228 | A | B |
| 229 | A | C |
| 230 | A | A |
| 231 | A | A |
| 232 | A | A |
| 233 | A | B |
| 234 | A | A |
| 235 | A | A |
| 236 | A | A |
| 237 | A | A |
| 238 | D | D |
| 239 | A | A |
| 240 | A | A |
| 241 | B | B |
| 242 | A | B |
| 243 | A | A |
| 244 | A | A |
| 245 | A | A |
| 246 | A | A |
| 247 | A | A |
| 248 | A | A |
| 249 | A | A |
| 250 | A | A |
| 251 | A | A |
| 252 | A | A |
| 253 | A | A |
| 254 | A | A |
| 255 | B | B |
| 256 | A | B |
| 257 | A | A |
| 258 | A | A |
| 259 | B | B |
| 260 | A | A |
| 261 | A | A |
| 262 | A | B |

Binding constants ($K_i$) for Examples 1 to 78 and 81 in the Human $H_3$ and Rat $H_3$ methods described herein are expressed by letter descriptor to indicate the following ranges: A is 0.1-100 nM; B is 101-500 nM; C is 501-1000 nM; and D is >1000 nM.

Compounds of the invention either have demonstrated or are expected to demonstrate inhibition of $H_3$ and thereby for utility for treatment of the indications described herein.

Publications cited throughout this disclosure are incorporated in their entirety herein by reference.

REFERENCES

Alguacil L. F.; Perez-Garcia C. Histamine $H_3$ Receptor: A potential drug target for the treatment of central nervous systems disorders. *Current Drug Targets-CNS & Neurological Disorders* 2003, 2, 303-131.

Arrang, J. M.; Garbarg, M.; Schwartz, J. C., Auto-inhibition of brain histamine release mediated by a novel class ($H_3$) of histamine receptor. *Nature* 1983, 302, (5911), 832-7.

Celanire, S.; Wijtmans, M.; Talaga, P.; Leurs, R.; de Esch, I. J., Keynote review: histamine $H_3$ receptor antagonists reach out for the clinic. *Drug Discov Today* 2005, 10, (23-24), 1613-27.

Chazot P. L.; Hann V. $H_3$ histamine receptor isoforms: New therapeutic targets in the CNS? *Current Opinions in Investigational Drugs* 2001, 2, 1428-1431.

Chen Z. Effect of histamine $H_3$-receptor antagonist clobenprobit on spatial memory of radial maze performance in rats. *Acta Pharmacol Sin* 2000, 21, 905-910.

Esbenshade, T. A.; ox, G. B.; Cowart, M. D. Histamine $H_3$ receptor antagonists: Preclinical promise for treating obesity and cognitive disorders. *Molecular interventions* 2006, 6, 77-88.

Fox G. B.; Pan J. B.; Esbenshade T. A.; Bennani Y. L.; Black L. A.; Faghih R.; Hancock A. A.; Decker M. W. Effects of histamine $H_3$ receptor ligands GT-2331 and ciproxifan in a repeated acquisition response in the spontaneously hypertensive rat pup. *Behav. Brain Res.* 2002, 131, 151-161.

Fox G. B.; Pan J. B.; Radek R. J.; Lewis A. M.; Bitner R. S.; Esbenshade T. A.; Faghih R.; Bennani Y. L.; Williams W.; Yao B. B. Decker M. W.; Hancock A. A. Two novel and selective nonimidazole $H_3$ receptor Antagonists A-304121 and A-317920: II. In vivo behavioral and neurophysiological characterization. *J. Pharmacol. Exper. Ther.* 2003, 305, 897-908.

Hancock, A. A.; Esbenshade, T. A.; Krueger, K. M.; Yao, B. B., Genetic and pharmacological aspects of histamine $H_3$ receptor heterogeneity. *Life Sci* 2003, 73, (24), 3043-72.

Hancock, A. A.; Fox, G. B. Persepectives on cognitive domains, $H_3$ receptor ligands and neurological disease. *Expert Opin. Investig. Drugs,* 2004, 13, 1237-1248.

Komater V. A.; Browman K. E.; Curzon P.; Hancock A. A., Decker M. W.; Fox B. $H_3$ receptor blockade by thioperamide enhances cognition in rats without inducing locomotor sensitization. *Psychopharmacology* 2003, 167, 363-372.

Leurs R.; Blandina P.; Tedford C.; Timmerman H. Therapeutic potential of histamine $H_3$ receptor agonists and antagonists. *Trends in Pharmacology* 1998, 19, 177-183.

Leurs, R.; Bakker, R. A.; Timmerman, H.; de Esch, I. J., The histamine H₃ receptor: from gene cloning to H₃ receptor drugs. *Nat Rev Drug Discov* 2005, 4, (2), 107-20.

Lin, J. S.; Sakai, K.; Vanni-Mercier, G.; Arrang, J. M.; Garbarg, M.; Schwartz, J. C.; Jouvet, M., Involvement of histaminergic neurons in arousal mechanisms demonstrated with H₃-receptor ligands in the cat. *Brain Res* 1990, 523, (2), 325-30.

Lloyd G. K.; Williams M. Neuronal nicotinic acetylcholine receptors as novel drug targets. *J Pharmacol Exp Ther.* 2000, 292, 461-467.

Monti, J. M.; Jantos, H.; Ponzoni, A.; Monti, D., Sleep and waking during acute histamine H₃ agonist BP 2.94 or H₃ antagonist carboperamide (MR 16155) administration in rats. *Neuropsychopharmacology* 1996, 15, 31-5.

Orsetti M.; Ferretti C.; Gamalero S. R.; Ghi P. Histamine H₃-receptor blockade in the rat nucleus basalis magnocellularis improves place recognition memory. *Psychopharmacology* 2002, 159, 133-137.

Parmentier R.; Ohtsu H.; Djebbara-Hannas Z.; Valatx J-L.; Watanabe T.; Lin J-S. Anatomical, physiological, and pharmacological characteristics of histidine decarboxylase knock-out mice: evidence for the role of brain histamine in behavioral and sleep-wake control. *J. Neurosci.* 2002, 22, 7695-7711.

Passani, M. B.; Lin, J. S.; Hancock, A.; Crochet, S.; Blandina, P., The histamine H₃ receptor as a novel therapeutic target for cognitive and sleep disorders. *Trends Pharmacol Sci* 2004, 25, 618-25.

Repka-Ramirez M. S, New concepts of histamine receptors and actions. *Current Allergy and Asthma Reports* 2003, 3, 227-231.

Ritz A.; Curley J.; Robertson J.; Raber J. Anxiety and cognition in histamine H₃ receptor−/− mice. *Eur J Neurosci* 2004, 19, 1992-1996.

Rouleau, A.; Heron, A.; Cochois, V.; Pillot, C.; Schwartz, J. C.; Arrang, J. M., Cloning and expression of the mouse histamine H₃ receptor: evidence for multiple isoforms. *J Neurochem* 2004, 90, 1331-8.

Vanni-Merci G.; Gigout S.; Debilly G.; Lin J. S. Waking selective neurons in the posterior hypothalamus and their response to histamine H₃-receptor ligands: an electrophysiological study in freely moving cats. *Behav Brain Res* 2003, 144, 227-241.

Witkin, J. M.; Nelson, D. L., Selective histamine H₃ receptor antagonists for treatment of cognitive deficiencies and other disorders of the central nervous system. *Pharmacol Ther* 2004, 103, 1-20.

Yao, B. B.; Sharma, R.; Cassar, S.; Esbenshade, T. A.; Hancock, A. A., Cloning and pharmacological characterization of the monkey histamine H₃ receptor. *Eur J Pharmacol* 2003, 482, (1-3), 49-60.

What is claimed:

1. A method for palliative treatment of a patient afflicted by a disease or disorder which is narcolepsy, a sleep/wake disorder, attention deficit hyperactivity disorder (ADHD), Alzheimer's disease, schizophrenia, or a cognition/cognitive disorder, comprising administering to the patient in need thereof a therapeutically effective amount of a compound according to formula Ie:

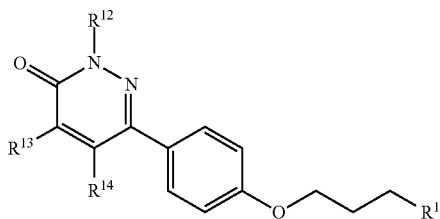

or a stereoisomeric form, mixture of stereoisomeric forms, or a pharmaceutically acceptable salt thereof, wherein:

$R^1$ is selected from a piperidinyl or pyrrolidinyl ring, optionally substituted with 1 to 3 $R^{20}$ groups;

$R^{12}$ is H, $C_1$-$C_6$ alkyl, cycloalkyl, aryl, arylalkyl, heteroaryl, heterocycloalkyl, C(=O)$R^{27}$, or CO$_2R^{27}$, wherein the $C_1$-$C_6$ alkyl, cycloalkyl, aryl, arylalkyl, heteroaryl, or heterocycloalkyl group is optionally substituted with 1 to 3 $R^{20}$ groups;

$R^{13}$ and $R^{14}$ are each independently H, $C_1$-$C_6$ alkyl, aryl, arylalkyl $C_1$-$C_6$alkoxyl, S(=O)$_y$—$C_1$-$C_6$ alkyl, cycloalkyl, heterocycloalkyl, or heteroaryl;

or $R^{13}$ and $R^{14}$, are taken together with the carbon atoms through which they are connected to form a fused phenyl, thienyl, pyrrolyl, oxazolyl, pyridinyl, cyclopentyl or cyclohexyl ring, wherein the fused phenyl, thienyl, pyrrolyl, oxazolyl, pyridinyl, cyclopentyl or cyclohexyl ring is optionally substituted with 1 to 3 $R^{20}$ groups;

$R^{20}$ at each occurrence is independently, H, F, Cl, Br, I, OR$^{21}$, NR$^{23}$R$^{24}$, NHOH, NO$_2$, CN, CF$_3$, $C_1$-$C_6$ alkyl optionally substituted with OR$^{26}$, $C_2$-$C_6$ alkenyl, $C_2$-$C_6$ alkynyl, $C_3$-$C_7$ cycloalkyl($C_0$-$C_4$ alkyl), 3- to 7-membered heterocycloalkyl($C_0$-$C_4$ alkyl), phenyl, 5- or 6-membered heteroaryl($C_0$-$C_4$alkyl), arylalkyl, (=O), C(=O)R$^{21}$, CO$_2$R$^{21}$, C(=O)R$^{21}$, C(=O)NR$^{23}$R$^{24}$, NR$^{27}$C(=O) R$^{21}$, NR$^{27}$C(=O)OR$^{21}$, C(=O)NR$^{23}$R$^{24}$, NR$^{27}$C(=OS)R$^{21}$, or S(O)$_q$R$^{21}$;

each $R^{21}$ is independently H, $C_1$-$C_6$ alkyl, aryl, or arylalkyl;

each $R^{23}$ and $R^{24}$ is independently selected from H, $C_1$-$C_6$ alkyl, and aryl, or $R^{23}$ and $R^{24}$, together with the nitrogen atom to which they are attached, form a 3 to 7 membered heterocyclic ring optionally substituted with =O;

$R^{26}$ is H, $C_1$-$C_6$alkyl, aryl, or alkylaryl;

$R^{27}$ is H, or $C_1$-$C_6$ alkyl;

q is 0, 1, or 2; and y is 0, 1, or 2.

2. The method according to claim 1, wherein in the compound $R^{13}$ and $R^{14}$ are taken together with the carbon atoms through which they are connected to form a fused phenyl, thienyl, oxazolyl, pyridinyl, cyclopentyl or cyclohexyl ring, wherein the fused phenyl, thienyl, pyrrolyl, oxazolyl, pyridinyl, cyclopentyl or cyclohexyl ring is optionally substituted with 1 to 3 $R^{20}$ groups.

3. The method according to claim 1, wherein in the compound $R^{12}$ is H, $C_1$-$C_6$ alkyl, cycloalkyl, aryl, arylalkyl, or heteroaryl, wherein the $C_1$-$C_6$ alkyl, cycloalkyl, aryl, arylalkyl, or heteroaryl is optionally substituted with 1 to 3 $R^{20}$ groups.

4. The method according to claim 1, wherein in the compound $R^{13}$ and $R^{14}$ are each independently H or $C_1$-$C_6$ alkyl.

5. The method according to claim 1, wherein in the compound $R^1$ is:

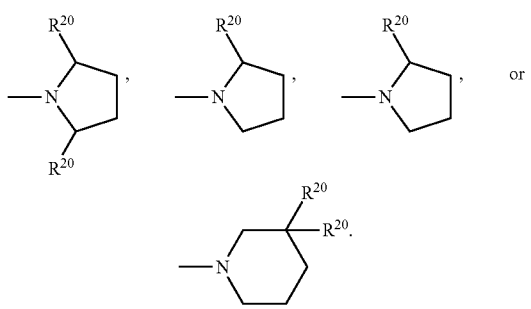

6. The method according to claim 5, wherein in the compound $R^1$ is:

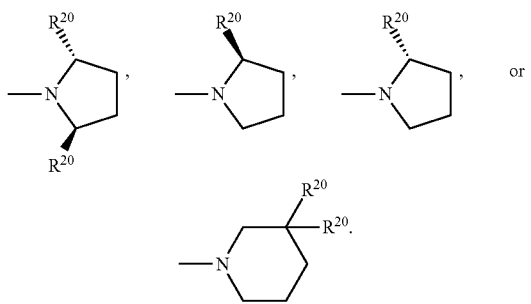

7. The method according to claim 6, wherein in the compound $R^{20}$ is F, Cl, $CF_3$, $NR^{23}R^{24}$, or $C_1$-$C_6$ alkyl optionally substituted with $OR^{26}$, $C_3$-$C_7$ cycloalkyl($C_0$-$C_4$ alkyl), or 3- to 7-membered heterocycloalkyl($C_0$-$C_4$alkyl).

8. The method according to claim 7, wherein in the compound $R^{20}$ is $C_1$-$C_6$ alkyl optionally substituted with $OR^{26}$.

9. The method according to claim 1, wherein the disease or disorder is a sleep/wake disorder.

10. The method according to claim 1, wherein the disease or disorder is attention deficit hyperactivity disorder (ADHD).

11. The method according to claim 1, wherein the disease or disorder is Alzheimer's disease.

12. The method according to claim 1, wherein the disease or disorder is schizophrenia.

13. The method according to claim 1, wherein the disease or disorder is a cognition/cognitive disorder.

14. A method for palliative treatment of a patient afflicted by a disease or disorder selected from narcolepsy, a sleep/wake disorder, attention deficit hyperactivity disorder (ADHD), Alzheimer's disease, schizophrenia, or a cognition/cognitive disorder, comprising administering to the patient in need thereof a therapeutically effective amount of a compound of formula Ie that is:

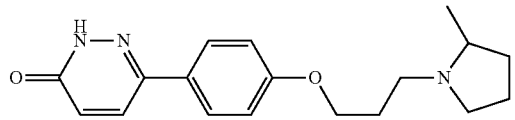 [SMILES: CC1CCCN1CCCOc1ccc(-c2ccc(=O)[nH]n2)cc1]

or a stereoisomer, mixture of stereoisomers or a pharmaceutically acceptable salt thereof.

15. The method according to claim 14, wherein the compound is

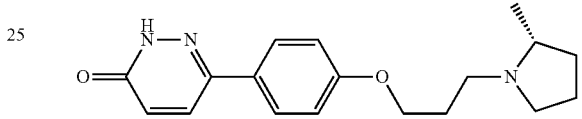

or a pharmaceutically acceptable salt thereof.

16. The method according to claim 15 comprising administering a pharmaceutically acceptable salt of the compound.

17. The method according to claim 14, wherein the disease or disorder is a sleep/wake disorder.

18. The method according to claim 14, wherein the disease or disorder is a cognitive/cognition disorder.

19. The method according to claim 14, wherein the disease or disorder is attention deficit hyperactivity disorder (ADHD).

20. The method according to claim 14, wherein the disease or disorder is Alzheimer's disease.

21. The method according to claim 14, wherein the disease or disorder is schizophrenia.

\* \* \* \* \*